(12) United States Patent
Ohtake et al.

(10) Patent No.: US 6,323,235 B1
(45) Date of Patent: Nov. 27, 2001

(54) BENZENE-CONDENSED HETEROCYCLIC DERIVATIVES AND THEIR USES

(76) Inventors: Atsushi Ohtake, 1-31-22 Tsunishi; Kazuhiro Hoshi, 1-31-17 Tsunishi, both of Kamakura-shi, Kanagawa 248; Shunji Tsukamoto, 734-2-8 Nakatogari, Nagaizumi-cho, Sunto-gun, Shizuoka 411; Takahiro Takeda; Naohiro Yamada, both of 1-31-22 Tsunishi, Kamakura-shi, Kanagawa 248; Kazuhisa Matsumoto, 2-3-6 Tsunishi, Kamakura-shi, Kanagawa 248; Michihiro Ohno, 1111 Tebiro, Kamakura-shi, Kanagawa 248; Kiyotaka Ohno, deceased, late of Fujisawa-shi, all of (JP), by Makiko Ohno, legal representative ( * ) Notice: Subject to any disclaimer, the term of this patent is extended or adjusted under 35 U.S.C. 154(b) by 0 days.

(21) Appl. No.: 09/482,279

(22) Filed: Jan. 13, 2000

Related U.S. Application Data (6262) Division of application No. 08/700,477, filed as application No. PCT/JP96/00011 on Jan. 8, 1996, now Pat. No. 6,043,264.

(30) Foreign Application Priority Data

Jan. 6, 1995 (JP) .......................................... 7-788

(51) Int. Cl.$^7$ ..................... C07D 209/18; A61K 31/404
(52) U.S. Cl. ................... 514/415; 514/419; 548/491; 548/503; 548/509; 548/510
(58) Field of Search ................... 514/415, 419; 548/491, 503, 509, 510

(56) References Cited

U.S. PATENT DOCUMENTS

| | | | |
|---|---|---|---|
| 4,933,351 | 6/1990 | Atkinson et al. | 514/320 |
| 5,232,945 | 8/1993 | Hulin | 514/456 |
| 5,385,931 | 1/1995 | Bigg et al. | 514/443 |
| 5,668,180 | 9/1997 | Lesieur et al. | 514/630 |
| 5,703,121 | 12/1997 | Lesieur et al. | 514/469 |
| 6,069,156 | * 5/2000 | Oku et al. | 514/339 |

FOREIGN PATENT DOCUMENTS

| | | |
|---|---|---|
| 165810 | 12/1985 | (EP) . |
| 337766 | * 10/1989 | (EP) . |
| 0548949 A2 | 6/1993 | (EP) . |
| 05081187 Al | 2/1994 | (EP) . |

OTHER PUBLICATIONS

FitzGerald, "Prostaglandins and Related Compounds", *Cecil Textbook of Medicine*, 20$^{th}$ Edition, vol. 2, pp. 1187–1194 (1996).

* cited by examiner

*Primary Examiner*—Mukund J. Shah
*Assistant Examiner*—Deepak R. Rao

(57) ABSTRACT

Novel compounds having strong $TXA_2$ receptor antagonist activities and $PGI_2$ receptor agonist activities, which are effective for therapy and prevention of diseases related to $TXA_2$, are disclosed. The compound of the present invention is represented by the following formula (I).

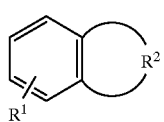

(I)

(wherein the meanings of the symbols in the formula are as described in the specification).

13 Claims, No Drawings

BENZENE-CONDENSED HETEROCYCLIC DERIVATIVES AND THEIR USES

This application is a divisional of Ser. No. 08/700,477 filed Jun. 26, 1997 now U.S. Pat. No. 6,043,264.

TECHNICAL FIELD

The present invention relates to a novel benzene-condensed heterocyclic derivative and to an antagonist against thromboxane $A_2$ (hereinafter referred to as "$TXA_2$") receptor, comprising the compound as an active ingredient.

BACKGROUND ART $TXA_2$ discovered by Samuelsson et al. in 1975 has a strong platelet aggregation activity as well as vascular smooth muscle-contracting activity and bronchial smooth muscle-contracting activity (Proc. Natl. Acad. Sci. U.S.A., 72, 2994 (1975)). On the other hand, plastaglandin $I_2$ ($PGI_2$) is known as a compound having activities opposite to the above-mentioned activities, that is, as a compound having a strong platelet aggregation inhibiting activity and vasodilation activity (Nature, 263, 663(1976)). Since these two compounds are synthesized from arachidonic acid in the body and since their activities are strong, it is said that the balance between $TXA_2$ and $PGI_2$ is important for keeping the homeostasis of circulatory system. Therefore, if this balance is inclined to the side of $TXA_2$, activation of platelets and subsequent thrombus formation and vasoconstriction are caused, which is thought to be a cause of circulatory disorders including ischemic heart diseases such as angina pectoris and myocardial infarction, cerebrovascular diseases, renal disorders and the like. Further, since $TXA_2$ has a strong bronchial smooth muscle-contracting activity, it is thought that $TXA_2$ also has a relationship to bronchial asthma. Thus, inhibition of activities of $TXA_2$ is thought to be effective for therapies of circulatory disorders including ischemic heart diseases such as angina pectoris and myocardial infarction, cerebrovascular diseases and renal disorders, as well as bronchial asthma. So far, as the drugs to inhibit the activities of $TXA_2$, a $TXA_2$ receptor antagonist (Circulation, 81, Suppl. I, I-69(1990); Medicinal Research Reviews, 11, 503(1991)), and an inhibitor of $TXA_2$ synthetase have been reported.

However, no drugs which sufficiently inhibit the activities of $TXA_2$ have been obtained yet.

DISCLOSURE OF THE INVENTION

Accordingly, an object of the present invention is to provide an excellent $TXA_2$ receptor antagonist.

The present inventors searched a $TXA_2$ receptor antagonist having a novel structure to discover benzene-condensed heterocyclic derivatives having strong $TXA_2$ receptor antagonist activities, thereby completing the present invention.

That is, the present invention provides a benzene-condensed heterocyclic derivative of the formula (I):

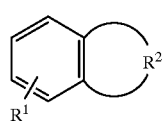

(I)

(wherein $R^1$ is —X—$(CH_2)_n$COOR (wherein X is —O—, —S— or —CH_2—, $R^3$ is hydrogen, $C_1$–$C_5$ lower alkyl, or an atom or group which gives a pharmaceutically acceptable salt, and n is an integer of 1 to 3);

$R^2$ is i) —$CR^4$=$CR^5$—O—, ii) —$CR^5$=$CR^4$—O—, or iii) —$NR^4$–$CR^5R^6$—$CHR^7$— (wherein $R^4$ is —$(CH_2)_m$—Y—$R^8$ (wherein m is an integer of 1 to 4, Y is

1) —O—,

2) —$CH_2$—,

3) —$S(O)_p$— (p is an integer of 0 to 2),

4) —CO—,

5) —CH(OH)—,

6) —$NR^9SO_2$—, (wherein $R^9$ is
 a) hydrogen,
 b) $C_1$–$C_5$ alkyl,
 c) phenyl (which may be substituted),
 d) $C_1$–$C_5$ alkyl substituted with phenyl (which may be substituted)

7) —$NR^9$CO— (wherein $R^9$ represents the same meanings as described above)

8) —$CONR^9$— (wherein $R^9$ represents the same meanings as described above)

9) —$NR^9$— (wherein $R^9$ represents the same meanings as described above)

10) —O—N=$CR^9$— (wherein $R^9$ represents the same meanings as described above), or 11) the group represented by the formula (II):

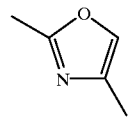

(IIa)

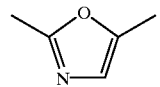

(IIb)

$R^8$ is 1) phenyl, thienyl, furyl, naphthyl or $C_3$–$C_8$ cycloalkyl, 2) substituted phenyl, substituted thienyl, substituted furyl or substituted naphthyl, 3) $C_1$–$C_5$ alkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy;

4) $C_2$–$C_5$ alkenyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy;

5) $C_3$–$C_5$ alkynyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy;

6) $C_2$–$C_8$ alkoxyalkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy;

7) $C_1$–$C_5$ hydroxyalkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy;

8) $C_2$–$C_8$ alkylthioalkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy;

9) $C_1$–$C_5$ aminoalkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy; or 10) —$CH_2$—C(O)—$R^{10}$ (wherein $R^{10}$ is phenyl (which may be substituted) or $C_1$–$C_5$ alkyl substituted with one or two phenyl groups (which may be substituted);

$R^5$ is
1) hydrogen,
2) $C_1$–$C_5$ alkyl,
3) $C_1$–$C_5$ hydroxyalkyl or acetoxyalkyl,
4) $C_1$–$C_5$ alkyl substituted with one or two phenyl groups (which may be substituted), or
5) $C_2$–$C_8$ alkoxyalkyl substituted with one or two phenyl groups (which may be substituted);

$R^6$ and $R^7$ represent hydrogen or $R^6$ and $R^7$ are covalently bonded to represent a double bond)).

The present invention also provides an antagonist against $TXA_2$ receptor, comprising the above-described compound of the present invention as an active ingredient.

The compounds of the present invention have strong $TXA_2$ receptor antagonist activities and $PGI_2$ receptor agonist activities, so that they are effective for therapy and prevention of diseases related to $TXA_2$.

BEST MODE FOR CARRYING OUT THE INVENTION

As mentioned above, the compound of the present invention is represented by the above-described formula (I).

Although the meanings of $R^1$ and $R^2$ in formula (I) are described above, the meanings will now be described in more detail. It should be noted that, in the present specification, the term "lower" in phrases such as "lower alkyl" means that the number of carbon atoms is 1 to 5, unless otherwise specified.

In cases where $R^3$ is a pharmaceutically acceptable cation, examples of the cation include metal cations, ammonium, amine cations and quaternary ammonium cations. Especially preferred metal cations are those derived from alkaline metals such as lithium, sodium and potassium, and those derived from alkaline earth metals such as magnesium and calcium. Needless to say, cations of, for example, aluminum, zinc and iron are also included in the present invention.

The pharmaceutically acceptable amine cations are those derived from primary, secondary or tertiary amines. Examples of the suitable amines include methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and similar aliphatic, alicyclic and heterocyclic amines having up to 18 carbon atoms such as 1-methylpiperidine, 4-ethylmorpholine, 1-isopropylpyrrolidine, 2-methylpyrrolidine, 4-dimethylpiperadine, 2-methylpiperidine and the like; and water-soluble amines and amines having hydrophilic groups, such as mono-, di-, and triethanolamine, ethyldiethylamine, N-butylethanolamine, 2-amino-1-butanol, 2-amino-2-ethyl-1,3-propanediol, tris(hydroxymethyl)aminomethane, N-phenylethanolamine, N-(p-tert-aminophenyl)diethanolamine, galactamine, N-methylglutamine, N-methylglucosamine, ephedrine, phenylephrine, epinephrine, procaine and the like; and basic amino acids such as lysine, arginine and the like. In cases where $R^3$ represents a $C_1$–$C_5$ alkyl group, examples of $R^3$ include methyl, ethyl, propyl, butyl, pentyl, isopropyl, sec-butyl, t-butyl, isobutyl, 1-methylbutyl, 3-methylbutyl, 2,2-dimethylpropyl and the like.

In cases where $R^5$ represents a $C_1$–$C_5$ alkyl, examples of $R^5$ include methyl, ethyl, propyl, butyl, pentyl, isopropyl, sec-butyl, t-butyl, isobutyl and the like.

In cases where $R^5$ represents a $C_1$–$C_5$ hydroxyalkyl, examples of $R^5$ include hydroxymethyl, 2-hydroxyethyl, 1-hydroxyethyl, 1-hydroxy-1-methylethyl, 3-hydroxypropyl, 2-hydroxypropyl, 1-hydroxypropyl, 4-hydroxypentyl, 5-hydroxybutyl and the like.

In cases where $R^5$ represents $C_1$–$C_5$ alkyl substituted with one or more phenyl groups (which may be substituted), examples of $R^5$ include benzyl, phenetyl, phenylpropyl, phenylbutyl, phenylpentyl, diphenylmethyl, 2,2-diphenylethyl, 1,3-diphenylpropyl, 3,3-diphenylpropyl, 3,3-diphenyl-2-methylpropyl, 3,3-diphenylbutyl, 1,4-diphenylbutyl, 2,4-diphenylbutyl, 3,4-diphenylbutyl, 4,4-diphenylbutyl, 4,4-diphenyl-2-methylbutyl, 4,4-diphenyl-3-methylbutyl, 4,4-diphenylpentyl, 1,5-diphenylpentyl, 4,5-diphenylpentyl, 5,5-diphenylpentyl and the like.

In cases where $R^5$ represents $C_2$–$C_8$ alkoxyalkyl substituted with one or two phenyl groups (which may be substituted), examples of $R^5$ include benzyloxyethyl, 3-methoxy-3-phenylpropyl, 2-(diphenylmethoxy)-2-methylethyl, 2-(diphenylmethoxy)-1-methylethyl, 3-(diphenylmethoxy)propyl, 4-(diphenylmethoxy)butyl, 5-(diphenylmethoxy)pentyl, 6-(diphenylmethoxy)hexyl, 7-(diphenylmethoxy)heptyl, 2-(2,2-diphenylethoxy)ethyl, (diphenylethoxy)propyl, 4-(2,2-diphenylethoxy)butyl, 6-(2,2-diphenylethoxy)hexyl and the like.

Examples of the substituents in the phenyl group in $R^5$ include lower alkyl groups, phenyl, hydroxy, lower alkyloxy, phenoxy, halogen, trifluoromethyl, cyano, nitro, amino, lower alkylamino and the like. Preferred lower alkyl groups include methyl, ethyl, propyl, isopropyl, butyl, isobutyl, sec-butyl, t-butyl, pentyl and the like. Preferred lower alkyloxy groups include methoxy, ethoxy, propyloxy, isopropyloxy, butyloxy, isobutyloxy, sec-butyloxy, t-butyloxy, pentyloxy and the like. Preferred halogens include fluorine, chlorine, bromine and iodine. Preferred lower alkylamino groups include methylamino, dimethylamino, ethylamino, diethylamino, diisopropylamino, di-t-butylamino and the like.

The thienyl group in $R^8$ is 2-thienyl or 3-thienyl; the furyl group is 2-furyl or 3-furyl; and the naphthyl group is 1-naphthyl or 2-naphthyl.

In cases where $R^8$ represents a $C_1$–$C_5$ alkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy, examples of $R^8$ include benzyl, phenetyl, phenylpropyl, phenylbutyl, phenylpentyl, diphenylmethyl, 2,2-diphenylethyl, 1,3-diphenylpropyl, 3,3-diphenylpropyl, 3,3-diphenyl-2-methylpropyl, 3,3-diphenylbutyl, 1,4-diphenylbutyl, 2,4-diphenylbutyl, 3,4-diphenylbutyl, 4,4-diphenylbutyl, 4,4-diphenyl-2-methylbutyl, 4,4-diphenyl-3-methylbutyl, 4,4-diphenylpentyl, 1,5-diphenylpentyl, 4,5-diphenylpentyl, 5,5-diphenylpentyl, 2-thienylmethyl, 3-thienylmethyl, 2-furylmethyl, 3-furylmethyl, 1-naphthylmethyl, 2-naphtylmethyl, cyclopentylmethyl, cyclohexylmethyl, phenoxymethyl, phenyl(2-thienyl)methyl, phenyl( 2-furyl) methyl, bis(2-thienyl)methyl, bis(2-furyl)methyl, dicyclohexylmethyl and the like.

In cases where $R^8$ represents a $C_2$–$C_5$ alkenyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy, examples of $R^8$ include 2-phenylvinyl, 3-phenyl-2-propenyl, 2-phenyl-1-methylvinyl, 4-phenyl-3-butenyl, 5-phenyl-4-pentenyl, 2,2-diphenylvinyl, 3,3-diphenyl-2-propenyl, 3,3-diphenyl-1-propenyl, 4,4-diphenyl-3-butenyl, 1,4-diphenyl-3-butenyl, 2,4-diphenyl-3-butenyl, 3,4-diphenyl-2-butenyl, 4,4-diphenyl-2-butenyl, 4,4-diphenyl-2-methyl-3-butenyl, 4,4-diphenyl-3-methyl-3-butenyl, 5,5-diphenyl-4-pentenyl, 1,5-diphenyl-4-pentenyl, 4,5-diphenyl-3-pentenyl, 4,4-diphenyl-2-pentenyl, 3,3-bis(2-thienyl)-2-propynyl, 3,3-bis(2-furyl)-2-propynyl, 3,3-bis(1-naphthyl)-2-propynyl, 4-cyclopentyl-2-butenyl, 4-phenoxy-2-butenyl and the like.

In cases where $R^8$ represents a $C_3$–$C_5$ alkynyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy, examples of $R^8$ include 3-phenyl-2-propynyl, 4-phenyl-2-butynyl, 5-phenyl-3-pentynyl, 3,3-diphenyl-1-propynyl, 3,3-diphenyl-1-butynyl, 4,4-diphenyl-2-butynyl, 5,5-diphenyl-3-pentynyl, 4,4-bis(2-thienyl)-2-butynyl, 4,4-bis(2-furyl)-2-butynyl, 4,4-bis(1-naphthyl)-2-butynyl, 4,4-dicyclohexyl-2-butynyl, 4-phenoxy-2-butynyl and the like.

In cases where $R^8$ represents a $C_2$–$C_8$ alkoxyalkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy, examples of $R^8$ include 2-benzyloxyethyl, 3-methoxy-3-phenylpropyl, 2-(diphenylmethoxy)-1-methylethyl, 3-(diphenylmethoxy)propyl, 4-(diphenylmethoxy)butyl, 5-(diphenylmethoxy)pentyl, 6-(diphenylmethoxy)hexyl, 7-(diphenylmethoxy)heptyl, 2-(2,2-diphenylethoxy)ethyl, 3-(2,2-diphenylethoxy)propyl, 4-(2,2-diphenylethoxy)butyl, 6-(2,2-diphenylethoxy)hexyl, 3-(bis(2-thienyl)methoxy)propyl, 3-(bis(2-furyl)methoxy)propyl, 3-(bis(1-naphthyl)methoxy)propyl, 3-(dicyclohexylmethoxy)propyl, 3-(phenoxymethoxy)propyl and the like.

In cases where $R^8$ represents a $C_1$–$C_5$ hydroxyalkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy, examples of $R^8$ include 2-hydroxy-2-phenylethyl, 1-hydroxy-3-phenylpropyl, 2-hydroxy-3-phenylpropyl, 3,3-diphenyl-2-hydroxypropyl, 3,3-diphenyl-2-methyl-2-hydroxypropyl, 4,4-diphenyl-2-hydroxybutyl, 4,4-diphenyl-3-hydroxybutyl, 4,4-diphenyl-3-methyl-2-hydroxybutyl, 5,5-diphenyl-2-hydroxypentyl, 5,5-diphenyl-3-hydroxypentyl, 1-hydroxy-3-(2-thyienyl)propyl, 1-hydroxy-3-(2-furyl)propyl, 1-hydroxy-3-(1-naphthyl)propyl, 1-hydroxy-3-cyclohexylpropyl, 1-hydroxy-3-phenoxypropyl and the like.

In cases where $R^8$ represents a $C_2$–$C_8$ alkylthioalkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy, examples of $R^8$ include 2-(diphenylmethylthio)ethyl, 3-(diphenylmethylthio)propyl, 5-(diphenylmethylthio)pentyl, 2-(2-diphenylmethylthio)ethyl, 3-(2-diphenylmethylthio)propyl, 2-(bis(2-thienyl)methylthio)ethyl, 2-(bis(2-furyl)methylthio)ethyl, 2-(bis(1-naphthyl)methylthio)ethyl, 2-(dicyclohexylmethlthio)ethyl, 2-(phenoxymethylthio)ethyl and the like.

In cases where $R^8$ represents a $C_1$–$C_5$ aminoalkyl which is substituted with one or two substituents selected from the group consisting of phenyl (which may be substituted), thienyl (which may be substituted), furyl (which may be substituted), naphthyl (which may be substituted), $C_3$–$C_8$ cycloalkyl and phenoxy, examples of $R^8$ include diphenylaminomethyl, 2-(diphenylamino)ethyl, 3-(diphenylamino)propyl, 4-(diphenylamino)butyl, 5-(diphenylamino)pentyl, 2-(bis(2-thienyl)amino)ethyl, 2-(bis(2-furyl)amino)ethyl, 2-(bis(1-naphthyl)amino)ethyl, 2-(dicyclohexylamino)ethyl and the like.

Examples of the substituents in phenyl, naphthyl, furyl and thienyl in $R^8$ include lower alkyl groups, phenyl, hydroxy, lower alkyloxy groups, phenoxy, halogens, trifluoromethyl, cyano, nitro, amino, lower alkylamino groups and the like. Preferred examples of the lower alkyl groups include methyl, ethyl, propyl, isopropyl, butyl, isobutyl, sec-butyl, pentyl and the like. Preferred examples of the lower alkyloxy groups include methoxy, ethoxy, propyloxy, isopropyloxy, butyloxy, isobutyloxy, sec-butyloxy, t-butyloxy, pentyloxy and the like. Preferred examples of the halogens include fluorine, chlorine, bromine and iodine. Preferred examples of the lower alkylamino groups include methylamino, dimethylamino, ethylamino, diethylamino, diisopropylamino, di-t-butylamino and the like.

In cases where $R^9$ represents a $C_1$–$C_5$ alkyl, examples of $R^9$ include methyl, ethyl, propyl, butyl, pentyl, isopropyl, sec-butyl, t-butyl, isobutyl and the like.

In cases where $R^9$ represents a $C_1$–$C_5$ alkyl substituted with phenyl (which may be substituted), examples of $R^9$ include benzyl, phenetyl, 3-phenylpropyl, 4-phenylbutyl, 5-phenylpentyl and the like.

Examples of the substituents in the phenyl group in $R^9$ include lower alkyl groups, phenyl, hydroxy, lower alkyloxy groups, phenoxy, halogens, trifluoromethyl, cyano, nitro, amino, lower alkylamino groups and the like. Preferred examples of the lower alkyl groups include methyl, ethyl, propyl, isopropyl, butyl, isobutyl, sec-butyl, t-butyl, pentyl and the like. Preferred examples of the lower alkyloxy groups include methoxy, ethoxy, propyloxy, isopropyloxy, butyloxy, isobutyloxy, sec-butyloxy, t-butyloxy, pentyloxy and the like. Preferred examples of the halogens include fluorine, chlorine, bromine and iodine. Preferred examples of the lower alkylamino groups include methylamino, dimethylamino, ethylamino, diethylamino, diisopropylamino, di-t-butylamino and the like.

In cases where $R^{10}$ represents a $C_1$–$C_5$ alkyl substituted with one or two phenyl groups (which may be substituted), examples of $R^{10}$ include benzyl, phenetyl, 3-phenylpropyl, 4-phenylbutyl, 5-phenylpentyl, diphenylmethyl, 2,2-diphenylethyl, 1,3-diphenylpropyl, 3,3-diphenylpropyl, 3,3-diphenyl-2-methylpropyl, 3,3-diphenylbutyl, 1,4-diphenylbutyl, 2,4-diphenylbutyl, 3,4-diphenylbutyl, 4,4-diphenylbutyl, 4,4-diphenyl-2-methylbutyl, 4,4-diphenyl-3-methylbutyl, 4,4-diphenylpentyl, 1,5-diphenylpentyl, 4,5-diphenylpentyl, 5,5-diphenylpentyl and the like.

Some of the compounds represented by the formula (I) comprise asymmetric carbon atoms and include geometrical isomers. The formula (I) includes all of the possible stereo isomers and geometrical isomers.

Specific examples of the compounds according to the present invention will now be enumerated. However, the present invention is not restricted by the specific examples by any means.

(3-((phenoxyacetylamino)methyl)benzofuran-7-yloxy) acetic acid,
(3-((2-phenoxyethylsulfonylamino)methyl)benzofuran-7-yloxy)acetic acid,
(3-((phenylsulfonylamino)methyl)benzofuran-7-yloxy) acetic acid,
(3-((benzylsulfonylamino)methyl)benzofuran-7-yloxy) acetic acid,
(3-((2-phenylethylsulfonylamino)methyl)benzofuran-7-yloxy)acetic acid,
(3-((3-phenylpropylsulfonylamino)methyl)benzofuran-7-yloxy)acetic acid,
(3-((4-phenylbutylsulfonylamino)methyl)benzofuran-7-yloxy)acetic acid,
(3-((5-phenylpentylsulfonylamino)methyl)benzofuran-7-yloxy)acetic acid,
(3-((2-naphthylsulfonylamino)methyl)benzofuran-7-yloxy) acetic acid,
(3-((benzylsulfonylamino)methyl)-2-methylbenzofuran-7-yloxy) acetic acid,
(3-((2-phenylethylsulfonylamino)methyl)-2-methylbenzofuran-7-yloxy)acetic acid,
(3-((3-phenylpropylsulfonylamino)methyl)-2-methylbenzofuran-7-yloxy)acetic acid,
(3-((2-phenylethylsulfonylamino)methyl)-2-isopropylbenzofuran-7-yloxy)acetic acid,
(3-(2-(benzylsulfonylamino)ethyl)benzofuran-7-yloxy) acetic acid,
(3-(2-(N-benzylbenzylsulfonylamino)ethyl)benzofuran-7-yloxy)acetic acid,
(3-(2-(benzylsulfonylamino)ethyl)-2-methylbenzofuran-7-yloxy)acetic acid,
(3-(2-(2-phenylethylsulfonylamino)ethyl)-2-methylbenzofuran-7-yloxy)acetic acid,
(3-(2-(2,2-diphenylethylsulfonylamino)ethyl)benzofuran-7-yloxy)acetic acid,
(3-(2-(3,3-diphenylpropylsulfonylamino)ethyl)benzofuran-7-yloxy)acetic acid,
(3-(2-(2-phenylethylthio)ethyl)-2-methylbenzofuran-7-yloxy)acetic acid,
(3-(2-(2-phenylethylsulfinyl)ethyl)-2-methylbenzofuran-7-yloxy)acetic acid,
(3-(2-(2-phenylethylsulfonyl)ethyl)-2-methylbenzofuran-7-yloxy)acetic acid,
(3-(2-(diphenylmethylideneaminoxy)ethyl)-2-methylbenzofuran-7-yloxy)acetic acid,
(3-((4-phenyloxazole-2-yl)methyl)benzofuran-7-yloxy) acetic acid,
(3-((4-(2-phenylethyl)oxazole-2-yl)methyl)benzofuran-7-yloxy)acetic acid,
(3-(2-(3-phenylpropyloxy)ethyl)benzofuran-7-yloxy)acetic acid,
(3-(2-benzyloxyethyl)benzofuran-7-yloxy)acetic acid,
(3-(2-diphenylmethoxy)ethyl)benzofuran-7-yloxy)acetic acid,
(3-(2-(3,3-diphenylpropyloxy)ethyl)benzofuran-7-yloxy) acetic acid,
(3-(2-(4-phenylbenzyloxy)ethyl)benzofuran-7-yloxy)acetic acid,
(3-(2-(2-oxo-2-phenylethoxy)ethyl)benzofuran-7-yloxy) acetic acid,
(3-((3,3-diphenylpropyloxy)methyl)benzofuran-7-yloxy) acetic acid,
(3-((2,2-diphenylethoxy)methyl)benzofuran-7-yloxy)acetic acid,
(3-(diphenylmethoxymethyl)benzofuran-7-yloxy)acetic acid,
(3-((2-phenylpropyloxy)methyl)benzofuran-7-yloxy)acetic acid,
(3-((1-benzyl-2-phenylethoxy)methyl)benzofuran-7-yloxy) acetic acid,
(3-((1-methyl-2-phenylethoxy)methyl)benzofuran-7-yloxy) acetic acid,
(3-((2-phenyl-2-methoxy-1-methylethoxy)methyl) benzofuran-7-yloxy)acetic acid,
(3-((2-phenylbutyloxy)methyl)benzofuran-7-yloxy)acetic acid,
(3-((2-phenoxyethoxy)methyl)benzofuran-7-yloxy)acetic acid,
(3-((2-(diphenylmethoxy)ethoxy)methyl)benzofuran-7-yloxy)acetic acid,
(3-((2-methyl-2-phenoxypropyloxy)methyl)benzofuran-7-yloxy)acetic acid,
(3-(2-(2-(diphenylmethoxy)ethoxy)ethyl)benzofuran-7-yloxy)acetic acid,
(3-((3-diphenylmethoxy)propyloxy)methyl)benzofuran-7-yloxy)acetic acid,
(3-(2-(diphenylmethylsulfonyl)ethyl)benzofuran-7-yloxy) acetic acid,
(3-(2-(diphenylmethylthio)ethyl)benzofuran-7-yloxy)acetic acid,
(3-(2-(bis(4-methoxyphenyl)methylthio)ethyl)benzofuran-7-yloxy)acetic acid,
(3-(2-(bis(4-hydroxyphenyl)methylthio)ethyl)benzofuran-7-yloxy)acetic acid,
(3-(2-(bis(4-chlorophenyl)methylthio)ethyl)benzofuran-7-yloxy)acetic acid,
(3-(2-(bis(4-fluorophenyl)methylthio)ethyl)benzofuran-7-yloxy)acetic acid,
(3-(2-(diphenylmethylthio)ethyl)benzofuran-6-yloxy)acetic acid,
(3-((3,3-diphenylpropylthio)methyl)benzofuran-7-yloxy) acetic acid,
(3-(3-diphenylmethylthio)propyl)benzofuran-7-yloxy) acetic acid,
(3-(3-(2,2-diphenylmethylthio)propyl)benzofuran-7-yloxy) acetic acid,
(3-(3-(3,3-diphenylpropylthio)propyl)benzofuran-7-yloxy) acetic acid,
(3-((diphenylmethylthio)methyl)benzofuran-7-yloxy)acetic acid,
(3-((2,2-diphenylmethylthio)methyl)benzofuran-7-yloxy) acetic acid, (3-(2-(2,2-diphenylmethylthio)ethyl)benzofuran-7-yloxy) acetic acid,
(3-(2-(3,3-diphenylpropylthio)ethyl)benzofuran-7-yloxy) acetic acid,
(3-(2-(diphenylmethylthio)ethyl)-2-methylbenzofuran-7-yloxy)acetic acid,
(3-(2-(diphenylmethylthio)ethyl)-2-hydroxymethylbenzofuran-7-yloxy)acetic acid,
(3-(2-(diphenylmethylthio)ethyl)-2-(2-hydroxyethyl)benzofuran-7-yloxy)acetic acid,
(3-(2-(diphenylmethylthio)ethyl)-2-(3-hydroxypropyl)benzofuran-7-yloxy)acetic acid,
(3-((3,3-diphenyl-2-propenyloxy)methyl)benzofuran-7-yloxy)acetic acid,
(3-((2-(diphenylamino)ethoxy)methyl)benzofuran-7-yloxy) acetic acid,
(3-((2-(diphenylmethoxy)propyloxy)methyl)benzofuran-7-yloxy)acetic acid,
(3-((1-methyl-2-(diphenylmethoxy)ethoxy)methyl) benzofuran-7-yloxy)acetic acid,
(3-(2-hydroxy-5,5-diphenylpropyl)benzofuran-7-yloxy) acetic acid,
(2-((3,3-diphenylpropyloxy)methyl)benzofuran-7-yloxy) acetic acid,
(2-((2,2-diphenylethoxy)methyl)benzofuran-7-yloxy)acetic acid,
(2-((3-diphenylmethoxy)propyloxy)methyl)benzofuran-7-yloxy)acetic acid,
(2-((2-(diphenylmethoxy)ethoxy)methyl)benzofuran-7-yloxy)acetic acid,
(2-(diphenylmethoxymethyl)benzofuran-7-yloxy)acetic acid,
(1-(2-(p-tolylsulfonylamino)ethyl)indole-4-yloxy)acetic acid,
(1-(2-(2-phenylethylsulfonylamino)ethyl)indole-4-yloxy) acetic acid,
(1-(2-(phenylsulfonylamino)ethyl)indole-4-yloxy)acetic acid,
(1-(2-(benzylsulfonylamino)ethyl)indole-4-yloxy)acetic acid,
(1-(2-(3-phenylpropyloxy)ethyl)indole-4-yloxy)acetic acid,
(1-(2-(2-phenylethoxy)ethyl)indole-4-yloxy)acetic acid,
(1-(2-(2,2-diphenylethoxy)ethyl)indole-4-yloxy)acetic acid,
(1-(2-(diphenylmethoxy)ethyl)indole-4-yloxy)acetic acid,
(1-(2-(3,3-diphenylpropyloxy)ethyl)indole-4-yloxy)acetic acid,
(1-(5-phenylpentyl)indole-4-yloxy)acetic acid,
(1-(2-diphenylmethylthio)ethyl)indole-4-yloxy)acetic acid,
(1-(4,4-diphenylbutyl)indole-4-yloxy)acetic acid,
(1-(2-(N-(diphenylmethyl)amino)ethyl)indole-4-yloxy) acetic acid,
(1-(2-(N,N-dibenzylamino)ethyl)indole-4-yloxy)acetic acid,
(1-(2-(diphenylmethylthio)ethyl)indoline-4-yloxy)acetic acid,
(1-(2-(diphenylmethoxy)ethyl)indoline-4-yloxy)acetic acid,
(1-(2-(2,2-diphenylethoxy)ethyl)indoline-4-yloxy)acetic acid,
(1-(2-(3,3-diphenylpropyloxy)ethyl)indoline-4-yloxy)acetic acid,
3-(3-(2-diphenylmethoxyethyl)benzofuran-7-yloxy) propionic acid,
4-(3-(2-diphenylmethoxyethyl)benzofuran-7-yloxy)butyric acid,
(3-(2-diphenylmethoxyethyl)benzofuran-7-ylthio)acetic acid,
(3-(3-(2-diphenylmethoxyethyl)benzofuran-7-ylthio) propionic acid,
4-(3-(2-diphenylmethoxyethyl)benzofuran-7-ylthio)butyric acid,
3-(3-(2-diphenylmethoxyethyl)benzofuran-7-yl)propionic acid,
4-(3-(2-diphenylmethoxyethyl)benzofuran-7-yl)butyric acid, and
5-(3-(2-diphenylmethoxyethyl)benzofuran-7-yl)valeric acid, as well as methyl ester, ethyl ester, propyl ester, isopropyl ester, butyl ester, t-butyl ester, pentyl ester and the like of these compounds.

Examples of the process for producing some of the compounds within the scope of the present invention will now be described. However, the present invention is not restricted by these.

Among the compounds within the scope of the present invention, those in which $R^1$ is —$OCH_2COOH$ or —$OCH_2COOMe$, and $R^2$ is —$CR^4$=$CR^5$—O— (wherein $R^4$ is as described above and $R^5$ is hydrogen, $C_1$–$C_5$ alkyl, or $C_1$–$C_5$ hydroxyalkyl) may be produced using as the starting material the intermediate (6) which may be produced by the Production Process A.

It should be noted that in the steps hereinbelow described, those for which the reaction temperature is not described can be carried out at room temperature.

Reaction Equation 1

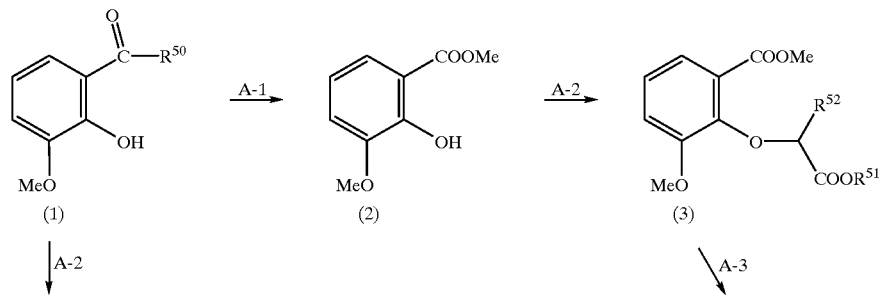

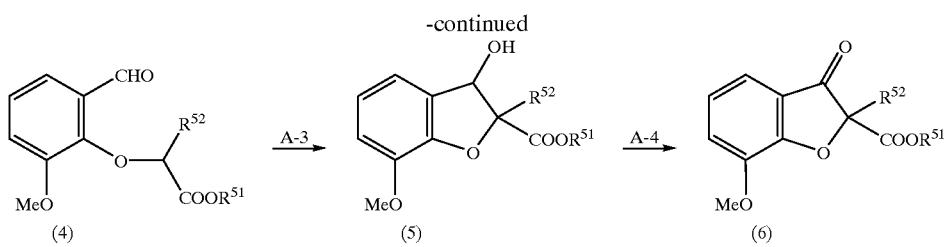

Production Process A (wherein $R^{50}$ is hydrogen or hydroxyl group, $R^{51}$ is $C_1$–$C_5$ alkyl, $R^{52}$ is hydrogen or $C_1$–$C_5$ alkyl)

As the material of the Production Process A, o-vanillin ($R^{50}$=H) or 3-methoxysalicylic acid ($R^{50}$=OH), which are easily and commercially available, may be employed.

Step A-1 is an esterification step of 3-methoxysalicylic acid. This step may be carried out by employing various esterification reaction, and may easily be carried out by heating the starting material with a catalytic amount or an acid in methanol. The reaction temperature is preferably from 30° C. to the refluxing temperature of methanol. As the acid catalyst, hydrochloric acid, sulfuric acid and p-toluenesulfonic acid are best preferred.

Step A-2 is an alkylation step of o-vanillin ester or 3-methoxysalicylic acid ester. This step is carried out by reacting the hydroxyl group of o-vanillin ester or 3-methoxysalicylic acid ester with $R^{51}$ ester of $C_1$–$C_6$ 2-bromoalkylcarboxylic acid in the presence of a base. Preferred examples of the base include potassium carbonate, sodium hydride, potassium hydroxide and sodium hydroxide. Various polar solvents may be employed, and methanol, acetone and DMF are best preferred.

Step A-3 is a cyclization step. This step is carried out by generating an anion at the α-position of the ester by using a base, and by making the aldehyde and ester in the molecule nucleophilically attack it. As the base, various bases may be used. Although potassium t-butoxide and sodium hydride are preferably used as the base, the base is not limited thereto. Various solvents may be employed, and toluene, THF, dimethoxyethane or DMF is preferably employed. The reaction temperature is preferably between −20° C. and 120° C.

Step A-4 is an oxidation step of hydroxyl group. A number of methods for carrying out oxidation reaction are known. This step can be sufficiently carried out by using a chromic acid-based oxidizing agent having a good ease of handling, although the oxidizing agent is not restricted thereto.

Among the compounds within the scope of the present invention, those in which $R^1$ is —$OCH_2COOH$— or —$OCH_2COOMe$ and $R^2$ is —$CR^4$=$CR^5$—O— (wherein $R^4$ is —$CH_2NHSO_2$—$R^8$ or —$CH_2NHCO$—$R^8$, and $R^5$ is hydrogen or $C_1$–$C_5$ alkyl) may be produced by Production Process B.

Reaction Equation 2

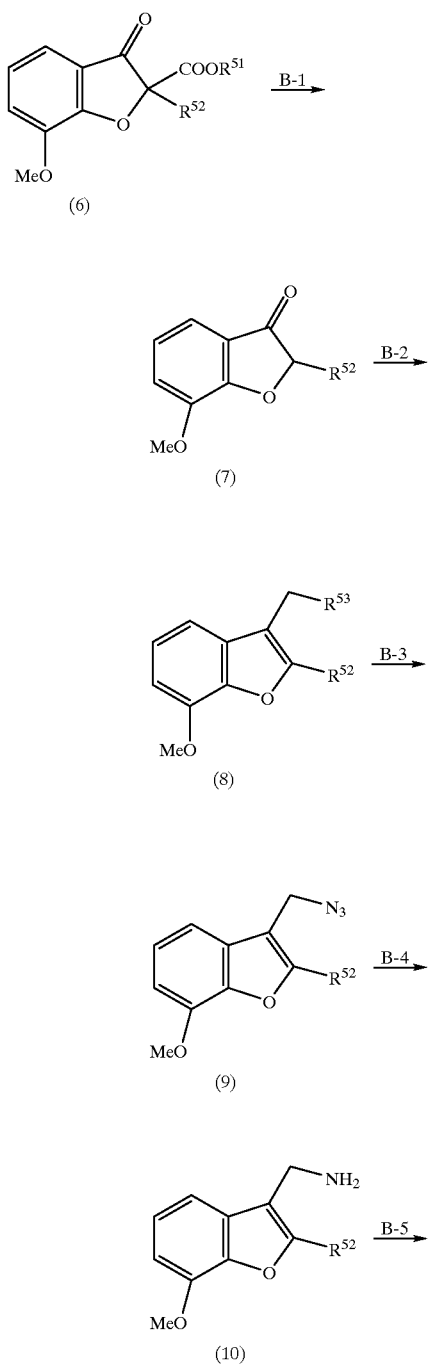

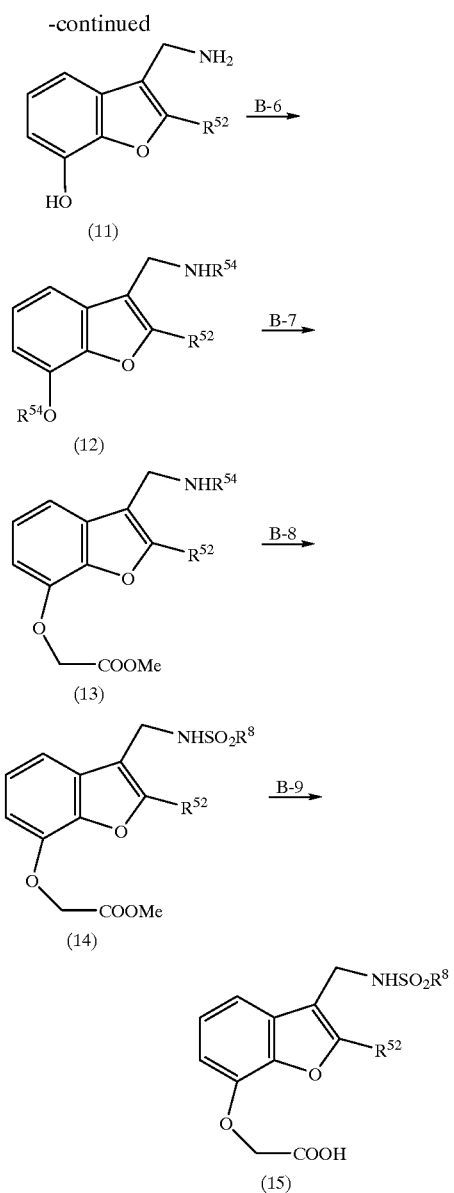

Production Process B
(wherein $R^{51}$ and $R^{52}$ represent the same meanings as described above, $R^{53}$ is chlorine or bromine, $R^{54}$ is acyl and $R^8$ represents the same meanings as described above).

Step B-1 is a decarboxylation step. This step is carried out by heating the starting material to reflux in water-containing dioxane, water-containing t-butyl alcohol or acetic acid in the presence of an acid. As the acid, hydrochloric acid or sulfuric acid is especially preferably used. Among the compounds (7) obtained by this step, those in which $R^{52}$ is hydrogen may also be obtained by a known method (J. Org. Chem., 53, 423–425, (1988)).

Step B-2 is a step of introducing methyl group substituted with an eliminating group $R^{53}$ into the ketone (7). This step is carried out by making the ketone (7) nucleophilically attack chloromethyllithium or bromomethyllithium. An example of the process for producing chloromethyllithium and bromomethyllithium used in this step is described in references (Tetrahedron, 27, 6109–6114(1971), and Tetrahedron, 28, 3009–3013(1972)). As the solvent, aprotic solvents are employed. Although ether, THF or dimethoxyethane is preferably employed as the solvent, the solvent is not restricted thereto. The reaction is carried out at a temperature between −100° C. and 0° C., preferably between −78° C. and −60° C.

Step B-3 is a step of introducing azide into the compound (9). This step is carried out by heating the compound (8) and sodium azide to the refluxing temperature of the solvent. As the solvent, THF/water or methanol/water mixed solvent is preferably employed.

Step B-4 is a reduction step of azide. Various reducing agents may be employed, and lithium aluminum hydride or diisobutylaluminum hydride is preferably employed. However, the reducing agent is not restricted to these.

Step B-5 is a deprotection step of phenolic methyl ether. This step is carried out by heating the compound (10) with sodium salt or potassium salt of a thiol. As the thiol, lower alkylthiols are preferably employed, and propanethiol is best preferred. As the solvent, DMF is preferably used. The reaction temperature is 50–150° C., preferably 80–120° C.

Step B-6 is a step of introducing acyl groups. By this step, both of the amino group and the hydroxyl of the compound (11) are protected by the acyl groups. As the acyl group, acetyl group and benzoyl group, as well as derivatives thereof may be employed. The reaction may be carried out under normal conditions. For example, the reaction may be carried out by reacting the compound (11) with the corresponding acid chloride or acid anhydride in the presence of a tertiary amine such as triethylamine or pyridine, in THF, dichloromethane or DMF. Alternatively, Step B-5 and Step B-6 may be successively carried out without isolating the compound (11), thereby directly deriving the compound (12) from the compound (10).

Step B-7 is a step of deprotecting the phenolic acyl group and introducing an acetic acid unit. This step is carried out by selectively deprotecting the phenolic acyl group alone using a base, and then by treating the resultant with methyl bromoacetate changing the solvent to DMF. As the base, potassium carbonate, potassium hydroxide or sodium hydroxide is preferably used. As the solvent, although methanol or ethanol may preferably be used, THF or dioxane may also be used.

Step B-8 is a step for converting the amide (13) to sulfonamide (14). This step is carried out by heating the compound (13) in methanol with an acid to the refluxing temperature thereby converting the compound (13) to an amine, and then reacting the resultant with the corresponding sulfonyl chloride in the presence of triethylamine or pyridine changing the solvent to dichloromethane, DMF or THF. The reaction may also be carried out by using the amine as a solvent. As the acid, hydrochloric acid or sulfuric acid is preferably employed.

Step B-9 is a hydrolysis step of methyl ester. This step is carried out by treating the compound (14) with an aqueous solution of a base in methanol. As the base, sodium hydroxide, potassium hydroxide or lithium hydroxide is preferably employed.

Among the compounds within the scope of the present invention, those in which $R^1$ is —OCH$_2$COOH or —OCH$_2$COOMe and $R^2$ is —CR$^4$═CR$^5$—O— (wherein $R^4$ is —CH$_2$—CH$_2$—NHSO$_2$—R$^8$ and $R^5$ is hydrogen or $C_1$–$C_5$ alkyl) may be produced by the Production Process C.

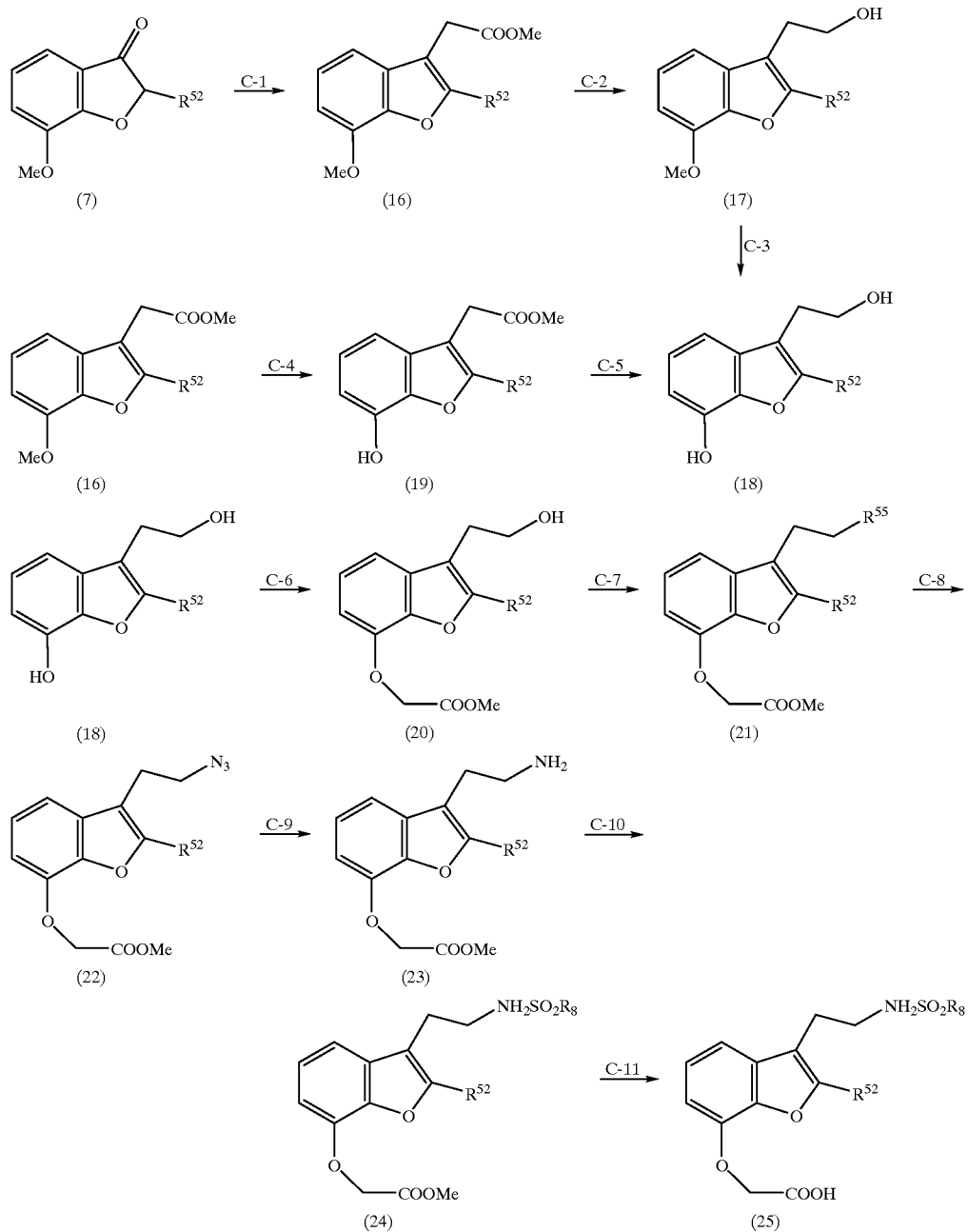

Reaction Equation 3

Production Process C
(wherein $R^8$ and $R^{52}$ represent the same meanings as described above, and $R^{55}$ is bromine, p-toluenesulfonyloxy or methanesulfonyloxy).

Step C-1 is a step of introducing an acetic acid unit to the compound (7) which can be obtained by Production Process B. This step is carried out by Wittig reaction using methyl (triphenylphosphoranilidene)acetate or Reformatsky reaction using methyl bromoacetate and zinc, and subsequent dehydration reaction. As the solvent for the Wittig reaction, toluene or xylene is preferably employed, and the reaction may usually be carried out at the refluxing temperature. In case of employing the Reformatsky reaction, an aprotic solvent, preferably ether or THF, is employed. The reaction temperature is between −78° C. and 100° C., preferably between −20° C. and 50° C. The dehydration reaction is carried out by treating the obtained tertiary alcohol with an acid catalyst. As the acid catalyst, formic acid, hydrochloric acid, sulfuric acid or p-toluenesulfonic acid may preferably be employed. However, the acid catalyst is not restricted thereto.

Step C-2 is a reduction step of the methyl ester. Various methods for reducing esters are known and various methods may be applied to this step. A method using lithium aluminum hydride or diisobutylaluminum hydride is preferred because the process is simple and the yield is high. However, needless to say, the reduction method is not limited to this. As the solvent, ether, THF or toluene is preferably used.

Step C-3 is a deprotecting step of methyl ether. This step is carried out in the similar manner as in Step B-5.

The compound (18) may also be obtained by Step C-4 and Step C-5.

Step C-4 is a step of deprotection of methyl ether by a Lewis acid. As the Lewis acid, various acids may be employed. Although boron tribromide is preferably used, the Lewis acid is not restricted thereto. As the solvent, benzene, toluene, dichloromethane, or tetrachloromethane is preferably employed. The reaction temperature is selected from the range between −80° C. and 25° C. Preferably, the Lewis acid is added at a temperature of −80° C. to −60° C. and the temperature is then raised to a temperature between 0° C. and 30° C. to complete the reaction.

Step C-5 is a reduction step of methyl ester, and may be carried out in the similar manner as in Step C-2.

Step C-6 is a step of introducing an acetic acid unit. In this step, after removing the hydrogen atom of the phenolic hydroxyl group by a base, the resultant is subjected to a coupling reaction with methyl bromoacetate. As the base, potassium carbonate, potassium hydroxide or sodium hydroxide is preferably employed. As the reaction solvent, polar solvents may be used and DMF is preferably employed.

Step C-7 is a step of converting hydroxyl group into bromine, p-toluenesulfonyloxy or methanesulfonyloxy group. In cases where $R^{55}$ is bromine, as a brominating agent, thionyl bromide, triphenylphosphine+tetrabromomethane, or triphenylphosphine+N-bromosuccinimide is preferably employed, although the brominating agent is not restricted thereto. As a solvent, DMF, THF or ether is preferably employed. Alternatively, thionyl bromide may be used as the solvent without using a separate solvent. The reaction temperature is selected from the range between −20° C. and 100° C., preferably between −20° C. and 50° C. In cases where $R^{55}$ is p-toluenesulfonyloxy or methanesulfonyloxy, the desired product may be obtained by tosylating or mesylating the hydroxyl group by a conventional method. That is, the desired product may be obtained by tosylating or mesylating the hydroxyl group by p-toluenesulfonyl chloride or methanesulfonyl chloride in THF, DMF or dichloromethane in the presence of triethylamine or pyridine.

Step C-8 is a step of introducing an azide group. This step may be carried out in the similar manner as in Step B-3.

Step C-9 is a step of reducing azide. This step may be carried out by reducing the compound (22) using palladium-carbon as a catalyst in hydrogen atmosphere. As the solvent, methanol or THF is preferably employed. The reaction temperature is between 0° C. and 50° C.

Step C-10 is a step of converting amino group into sulfonamide. This step is carried out by reacting the compound (33) with a corresponding sulfonyl chloride in the presence of a tertiary amine. As the tertiary amine, triethylamine, pyridine or diisopropylethylamine is preferably employed, although the tertiary amine is not restricted thereto. As the solvent, THF or dichloromethane is preferably employed. However, the tertiary amine may be used as the solvent.

Step C-11 is a hydrolysis step of methyl ester, and may be carried out in the similar manner as in Step B-9.

Among the compounds within the scope of the present invention, those in which $R^1$ is —OCH$_2$COOH or —OCH$_2$COOMe, and $R^2$ is —CR$^4$=CR$^5$—O— (wherein R is —CH$_2$—Z—R$^8$ and $R^5$ is hydrogen or C$_1$–C$_5$ alkyl) may be produced by the Production Process D.

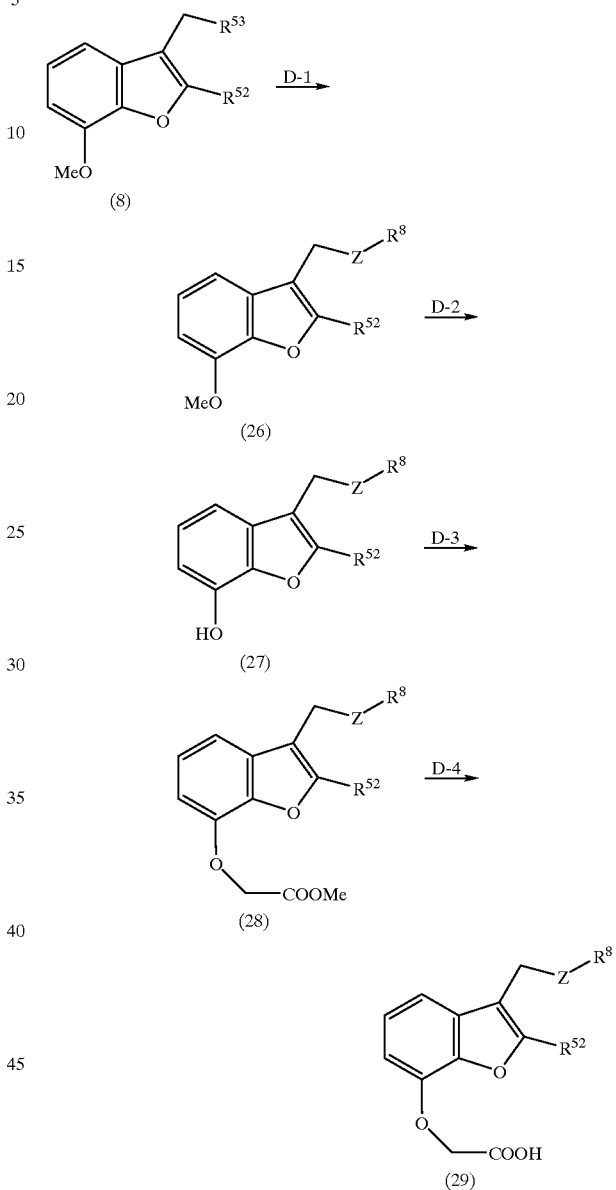

Reaction Equation 4

Production Process D (wherein $R^8$, $R^{52}$ and $R^{53}$ have the same meanings as described above, and Z is oxygen or sulfur).

Step D-1 is a step of etherification or thioetherification of the compound (8) obtained by Step B-2. This step is carried out by adding the compound (8) in a preliminarily prepared sodium salt or potassium salt of R$^8$—OH or R$^8$—SH. As the base, potassium metal, potassium hydride, potassium t-butoxide, sodium metal, or sodium hydride may be employed, and sodium hydride or potassium t-butoxide is preferably employed. In cases where Z is sulfur, potassium carbonate as a base may be added to a mixed solution of R$^8$—SH and the compound (8). Aprotic solvents, preferably THF, DMF or acetone, may be used as the solvent. The reaction temperature is selected from the range between −20° C. and 100° C., preferably between −10° C. and 30° C.

Step D-2 is a deprotection step of methyl ether, and may be carried out in the similar manner as in Step B-5.

Step D-3 is a step of introducing an acetic acid unit, and may be carried out in the similar manner as in Step C-6.

Step D-4 is a hydrolysis step of methyl ester and may be carried out in the similar manner as in Step B-9.

Among the compounds within the scope of the present invention, those in which $R^1$ is —$OCH_2COOH$ or —$OCH_2COOMe$, and $R^2$ is —$CR^4$=$CR^5$—O— (wherein $R^4$ is —$CH_2$—$CH_2$—O—$R^8$ and $R^5$ is hydrogen or $C_1$–$C_5$ alkyl) may be produced by the Production Process E.

Reaction Equation 5

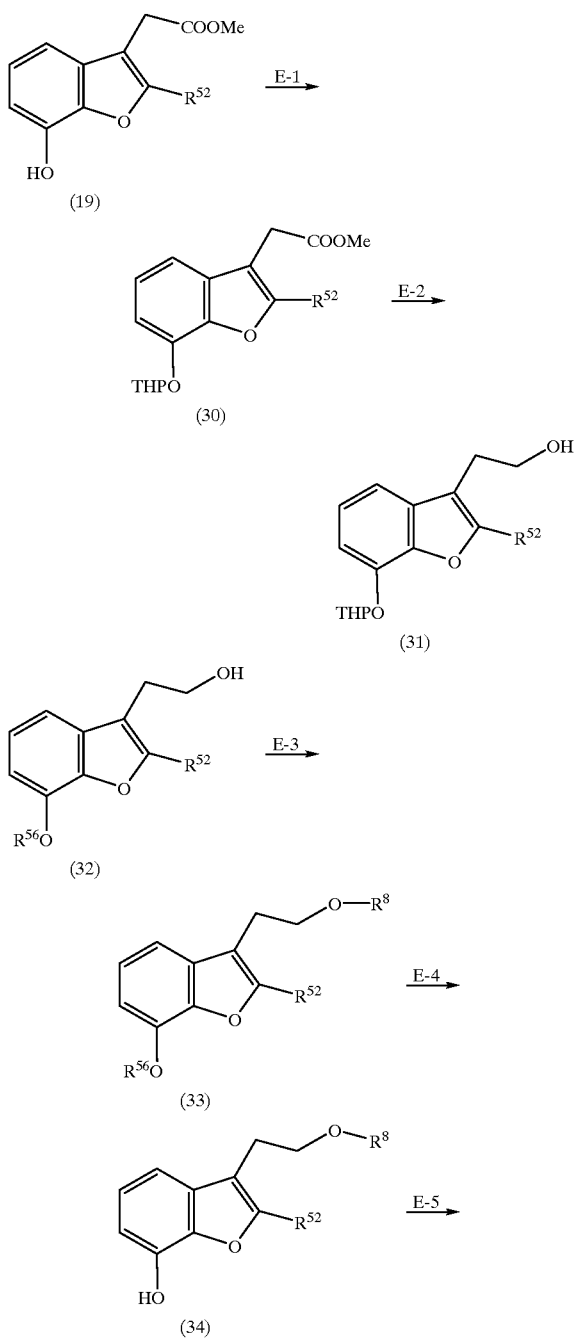

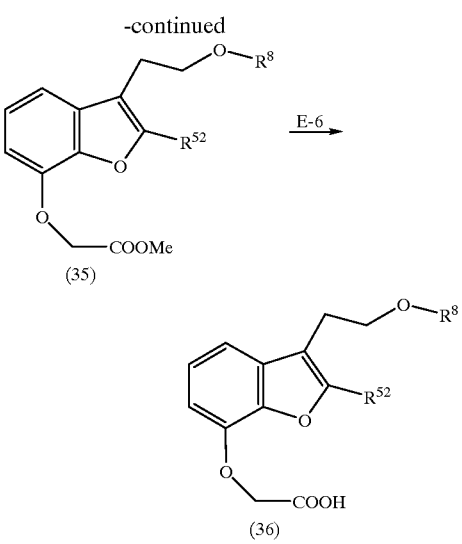

Production Process E
(wherein $R^8$ and $R^{52}$ represent the same meanings as described above, and $R^{56}$ represents methyl or tetrahydropyranyl).

Step E-1 is a step of protecting the hydroxyl group of the compound (19) which can be obtained by Step C-4, with tetrahydropyranyl group. This step may be carried out under the normal conditions for tetrahydropyranylation. That is, the step is carried out by reacting 2,3-dihydropyran with the compound (19) in the presence of a catalytic amount of p-toluenesulfonic acid.

Step E-2 is a reduction step of methyl ester and may be carried out in the similar manner as in Step C-2.

Steps E-3 and thereafter are carried out by using the compound (31) ($R^{56}$=THP) or the compound (17) ($R^{56}$=Me) which can be obtained by Step C-2 as a starting material.

Step E-3 is a step of introducing a side chain into the compound (32). This step is carried out by converting the hydroxyl group of the compound (32) into an alkoxide by a base and then by adding $R^8$—Cl or $R^8$—Br. As the base, potassium metal, potassium hydride, potassium t-butoxide, sodium metal, and sodium hydride may be employed, and potassium t-butoxide or sodium hydride is preferably employed. As the solvent, an aprotic solvent is used, and preferably THF or DMF is employed, although the solvent is not restricted thereto. The reaction temperature is selected from the range between −20° C. and 100° C., preferably between −10° C. and 30° C.

Step E-4 is a deprotection step of the protected hydroxyl group. In cases where $R^{56}$ is tetrahydropyranyl, this step is carried out by treating the compound (33) with an acid. As the acid, hydrochloric acid, sulfuric acid and acetic acid may be employed. As the solvent, THF, DMF, methanol, ethanol or dioxane, or a mixed solvent of one or more of these solvents and water is employed. The reaction temperature is selected from the range between 0° C. and 100° C., preferably between 10° C. and 50° C. In cases where $R^{56}$ is methyl, this step may be carried out in the similar manner as in Step B-5.

Step E-5 is a step of introducing an acetic acid unit into the compound (34), and may be carried out in the similar manner as in Step C-6.

Step E-6 is a hydrolysis step of methyl ester, and may be carried out in the similar manner as in Step B-9.

Among the compounds within the scope of the present invention, those in which $R^1$ is —$OCH_2COOH$ or —$OCH_2COOMe$, and $R^2$ is —$CR^4$=$CR^5$—O— (wherein $R^4$ is —$CH_2$—$H_2$—O—N=$CPh_2$ or —$CH_2$—$CH_2$—S(O)$_p$—$R^8$ (wherein p is an integer of 0–2) and $R^5$ is hydrogen or $C_1$–$C_5$ alkyl) may be produced by the Production Process F.

Production Process F
(wherein $R^8$, $R^{52}$, $R^{55}$ and $R^{56}$ represent the same meanings as described above, and $R^{57}$ is —O—N=$CPh_2$ or —S—$R^8$).

Step F-1 is a step of converting hydroxyl group into an eliminating group $R^{55}$, and may be carried out in the similar manner as in Step C-7.

Reaction Equation 6

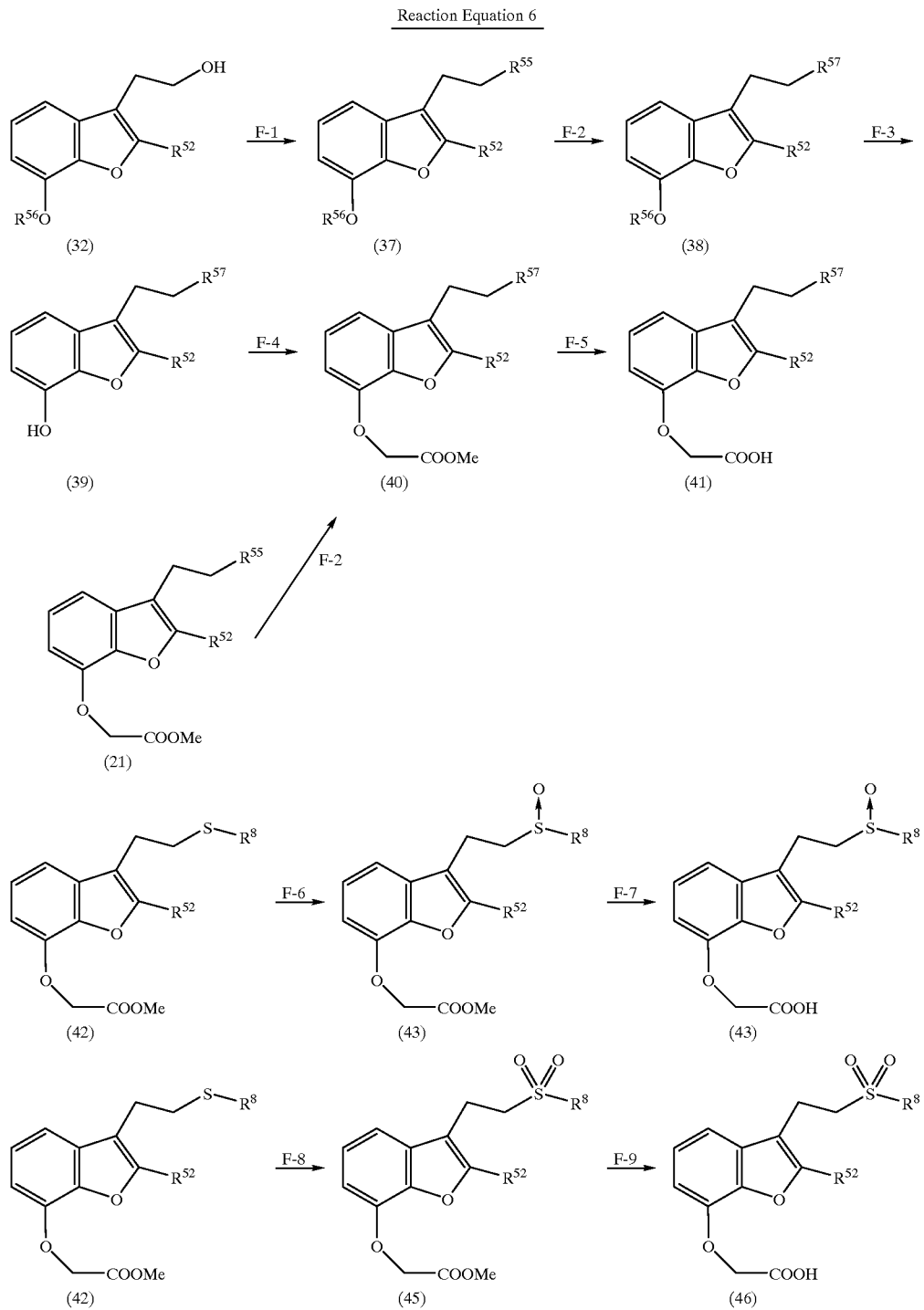

Step F-2 is a step of introducing a side chain into the compound (37). This step is carried out by removing the hydrogen atom of the hydroxyl group or thiol group of $Ph_2C=N-OH$ or $R^8-SH$ by a base and by adding the compound (37). As the base, potassium metal, potassium hydride, potassium t-butoxide, sodium metal, or sodium hydride may be employed, and potassium t-butoxide or sodium hydride is preferably employed, although the base is not restricted thereto. As the solvent, an aprotic solvent is used, and preferably THF or DMF is employed, although the solvent is not restricted thereto. The reaction temperature is selected from the range between −20° C. and 100° C., preferably between −10° C. and 25° C.

Step F-3 is a step of deprotecting the methyl or tetrahydropyranyl group, and may be carried out in the similar manner as in Step B-5 or Step E-4.

Step F-4 i s a step of introducing an acetic acid u nit into the compound (39), and may be carried out in the similar manner as in Step C-6.

The compound (40) obtained by Step F-4 may also be obtained by introducing a side chain into the compound (21) obtained by the Production Process C, in the similar manner as in Step E-2.

Step F-5 is a hydrolysis step of methyl ester, and may be carried out in the similar manner as in Step B-9.

Step F-6 is a step of oxidizing the sulfide (42) into a sulfoxide (43). This step is carried out by treating the compound (42) with N-bromosuccinimide in methanol.

Step F-8 is a step of converting the sulfide (42) into a sulfone (45). This step is carried out by treating the compound (42) with a peracid in dichloromethane. As the peracid, peracetic acid, perbenzoic acid, m-chloroperbenzoic acid and trifluoroperacetic acid may be employed, and m-chloroperbenzoic acid may preferably be employed. However, the peracid is not restricted to these. As the solvent, dichloromethane is preferably used. The reaction temperature may be −20° C. to 50° C., preferably 0° C. to 25° C.

Step F-7 and Step F-9 are hydrolysis steps of methyl ester and are carried out in the similar manner as in Step B-9.

Among the compounds within the scope of the present invention, those in which $R^1$ is $-OCH_2COOH$ or $-OCH_2COOMe$, and $R^2$ is $-CR^4=CR^5-O-$ (wherein $R^4$ is $-CH_2-CH_2-S-R^8$ and $R^5$ is hydroxymethyl) may be produced by the Production Process G.

Reaction Equation 7

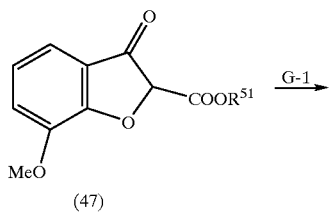

(47)

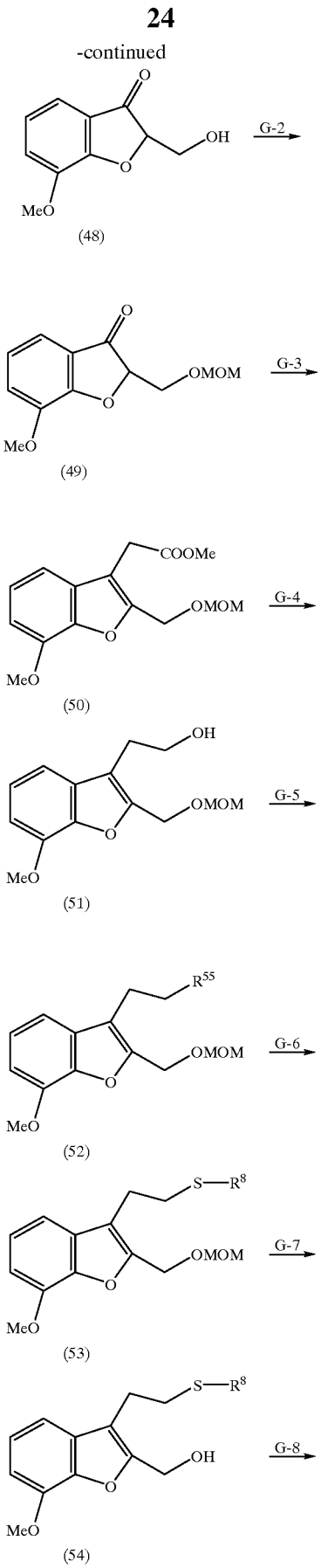

(48)

(49)

(50)

(51)

(52)

(53)

(54)

-continued

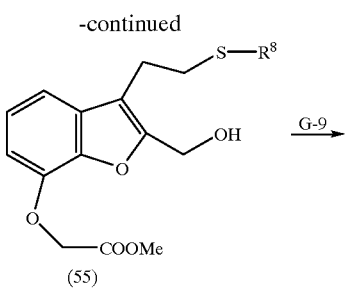
(55)

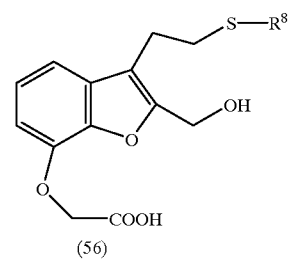
(56)

Production Process G
(wherein $R^8$, $R^{51}$ and $R^{55}$ have the same meanings as described above)

Step G-1 is a reduction step of ester. This step is carried out by firstly treating the compound (47) obtainable by the Step A with a base to convert the compound into an enolate, and then reducing the ester alone by a reducing agent. As the base, sodium metal and sodium hydroxide may preferably be employed. As the reducing agent, various compounds may be employed. Preferred reducing agents are lithium aluminum hydride and diisobutylalminum hydride. An aprotic solvent is used as the solvent and ether, THF and dioxane may preferably be employed. The reaction temperature is selected from the range between −78° C. and 100° C. Preferably, the step may be carried out by heating the reaction mixture to refluxing temperature after adding the base and then by cooling the reaction mixture to 0° C. followed by adding the reducing agent.

Step G-2 is a step of protecting the hydroxyl group of the compound (48) with methoxymethyl group. This step is carried out by treating the compound (48) with dimethoxymethane in the presence of phosphorus pentoxide. As the solvent, dichloromethane is preferably employed.

Step G-3 is a step of introducing an acetic acid unit, and may be carried out in the similar manner as in Step C-1.

Step G-4 is a reduction step of the ester, and may be carried out in the similar manner as in Step C-2.

Step G-5 is a step of converting the hydroxyl group of the compound (51) into an eliminating group, and is carried out in the similar manner as in Step C-7.

Step G-6 is a step of introducing thioether, and is carried out as in Step D-1.

Step G-7 is a deprotection step of methoxymethyl group. This step is carried out by treating the compound (53) with a catalytic amount of an acid. As the acid, p-toluenesulfonic acid or pyridinium p-toluenesulfonate is preferably employed. As the solvent, various alcohols are preferred, and t-butyl alcohol is especially preferred. The reaction is carried out at a temperature of 0° C. to 200° C. Preferably, the reaction is carried out at the refluxing temperature using t-butyl alcohol as the solvent.

Step G-8 is a step of deprotecting methyl ether and introducing acetic acid into phenol. This step may be carried out in the similar manner as in Step B-5 or Step C-6.

Step G-10 is a hydrolysis step of ester and may be carried out as in Step B-9.

Among the compounds within the scope of the present invention, those in which $R^1$ is —OCH$_2$COOH or —OCH$_2$COOMe, and $R^2$ is —CR$^4$=CR$^5$—O— (wherein $R^4$ is —CH$_2$—CH$_2$—S—R$^8$ and $R^5$ is hydroxyethyl) may be produced by the Production Process H.

Reaction Equation 8

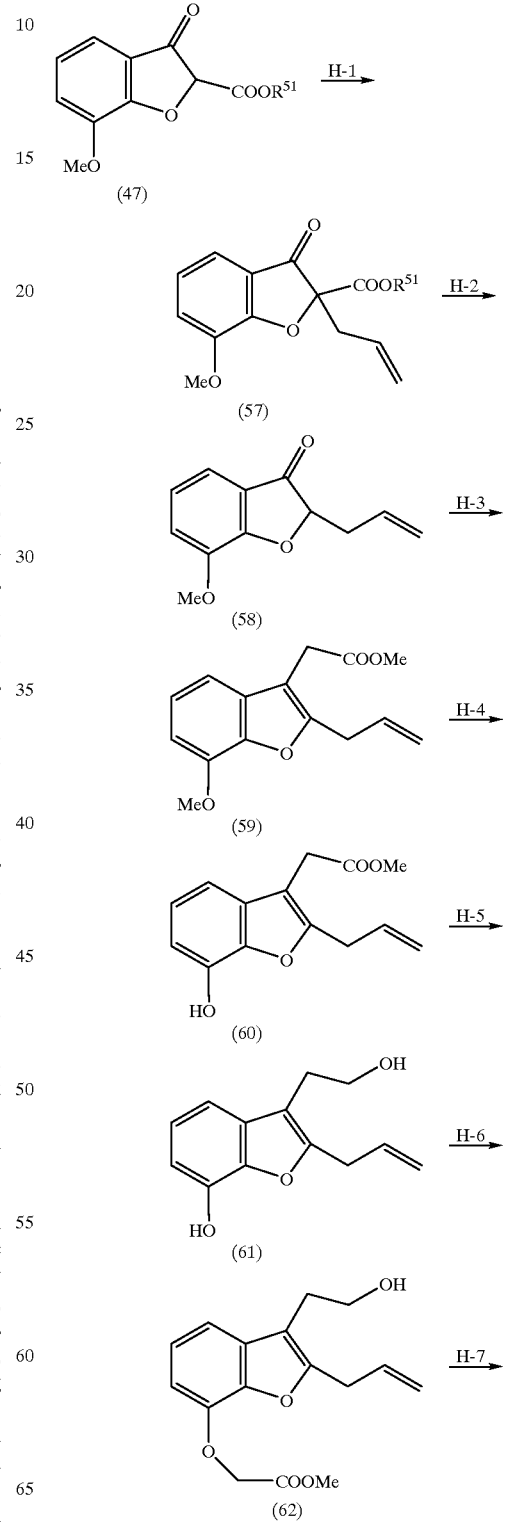

-continued

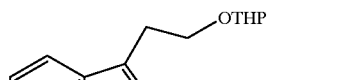

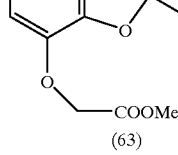
(63)

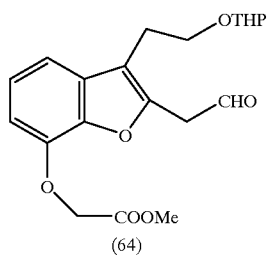
(64)

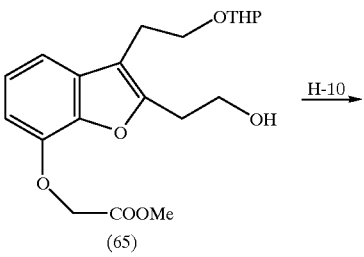
(65)

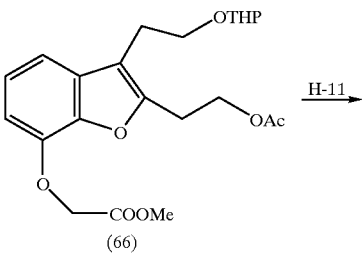
(66)

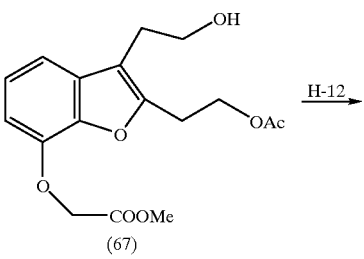
(67)

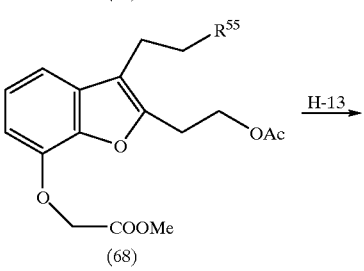
(68)

-continued

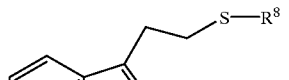

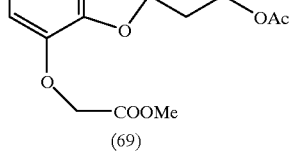
(69)

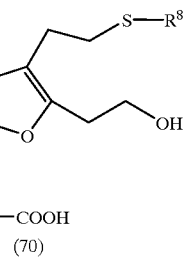
(70)

Production Process H (wherein $R^8$, $R^{51}$ and $R^{55}$ have the same meanings as described above)

Step H-1 is a step of introducing an allyl group. This step is carried out by converting the compound (47) into an enolate using a base, and then by treating the enolate with allyl bromide. As the base, sodium hydride is best preferred, although the base is not restricted to it. Various solvents may be used as the solvent, and DMF, THF, ether and toluene are preferred. This step may also be carried out by recovering by filtration the metal salt of the compound (47) obtained after completion of Step A-3, and treating the obtained metal salt with allyl bromide. Although a mixture of C-allyl compound and O-allyl compound is obtained by this Step, the O-allyl compound may be converted into the C-allyl compound by carrying out Claise rearrangement after extraction. The Claise rearrangement may easily be carried out by treating the mixture of the C-allyl compound and O-allyl compound in benzene or toluene at the refluxing temperature.

Step H-2 is a decarboxylation step and may be carried out in the similar manner as in Step B-1.

Step H-3 is a step of introducing an acetic acid unit and may be carried out as in Step C-1.

Step H-4 is a deprotection step of methyl group and may be carried out as in Step C-4.

Step H-5 is a reduction step of ester and may be carried out as in Step C-2.

Step H-6 is a step of introducing an acetic acid unit and may be carried out as in Step C-6.

Step H-7 is a step of protecting the hydroxyl group of the compound (62) with tetrahydropyranyl ether. This step is carried out by treating the compound (62) with dihydropyran in the presence of a catalytic amount of an acid. As the acid, hydrochloric acid, sulfuric acid and p-toluenesulfonic acid may preferably be employed. As the solvent, various solvents may be employed, and THF and dichloromethane are preferred.

Step H-8 is a step of cleaving the allyl group. This step is carried out by oxidatively cleaving the double bond by treating the compound (63) with an oxidizing agent. As the oxidizing agent, osmium tetroxide/sodium periodide or potassium permanganate is preferably used. As the solvent, dichloromethane and t-butyl alcohol are best preferred. The reaction temperature is preferably between −20° C. and 50° C.

Step H-9 is a reduction step of aldehyde. This step is a step of selectively reducing the aldehyde alone of the compound (64). As the reducing agent, sodium borohydride is preferably employed. As the solvent, methanol, ethanol, or THF/water mixture is preferably employed. The reaction temperature is preferably between −20° C. and 30° C.

Step H-10 is a step of protecting the hydroxyl group of the compound (65) with acetyl group. This step may be carried out by applying an ordinary acetylation reaction. The system of acetic anhydride/pyridine, acetyl chloride/triethylamine, and acetyl chloride/pyridine are preferred. As the solvent, dichloromethane, ether or THF is preferably employed. The reaction temperature is preferably −20° C. to 30° C.

Step H-11 is a step of deprotecting the tetrahydropyranyl group, and may be carried out in the similar manner as in Step E-4.

Step H-12 is a step of converting the hydroxyl group of the compound (67) to an eliminating group, and may be carried out as in Step C-7.

Step H-13 is a step of introducing a thioether side chain, and may be carried out as in Step D-1.

Step H-14 is a hydrolysis step of methyl ester. By this step, the acetyl group is also eliminated simultaneously. This step may be carried out as in Step B-9.

Among the compounds within the scope of the present invention, those in which $R^1$ is —OCH$_2$COOH or —OCH$_2$COOMe, and $R^2$ is —CR$^4$═CR$^5$—O— (wherein $R^4$ is —CH$_2$—CH$_2$—S—R$^8$ and $R^5$ is hydroxypropyl) may be produced by the Production Process I.

Reaction Equation 9

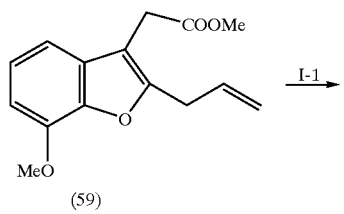
(59)

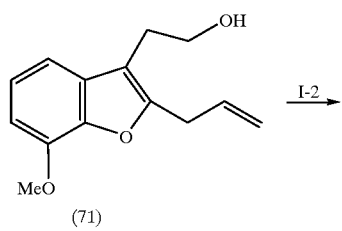
(71)

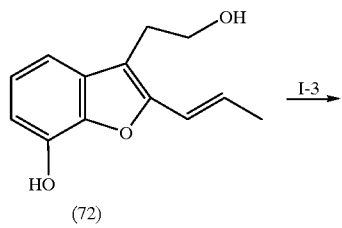
(72)

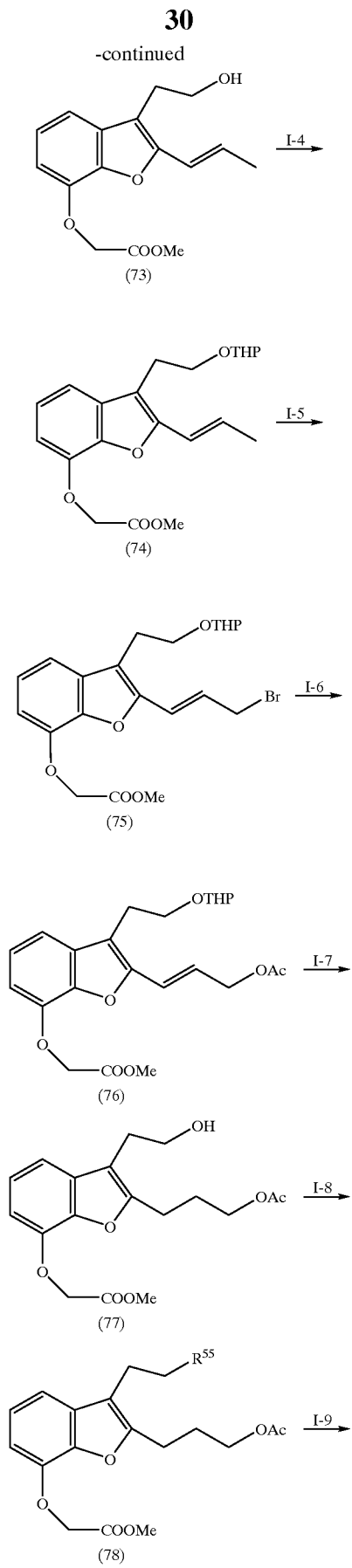

-continued

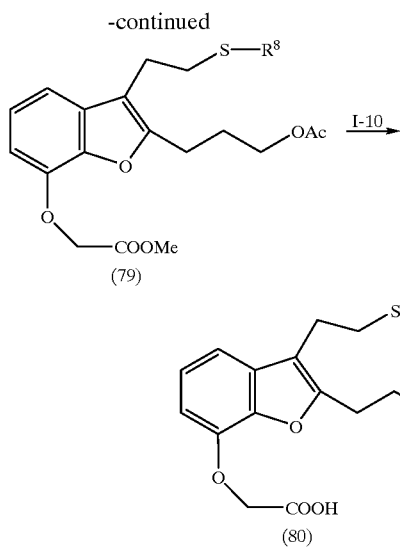

(79)

(80)

Production Process I
(wherein $R^8$ and $R^{55}$ have the same meanings as described above)

Step I-1 is a reduction step of ester, and may be carried out in the same manner as in Step C-2.

Step I-2 is a deprotection step of methyl group, and may be carried out as in Step B-5. By this step, isomerization of the double bond of the 2-allyl group is also carried out simultaneously.

Step I-3 is a step of introducing an acetic acid unit, and may be carried out as in Step C-6.

Step I-4 is a step of protecting the hydroxyl group of the compound (73) with tetrahydropyranyl group, and may be carried out as in Step H-7.

Step I-5 is a step of introducing bromine into the compound (74). In this step, bromine is introduced into the allyl group which is a side chain at the 2-position, by using N-bromosuccinimide. As the solvent, benzene, tetrachloromethane or chloroform is preferably employed, and the reaction is preferably carried out at the refluxing temperature of the solvent. The reaction may also be carried out adding a peracid or azoisobutylonitrile (AIBN) as a radical initiator.

Step I-6 is a step of introducing an acetoxy group. This step is carried out by treating the compound (75) with a metal salt of acetic acid. As the metal, sodium and potassium are preferred. As the solvent, DMF or THF is preferably employed. The reaction may be carried out at a temperature between 20° C. and 100° C.

Step I-7 is a reduction step of the double bond. This step may be carried out by catalytic hydrogenation using a catalyst. As the catalyst, palladium metal and platinum oxide, as well as these catalysts carried on a carrier are preferred. As the solvent, methanol, ethanol and THF are preferred. The reaction temperature may be 0° C. to 50° C. By this step, deprotection of the tetrahydropyranyl group is also carried out simultaneously.

Step I-8 is a step of converting the hydroxyl group of the compound (77) into an eliminating group, and may be carried out in the similar manner as in Step C-7.

Step I-9 is a step of introducing a thioether side chain, and may be carried out as in Step D-1.

Step I-10 is a hydrolysis step of methyl ester. By this step, the acetyl group is also eliminated simultaneously. This step may be carried out as in Step B-9.

Among the compounds within the scope of the present invention, those in which $R^1$ is —$OCH_2COOH$ or —$OCH_2COOMe$, and $R^2$ is —$CR^4$=$CR^5$—O— (wherein $R^4$ is —$CH_2$—$CH_2$—$CH_2$—S—$R^8$) may be produced by the Production Process J.

(Reaction Equation 10)

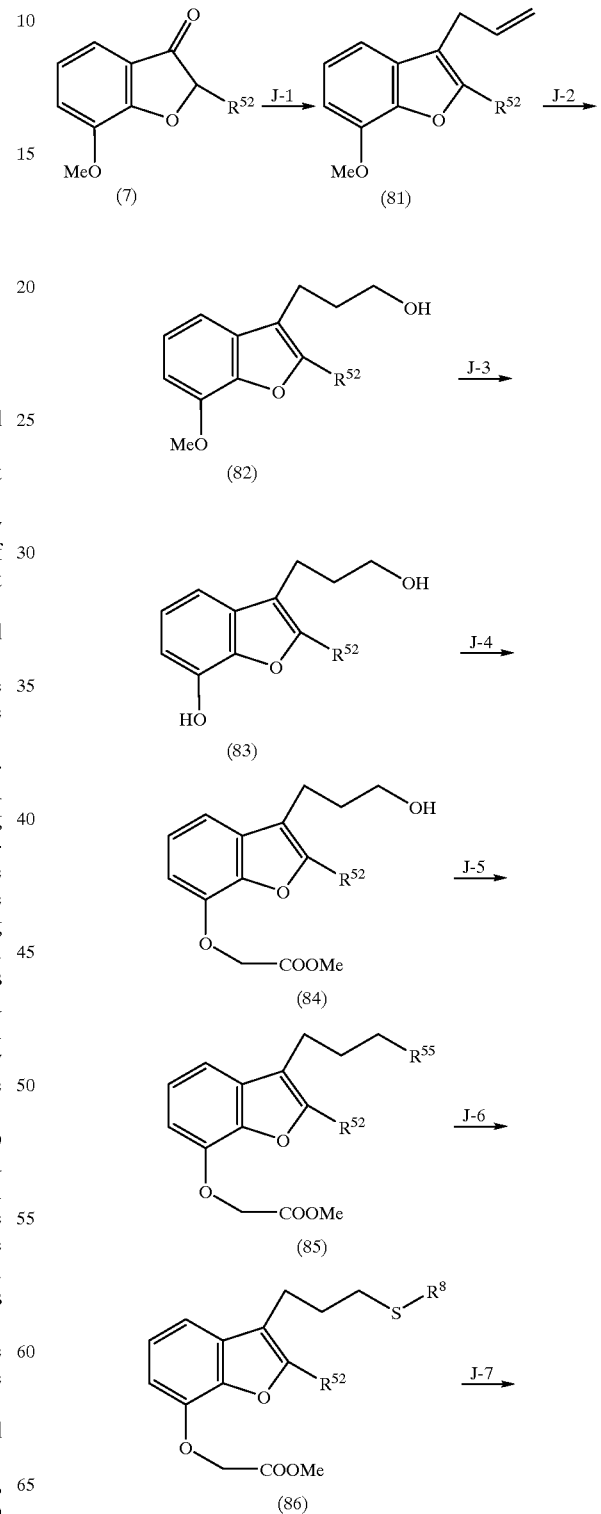

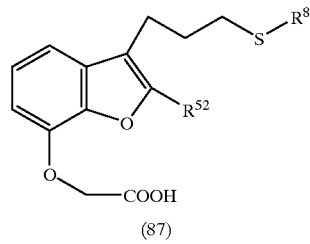

(87)

Production Process J (wherein $R^8$, $R^{52}$ and $R^{55}$ have the same meanings as described above)

Step J-1 is a step of introducing an allyl group. This step may be carried out by reacting the compound (7) with allyllithium or an allyl Grignard reagent in the presence of cerium chloride, and by dehydrating the generated tertiary alcohol. As the solvent, aprotic solvents may be employed and THF and ether are preferred. The reaction temperature is selected from the range between −78° C. and 10° C. The dehydration reaction may preferably be carried out by refluxing the resultant in benzene in the presence of an acid catalyst. As the acid catalyst, p-toluenesulfonic acid is preferably employed.

Step J-2 is a step of oxidizing the double bond of the compound (81). This step is carried out by hydroboration and subsequent oxidation reaction. As the borane derivative, various borane derivatives such as diborane, borane complexes, and alkyl boranes may be employed, and complex between borane and dimethylsulfide, and complex between borane and THF are preferred. As the solvent, THF or ether is preferably employed. The reaction temperature is preferably −20° C. to 50° C. The oxidation reaction is preferably carried out by using a peracid or hydrogen peroxide under alkyl condition. As the solvent, methanol or ethanol is preferably employed. The reaction temperature is preferably 10° C. to 50° C.

Step J-3 is a deprotection step of methyl group, and may be carried out in the similar manner as in Step C-4.

Step J-4 is a step of introducing an acetic acid unit, and may be carried out as in Step C-6.

Step J-5 is a step of converting the hydroxyl group of the compound (84) into an eliminating group, and may be carried out as in Step C-7.

Step J-6 is a step of introducing a thioether side chain, and may be carried out as in Step D-1.

Step J-7 is a hydrolysis step of methyl ester, and may be carried out as in Step B-9.

Among the compounds within the scope of the present invention, those in which $R^1$ is —OCH$_2$COOH or —OCH$_2$COOMe, and $R^2$ is —CR$^4$=CR$^5$—O— (wherein R is —CH$_2$—CH(OH)—R$^8$ and $R^5$ is hydrogen or $C_1$–$C_5$ alkyl) may be produced by the Production Process K.

Reaction Equation 11

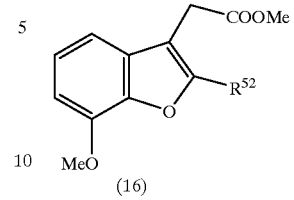

(16)

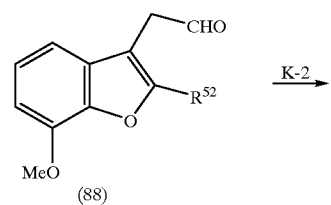

(88)

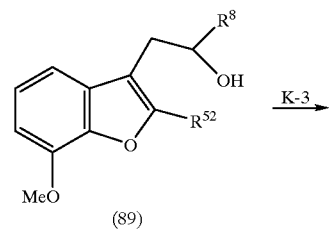

(89)

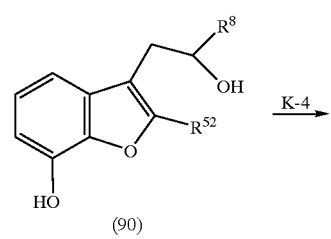

(90)

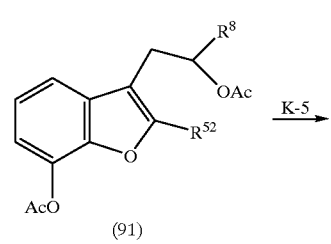

(91)

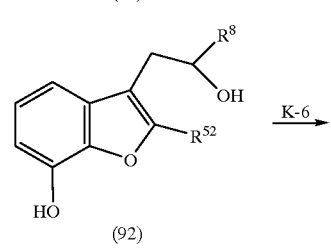

(92)

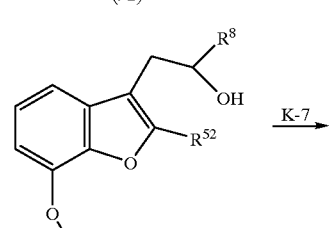

(93)

Production Process K (wherein $R^8$ and $R^{52}$ have the same meanings as described above)

Step K-1 is a step of reducing methyl ester into aldehyde. Various reducing agents may be employed, and diisobutylaluminum hydride is preferably employed. As the solvent, aprotic solvents may be employed, and dichloromethane and THF are preferred. The reaction may be carried out at a temperature of −100° C. to 10° C.

Step K-2 is a step of introducing a side chain. This step may be carried out by reacting $R^8$—Li or $R^8$—Mg—$R^{58}$ (wherein $R^{58}$ is chlorine or bromine) with the compound (88). As the solvent, aprotic solvents may be employed, and THF and ether are especially preferred. The reaction may be carried out at a temperature of −78° C. to 10° C.

Step K-3 is a deprotection step of methyl ether and may be carried out in the similar manner as in Step B-5.

Step K-4 is a step of protecting hydroxyl group with acetyl group, and may be carried out as in Step H-10.

Step K-5 is a deprotection step of acetyl group. This step is carried out by treating the compound (91) with a base. As the base, potassium carbonate, potassium hydroxide and sodium hydroxide are preferred. As the solvent, methanol, ethanol and mixtures of each of these alcohols with water are best preferred. The reaction may be carried out at a temperature of 0° C. to 50° C.

Step K-6 is a step of introducing an acetic acid unit, and may be carried out as in Step C-6.

Step K-7 is a hydrolysis step of methyl ester, and may be carried out as in Step B-9.

Among the compounds within the scope of the present invention, those in which $R^1$ is —OCH$_2$COOH or —OCH$_2$COOMe, and $R^2$ is —CR$^4$=CR$^5$—O— (wherein $R^4$ is —O—CH$_2$—W—$R^8$ (wherein W is represented by formula (IIa) and $R^5$ is hydrogen or $C_1$-$C_5$ alkyl) may be produced by the Production Process L.

Reaction Equation 12

Production Process L (wherein $R^8$ and $R^{52}$ have the same meanings as described above)

Step L-1 is a hydrolysis step of methyl ester, and may be carried out in the similar manner as in Step B-9.

Step L-2 is an alkylation step of the carboxylic acid (95). This step is carried out by converting the carboxylic acid (95) into a salt using a base and then by condensing the resultant with $R^8$—CO—CH$_2$—OH. Alternatively, this step is carried out by condensing $R^8$—CO—CH$_2$—OH and the carboxylic acid using a dehydrating agent. As the base, potassium carbonate, potassium hydroxide, sodium hydroxide and sodium hydride are preferably employed, although the base is not restricted thereto. As the dehydrating agent, dicyclohexylcarbodiimide is preferably used, although the dehydrating agent is not restricted thereto. As the solvent used when using the base, THF or DMF is preferably employed. Alternatively, after converting the carboxylic acid into a salt in methanol, the reaction may be carried out using the methanol as a solvent. The reaction temperature is preferably 0° C. to 50° C. As the solvent used when the dehydrating agent is used, THF, DMF, benzene or toluene is preferably employed. The reaction temperature is preferably 0° C. to 50° C.

Step L-3 is a step of constructing oxazole ring. This step is carried out by heating the compound (96) with ammonium acetate to reflux in acetic acid.

Step L-4 is a deprotection step of methyl ether, and may be carried out in the similar manner as in Step B-5.

Step L-5 is a step of introducing an acetic acid unit, and may be carried out as in Step C-6.

Step L-6 is a hydrolysis step of methyl ester, and may be carried out as in Step B-9.

Among the compounds within the scope of the present invention, those in which $R^1$ is —OCH$_2$COOH or —OCH$_2$COOEt, and $R^2$ is —CHR$^5$—CHR$^4$—O— (wherein $R^4$ is —CH$_2$—O—R$^{80}$ and $R^5$ is hydrogen) may be produced by the Production Process M.

Reaction Equation 13

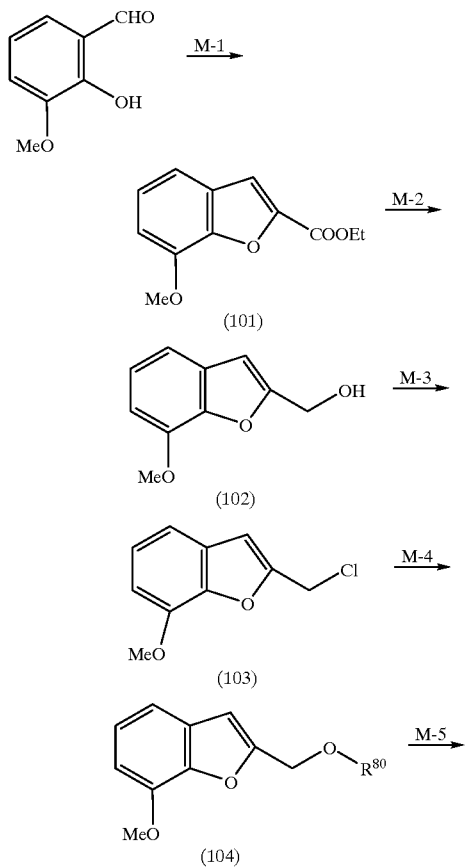

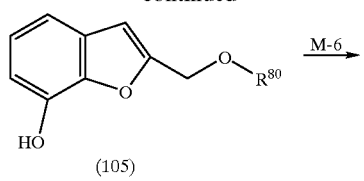

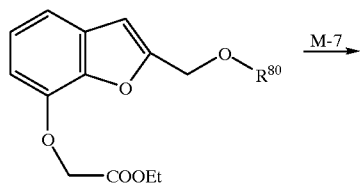

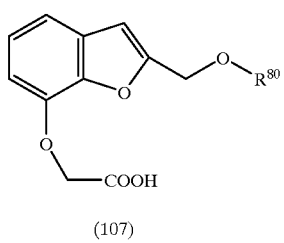

Production Process M (wherein $R^{80}$ represents $C_1$–$C_5$ alkyl substituted with one or two allyl groups, or $C_1$–$C_8$ alkoxyalkyl substituted with one or two allyl groups).

Step M-1 is a step of converting o-vanillin to benzofuran. In this step, by heating o-vanillin and ethyl bromoacetate in the presence of a base, O-alkylation of o-vanillin, cyclization and dehydration are attained so that the benzofuran ring is constructed in a single step. As the base, potassium carbonate is preferably employed, although the base is not restricted thereto. As the solvent, DMF is preferably employed. The reaction temperature may be 50° C. to 150° C., preferably 80° C. to 120° C.

Step M-2 is a reduction step of ethyl ester, and may be carried out in the similar manner as in Step C-2.

Step M-3 is a step of converting hydroxyl group into chlorine. This step is carried out by treating the compound (102) with thionyl chloride. Pyridine may be added to the reaction solution. As the solvent, dichloromethane or DMF is preferably employed, and pyridine may also be used as the solvent. The reaction may also be carried out by adding thionyl chloride to the compound (102) without using a solvent.

Step M-4 is a step of introducing a side chain, and may be carried out as in Step D-1.

Step M-5 is a deprotection step of methyl ether, and may be carried out as in Step B-5.

Step M-6 is a step of introducing an acetic acid unit, and may be carried out as in Step C-6 except that ethyl bromoacetate is used in place of methyl bromoacetate.

Step M-7 is a hydrolysis step of methyl ester, and may be carried out as in B-9.

Among the compounds within the scope of the present invention, those in which $R^1$ is —OCH$_2$COOH or —OCH$_2$COOMe, and $R^2$ is —NR$^4$—CR$^5$R$^6$—CHR$^7$— (wherein $R^6$ and $R^7$ represent covalent bond, $R^4$ is —CH$_2$—CH$_2$—NHSO$_2$—R$^8$ and $R^5$ is hydrogen) may be produced by the Production Process N.

Reaction Equation 14

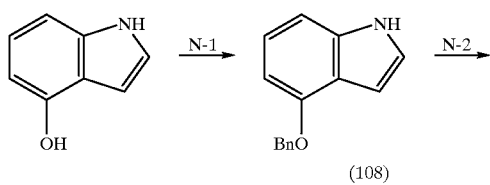
(108)

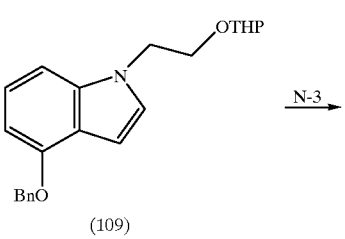
(109)

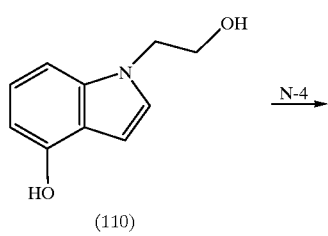
(110)

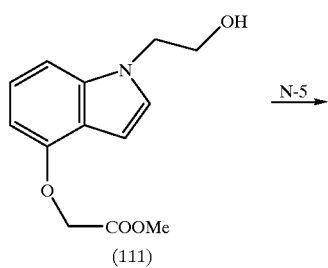
(111)

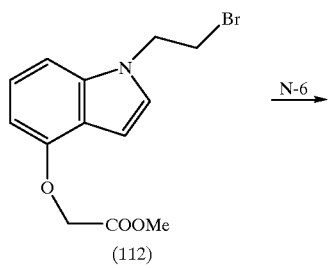
(112)

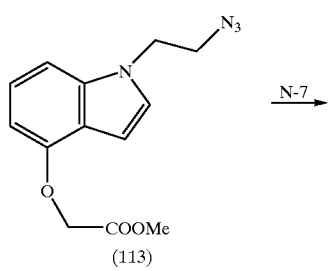
(113)

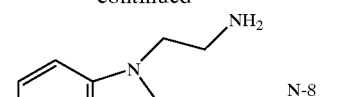
(114)

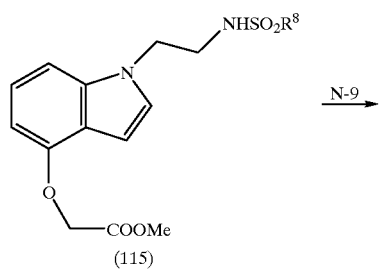
(115)

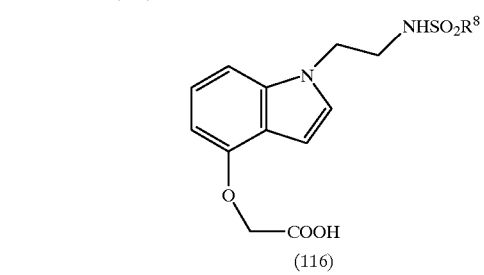
(116)

Production Process N (wherein $R^8$ represents the same meanings as described above)

As the starting material of this production process, easily and commercially available 4-hydroxyindole is used.

Step N-1 is a step of protecting the hydroxyl group in 4-hydroxyindole with benzyl ether. This step is carried out under usual benzylation conditions. Although this reaction may preferably be carried out in DMF using sodium hydroxide as a base, the reaction conditions are not restricted thereto.

Step N-2 is an N-alkylation step of the compound (108). This step is carried out by eliminating the hydrogen atom in NH by using a base, and then reacting the resultant with tetrahydropyranyl ether of ethylene bromohydrin. As the base, potassium metal, potassium hydride, potassium t-butoxide, sodium metal, sodium hydride and the like may be employed. Among these, sodium hydride is preferred, although the base is not restricted to this. As the solvent, THF, DMF, ether or dimethoxyethane is employed, and DMF is preferred. The reaction may be carried out at a temperature of −20° C. to 50° C., preferably −10° C. to 10° C.

Step N-3 is a deprotection step of benzyl ether. This step is carried out by catalytic hydrogenation using palladium-carbon as a catalyst. By this step, not only the benzyl ether, but also the tetrahydropyranyl ether may be deprotected. As the solvent, methanol or ethanol is preferably employed. The reaction may be carried out at a temperature of 0° C. to 50° C.

Step N-4 is a step of introducing an acetic acid unit, and may be carried out as in Step C-6.

Step N-5 is a step of converting hydroxyl group into bromine, and may be carried out as in Step C-7.

Step N-6 is a step of introducing an azide group, and may be carried out as in B-3.

Step N-7 is a reduction step of azide group, and may be carried out as in Step C-9.

Step N-8 is a step of converting the amino group of the compound (114) into sulfonamide, and may be carried out as in Step C-10.

Step N-9 is a hydrolysis step of methyl ester, and may be carried out as in Step B-9.

Among the compounds within the scope of the present invention, those in which $R^1$ is —OCH$_2$COOH or —OCH$_2$COOMe, and $R^2$ is —NR$^4$—CR$^5$—R$^6$—CHR$^7$— (wherein $R^4$ is —CH$_2$—CH$_2$—O—R$^8$, $R^5$ is hydrogen, and both of $R^6$ and $R^7$ represent hydrogen or covalent bond) may be produced by the Production Process O.

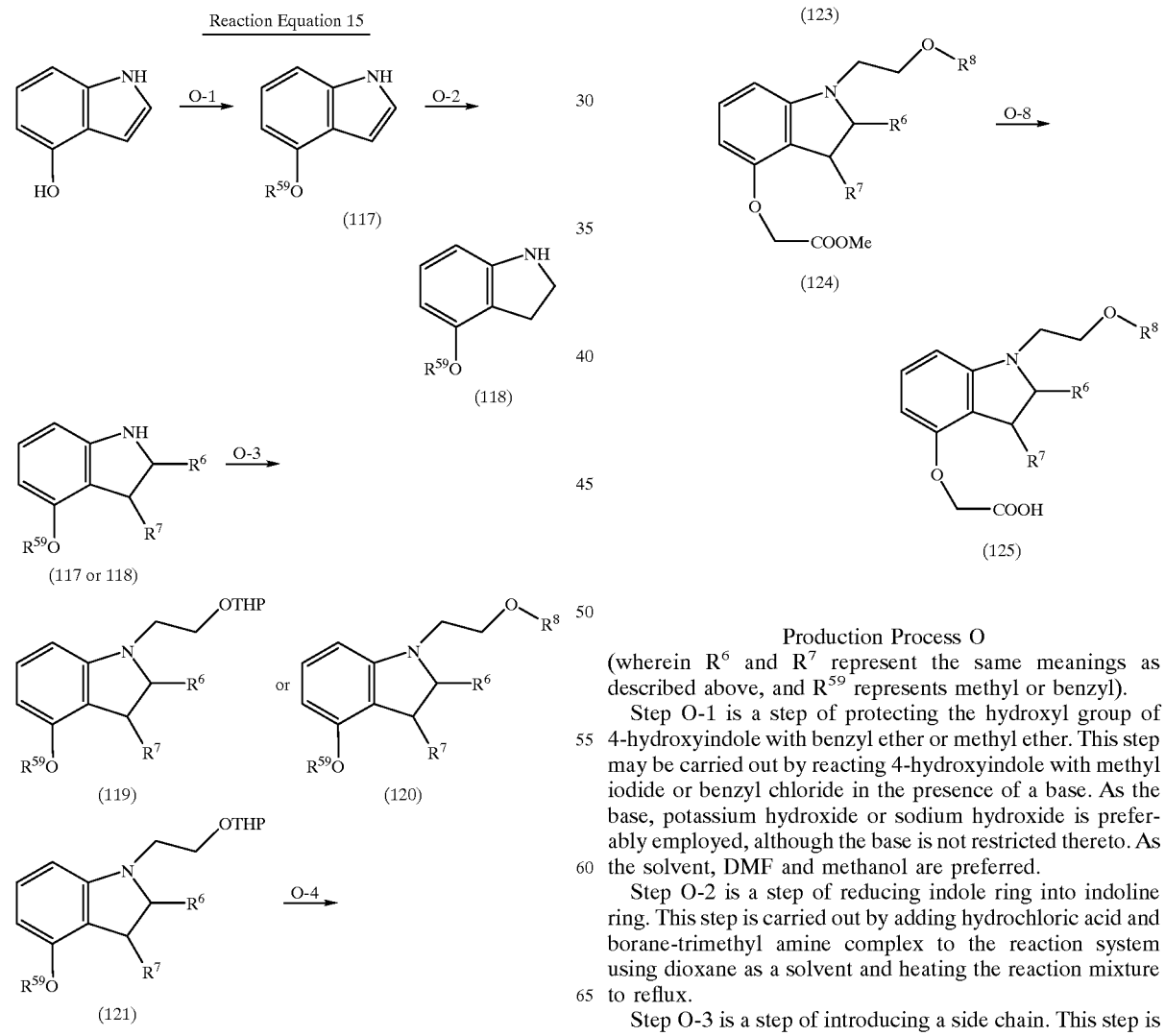

Production Process O
(wherein $R^6$ and $R^7$ represent the same meanings as described above, and $R^{59}$ represents methyl or benzyl).

Step O-1 is a step of protecting the hydroxyl group of 4-hydroxyindole with benzyl ether or methyl ether. This step may be carried out by reacting 4-hydroxyindole with methyl iodide or benzyl chloride in the presence of a base. As the base, potassium hydroxide or sodium hydroxide is preferably employed, although the base is not restricted thereto. As the solvent, DMF and methanol are preferred.

Step O-2 is a step of reducing indole ring into indoline ring. This step is carried out by adding hydrochloric acid and borane-trimethyl amine complex to the reaction system using dioxane as a solvent and heating the reaction mixture to reflux.

Step O-3 is a step of introducing a side chain. This step is carried out by eliminating the hydrogen atom in NH of indole (117) or indoline (118) by using a base, and adding $R^8$—O—$CH_2$—$CH_2$—Br. As the base, sodium hydride or phenyllithium is preferably employed, although the base is not restricted thereto. As the solvent, an aprotic solvent, preferably DMF, may be employed. The reaction temperature is between −20° C. and 50° C. Preferably, the base and the material of the side chain are added at 0° C. and then the temperature is raised to room temperature to complete the reaction. The compound (120) obtained by this step may also be obtained by the same method as described above except that tetrahydropyranyl ether of ethylenebromohydrine is used in place of $R^8$—O—$CH_2$—$CH_2$—Br to obtain the compound (119), and then by carrying out Steps O-4 and O-5 described below.

Step O-4 is a deprotection step of tetrahydropyranyl ether. This step is carried out by hydrolyzing the compound (121) with an acid. As the acid, hydrochloric acid or sulfuric acid is preferably employed. As the solvent, THF, methanol, ethanol, or a mixture of each of these solvents and water is preferably employed.

Step O-5 is an O-alkylation step of the compound (122), and may be carried out in the similar manner as in Step E-3.

Step O-6 is a deprotection step of $R^{59}$. In cases where $R^{59}$ is methyl, the step may be carried out as in B-5. In cases where $R^{59}$ is benzyl, the step may be carried out as in Step N-3.

Step O-7 is a step of introducing acetic acid unit, and may be carried out as in Step C-6.

Step O-8 is a hydrolysis step of methyl ester, and may be carried out as in Step B-9.

Among the compounds within the scope of the present invention, those in which $R^1$ is —$OCH_2COOH$ or —$OCH_2COOMe$, and $R^2$ is —$NR^4$—$CR^5R^6$—$CHR^7$— (wherein $R^6$ and $R^7$ represent covalent bond, $R^4$ is —$CH_2$—$CH_2$—$NR^6$—$R^8$ and $R^5$ is hydrogen) may be produced by the Production Process P.

Reaction Equation 16

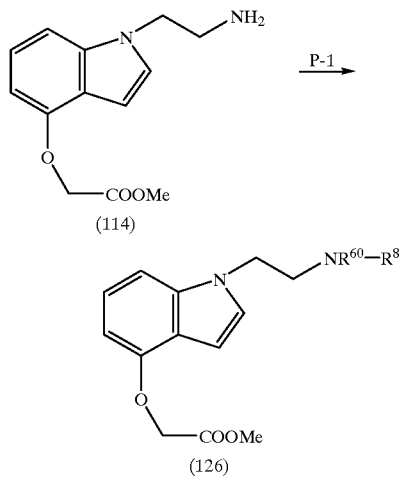

-continued

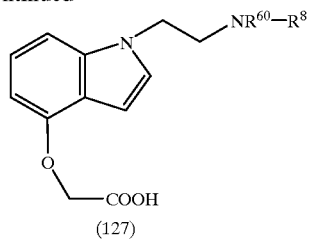

Production Process P (wherein $R^8$ represents the same meanings as described above, and $R^{60}$ represents hydrogen or benzyl).

Step P-1 is an N-alkylation step of the compound (114). In cases where $R^{60}$ is hydrogen, this step is carried out by reacting the compound (114) with $R^8$—Cl or $R^8$—Br in the presence of a base. In cases where $R^{60}$ is benzyl, this step is carried out by using benzyl bromide. As the base, various tertiary amines and potassium carbonate may be employed, and potassium carbonate, pyridine, triethylamine and diisopropylethylamine are preferred. As the solvent, DMF and acetonitrile are preferred. The reaction temperature is preferably 20° C. to 150° C.

Step P-2 is a hydrolysis step of methyl ester, and may be carried out as in Step B-9.

Among the compounds within the scope of the present invention, those in which $R^1$ is —$OCH_2COOH$ or —$OCH_2COOMe$, and $R^2$ is —$NR^4$—$CR^5R^6$—$CHR^7$— (wherein $R^4$ is $C_2$–$C_{10}$ alkyl substituted with one or two phenyl groups (which may be substituted), $R^5$ is hydrogen, and both of $R^6$ and $R^7$ represent hydrogen or covalent bond) may be produced by the Production Process Q.

Reaction Equation 17

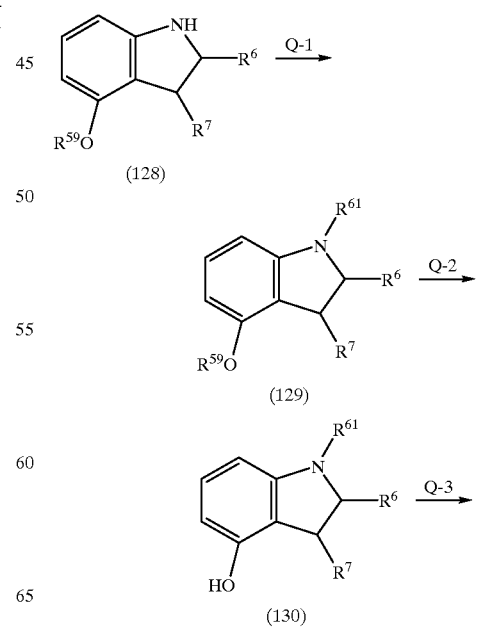

-continued (131)

(132)

Production Process Q (wherein $R^6$, $R^7$ and $R^{59}$ represent the same meanings as described above, and $R^{61}$ represents $C_2$–$C_{10}$ alkyl substituted with one or two phenyl groups (which may be substituted).

Step Q-1 is a step of introducing a side chain. This step is carried out by eliminating the hydrogen atom of NH in indole or indoline by using a base and by adding $R^{61}$—Br or $R^{61}$—Cl. As the base, sodium hydride or phenyllithium is preferably employed, although the base is not restricted thereto. As the solvent, aprotic solvents may be employed, and DMF is preferably employed. The reaction temperature is selected from the range between –20° C. and 50° C.

Step Q-2 is a deprotection step of $R^{59}$. In cases where $R^{59}$ is methyl, this step may be carried out as in Step B-5. In cases where $R^{59}$ is benzyl, this step may be carried out as in Step N-3.

Step Q-3 is a step of introducing an acetic acid unit, and may be carried out as in Step C-6.

Step Q-4 is a hydrolysis step of methyl ester, and may be carried out as in Step B-9.

Among the compounds within the scope of the present invention, those in which $R^1$ is —OCH$_2$COOH or —OCH$_2$COOMe, and $R^2$ is —NR$^4$—CR$^5$R$^6$—CHR$^7$— (wherein $R^4$ is —CH$_2$—CH$_2$—S—R$^8$, $R^5$ is hydrogen, and both of $R^6$ and $R^7$ represent hydrogen or covalent bond) may be produced by the Production Process R.

Reaction Equation 18

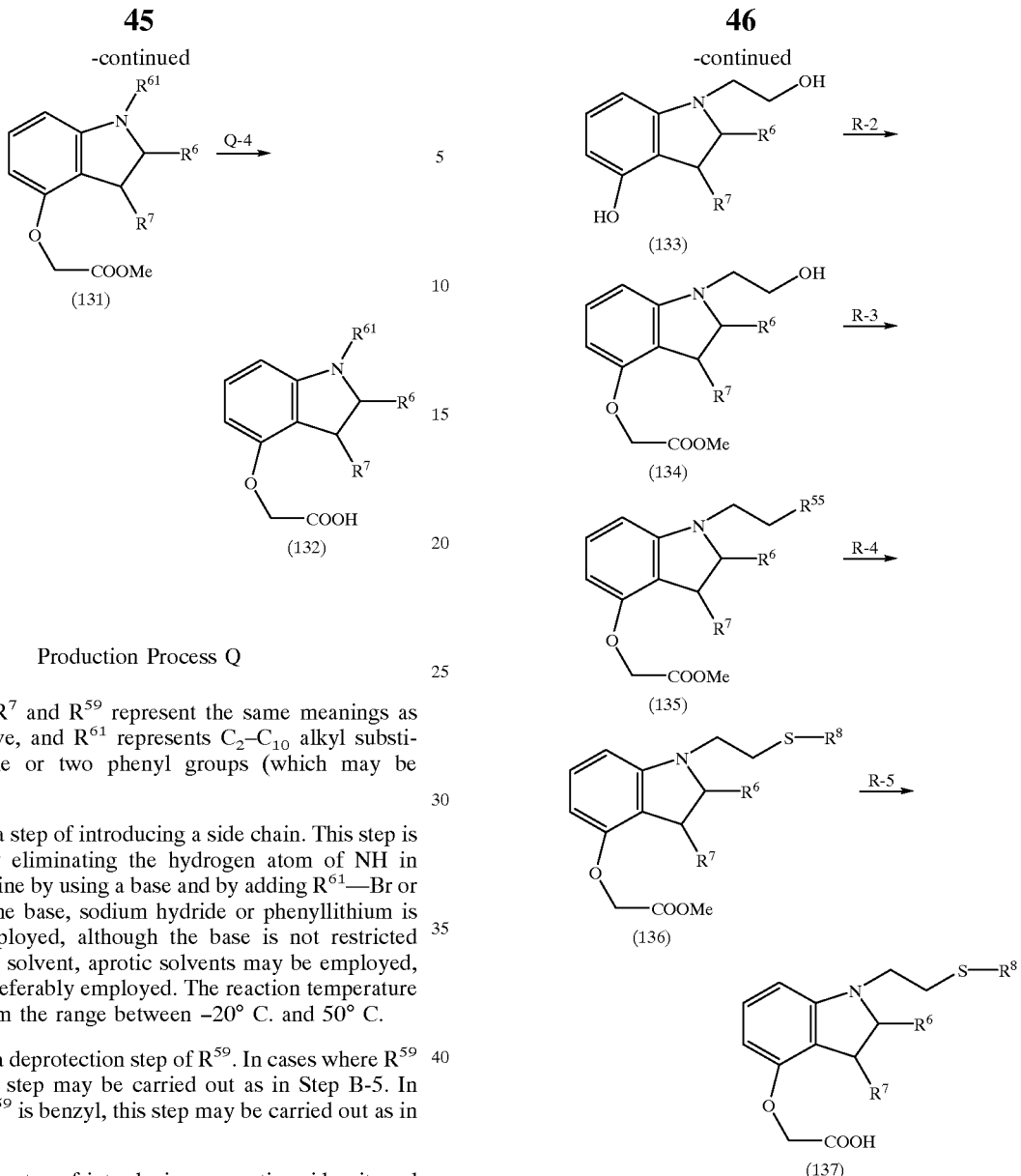

Production Process R (wherein $R^6$, $R^7$, $R^8$, $R^{55}$ and $R^{59}$ represent the same meanings as described above).

Step R-1 is a step of deprotecting $R^{59}$ of the compound (122) which can be obtained by Step O-4. In cases where $R^{59}$ is methyl, this step may be carried out as in Step B-5. In cases where $R^{59}$ is benzyl, this step may be carried out as in Step N-3.

Step R-2 is a step of introducing an acetic acid unit, and may be carried out as in Step C-6.

Step R-3 is a step of converting hydroxyl group into eliminating group $R^{55}$, and may be carried out as in Step C-7.

Step R-4 is a step of introducing a side chain, and may be carried out as in Step D-1.

Step R-5 is a hydrolysis step of methyl ester, and may be carried out as in Step B-9.

Although the compound of the present invention is represented by a structural formula of an optically active compound, the general formula includes d-, l- and d,l-isomers. The processes A to R can be equally applied to d-, l- and dl-isomers.

In cases where the processes A to R are carried out using a dl compound, the compound represented by the formula [I] obtained in the form of racemate may easily be separated into d- or l-isomer by column chromatography or the like.

The compounds of the present invention have strong $TXA_2$ receptor antagonist activities and $PGI_2$ receptor agonist activities, so that they have pharmacological activities such as activity to inhibit platelet aggregation, vasoconstriction inhibition activity and activity to inhibit contraction of bronchial muscle. Therefore, they are effective in therapy and prevention of hypertension, myocardial infarction, angina pectoris, thrombus formation after PTCA, cerebral infarction, transient cerebral ischemic attack, peripheral circulatory disturbance (Buerger's disease, Raynaud's disease, Behcet's disease, thrombotic thrombocytopenic purpura, hepatic disorders, renal disorders and the like), arteriosclerosis, platelet function disorder accompanied by diabetes, retinal vascular occlusion, hyperlipidemia, lupus nephritis, vibration disease, bronchial asthma, allergies and the like. To this end, the compound according to the present invention may usually be administered by intravenous, intraarterial, intramuscular, percutaneous, subcutaneous or oral administration. In case of oral or rectal administration, the compound is usually administered 1 to 4 times a day at a dose of 1 µg/kg/day to 100 mg/kg/day. In case of intravenous drip infusion or intraarterial injection, good results are obtained by administering the compound at a dose of 1 ng/kg/min. to 100 µg/kg/min. In case of usual intravenous, intramuscular or subcutaneous injection, the compound is usually administered 1 to 4 times a day at a dose of 0.1 µg/kg/day to 100 mg/kg/day. When the compound is administered, the dose is selected from the ranges mentioned above depending on the age, sex and conditions of the patient and on the times of administration.

The compounds of the present invention may be orally administered in the form of a solid containing a vehicle such as starch, lactose, sucrose, glucose, microcrystalline cellulose or a kind of clay, a coloring agent, lubricant, binding agent, disintegrating agent, or a coating agent. Alternatively, the compounds of the present invention may be administered parenterally in the form of a sterilized solution. The solution may contain another solute, such as sodium chloride or glucose enough to make the solution isotonic. Since the compounds of the present invention have chemical structural stabilities, there is no difficulties in formulating the compounds. Thus, the compounds may be formulated into a wide variety of preparations such as formulations for oral administration (tablets, powder, granules), various injection solutions, suppositories, ointments, lotions and the like.

Examples of a part of the present invention will now be described.

Reference Example 1

Methyl 3-methoxy salicylate

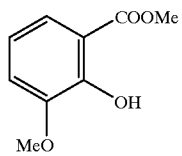

3-methoxysalicylic acid (23.8 g) was dissolved in anhydrous methanol (400 ml) and concentrated sulfuric acid (2.5 ml) was added, followed by stirring the mixture for 25 hours. After evaporating the solvent under reduced pressure, the residue was poured into water and the resultant was extracted with ethyl acetate. The organic layer was washed with saturated sodium hydrogen carbonate solution, water and with saturated brine, and then dried over magnesium sulfate. After removing magnesium sulfate by filtration, the solvent was evaporated off. The obtained compound was recrystallized from ethyl acetate/n-hexane to obtain the desired product (24.6 g, yield: 96%).

m.p.: 64.0–64.5° C. (recrystallized from ethyl acetate/n-hexane)

IR (KBr method) 3342, 1688, 1628, 1597, 1510, 1466, 1379, 1346, 1274, 1224, 1191, 1145, 1079, 998, 940, 853, 789, 762, 741, 723, 679, 650, 586, 528, 441 $cm^{-1}$ NMR (300 MHz $CDCl_3$) δ11.01(1H,s),7.44(1H,dd,J=2,8 Hz),7.05(1H,dd,J=2,8 Hz), 6.83(1H,t,J=8 Hz),3.96(3H,s), 3.91(3H,s)

EI-MS m/e 182($M^+$)

Reference Example 2

Methyl 2-methoxycarbonylmethyloxy-3-methoxy benzoate

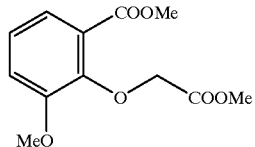

Methyl 3-methoxysalicylic acid (22.5 g) and methyl bromoacetate (20.4 g) were dissolved in DMF (370 ml) and anhydrous potassium carbonate (20.2 g) was added, followed by stirring the mixture at room temperature for 30 hours. After removing the solvent by evaporation under reduced pressure, the residue was poured into water and the resultant was extracted with ethyl acetate. The organic layer was washed with water and saturated brine, and dried over magnesium sulfate. After removing magnesium sulfate by filtration, the solvent was evaporated off. The obtained residue was purified by distillation under reduced pressure (bp. 157–159° C./6 mmHg) to obtain the desired compound (23.2 g, yield: 91%).

m.p.: 71° C. (recrystallized from ethyl acetate/n-hexane)

IR (KBr method) 3342, 1688, 1628, 1597, 1510, 1466, 1379, 1346, 1274, 1224, 1191, 11 45, 1079, 998, 940, 853, 789, 762, 741, 723, 679, 650, 586, 528, 441 $cm^{-1}$ NMR(300 MHz $CDCl_3$) δ7.33(1H,dd,J=2,8 Hz),7.12(1H, t,J=8 Hz),7.06(1H,dd, J=2,8 Hz),4.69(2H,s),3.89(3H,s),3.86 (3H,s),3.82(3H,s)

EI-MS m/e 254($M^+$)

Reference Example 3

Methyl 3-hydroxy-7-methoxybenzofuran-2-carboxylate

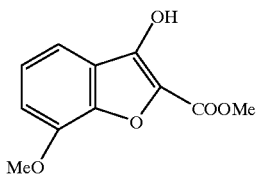

Sodium hydride (752 mg) was washed with n-hexane and dried under reduced pressure. Methyl 2-methoxycarbonylmethyloxy-3-methoxy benzoate (4.68 g) was dissolved in toluene (50 ml) and the solution was added to the sodium hydride, followed by stirring the mixture at 100° C. for 22 hours. The reaction solution was poured into 1N hydrochloric acid and extracted with ethyl acetate. The organic layer was washed with water and saturated brine, and dried over magnesium sulfate. After removing magnesium sulfate by filtration, the solvent was evaporated off. The obtained residue was recrystallized from ethyl acetate/n-hexane to obtain the desired compound (2.53 g, yield: 63%).

m.p.: 114° C. (recrystallized from ethyl acetate/n-hexane)

IR (KBr method) 3342, 1688, 1628, 1597, 1510, 1466, 1379, 1346, 1274, 1224, 1191, 1145, 1079, 998, 940, 853, 789, 762, 741, 723, 679, 650, 586, 528, 441 cm$^{-1}$ NMR(300 MHz CDCl$_3$) δ8.07(1H,bs),7.32(1H,dd,J=1,8 Hz),7.22(1H,t,J=8 Hz), 6.97(1H,dd,J=1,8 HZ),4.00(3H,s), 3.99(3H,s)

EI-MS m/e 222(M$^+$)

Reference Example 4

Methyl 7-methoxy-3-oxo-2-(2-propenyl)-2,3-dihydrobenzofuran-2-carboxylate

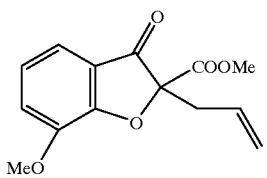

Methyl 3-methoxy-2-(methoxycarbonylmethoxy) benzoate (19.39 g) was dissolved in toluene (200 ml). To this solution, sodium hydride (3.36 g) was added and the resultant was stirred at room temperature for 20 minutes, followed by refluxing the mixture for 2 hours. Toluene was evaporated off under reduced pressure and the residue was dissolved in DMF (150 ml). To this solution, acetic acid (2 ml) was added and the solvent was evaporated off under reduced pressure. The residue was dissolved in toluene (200 ml) and the solution was refluxed for 1 hour. The reaction solution was cooled to room temperature and poured into water (150 ml), followed by separating the organic layer. The aqueous layer was extracted with ethyl acetate (100 ml) and the organic layers were combined. The resultant was washed with saturated aqueous sodium hydrogen carbonate solution and with saturated brine, followed by drying the resultant over sodium sulfate. After removing sodium sulfate by filtration, the solvent was evaporated off, and the residue was purified by column chromatography (solvent: hexane/ethyl acetate=3/1) using silica gel to obtain the desire compound (18.42 g, yield: 92%).

IR (liquid film method) 2970, 1745, 1718, 1640, 1617, 1600, 1506, 1440, 1350, 1261, 1194, 1170, 1153, 1125, 1081, 1065, 1013, 965, 936, 888, 847, 808, 771, 731 cm$^{-1}$ NMR(300 MHz CDCl$_3$) δ7.24(1H,dd,J=7.7,1.4 Hz),7.15 (1H,dd,J=8.0,1.4 Hz), 7.06(1H,t,J=7.7 Hz), 5.67(1H,ddt,J= 17.3,10.1,7.1 Hz),5.27–5.20(1H,m),5.11–5.07(1H,m),3.99, 3.75(each3H,s), 3.08(1H,ddt,J=14.5,7.2,1.1 Hz),2.91(1H, ddt,J=14.6,7.7.4, 1.1 Hz)

EI-MS m/e 262(M$^+$)

Reference Example 5

7-methoxy-3-oxo-2-(2-propenyl)-2,3-dihydrobenzofuran

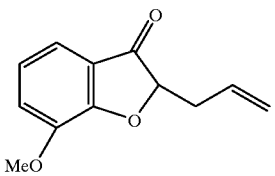

Methyl 7-methoxy-3-oxo-2-(2-propenyl)-2,3-dihydrobenzofuran-2-carboxylate (18.42 g) and concentrated sulfuric acid (2 ml) were dissolved in t-butyl alcohol (150 ml) and the solution was refluxed for 22.5 hours. After cooling the reaction solution to room temperature, the reaction solution was neutralized with saturated aqueous sodium hydrogen carbonate and then washed with saturated brine, followed by drying the resultant over sodium sulfate. After removing sodium sulfate by filtration, the solvent was evaporated under reduced pressure, and the residue was purified by column chromatography (solvent:hexane/ethyl acetate=4/1) using silica gel to obtain the desired compound (11.39 g, yield: 79%).

IR (liquid film method) 3080, 3014, 2940, 2844, 1717, 1644, 1603, 1506, 1441, 1352, 1319, 1270, 1209, 1185, 1168, 1091, 1064, 1029, 1011, 922, 876, 855, 797, 752, 733 cm$^{-1}$ NMR (300 MHz CDCl$_3$) δ7.24(1H,dd,J=7.7,1.1 Hz),7.15 (1H,dd,J=7.7,1.1 Hz), 7.02(1H,t,J=7.7 Hz), 5.82(1H,ddt,J= 17.3,10.1,6.9 Hz), 5.24(1H,ddd,J=7.3,1.6,1.4 Hz)), 5.14–5.09(1H,m), 4.68(1H,dd,J=6.8,4.7 Hz),3.96(3H,s), 2.89–2.78(1H,m), 2.66–2.55(1H,m)

EI-MS m/e 204(M$^+$)

Reference Example 6

3-bromomethyl-7-methoxybenzofuran

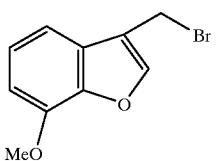

7-methoxy-2,3-dihydrobenzofuran-3-one (1.00 g) which is obtained by the process described in a reference (J. Org.

Chem. 53, 423–425(1988) and dibromomethane (1.3 ml) were dissolved in tetrahydrofuran (30 ml) and the solution was cooled to −78° C. To this solution, n-butyllithium (1.62 M, 14.8 ml) was added dropwise for 10 minutes, and the resulting solution was stirred at −78° C. for 30 minutes. To this reaction solution, acetic acid (2 ml) was added and the solution was poured into water layer (30 ml). The water layer was extracted twice with ethyl acetate (20 ml) and the organic layers were combined. The resultant was washed with saturated brine and dried over sodium sulfate. After removing sodium sulfate by filtration, the solvent was evaporated off. The obtained residue was dissolved in benzene (30 ml) and p-toluenesulfonic acid (121 mg) was added thereto, followed by stirring the mixture at room temperature for 10.5 hours. The solvent was removed under reduced pressure and the residue was purified by column chromatography (solvent: hexane/ethyl acetate=15/1) using silica gel to obtain the desired compound (607 mg, yield: 41%).

m.p.: 66–67° C. (recrystallized from hexane/ethyl acetate)

IR (KBr method) 3118, 1626, 1595, 1493, 1468, 1433, 1361, 1286, 1270, 1216, 1203, 1178, 1149, 1108, 1046, 922, 822, 783, 741, 719, 681, 656, 607, 582 cm$^{-1}$ NMR(900 MHz CDCl3) δ7.69(1H,s),7.29–7.22(2H,m), 6.85(1H,dd,J=2.9,6.0 Hz), 4.61(2H,d,J=0.7 Hz),4.01(3H,s)

EI-MS m/e 241(M$^+$)

Reference Example 7

3-chlromethyl-7-methoxybenzofuran

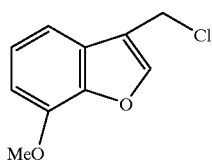

The same procedure as in Reference Example 6 was repeated except that chlorobromomethane was used in place of dibromomethane to obtain the desired compound (2.23 g, yield: 37%) from 7-methoxy-2,3-dihydrobenzofuran-3-one (5.03 g).

IR (KBr method) 3120, 2966, 1626, 1595, 1495, 1466, 1456, 1435, 1363, 1288, 1272, 1203, 1180, 1156, 1133, 1112, 1060, 1044, 924, 824, 783, 737, 721, 694, 677, 627, 605 cm$^{-1}$ NMR (90 MHz CDCl$_3$) δ7.67(1H,s),7.28–7.21(2H,m), 6.89(1H,m,), 4.74(2H,d,J=0.7 Hz),4.01(3H,s)

EI-MS m/e 196(M$^+$)

Reference Example 8

3-azidomethyl-7-methoxybenzofuran

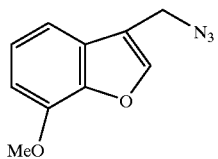

3-bromomethyl-7-methoxybenzofuran (565 mg) and sodium azide (230 mg) were dissolved in methanol-water (5:1, 10 ml) and the solution was refluxed for 1 hour. After cooling the reaction solution to room temperature, the reaction solution was poured into water layer (30 ml) and extracted twice with ethyl acetate (20 ml). The organic layers were combined and washed with saturated brine, followed by drying the resultant over sodium sulfate. After removing sodium sulfate, the solvent was removed under reduced pressure and the residue was purified by column chromatography (solvent: hexane/ethyl acetate=9/1) using silica gel to obtain the desired compound (452 mg, yield: 95%).

IR (liquid film method) 2944, 2844, 2104, 1628, 1593, 1495, 1437, 1361, 1344288, 1270, 1245, 1212, 1180, 1149, 1106, 1052, 787, 729 cm$^{-1}$ NMR (90 MHz CDCl$_3$) δ7.66(1H,s),7.26–7.19(2H,m), 6.90–6.80(1H,m),4.45(2H,s)0.03(3H,s)

EI-MS m/e 203(M$^+$)

Reference Example 9

7-acetoxy-3-((acetylamino)methyl)benzofuran

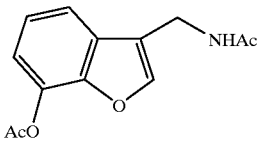

3-azidomethyl-7-methoxybenzofuran (325 mg) was dissolved in diethyl ether (10 ml) and the solution was cooled to 0° C. To this solution, lithium aluminum hydride (91 mg) was added and the resulting solution was stirred at 0° C. for 1 hour and then at room temperature for 1.5 hours. To the reaction solution, saturated aqueous sodium hydrogen carbonate was added and the solution was dried over magnesium sulfate, followed by filtration. After concentrating the filtrate, the residue was dissolved in dimethylformamide (7 ml). To this solution, potassium t-butoxide (415 mg) and n-propanethiol (0.34 ml) were added and the solution was stirred at 100° C. for 1.5 hours. After the reaction, the reaction solution was cooled to 0° C. and pyridine (1.2 ml) and acetyl chloride (1.05 ml) were added, followed by stirring the resulting solution for 40 minutes. The reaction solution was poured into water layer (30 ml) and extracted twice with ethyl acetate (20 ml). The organic layers were combined and washed with 1N hydrochloric acid (20 ml) and with saturated brine, followed by drying the resultant over sodium sulfate. After removing the sodium sulfate by filtration, the solvent was removed under reduced pressure and the residue was purified by column chromatography (solvent: chloroform/methanol=95/5) using silica gel to obtain the desired compound (260 mg, yield: 66%).

m.p.: 138–139° C. (recrystallized from hexane/ethyl acetate)

IR (KBr method) 3298, 1763, 1651, 1591, 1560, 1522, 1510, 1493, 1475, 1460, 1437, 1375, 1344, 1296, 1284, 1251, 1218, 1191, 1170, 1145, 1098, 1083, 1052, 1019, 967, 899, 876 cm$^{-1}$ NMR (90 MHz CDCl$_3$) δ7.57(1H,s),7.54–7.03(3H,m), 4.55(2H,d,J=5.7 Hz), 2.40(3H,s),2.01(3H,s)

EI-MS m/e 247(M$^+$)

Reference Example 10

7-phenoxyacetoxy-3-((phenoxyacetylamino)methyl)benzofuran

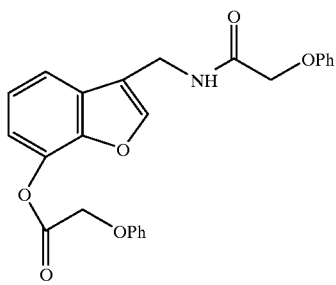

The same procedure as in Reference Example 4 was repeated except that phenoxyacetyl chloride was used in place of acetyl chloride to obtain the desired compound (278 mg, yield: 29%) from 3-azidomethyl-7-methoxybenzofuran (452 mg).

m.p.: 117–118° C. (recrystallized from hexane/ethyl acetate)

IR (KBr method) 3622, 3418, 3126, 1794, 1783, 1688, 1626, 1601, 1589, 1535, 1491, 1458, 1437, 1365, 1344, 1301, 1290, 1249, 1236, 1197, 1172, 1149, 1089, 1075, 1060, 1015, 967, 851, 837, 824, 801, 768, 750 cm$^{-1}$ NMR (90 MHz CDCl$_3$) δ7.56(1H,s),7.53–6.83(13H,m), 4.99(2H,s), 4.65(2H,d,J=5.5 Hz),4.55(2H,s)

EI-MS m/e 431(M$^+$)

Reference Example 11

3-(diphenylmethylthiomethyl)-7-methoxybenzofuran

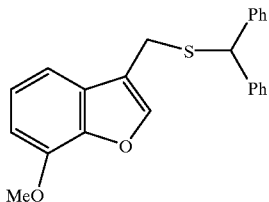

Under argon atmosphere, diphenylmethanethiol (121 mg) was dissolved in DMF (2 ml) and the solution was stirred at room temperature. To this solution, potassium t-butoxide (81 mg) and 3-chloromethyl-7-methoxybenzofuran (118 mg) were added and the solution was stirred at room temperature. After confirming vanishment of the materials, the reaction solution was poured into saturated aqueous ammonium chloride solution (5 ml) and the resulting solution was extracted three times with ethyl acetate (10 ml). The organic layers were combined and washed with saturated brine, followed by drying the resultant over sodium sulfate. After removing the sodium sulfate by filtration, the solvent was removed under reduced pressure and the residue was purified by column chromatography (solvent: hexane/ethyl acetate=20/1) using silica gel to obtain the desired compound (183 mg, yield: 85%).

IR (liquid film method) 1626, 1589, 1493, 1452, 1433, 1354, 1274, 1203, 1180, 1156, 1100, 1046, 789, 739, 704 cm$^{-1}$ NMR (400 MHz CDCl$_3$) δ7.39–7.15(13H,m),6.83(1H,dd, J=7.8,1.0 Hz), 5.00(1H,s),4.02(3H,s),3.63(2H,s)

EI-MS m/e 360(M$^+$)

Reference Example 12

3-(diphenylmethylthiomethyl)-7-hydroxybenzofuran

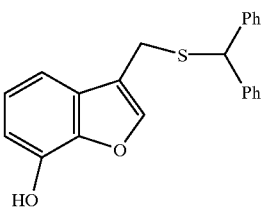

Under argon atmosphere, 3-(diphenylmethylthiomethyl)-7-methoxybenzofuran (45 mg) was dissolved in DMF (3 ml) and the solution was stirred at room temperature. To this solution, n-propanethiol (0.20 ml) and potassium t-butoxide (47 mg) were added and the resulting solution was stirred at 100° C. After confirming vanishment of the materials, the reaction mixture was poured into saturated aqueous ammonium chloride solution (5 ml) and the resulting solution was extracted three times with ethyl acetate (10 ml). After combining the organic layers, the resultant was washed with saturated brine and dried over sodium sulfate. After removing the sodium sulfate by filtration, the solvent was removed under reduced pressure and the residue was purified by column chromatography (solvent: hexane/ethyl acetate=5/1-3/1) using silica gel to obtain the desired compound (26 mg, yield: 60%).

IR (liquid film method) 3400, 1622, 1491, 1448, 1357, 1274, 1222, 1183, 1096, 969, 785, 733, 702 cm$^{-1}$ NMR (400 MHz CDCl$_3$) δ7.39–7.09(13H,m),6.85(1H,dd, J=7.8,1.0 Hz), 5.47(1H,br s),5.02(1H,s),3.63(3H,d,J=1.0 Hz)

EI-MS m/e 346(M$^+$)

Reference Example 13

Methyl 7-methoxybenzofuran-3-acetate

7-methoxy-2,3-dihydrobenzofuran-3-one (10.36 g) and methyl(triphenylphosphoranilidene)acetate (26.92 g) were added to xylene (200 ml) and the mixture was refluxed for 28 hours. After cooling the reaction solution to room temperature, cyclohexane (100 ml) was added to the reaction solution, and the resultant was filtered. The filtrate was concentrated and the residue was purified by column chromatography (solvent: hexane/ethyl acetate=5/1) using silica gel to obtain the desired compound (12.37 g, yield: 91%).

IR (liquid film method) 2956, 1738, 1628, 1591, 1495, 1437, 1363, 1319, 1270, 1207, 1168, 1100, 1050, 1009, 787, 733, 625 cm$^{-1}$ NMR (90 MHz CDCl$_3$) δ7.63(1H,s),7.25–7.13(2H,m), 6.80(1H,dd,J=5.5,3.3 Hz), 4.00(3H,s),3.72(3H,s),3.69(2H,d, J=1.1 Hz)

EI-MS m/e 220(M$^+$)

Reference Example 14

Methyl (7-methoxy-2-(2-propenyl)benzofuran-3-yl)acetate

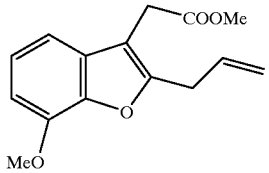

THF (10 ml) was added to zinc powder (5.92 g) and then a catalytic amount of iodine was added. While vigorously stirring the resulting solution, a small amount of a solution of 7-methoxy-3-oxo-2-(2-propenyl)-2,3-dihydrobenzofuran (6.16 g) and methyl bromoacetate (8.9 ml) in THF (90 ml) was added at room temperature. After confirming generation of heat, the reaction solution was cooled to 0° C. and the remainder of the solution was added dropwise for 15 minutes. The reaction solution was stirred at 0° C. for 3 hours, cooled to room temperature and was stirred for another 2.5 hours. Acetic acid (5.5 ml) was added to the reaction solution and the resultant was filtered through Celite. After removing the solvent under reduced pressure, the residue was dissolved in toluene (100 ml) and p-toluenesulfonic acid (536 mg) was added thereto, followed by stirring the resulting mixture at room temperature for 2 hours. The reaction solution was poured into water (150 ml) and the resultant was extracted twice with ethyl acetate (50 ml). After combining the organic layers, the resultant was washed with saturated aqueous sodium hydrogen carbonate solution and with saturated brine, and dried over sodium sulfate. After removing the sodium sulfate by filtration, the solvent was removed under reduced pressure and the residue was purified by column chromatography (solvent: hexane/ethyl acetate=3/1) using a silica gel to obtain the desired compound (5.23 g, yield: 67%).

m.p.: 65–66° C. (recrystallized from hexane/ethyl acetate)

IR (KBr method) 2998, 2950, 1735, 1628, 1591, 1498, 1441, 1425, 1386, 1329, 1308, 1280, 1266, 1231, 1213, 1198, 1181, 1166, 1144, 1094, 1069, 1007, 992, 916, 899, 849, 827, 783, 761, 726 cm$^{-1}$ NMR (300 MHz CDCl$_3$) δ7.15(1H,t,J=7.7 Hz),7.09(1H, dd,J=7.7,1.4 Hz), 6.77(1H,dd,J=7.4,1.4 Hz), 5.82(1H,ddt,J= 17.2,10.2,6.3 Hz), 5.15(1H,dq,J=25.6,1.6 Hz),3.99,3.68 (each3H,s),3.63(2H,s), 3.57(2H,dt,J=6.3,1.6 Hz)

EI-MS m/e 260(M$^+$)

Reference Example 15

Methyl (7-hydroxybenzofuran-3-yl)acetate

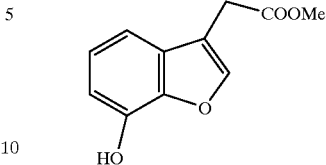

Methyl (7-methoxybenzofuran-3-yl)acetate (12.37 g) was dissolved in dichloromethane (50 ml) and the solution was cooled to −78° C. To this solution, boron tribromide (1.0 M, 120 ml) was added dropwise for 50 minutes. Thereafter, the temperature was raised to room temperature and the reaction solution was stirred at this temperature for 3 hours. After completion of the reaction, the reaction solution was cooled to −78° C. and methanol (100 ml) was added thereto. After neutralizing the reaction mixture by adding sodium hydrogen carbonate, the resulting solution was filtered. The filtrate was concentrated and poured into water layer (300 ml) and the resultant was extracted twice with ether (150 ml). After combining the organic layers, the resultant was washed with saturated brine and dried over sodium sulfate. After removing the sodium sulfate by filtration, the solvent was removed under reduced pressure and the residue was purified by column chromatography (solvent: hexane/ethyl acetate=2/1) using silica gel to obtain the desired compound (10.53 g, yield: 91%).

m.p.: 58–59° C. (recrystallized from cyclohexane/ethyl acetate)

IR (KBr method) 3284, 1698, 1593, 1495, 1473, 1365, 1294, 1261, 1180, 1129, 1093, 1015, 977, 772, 727 cm$^{-1}$ NMR(90 MHz CDCl$_3$) δ7.66(1H,s),7.31–7.09(2H,m), 6.87(1H,dd,J=4.2,4.8 Hz), 5.58(1H,brm),3.79(3H,s),3.75 (2H,d,J=1.1 Hz)

Reference Example 16

7-hydroxy-3-(2-hydroxyethyl)benzofuran

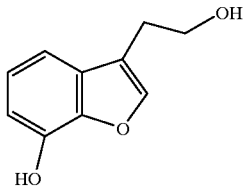

Methyl (7-hydroxybenzofuran-3-yl)acetate (1.46 g) was dissolved in THF (30 ml) and the solution was cooled to 0° C. To this solution, lithium aluminum hydride (269 mg) was added and the solution was stirred for 3.5 hours. After making the pH of the reaction solution not more than 2 by adding 1N hydrochloric acid, the reaction solution was poured into water layer (50 ml) and the resultant was extracted twice with ethyl acetate (20 ml). After combining the organic layers, the resultant was washed with saturated brine and dried over sodium sulfate. After removing the sodium sulfate by filtration, the solvent was removed under reduced pressure and the residue was purified by column chromatography (solvent: hexane/ethyl acetate=1/1) using silica gel to obtain the desired compound (1.09 g, yield: 86%).

m.p.: 116–117° C. (recrystallized from hexane/ethyl acetate)

IR (KBr method) 3416, 3090, 2982, 2940, 1597, 1491, 1477, 1408, 1363, 1319, 1267, 1185, 1168, 1137, 1098, 1054, 1017, 980, 934, 855, 799, 787, 739, 704, 634, 572, 557, 545 cm$^{-1}$ NMR (90 MHz CDCl$_3$) δ7.48(1H,s),7.08–7.02(2H,m), 6.92–6.75(1H,m), 3.89(2H,t,J=6.6 Hz),2.90(2H,t,J=5.5 Hz)

EI-MS m/e 178(M$^+$)

Reference Example 17

Methyl (3-(2-hydroxyethyl)benzofuran-7-yloxy)acetate

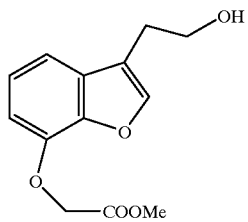

7-hydroxy-3-(2-hydroxyethyl)benzofuran (1.09 g), methyl bromoacetate (0.86 ml) and potassium carbonate (930 mg) were added to DMF (50 ml) and the mixture was stirred at room temperature for 18 hours. After filtering the reaction solution, the filtrate was concentrated and added to water layer (150 ml), followed by extracting the resultant twice with ethyl acetate (20 ml). After combining the organic layers, the resultant was washed with saturated brine and dried over sodium sulfate. After removing the sodium sulfate by filtration, the solvent was removed under reduced pressure and the residue was purified by column chromatography (solvent: hexane/ethyl acetate=1/1) using silica gel to obtain the desired compound (1.48 g, yield: 97%).

IR (KBr method) 3500, 3456, 3422, 2860, 1746, 1715, 1673, 1630, 1586, 1495, 1481, 1450, 1435, 1379, 1270, 1207, 1156, 1098, 1085, 1062, 1040, 1009, 953, 868, 830, 787, 745, 731 cm$^{-1}$ NMR (90 MHz CDCl$_3$) δ7.53(1H,s),7.26–7.13(2H,m), 6.78(1H,dd,J=6.6,2.6 Hz), 4.88(2H,s),4.03–3.89(2H,m), 3.81(3H,s), 2.93(2H,dt,J=6.2,0.9 Hz)

Reference Example 18

Methyl (3-(2-bromoethyl)benzofuran-7-yloxy)acetate

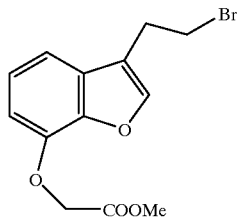

Methyl (3-(2-hydroxyethyl)benzofuran-7-yloxy)acetate (1.30 g) was dissolved in THF (15 ml) and the solution was cooled to 0° C. To this solution, triphenylphosphine (2.05 g) and N-bromosuccinimide (NBS, 1.39 g) were added and the resulting solution was stirred for 1 hour. Hexane (10 ml) was added to the reaction solution and the reaction solution was filtered through Celite. The filtrate was poured into water layer (50 ml) and extracted twice with ethyl acetate (20 ml). The organic layers were combined and washed with saturated brine, followed by drying the resultant over sodium sulfate. After removing the sodium sulfate by filtration, the solvent was removed under reduced pressure and the residue was purified by column chromatography (solvent: hexane/ethyl acetate=3/1) using silica gel to obtain the desired compound (1.39 g, yield: 85%).

m.p.: 58–59° C. (recrystallized from hexane/ethyl acetate)

IR (KBr method) 3110, 2956, 2916, 1767, 1628, 1591, 1499, 1435, 1390, 1365, 1296, 1278, 1214, 1203, 1149, 1116, 1085, 988, 948, 905, 84583, 745, 729, 650, 590, 545cm$^{-1}$ NMR (90 MHz CDCl$_3$) δ7.54(1H,s),7.20–7.14(2H,m), 6.81(1H,m),4.88(2H,s), 3.81(3H,s),3.73–3.56(2H,m), 3.32–3.24(2H,m)

EI-MS m/e 312(M$^+$)

Reference Example 19

Methyl (3-(2-methanesulfonyloxyethyl)benzofuran-7-yloxy)acetate

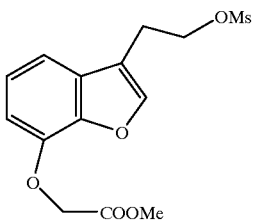

Methyl (3-(2-hydroxyethyl)benzofuran-7-yloxy)acetate (4.12 g) was dissolved in dichloromethane (120 ml) and triethylamine (3 ml) and methanesulfonyl chloride (1.35 ml) were added to the solution, followed by stirring the resulting solution at 0° C. for 1.5 hours. The reaction mixture was then poured into 1N hydrochloric acid and the resultant was extracted with dichloromethane. The organic layer was washed with water, saturated aqueous sodium hydrogen carbonate solution, water, and with saturated saline, and dried over sodium sulfate. After removing the sodium sulfate by filtration, the solvent was removed under reduced pressure. The residue was recrystallized from n-hexane/ethyl acetate to obtain the desired compound (5.25 g, yield: 97%).

m.p.: 102.0° C. (recrystallized from ethyl acetate/n-hexane)

IR (KBr method) 3130, 1763, 1630, 1586, 1493, 1439, 1354, 1288, 1203, 1172, 1091, 984, 963, 907, 843, 793, 758, 735, 717, 526, 472 cm$^{-1}$ NMR (300 MHz CDCl$_3$) δ7.56(1H,s),7.21(1H,dd,J=2,8 Hz),7.17(1H,t,J=8 Hz), 6.79(dd,1H,J=2,8 Hz),4.89(2H,s), 4.48(2H,t,J=7 Hz), 3.92(3H,s),3.81(3H,s),3.15(2H,dt,J=1,7 Hz)

EI-MS m/e 328(M$^+$)

Reference Example 20

Methyl (3-(2-azidoethyl)benzofuran-7-yloxy)acetate

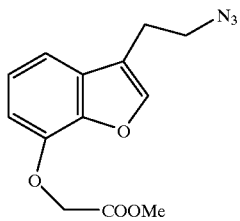

By the similar method as in Reference Example 8, the desired compound (654 mg, yield: 90%) was obtained from methyl (3-(2-bromoethyl)benzofuran-7-yloxy)acetate (830 mg).

IR (KBr method) 3114, 2914, 2086, 1771, 1630, 1593, 1576, 1493, 1448, 1435, 1392, 1365, 1288, 1270, 1245, 1210, 1187, 1149, 1096, 1062, 1040, 949, 903, 855, 777, 741, 729, 665, 630, 605 cm$^{-1}$ NMR (90 MHz CDCl$_3$) δ7.51(1H,s),7.20–7.14(2H,m), 6.78(1H,dd,J=5.4,3.5 Hz), 4.88(2H,s),3.80(3H,s),3.58(2H,t, J=7.1 Hz), 2.94 (2H,t,J=7.1 Hz)

Reference Example 21

Methyl (3-(2-hydroxyethyl)-2-(2-propenyl) benzofuran-7-yloxy)acetate

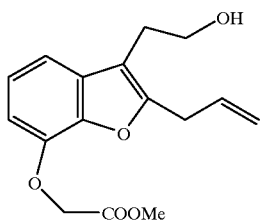

Methyl (7-methoxy-2-(2-propenyl)benzofuran-3-yl) acetate (464 mg) was dissolved in dichloromethane (4 ml) and the solution was cooled to 0° C. To this solution, boron tribromide (1.0 M, 3.9 ml) was added and the solution was stirred for 2 hours. Saturated aqueous sodium hydrogen carbonate solution was added to the reaction solution and the resulting solution was poured into water layer (50 ml), followed by extracting the resultant twice with ethyl acetate (30 ml). The organic layers were combined and washed with saturated brine, followed by drying over sodium sulfate. After removing sodium sulfate by filtration, the solvent was removed under reduced pressure and the residue was dissolved in THF (15 ml). This solution was cooled to 0° C. and lithium aluminum hydride (91 mg) was added, followed by stirring the resulting mixture at 0° C. for 30 minutes and then at room temperature for 1.5 hours. Ethyl acetate was added to the reaction solution to quench the lithium aluminum hydride, and water (0.2 ml) and acetic acid (0.5 ml) were added, followed by stirring the solution at room temperature for 30 minutes. To this solution, sodium hydrogen carbonate (600 mg) and magnesium sulfate were added and the solution was filtered through Celite. After removing the solvent under reduced pressure, the residue was dissolved in DMF (5 ml). To this solution, methyl bromoacetate (0.5 ml) and potassium carbonate (606 mg) were added and the solution was stirred at room temperature for 17 hours. The reaction solution was poured into water (80 ml) and the resultant was extracted twice with ethyl acetate (20 ml). The organic layers were combined and washed with saturate brine, followed by drying the resultant over sodium sulfate. After removing the sodium sulfate by filtration, the solvent was removed under reduced pressure and the residue was purified by column chromatography (solvent: hexane/ethyl acetate=1/1) using silica gel to obtain the desired compound (450 mg, yield: 87%).

IR (liquid film method) 3402, 3012, 2956, 2884, 1744, 1628, 1591, 1493, 1441, 1381, 1294, 1203, 1085, 1048, 996, 919, 855, 781, 733 cm$^{-1}$ NMR (300 MHz CDCl$_3$) δ7.16–7.08(2H,m),6.73(1H,dd, J=7.1,1.6 Hz), 5.99(1H,ddt,J=17.0,10.2,6.3 Hz),5.19–5.10 (2H,m), 4.89(2H,s),3.85(2H,t,J=6.3 Hz),3.81(3H,s), 3.56 (2H,dt,J=6.3,1.6 Hz),2.89(2H,t,J=6.3 Hz)

EI-MS m/e 290(M$^+$)

Reference Example 22

Methyl (2-(2-propenyl)-3-(2-tetrahydropyranyloxyethyl)benzofuran-7-yloxy) acetate

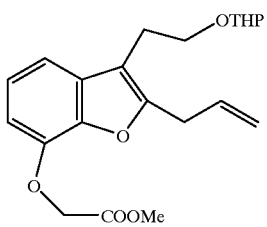

Methyl (3-(2-hydroxyethyl)-2-(2-propenyl) benzofuranyloxy)acetate (450 mg) was dissolved in THF (2 ml). To this solution, 2,3-dihydropyrane (0.212 ml) and p-toluenesulfonic acid (15 mg) were added and the solution was stirred at room temperature for 1.5 hours. The reaction solution was poured into water (50 ml) and the resultant was extracted twice with ethyl acetate (20 ml). The organic layers were combined and washed with saturated brine, followed by drying the resultant over sodium sulfate. After removing the sodium sulfate by filtration, the solvent was removed under reduced pressure and the residue was purified by column chromatography (solvent: hexane/ethyl acetate=3/1) using silica gel to obtain the desired compound (544 mg, yield: 94%).

IR (liquid film method) 2946, 2872, 1767, 1742, 1628, 1591, 1493, 1441, 1381, 1352, 1292, 1201, 1137, 1122, 1079, 1035, 994, 971, 907, 870, 855, 781, 733 cm$^{-1}$ NMR (300 MHz CDCl$_3$) δ7.16(1H,dd,J=8.0,1.1 Hz),7.09 (1H,t,J=8.0 Hz), 6.70(1H,dd,J=8.0,1.1 Hz), 5.98(1H,ddt,J= 17.0,10.2,6.3 Hz), 5.20–5.09(2H,m),4.88(2H,s),4.59–4.57 (1H,brm), 3.94(1H,dt,J=9.6,6.9 Hz),3.81(3H,s),3.80–3.72 (1H,m), 3.61–3.53(3H,m),3.49–3.41(1H,m),2.92(2H,t,J=6.9 Hz), 1.84–1.45 (6H,m)

EI-MS m/e 374(M$^+$)

Reference Example 23

Methyl (2-(2-hydroxyethyl)-3-(2-tetrahydropyranyloxyethyl)benzofuran-7-yl)acetate

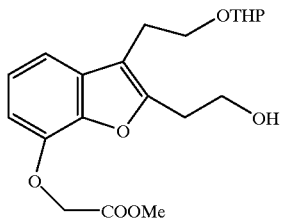

Methyl (2-(2-propenyl)-3-(2-tetrahydropyranyloxyethyl) benzofuran-7-yloxy)acetate (0.97 g) and osmium tetroxide (0.07 M solution in t-butyl alcohol, 0.37 ml) were dissolved in dioxane/water (3:1) and the solution was cooled to 0° C. To this solution, sodium periodate (1.38 g) was added for 10 minutes. After stirring the reaction solution at 0° C. for 30 minutes, the solution was stirred at room temperature for additional 30 minutes. The reaction solution was filtered through Celite and the precipitate was washed with THF (12 ml). The filtrate was cooled to 0° C. and sodium borohydride (98 mg) was added, followed by stirring the resultant for 40 minutes. The reaction solution was poured into water (50 ml) and the resultant was extracted twice with ethyl acetate (20 ml). The organic layers were combined and washed with 1N hydrochloric acid, saturated aqueous sodium hydrogen carbonate and saturated brine, followed by drying the resultant over sodium sulfate. After removing the sodium sulfate by filtration, the solvent was removed under reduced pressure and the residue was purified by column chromatography (solvent: hexane/ethyl acetate=1/1)using silica gel to obtain the desired compound (412 mg, yield: 42%).

IR (liquid film method) 3444, 2952, 2874, 1765, 1744, 1628, 1591, 1493, 1441, 1381, 1354, 1325, 1288, 1203, 1137, 1122, 1104, 1069, 1035, 971, 907, 870, 814, 781, 735 cm$^{-1}$ NMR (300 MHz CDCl$_3$) δ7.14(1H,dd,J=8.0,1.4 Hz),7.09 (1H,t,J=7.7 Hz), 6.70(1H,dd,J=7.7,1.4 Hz), 4.87(2H,s), 4.54– 4.52(1H,brm),4.11–4.04(1H,m),3.93(2H,t,J=5.8 Hz), 3.81(3H,s),3.71–3.58(3H,m),3.43–3.35(1H,m), 3.05(2H,t, J=5.8 Hz),2.96(2H,t,J=6.31 Hz),1.76–1.42(6H,m)

EI-MS m/e 378(M$^+$)

Reference Example 24

Methyl (2-(2-acetoxyethyl)-3-(2-hydroxyethyl) benzofuran-7-yloxy)acetate

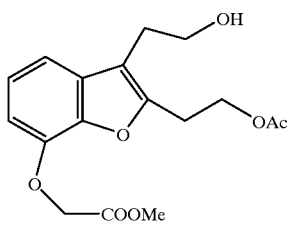

Methyl (2-(2-hydroxyethyl)-3-(2-tetrahydropyranyloxyethyl)benzofuran-7-yloxy)acetate (403 mg), pyridine (0.13 ml) and acetic anhydride (0.3 ml) were dissolved in THF (5 ml) and the solution was stirred at room temperature for 16 hours. The reaction solution was poured into water (50 ml) and the organic layer was separated, followed by extraction twice with ethyl acetate (20 ml). The organic layers were combined and washed with 1N hydrochloric acid, saturated aqueous sodium hydrogen carbonate solution and with saturated brine, followed by drying the resultant over sodium sulfate. After removing sodium sulfate by filtration, the solvent was removed under reduced pressure and the residue was dissolved in methanol (4 ml). To this solution, 1N hydrochloric acid (1 ml) was added and the solution was stirred at room temperature for 2 hours. The reaction solution was poured into water (50 ml) and the resultant was extracted twice with ethyl acetate (20 ml). The organic layers were combined and washed with saturated aqueous sodium hydrogen carbonate solution and with saturated brine, followed by drying the resultant over sodium sulfate. After removing the sodium sulfate by filtration, the solvent was removed under reduced pressure and the residue was purified by column chromatography (solvent: hexane/ethyl acetate=1/2) using silica gel to obtain the desired compound (412 mg, yield: 42%).

m.p.: 80–81° C. (recrystallized from hexane/ethyl acetate)

IR (KBr method) 3322, 3220, 2960, 1734, 1632, 1497, 1475, 1452, 1439, 1371, 1311, 1296, 1270, 1247, 1210, 1174, 1102, 1067, 1052, 1011, 864, 777, 733 cm$^{-1}$ NMR (300 MHz CDCl$_3$) δ7.14–7.09(2H,m),6.74(1H,dd, J=7.4,2.5 Hz),4.88(2H,s), 4.43(2H,t,J=6.6 Hz),3.87(2H,t,J= 6.3 Hz),3.81(3H,s), 3.13(2H,t,J=6.6 Hz),2.90(2H,t,J=6.3 Hz),2.03(3H,s)

EI-MS m/e 336(M$^+$)

Reference Example 25

Methyl (3-(2-hydroxyethyl)-2-(1-propenyl) benzofuran-7-yloxy)acetate

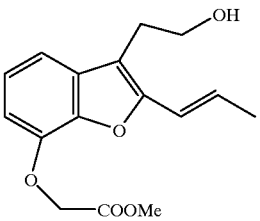

3-(2-hydroxyethyl)-7-methoxy-2-(2-propenyl) benzofuran (1.43 g), n-propanethiol (0.84 ml) and potassium t-butoxide (968 mg) were dissolved in DMF (15 ml) and the solution was stirred at room temperature for 5 minutes and then at 100° C. for 5 hours. After cooling the reaction temperature to room temperature, methyl bromoacetate (0.87 ml) was added and the solution was stirred at room temperature for 2 hours. The reaction solution was poured into water (150 ml) and the resultant was extracted twice with ethyl acetate (20 ml). The organic layers were combined and washed with saturated aqueous sodium hydrogen carbonate solution and with saturated brine, followed by drying the resultant over sodium sulfate. After removing the sodium sulfate by filtration, the solvent was removed under reduced pressure and the residue was purified by column chromatography (solvent: hexane/ethyl acetate=3/1) using silica gel to obtain the desired compound (630 mg, yield: 35%).

IR (liquid film method) 3380, 3042, 2956, 2880, 1742, 1624, 1593, 1493, 1437, 1377, 1299, 1205, 1110, 1085, 1048, 959, 781, 735 cm$^{-1}$ NMR (300 MHz CDCl$_3$) δ7.14–7.08(2H,m),6.76(1H,dd, J=7.1,1.6 Hz),6.61–6.38(2H,m),4.92(2H,s),3.85(2H,t,J=6.6 Hz),3.82(3H,s), 2.93(2H,t,J=6.3 Hz),1.94(2H,dd,J=6.6,1.4 Hz)

EI-MS m/e 290(M$^+$)

Reference Example 26

Methyl (2-(1-propenyl)-3-(2-tetrahydropyranyloxyethyl)benzofuran-7-yloxy)acetate

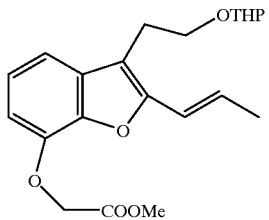

By the method similar to Reference Example 22, the desired compound (741 mg, yield: 93%) was obtained from methyl (3-(2-hydroxyethyl)-2-(1-propenyl)benzofuran-7-yloxy)acetate (620 mg).

IR (liquid film method) 3042, 2928, 2862, 1763, 1742, 1624, 1593, 1493, 1437, 1381, 1352, 1290, 1191, 1120, 1067, 1033, 963, 938, 907, 870, 814, 781, 733 cm$^{-1}$ NMR (300 MHz CDCl$_3$) δ7.15(1H,dd,J=8.0,1.1 Hz),7.07 (1H,t,J=8.0 Hz), 6.73(1H,dd,J=7.7,1.1 Hz),6.56–6.35(2H, m),4.91(2H,s),4.59–4.56(1H,brm),3.93(1H,dt,J=9.6,6.9 Hz),3.81(3H,s),3.82–3.72(1H,m),3.58(1H,dt,J=9.6,6.9 Hz), 3.48–3.40(1H,m), 2.95(2H,t,J=6.9 Hz),1.93(2H,d,J=5.2 Hz),1.86–1.44(6H,m)

EI-MS m/e 374(M$^+$)

Reference Example 27

Methyl (2-(3-acetoxy-1-propenyl)-3-(2-tetrahydropyranyloxyethyl)benzofuran-7-yloxy)acetate

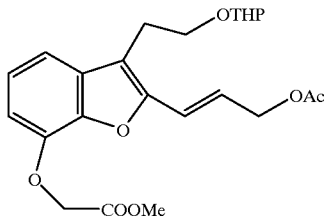

Methyl (2-(1-propenyl)-3-(2-tetrahydropyranyloxyethyl) benzofuran-7-yloxy)acetate (523 mg) was dissolved in benzene (5 ml) and NBS (299 mg) and azoisobutylonitrile (23 mg) were added, followed by stirring the mixture for 4 hours. The reaction solution was poured into water (50 ml) and the resultant was extracted twice with ethyl acetate (20 ml). The organic layers were combined and washed with saturated brine, followed by drying the resultant over sodium sulfate. After removing sodium sulfate by filtration, the solvent was removed under reduced pressure and the residue was dissolved in DMF (4 ml). Potassium acetate (205 mg) was added to this solution and the solution was stirred at room temperature for 50 minutes. The reaction solution was added to water (50 ml) and the resultant was extracted twice with ethyl acetate (20 ml). The organic layers were combined and washed with saturated brine and dried over sodium sulfate. After removing the sodium sulfate by filtration, the solvent was removed under reduced pressure and the residue was purified by column chromatography (solvent: hexane/ethyl acetate=2/1) using silica gel to obtain the desired compound (217 mg, yield: 36%).

IR (liquid film method) 2948, 2872, 1734, 1688, 1626, 1593, 1493, 1437, 1381, 1205, 1122, 1081, 1033, 963, 907, 870, 814, 783, 735 cm$^{-1}$ NMR (300 MHz CDCl$_3$) δ7.18(1H,dd,J=7.9,1.1 Hz),7.10 (1H,t,J=7.9 Hz), 6.77(1H,dd,J=7.9,1.1 Hz),6.69(1H,dt,J= 15.7,1.4 Hz),6.52(1H, dt,J=15.7,6.3 Hz),4.90(2H,s),4.77 (2H,dd,J=16.0,1.4 Hz), 4.57(1H,brm),3.95(1H,dt,J=9.3,6.9 Hz),3.82(3H,s), 3.77–3.69(1H,brm),3.59(1H,dt,J=9.6,6.9 Hz), 3.47–3.39(1H,brm),2.98(2H,t,J=6.9 Hz),2.12(3H,s), 1.84–1.44(6H,m)

EI-MS m/e 432(M$^+$)

Reference Example 28

Methyl (2-(3-acetoxypropyl)-3-(2-hydroxyethyl) benzofuran-7-yloxy)acetate

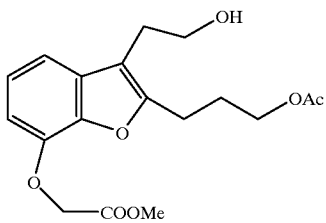

Methyl (2-(3-acetoxy-1-propenyl)-3-(2-tetrahydropyranyloxyethyl)benzofuran-7-yloxy)acetate (199 mg) was dissolved in methanol (4 ml) and 5% Pd/C (28 mg) was added to the solution, followed by stirring the solution at room temperature for 1.5 hours under hydrogen atmosphere. After filtering the reaction solution through Celite, the filtrate was evaporated under reduced pressure. The residue was purified by column chromatography (solvent: hexane/ethyl acetate=1/1)using silica gel to obtain the desired compound (80 mg, yield: 50%).

IR (liquid film method) 3410, 2958, 1734, 1628, 1591, 1493, 1441, 1369, 1247, 1199, 1106, 1046, 861, 781, 756, 735, 665 cm$^{-1}$ NMR (300 MHz CDCl$_3$) δ7.14–7.07(2H,m),6.71(1H,dd, J=6.9,2.2 Hz),4.88(2H,s), 4.12(2H,t,J=6.3 Hz),3.86(2H,t,J= 6.6 Hz),3.81(3H,s), 2.87(4H,m),2.09(2H,quint,J=7.1 Hz), 2.03(3H,s)

EI-MS m/e 350(M$^+$)

Reference Example 29

Methyl (7-tetrahydropyranyloxybenzofuran-3-yl) acetate

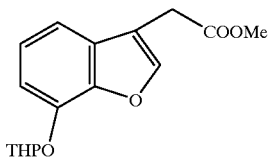

By the method similar to Reference Example 22, the desired compound (606 mg, yield 87%) was obtained from methyl (7-hydroxybenzofuran-3-yl)acetate (492 mg).

IR (liquid film method) 2878, 2854, 1734, 1628, 1591, 1491, 1458, 1437, 1390363, 1319, 1259, 1166, 1100, 1077, 1052, 1023, 988, 946, 903, 874, 82089, 735, 627, 567 cm$^{-1}$ NMR (90 MHz CDCl$_3$) δ7.63(1H,s),7.21–7.11(3H,m), 5.68(1H,m),4.15–3.50(2H,m)0.73(3H,s),3.70(2H,d,J=1.1 Hz),2.10–1.60(6H,m)

EI-MS m/e 290(M$^+$)

Reference Example 30

3-(2-hydroxyethyl)-7-tetrahydropyranyloxybenzofuran

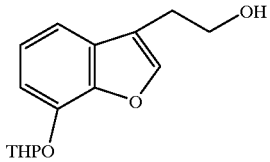

Methyl (7-tetrahydropyranyloxybenzofuran-3-yl)acetate (355 mg) was dissolved in THF (4 ml) and the solution was cooled to 0° C. To this solution, lithium aluminum hydride (47 mg) was added and the solution was stirred at room temperature for 30 minutes. Saturated aqueous sodium hydrogen carbonate was added to the reaction solution and the solution was filtered through Celite. The filtrate was poured into water layer (30 ml) and the resultant was extracted twice with ethyl acetate (20 ml). The organic layers were combined and washed with saturated saline, followed by drying the resultant over sodium sulfate. After removing the sodium sulfate by filtration, the solvent was removed under reduced pressure and the residue was purified by column chromatography (solvent: hexane/ethyl acetate=2/1) using silica gel to obtain the desired compound (289 mg, yield: 90%).

IR (liquid film method) 3348, 2950, 2878, 1628, 1589, 1491, 1435, 1390, 1359286, 1259, 1183, 1145, 1116, 1096, 1025, 944, 949, 903, 872, 787, 735, 408 cm$^{-1}$ NMR (90 MHz CDCl$_3$) δ7.50(1H,s),7.26–7.06(3H,m), 5.68(1H,m),4.16– 3.48(4H,m).91(2H,t,J=6.4 Hz),2.25–1.70 (6H,m)

EI-MS m/e 262(M$^+$)

Reference Example 31

3-(2-propenyl)-7-methoxybenzofuran

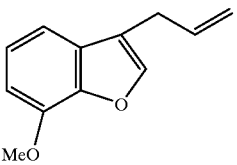

Cerium chloride (5.63 g) was placed in a dry eggplant type flask, and stirred at 150° C. under reduced pressure for 4 hours to dry. After replacing the atmosphere with nitrogen, the reaction mixture was cooled to room temperature. THF (30 ml) was added and the flask was left to stand overnight. The reaction mixture was cooled to 0° C. and allylmagnesium bromide (0.79 M solution in ether, 28.9 ml) was added dropwise. To this, 2,3-dihydro-3-oxo-7-methoxybenzofuran (2.5 g) was added and the resulting mixture was stirred at 0° C. for 1.5 hours. The reaction solution was poured into water (200 ml) and acetic acid (3 ml), and the resultant was extracted with ethyl acetate. The organic layer was washed with saturated aqueous sodium hydrogen carbonate solution and with saturated brine, followed by drying the resultant over sodium sulfate. After removing sodium sulfate by filtration, the solvent was evaporated off to obtain brown syrup (4.52 g). This syrup (4.52 g) was dissolved in benzene (20 ml) and p-toluenesulfonic acid monohydrate (50 mg) was added to the solution, followed by stirring the resulting solution at 60° C. for 30 minutes. The reaction solution was poured into 5% sodium hydrogen carbonate solution, and extracted with ethyl acetate. The organic layer was washed with saturated aqueous sodium hydrogen carbonate solution and with saturated brine, followed by drying the resultant over sodium sulfate. After removing the sodium sulfate by filtration, the solvent was removed under reduced pressure and the residue was purified by column chromatography (solvent: cyclohexane/diethyl ether=5/1-2/1) using silica gel. The main fraction was further purified by column chromatography (solvent: n-hexane/ethyl acetate=20/1) to obtain the desired compound (2.05 g, yield: 72%).

IR (liquid film method) 2914, 1738, 1628, 1591, 1495, 1437, 1361, 1284, 1267, 1096, 1048, 919, 785, 731 cm$^{-1}$ NMR (300 MHz CDCl$_3$) δ7.42(1H,s),7.13–7.16(2H,m), 6.80(1H,dd,J=3, 6 Hz),5.95–6.10(1H,m),5.09–5.23(2H,m), 4.10(3H,s),3.40–3.44(2H,m)

EI-MS m/e 188(M$^+$)

Reference Example 32

3-(3-hydroxypropyl)-7-methoxybenzofuran

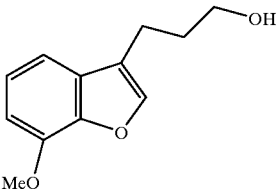

3-(2-propenyl)-7-methoxybenzofuran (2.19 g) was dissolved in anhydrous tetrahydrofuran (25 ml) under argon atmosphere and the solution was cooled to 0° C. Borane dimethylsulfide complex (2M solution in THF, 6.1 ml) was added and the solution was stirred at room temperature for 2 hours. The reaction solution was cooled to 0° C. and ethanol (20 ml), 3N aqueous sodium hydroxide solution (1.3 ml) and 30% hydrogen peroxide solution (1.5 ml) were added. After stirring the reaction solution at room temperature for another 15 minutes, the reaction mixture was poured into saturated aqueous ammonium chloride solution, and the resultant was extracted with ethyl acetate. The organic layer was washed with water and with saturated brine, and dried over sodium sulfate. After removing the sodium sulfate by filtration, the solvent was removed under reduced pressure and the residue was purified by column chromatography (solvent: cyclohexane/ethyl acetate=3/1-2/1) to obtain the desired compound (1.42 g, yield: 59%).

IR (liquid film method) 3378, 2944, 1626, 1589, 1493, 1437, 1361, 1286, 1267, 1203, 1180, 1143, 1094, 1060, 1038, 924, 785, 733 cm$^{-1}$ NMR (300 MHz CDCl$_3$) δ7.44(1H,s),7.16(1H,m),6.81 (1H,m),4.01(3H,s), 3.74(2H,t,J=6 Hz),2.77(2H,dt,J=1,8 Hz),1.98(2H,m), 1.49(1H,bs)

EI-MS m/e 206(M$^+$)

Reference Example 33

3-(3-hydroxypropyl)-7-hydroxybenzofuran

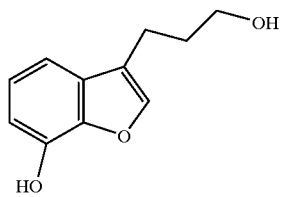

By the similar method as in Reference Example 15, the desired compound (996 mg, yield: 90%) was obtained from 3-(3-hydroxypropyl)-7-methoxybenzofuran (1.187 g).

m.p.: 101.0–101.5° C. (recrystallized from ethyl acetate/n-hexane)

IR (KBr method) 3446, 3140, 1493, 1379, 1299, 1272, 1185, 1098, 1046, 975, 911, 783, 727, 567, 509 cm$^{-1}$ NMR (300 MHz CDCl$_3$) δ7.49(1H,d,J=7 Hz),7.03(2H, m),6.70(1H,dd,J=2,7 Hz), 3.62(2H,t,J=7 Hz),2.72(2H,t,J=7 Hz),1.90(2H,quint,J=7 Hz)

EI-MS m/e 192(M$^+$)

Reference Example 34

Methyl (3-(3-hydroxypropyl)benzofuran-7-yloxy) acetate

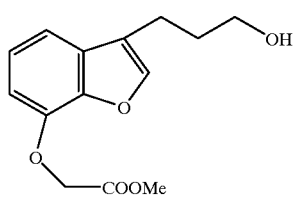

By the method similar to Reference Example 17, the desired compound (884 mg, yield: 83%) was obtained from 3-(3-hydroxypropyl)-7-hydroxybenzofuran (777 mg).

m.p.: 72–73° C. (recrystallized from ethyl acetate/n-hexane)

IR (KBr method) 3506, 1715, 1493, 1458, 1435, 1340, 1315, 1265, 1203, 1145, 1087, 1058, 1009, 729 cm$^{-1}$ NMR (300 MHz CDCl$_3$) δ7.45(1H,s),7.22(1H,m),7.14 (1H,m),6.78(1H,d,J=7 Hz), 4.89(2H,s),3.82(3H,s),3.74(2H, t,J=6 Hz),2.78(2H,t,J=6 Hz), 1.98(2H,quint,J=6 Hz)

EI-MS m/e 264(M$^+$)

Reference Example 35

Methyl (3-(3-bromopropyl)benzofuran-7-yloxy) acetate

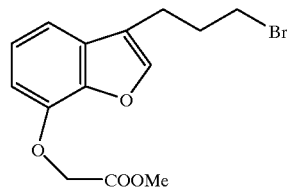

By the method similar to Reference Example 18, the desired compound (837 mg, yield: 95%) was obtained from (3-(3-hydroxypropyl)benzofuran-7-yloxy)acetate (710 mg).

IR (liquid film method) 1769, 1626, 1584, 1491, 1437, 1284, 1270, 1214, 1205, 1141, 1085, 783, 743 cm$^{-1}$ NMR (300 MHz CDCl$_3$) δ7.48(1H,s),7.21(1H,dd,J=1,8 Hz),7.15(1H,t,J=8 Hz), 6.78(1H,dd,J=1,8 Hz),4.89(2H,s), 3.82(3H,s), 3.45(2H,t,J=6 Hz),2.86(2H,t,J=6 Hz),2.24(2H, quint,J=6 Hz)

EI-MS m/e 326, 328(peak height ratio=1:1)(M$^+$)

Reference Example 36

3-(2-hydroxy-5,5-diphenylpentyl)-7-methoxybenzofuran

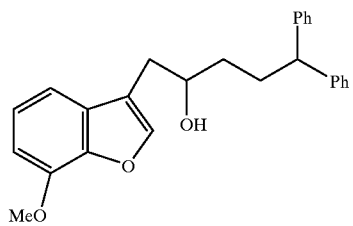

Under argon atmosphere, methyl (7-methoxybenzofuran-3-yl)acetate (82 mg) was dissolved in methylene chloride (2 ml) and the solution was stirred at −78° C. To this solution, diisobutylaluminum hydride (1.01 M solution in toluene (0.40 ml)) was added, and the resulting solution was stirred at −78° C. After confirming vanishment of the materials, saturated aqueous sodium sulfate solution (5 ml) was gradually added to the reaction solution and the resultant was extracted three times with ethyl acetate (10 ml). The organic layers were combined and washed with saturated brine, followed by drying the resultant over sodium sulfate. After removing sodium sulfate by filtration, the solvent was removed under reduced pressure to obtain a partially purified product. Under argon atmosphere, the obtained partially purified product was dissolved in THF (2 ml) and the solution was stirred at −78° C. To this solution, 3,3-diphenylmagnesium bromide was added and the temperature of the solution was gradually raised to room temperature. After confirming vanishment of the materials, saturated aqueous ammonium chloride solution (5 ml) was added to the reaction solution, and the resulting solution was extracted three times with ethyl acetate (10 ml). The organic layers were combined and washed with saturated brine, followed by drying the resultant over sodium sulfate. After removing the sodium sulfate by filtration, the solvent was removed under reduced pressure and the residue was purified by Lovar column chromatography (solvent: hexane/ethyl acetate=10/1) to obtain the desired compound (36 mg, yield: 25%).

IR (liquid film method) 2942, 1694, 1626, 1591, 1495, 1454, 1437, 1361, 1284, 1267, 1205, 1180, 1143, 1096, 1058, 926, 785, 733, 702 cm$^{-1}$ NMR (300 MHz CDCl$_3$) δ7.45(1H,s),7.40–6.94(12H,m), 6.81(1H,d,J=7.5 Hz), 4.01(3H,s),4.07–3.07(2H,m),2.82(1H, dd,J=14.4,3.9 Hz), 2.68(1H,dd,J=14.4,8.4 Hz),2.33–2.07 (2H,m),1.70–1.40(2H,m)

EI-MS m/e 386(M$^+$)

Reference Example 37

3-(2-acetoxy-5,5-diphenylpentyl)-7-acetoxybenzofuran

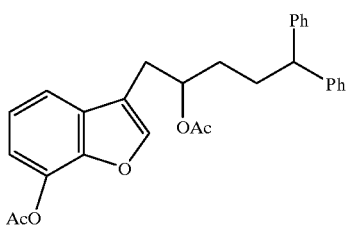

Under argon atmosphere, 3-(2-hydroxy-5,5-diphenylpentyl)- 7-methoxybenzofuran (130 mg) was dissolved in DMF and the solution was stirred at room temperature. To this solution, n-propanethiol (0.30 ml) and potassium t-butoxide (153 mg) were added and the solution was stirred at 100° C. After confirming vanishment of the materials, saturated aqueous ammonium chloride solution (5 ml) was added to the reaction solution and the resulting solution was extracted three times with ethyl acetate (10 ml). The organic layers were combined and washed with saturated brine, followed by drying over sodium sulfate. After removing sodium sulfate by filtration, the solvent was removed under reduced pressure and the residue was purified by Lovar column chromatography (solvent: hexane/ethyl acetate=2/1), thereby purifying the residue. The obtained compound was dissolved in methylene chloride (2 ml) and the solution was stirred at room temperature. To this solution, acetic anhydride (0.10 ml) and pyridine (0.10 ml) were added and the solution was stirred at room temperature. After confirming vanishment of the materials, saturated aqueous ammonium chloride solution (5 ml) was added to the reaction solution, and the resultant was extracted three times with ethyl acetate (10 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=2/1) using silica gel to obtain the desired compound (184 mg, yield: 100%).

NMR (300 MHz CDCl$_3$) δ7.46(1H,d,J=7.5 Hz),7.33(1H, s),7.29–7.12(11H,m), 7.05(1H,d,J=7.5 Hz),5.17(1H,tt,J= 6.0,6.0 Hz), 3.84(1H,t,J=7.8 Hz),2.91(1H,dd,J=14.4,5.7 Hz), 2.82(1H,dd,J=14.4,6.0 Hz),2.41(3H,s), 2.20–2.00(2H, m),2.01(3H,s),1.62–1.54(2H,m)

EI-MS m/e 456(M$^+$)

Reference Example 38

Ethyl 2-(2-formyl-6-methoxyphenoxy)propionate

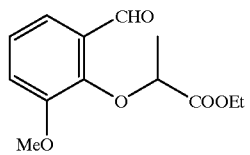

o-vanillin (24.20 g) was dissolved in DMF (300 ml) and potassium carbonate (15.4 g) and ethyl 2-bromopropionate (24.8 ml) were added to the solution, followed by stirring the solution at room temperature for 19.5 hours. The reaction solution was filtered and the filtrate was concentrated. The obtained residue was distilled to obtain the desired compound (36.98 g, yield: 93%).

b.p.: 129–130° C./0.4 mmHg

IR (liquid film method) 2988, 2944, 2900, 1744, 1694, 1586, 1483, 1458, 1394, 1377, 1309, 1251, 1205, 1131, 1096, 1067, 1044, 1019, 913, 785, 764, 743 cm$^{-1}$ NMR (90 MHz CDCl$_3$) δ10.61(1H,s),7.50–7.09(3H,m), 5.05(1H,q,J=7.0 Hz), 4.16(2H,q,J=7.0 Hz),3.88(3H,s),1.63 (3H,d,J=7.0 Hz), 1.23(3H,t,J=7.1 Hz)

EI-MS m/e 252(M$^+$)

Reference Example 39

Ethyl 7-methoxy-2-methyl-3-oxo-2,3-dihydrobenzofuran-2-carboxylate

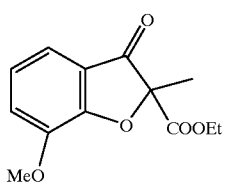

Sodium hydride (60% dispersion in oil, 6.61 g) was added to DMF (250 ml). To this solution, a solution of ethyl 2-(2-formyl-6-methoxyphenoxy)-propionate (34.56 g) in DMF (150 ml) was added dropwise at room temperature for 1 hour, and the resulting solution was stirred for another 30 minutes. Acetic acid (12 ml) was added to the reaction solution and the solution was concentrated. The solution was poured into water layer (300 ml) and the resultant was extracted twice with ethyl acetate (150 ml). The organic layers were combined and washed with saturated brine, followed by drying over sodium sulfate. After removing sodium sulfate by filtration, the solvent was removed under reduced pressure and the obtained residue was dissolved in dichloromethane (600 ml). To this solution, Celite (105 g) and pyridinium chlorochromate (44.52 g) were added and the solution was stirred at room temperature for 21 hours. Isopropyl alcohol (20 ml) was added to the reaction solution and the resulting solution was stirred for 15 minutes. One liter of hexane was added to the reaction solution and the resultant was filtered through Celite, followed by washing the precipitate with one liter of ether. The filtrate was washed with water (500 ml) and the aqueous layer was extracted with ether (200 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=5/1-3/1) using silica gel to obtain the desired compound (20.39 g, yield: 60%).

m.p.: 81–82° C. (recrystallized from hexane/ether)

IR (KBr method) 2978, 1717, 1657, 1649, 1618, 1603, 1508, 1466, 1439, 1375, 1284, 1253, 1199, 1176, 1127, 1110, 1077, 1065, 1009, 980, 940, 853, 841, 774, 750, 727, 671, 629 cm$^{-1}$ NMR (90 MHz CDCl$_3$) δ7.33–6.97(3H,m),4.21(2H,q,J=7.3 Hz),3.99(3H,s), 1.77(3H),1.23(3H,t,J=7.0 Hz)

EI-MS m/e 250(M$^+$)

Reference Example 40

7-methoxy-2-methyl-2,3-dihydrobenzofuran-3-one

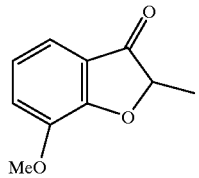

Methyl 7-methoxy-2-methyl-3-oxo-2,3-dihydrobenzofuran-2-carboxylate (18.38 g) was dissolved in dioxane-water (5:1, 300 ml) and 0.5 N sulfuric acid (37 ml) was added to the solution, followed by refluxing the resulting solution for 16 hours. The reaction solution was concentrated and poured into water layer (300 ml), followed by extracting the resultant three times with ether (150 ml). The organic layers were combined and washed with saturated aqueous sodium hydrogen carbonate solution and with saturated brine, followed by drying over sodium sulfate. After removing the sodium sulfate by filtration, the solvent was removed under reduced pressure and the residue was purified by column chromatography (solvent: hexane/ethyl acetate=9/1-5/1) using florisil to obtain the desired compound (4.69 g, yield: 36%).

m.p.: 60–61° C. (recrystallized from hexane/ether)

IR (KBr method) 2988, 2936, 1713, 1657, 1638, 1615, 1603, 1560, 1543, 1510, 1468, 1441, 1375, 1350, 1317, 1305, 1265, 1210, 1185, 1170, 1145, 1081, 1065, 973, 917, 899, 866, 824, 799, 758, 679, 642, 598, 555 cm$^{-1}$ NMR (90 MHz CDCl$_3$) δ7.31–6.99(3H,m),4.68(1H,q,J=7.2 Hz),3.97(3H,s), 1.56(3H,J=7.2 Hz)

EI-MS m/e 178(M$^+$)

Reference Example 41

3-azidomethyl-7-methoxy-2-methylbenzofuran

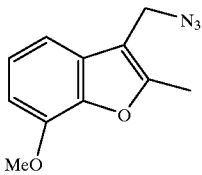

7-methoxy-2-methyl-2,3-dihydrobenzofuran-3-one (2.97 g) and dibromomethane (2.4 ml) were dissolved in THF (80 ml) and the solution was cooled to −78° C. To this solution, n-butyllithium (1.62 M, 21 ml) was added dropwise for 30 minutes, and the mixture was stirred at −78° C. for 20 minutes. Acetic acid (5 ml) was added to the reaction solution and the resultant was poured into water layer (100 ml). The aqueous layer was extracted twice with ethyl acetate (50 ml) and the organic layers were combined. The organic layer was washed with saturated brine and dried over sodium sulfate. Sodium sulfate was removed by filtration and the solvent was removed under reduced pressure. The obtained residue was dissolved in benzene (50 ml) and p-toluenesulfonic acid (286 mg) was added, followed by stirring the solution at 50° C. for 1.5 hours. The reaction solution was poured into water layer (50 ml) and the resultant was extracted twice with ethyl acetate (30 ml). The organic layers were combined and washed with saturated aqueous sodium hydrogen carbonate solution and with saturated brine, followed by drying over sodium sulfate. Sodium sulfate was removed by filtration and the solvent was removed under reduced pressure. The obtained residue was dissolved in methanol-water (5:1, 100 ml) and sodium azide (1.63 g) was added to the solution, followed by refluxing the resulting solution for 1 hour. The reaction solution was cooled to room temperature and then poured into water layer (100 ml), followed by extraction twice with ethyl acetate (50 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=9/1) using silica gel to obtain the desired compound (1.70 g, yield: 47%).

IR (liquid film method) 2942, 2108, 1628, 1595, 1495, 1439, 1321, 1278, 1232, 1210, 1178, 1114, 1091, 1062, 1044, 864, 781, 733, 634, cm$^{-1}$ NMR (90 MHz CDCl$_3$) δ7.20–6.77(3H,m),4.39(2H,s), 4.01(3H,s),2.50(3H,s)

EI-MS m/e 217(M$^+$)

Reference Example 42

7-acetoxy-3-(acetylamino)methyl-2-methylbenzofuran

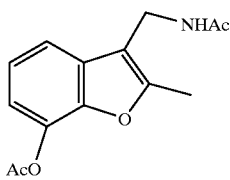

By the method similar to Reference Example 9, the desired compound (1.27 g, yield: 62%) was obtained from 3-azidomethyl-7-methoxy-2-methylbenzofuran (1.70 g).

m.p.: 139–141° C. (recrystallized from cyclohexane/ethyl acetate)

IR (KBr method) 3328, 2930, 1760, 1642, 1595, 1537, 1491, 1466, 1444, 1373, 1265, 1218, 1193, 1174, 1154, 1079, 1017, 855, 791,745, 73380 cm$^{-1}$ NMR (90 MHz CDCl$_3$) δ7.35(1H,dd,J=7.4,1.5 Hz),7.13 (1H,d,J=7.4 Hz), 6.96(1H,dd=7.4,1.6 Hz),5.8–5.6(1H,brm), 4.43(2H,d,J=5.3 Hz),2.39(3H,s),1.95(3H,s)

EI-MS m/e 261(M$^+$)

Reference Example 43

Methyl (7-methoxy-2-methylbenzofuran-3-yl) acetate

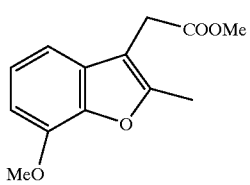

By the method similar to Reference Example 13, the desired compound (3.29 g, yield: 67%) was obtained from 7-methoxy-2-methyl-2,3-dihydrobenzofuran-3-one (3.74 g).

NMR (90 MHz CDCl$_3$) δ7.15–7.08(2H,m),6.78(1H,dd,J= 6.3,2.4 Hz),4.00(3H,s), 3.68(3H,s),3.60(2H,s),2.45(3H,s)

Reference Example 44

3-(2-hydroxyethyl)-7-methoxy-2-methylbenzofuran

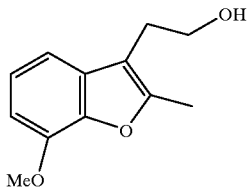

By the method similar to Reference Example 30, the desired compound (1.70 g, yield: 47%) was obtained from methyl (7-methoxy-2-methylbenzofuran-3-yl) acetate.

m.p.: 58–59° C. (recrystallized from hexane/ether)

IR (KBr method) 3356, 3272, 2970, 2946, 2920, 1624, 1591, 1493, 1468, 1450, 1441, 1282, 1214, 1187, 1170, 1093, 1062, 1046, 864, 775, 729 cm$^{-1}$ NMR (90 MHz CDCl$_3$) δ7.13–7.07(2H,m),6.74(1H,dd,J= 6.3,2.6 Hz),4.00(3H,s), 3.82(2H,m),2.87(2H,t,J=6.6 Hz), 2.44(3H,s),1.48(1H,brm)

EI-MS m/e 206(M$^+$)

Reference Example 45

Methyl (3-(2-hydroxyethyl)-2-methylbenzofuran-7-yloxy)acetate

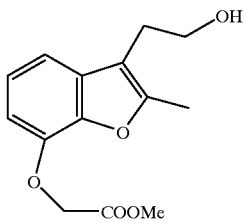

3-(2-hydroxyethyl)-7-methoxy-2-methylbenzofuran (2.34 g) was dissolved in DMF (60 ml) and potassium t-butoxide (2.71 g) and n-propanethiol (2.2 ml) were added to the solution, followed by stirring the resulting solution at 100° C. for 5 hours. The reaction mixture was cooled to room temperature and acetic acid (3 ml) was added. The reaction solution was concentrated, and poured into water layer (100 ml). The aqueous layer was extracted twice with ethyl acetate (50 ml). The organic layers were combined and washed with saturated brine, followed by drying over sodium sulfate. Sodium sulfate was removed by filtration and the solvent was removed under reduced pressure. The obtained residue was dissolved in DMF (50 ml), and potassium carbonate (1.66 g ) and methyl bromoacetate (1.7 ml) were added, followed by stirring the resulting solution at room temperature for 17.5 hours. The reaction solution was concentrated and poured into water layer (100 ml), followed by extraction twice with ether (50 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=2/1-1/1) using silica gel to obtain the desired compound (2.29 g, yield: 75%).

IR (liquid film method) 3568, 3390, 2956, 2882, 1760, 1626, 1591, 1493, 1437290, 1261, 1205, 1108, 1050, 855, 779, 733, 640, cm$^{-1}$ NMR (90 MHz CDCl$_3$) δ7.13–6.65(3H,m),4.86(2H,s), 3.85(1H,t,J=6.8 Hz), 3.80(3H),2.84(2H,d,J=6.8 Hz),2.43 (3H,s),1.58(1H,brs)

Reference Example 46

Methyl (3-(2-azidoethyl)-2-methylbenzofuran-7-yloxy)acetate

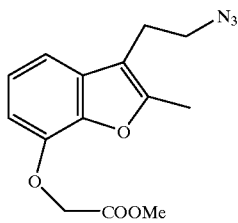

Methyl (3-(2-hydroxyethyl)-2-methylbenzofuran-7-yloxy acetate (390 mg) was dissolved in dichloromethane (7 ml) and the obtained solution was cooled to 0° C. To this solution, triethylamine (0.43 ml) and p-toluenesulfonyl chloride (443 mg) were added and the resulting solution was stirred at 0° C. for 1 hour and then at room temperature for 23 hours. The reaction solution was poured into water layer (30 ml) and the resultant was extracted twice with ethyl acetate (15 ml). The organic layers were combined and washed with saturated brine, followed by drying over sodium sulfate. Sodium sulfate was removed by filtration and the solvent was removed under reduced pressure. The residue was dissolved in THF-water (5:1, 10 ml) and sodium azide (354 mg) was added, followed by refluxing the resulting solution for 24 hours. The reaction solution was poured into water layer (50 ml) and the resultant was extracted twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=3/1) using silica gel to obtain the desired compound (250 mg, yield: 58%).

m.p.: 62–63° C. (recrystallized from hexane/ethyl acetate)

IR (KBr method) 2110, 1773, 1622, 1586, 1491, 1437, 1278, 1255, 1226, 1209, 1197, 1172, 1114, 791,737 cm$^{-1}$ NMR (90 MHz CDCl$_3$) δ7.13–7.07(2H,m),6.70(1H,dd,J= 5.3,3.5 Hz), 4.87(2H,s),3.81(3H,s),3.50(2H,t,J=7.2 Hz), 2.88(2H,t,J=7.0 Hz),2.45(3H,s)

EI-MS m/e 289(M$^+$)

Reference Example 47

Methyl (3-(2-bromoethyl)-2-methylbenzofuran-7-yloxy)acetate

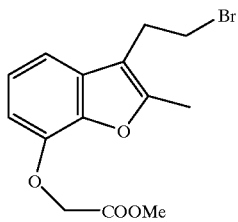

By the method similar to Reference Example 18, the desired compound (346 mg, yield: 88%) was obtained from methyl (3-(2-hydroxyethyl)-2-methylbenzofuran-7-yloxy) acetate (318 mg).

m.p.: 96–97° C. (recrystallized from hexane/ethyl acetate)

IR (KBr method) 2964, 2920, 1729, 1632, 1591, 1493, 1450, 1433, 1381, 1367, 1307, 1267, 1218, 1207, 1180, 1152, 1093, 1069, 1019, 1009, 965, 866, 781, 762, 729, 662 cm$^{-1}$ NMR (90 MHz CDCl$_3$) δ7.13–7.06(2H,m),6.69(1H,dd,J= 5.5,3.7 Hz), 4.87(2H,s),3.81(3H,s),3.49 (2H,dt,J=6.1,0.9 Hz), 3.17(2H,t,J=6.8 Hz),2.44(3H,s)

EI-MS m/e 326(M$^+$)

Reference Example 48

Methyl 2-(2-formyl-6-methoxyphenoxy)isovalerate

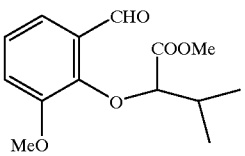

The same method as in Reference Example 38 was repeated except that methyl 2-bromoisovalerate (10.20 g) was used in place of ethyl 2-bromopropionate, to obtain the desired compound (6.78 g, yield: 54%) from o-vanillin (7.14 g).

b.p.: 121–122° C./0.2 mmHg

IR (liquid film method) 2970, 2882, 1746, 1694, 1586, 1483, 1392, 1371, 1309, 1249, 1212, 1185, 1131, 1114, 1085, 1067, 1019, 913, 787, 766 cm$^{-1}$ NMR (90 MHz CDCl$_3$) δ10.64(1H,s),7.50–7.07(3H,m), 4.96(1H,d,J=4.6 Hz), 3.85(3H,s),3.66(3H,s),2.32(1H,m), 1.14(3H,d,J=6.9 Hz), 1.10 (3H,d, J=7.0 Hz)

EI-MS m/e 266(M$^+$)

Reference Example 49

Methyl 2-isopropyl-7-methoxy-3-oxo-2,3-dihydrobenzofuran-2-carboxylate

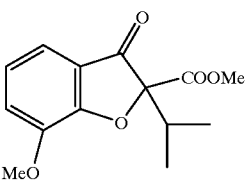

Potassium t-butoxide (5.62 g) was dissolved in DMF (150 ml) and the obtained solution was cooled to 0° C. To this solution, methyl 2-(2-formyl-6-methoxyphenoxy) isovalerate (11.10 g) solution in DMF (50 ml) was added dropwise for 40 minutes, and the resulting solution was stirred for another 30 minutes. Acetic acid (4 ml) was added to the reaction solution and the solution was concentrated. The resultant was poured into water layer (300 ml) and extracted twice with ethyl acetate (150 ml). The organic layers were combined and washed with saturated brine, followed by drying over sodium sulfate. After removing the sodium sulfate by filtration, the solvent was removed under reduced pressure and the obtained residue was dissolved in dichloromethane (250 ml). To this solution, Celite (70 g) and pyridinium dichromate (23.55 g) were added and the solution was stirred at room temperature for 19 hours. Isopropyl alcohol (20 ml) was added to the reaction solution and the solution was stirred for 15 minutes. Ether (200 ml) was added to the solution and the solution was filtered through Celite, followed by washing the obtained precipitate with ether (100 ml twice). The filtrate was concentrated and the residue was purified by column chromatography (solvent: hexane/ethyl acetate=5/1-3/1) using silica gel to obtain the desired compound (7.26 g, yield: 66%).

m.p.: 87–88° C. (recrystallized from cyclohexane/chloroform)

IR (KBr method) 2980, 2964, 2940, 1744, 1717, 1620, 1601, 1508, 1473, 1444, 1348, 1255, 1187, 1172, 1145, 1087, 1071, 1042, 1000, 959, 934, 849, 835, 799, 756, 731, 675, 667 cm$^{-1}$ NMR (90 MHz CDCl$_3$) δ7.29–7.02(3H,m),4.00(3H,s), 3.76(3H,s),2.90(1H,m), 1.15(3H,d,J=6.8 Hz),0.79(3H,d,J= 6.8 Hz)

EI-MS m/e 264(M$^+$)

Reference Example 50

2-isopropyl-7-methoxy-2,3-dihydrobenzofuran-3-one

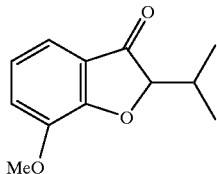

By the method similar to Reference Example 40, the desired compound (2.47 g, yield: 60%) was obtained from methyl 2-isopropyl-7-methoxy-3-oxo-2,3-dihydrobenzofuran-2-carboxylate.

m.p.: 46–47° C. (recrystallized from hexane)

IR (KBr method) 2972, 1717, 1613, 1601, 1506, 1462, 1439, 1286, 1265, 1249, 1210, 1181, 1170, 1089, 1067, 1052, 980, 909, 760 cm$^{-1}$ NMR (90 MHz CDCl$_3$) δ7.29–6.98(3H,m),4.47(1H,d,J= 3.8 Hz),3.97(3H,s), 2.40(1H),1.17(3H,d,J=7.1 Hz),0.92(3H, d,J=6.8 Hz)

EI-MS m/e 206(M$^+$)

Reference Example 51

3-azidomethyl-2-isopropyl-7-methoxybenzofuran

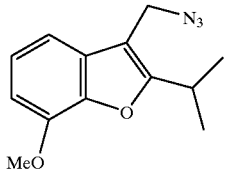

By the method similar to Reference Example 41, the desired compound (672 mg, yield: 30%) was obtained from 2-isopropyl-7-methoxy-2,3-dihydrobenzofuran-3-one (1.90 g).

IR (liquid film method) 2976, 2936, 2116, 2098, 1624, 1591, 1495, 1458, 1439, 1340, 1330, 1284, 1243, 1214, 1187, 1151, 1075, 1044, 870, 806, 775, 733 cm$^{-1}$ NMR (90 MHz CDCl$_3$) δ7.25–7.12(2H,m),6.78(1H,dd,J= 5.5,3.5 Hz),4.40(2H,s), 4.01(3H,s),3.23(1H,sept,J=6.8 Hz), 1.40(3H,d,J=6.8 Hz)

EI-MS m/e 245(M$^+$)

Reference Example 52

2-hydroxymethyl-2,3-dihydro-3-oxo-7-methoxybenzofuran

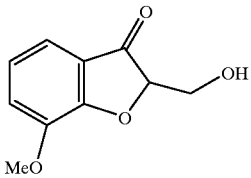

Sodium hydride (440 mg) was washed with n-hexane and dried under reduced pressure. Methyl 3-hydroxy-7-methoxybenzofuran-2-carboxylate (2.33 g) was dissolved in THF (200 ml) and the solution was added to the sodium hydride, followed by refluxing the resulting solution for 80 minutes. After cooling the solution to 0° C., aluminum lithium hydride (404 mg) was added, and the resulting solution was stirred at 0° C. for 2 hours. To the reaction solution, a 1:1 mixture (200 ml) of 1N hydrochloric acid and saturated brine was added and the organic layer was separated. The aqueous layer was extracted with ethyl acetate. The organic layers were combined and washed with saturated brine, followed by drying over magnesium sulfate. Magnesium sulfate was removed by filtration and the solvent was evaporated off. The residue was purified by column chromatography (solvent: ethyl acetate) to obtain the desired compound (1.76 g, yield: 87%).

m.p.: 103–104° C. (recrystallized from ethyl acetate/n-hexane)

IR (KBr method) 3426, 1696, 1615, 1603, 1510, 1437, 1274, 1185, 1168, 1100, 1079, 1052, 1027, 959, 876, 833, 777, 733, 683, 605, 588, 468 cm$^{-1}$ NMR (300 MHz CDCl$_3$) δ7.27(1H,dd,J=1,8 Hz),7.14 (1H,dd,J=1,8 Hz), 7.06(1H,t,J=8 Hz),4.72(1H,t,J=4 Hz), 4.15(2H,m),3.98(3H,s), 1.97 (1H,t,J=7 Hz)

EI-MS m/e 194(M$^+$)

Reference Example 53

2,3-dihydro-2-methoxymethoxymethyl-3-oxo-7-methoxybenzofuran

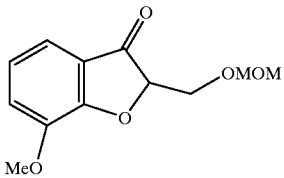

2,3-dihydro-2-hydroxymethyl-3-oxo-7-methoxybenzofuran (1.79 g) and dimethoxymethane (10 ml) were dissolved in dichloromethane (25 ml) and phosphorus pentoxide (3.47 g) was added to the obtained solution, followed by stirring the resulting solution at room temperature for 3.5 hours. The reaction mixture was added to saturated aqueous sodium hydrogen carbonate solution and extracted with ethyl acetate. The organic layers were combined and washed with water and with saturated brine, followed by drying over magnesium sulfate. Magnesium sulfate was removed by filtration and the solvent was evaporated off. The residue was purified by column chromatography (solvent: n-hexane/ethyl acetate=1/1) to obtain the desired compound (912 mg, yield: 58%).

m.p.: 71–72° C. (recrystallized from ethyl acetate/n-hexane)

IR (KBr method) 2960, 1715, 1615, 1603, 1510, 1448, 1282, 1181, 1077, 1064, 1038, 1000, 953, 920, 868, 772, 735, 565 cm$^{-1}$ NMR (300 MHz CDCl$_3$) δ7.26(1H,dd,J=1,7 Hz),7.13 (1H,dd,J=1,7 Hz), 7.03(1H,t,J=7 Hz),4.76(1H,dd,J=3,5 Hz), 4.61(1H,d,J=7 Hz), 4.58(1H,d,J=7 Hz),4.08(2H,m),3.97 (3H,s),3.31(3H,s)

EI-MS m/e 238(M$^+$)

Reference Example 54

Methyl (2,3-dihydro-2-methoxymethyl-3-hydroxy-7-methoxybenzofuran-3-yl)acetate

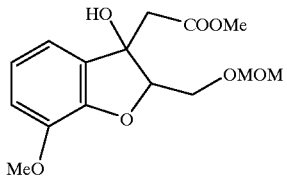

Zinc powder (793 mg) was stirred under reduced pressure for 1 hour to dry the powder. THF (5 ml) was added and the resultant was stirred at 0° C. 2,3-dihydro-2-methoxymethoxymethyl-3-oxo-7-methoxybenzofuran (815 mg) and methyl bromoacetate (1.5 ml) in THF (11 ml) were added dropwise at 0° C. Reaction was started by slightly heating the mixture and the mixture was stirred at 0° C. for 15 minutes and then at room temperature for 2.5 hours. A small amount of 5% aqueous citric acid solution was added to the reaction solution and the solvent was evaporated off. The residue was poured into 5% aqueous citric acid solution and the extracted with ethyl acetate. The organic layers were combined and washed with water and with saturated brine, followed by drying over magnesium sulfate. Magnesium sulfate was removed by filtration and the solvent was evaporated off. The residue was purified by column chromatography (solvent: n-hexane/ethyl acetate=3/2) to obtain the desired compound (990 mg, yield: 93%).

IR (liquid film method) 3474, 1738, 1624, 1599, 1497, 1462, 1441, 1280, 1212, 1154, 1114, 1042, 994, 919, 895, 874, 737 cm$^{-1}$ NMR (300 MHz CDCl$_3$) δ6.94(1H,dd,J=2,8 Hz),6.90 (1H,t,J=8 Hz), 6.83(1H,dd,J=2,8 Hz),4.90(1H,t,J=4 Hz), 4.67(1H,d,J=6 Hz), 4.64(1H,d,J=6 Hz),4.14(1H,d,J=1 Hz), 4.11(2H,d,J=4 Hz), 3.88(3H,s),3.74(3H,s),3.35(3H,s),3.07 (1H,dd,J=1,16 Hz), 2.87(1H,dd,J=1,16 Hz)

EI-MS m/e 312(M$^+$)

Reference Example 55

Methyl (2-methoxymethoxymethyl-7-methoxybenzofuran-3-yl)acetate

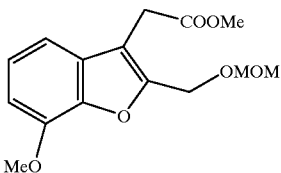

Methyl (2,3-dihydro-2-methoxymethoxymethyl-3-hydroxy-7-methoxybenzofuran-3-yl)acetate (990 mg) was dissolved in THF (25 ml) and formic acid (15 ml), and the obtained solution was stirred at room temperature for 15 hours. The reaction mixture was poured into saturated aqueous sodium hydrogen carbonate solution and extracted with ethyl acetate. The organic layer was washed with water and with saturated brine and dried over magnesium sulfate. Magnesium sulfate was removed by filtration and the solvent was evaporated off. The residue was purified by column chromatography (solvent: n-hexane/ethyl acetate=1/1) to obtain the desired compound (789 mg, yield: 75%).

IR (liquid film method) 2954, 1742, 1626, 1593, 1497, 1439, 1359, 1274, 1216, 1100, 1081, 1038, 922, 857, 785, 733 cm$^{-1}$ NMR (300 MHz CDCl$_3$) δ7.18(1H,t,J=8 Hz),7.13(1H,dd, J=2,8 Hz), 6.82(1H,dd,J=2,8 Hz),4.74(2H,s),4.69(2H,s), 4.00(3H,s), 3.76(2H,s),3.69(3H,s),3.41(3H,s)

EI-MS m/e 294(M$^+$)

Reference Example 56

2-methoxymethoxymethyl-3-(2-hydroxyethyl)-7-methoxybenzofuran

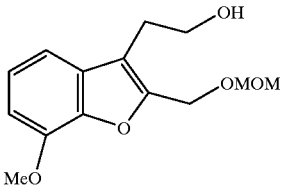

By the method similar to Reference Example 30, the desired compound (204 mg, yield: 95%) was obtained from methyl (2-methoxymethoxymethyl-7-methoxybenzofuran-3-yl)acetate (237 mg).

IR (liquid film method) 3404, 2946, 1626, 1591, 1495, 1439, 1359, 1284, 1216, 1154, 1098, 1038, 920, 859, 783, 735 cm$^{-1}$ NMR (300 MHz CDCl$_3$) δ7.17(1H,t,J=8 Hz),7.12(1H,dd, J=2,8 Hz), 6.83(1H,dd,J=2,8 Hz),4.73(2H,s),4.72(2H,s), 4.01(3H,s), 3.87(2H,q,J=6 Hz),3.42(3H,s),2.98(2H,t,J=6 Hz), 2.14 (1H,t,J=6 Hz)

EI-MS m/e 266(M$^+$)

Reference Example 57

2-methoxymethoxymethyl-3-(2-methanesulfonyloxyethyl)-7-methoxybenzofuran

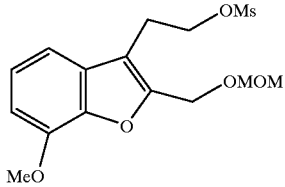

By the method similar to Reference Example 19, the desired compound (258 mg, yield: 99%) was obtained from 2-methoxymethoxymethyl-3-(2-hydroxyethyl)-7-methoxybenzofuran.

IR (liquid film method) 2950, 1626, 1591, 1497, 1466, 1441, 1357, 1284, 1214, 1176, 1102, 1038, 1006, 973, 955, 905, 814, 799, 785, 735 cm$^{-1}$ NMR (300 MHz CDCl$_3$) δ7.20(1H,t,J=7 Hz),7.14(1H,dd, J=1,7 Hz), 6.83(1H,dd,J=1,7 Hz),4.71(4H,s),4.44(2H,t,J=7 Hz), 4.01(3H,s),3.43(3H,s),3.18(2H,t,J=6 Hz),2.85(3H,s)

EI-MS m/e 344(M$^+$)

Reference Example 58

2-methoxymethoxymethyl-3-(2-(diphenylmethylthio)ethyl)-7-methoxybenzofuran

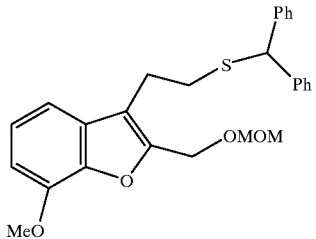

Sodium hydride (85 mg) was washed with n-hexane and dried under reduced pressure. Diphenylmethanethiol (396 mg) was dissolved in DMF (8 ml) and the obtained solution was added to the sodium hydride. 2-methoxymethoxymethyl-3-(2-methanesulfonyloxyethyl)-7-methoxybenzofuran (437 mg) was dissolved in DMF (6 ml) and the obtained solution was added to the above-mentioned solution, and the resulting solution was stirred at 60° C. for 15 hours. After evaporating off the solvent of the reaction mixture, the residue was poured into 5% aqueous citric acid solution and extracted with ethyl acetate. The organic layers were combined and washed with water and with saturated brine, followed by drying over magnesium sulfate. Magnesium sulfate was removed by filtration and the solvent was evaporated off. The residue was purified by column chromatography (solvent: n-hexane/ethyl acetate= 2/1) to obtain the desired compound (406 mg, yield: 71%).

m.p.: 110° C. (recrystallized from ethyl acetate/n-hexane)

IR (KBr method) 2930, 1624, 1589, 1493, 1452, 1439, 1375, 1346, 1284, 1212, 1135, 1077, 1029, 1013, 917, 857, 754, 743, 735, 704, 692, 625, 588, 511, 497 cm$^{-1}$ NMR (300 MHz CDCl$_3$) δ7.37–7.41(4H,m),7.19–7.33 (6H,m),7.08(1H,t,J=8 Hz), 6.83(1H,dd,J=1,8 Hz),6.78(1H, dd,J=1,8 Hz),5.15(1H,s), 4.64(2H,s),4.62(2H,s),3.99(3H,s), 3.39(3H,s), 2.95(2H,t,J=7 Hz),2.66(2H,t,J=7 Hz)

EI-MS m/e 448(M$^+$)

Reference Example 59

Methyl (2-methoxymethoxymethyl)-3-(2-diphenylmethylthio)ethyl)-benzofuran-7-yloxy) acetate

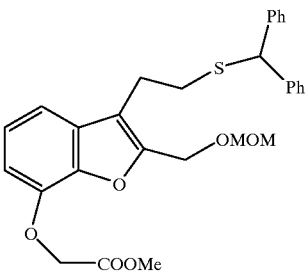

Potassium t-butoxide (465 mg) was dried under reduced pressure. n-propanethiol (0.4 ml) was dissolved in DMF (5 ml) and the obtained solution was stirred at room temperature. 2-methoxymethoxymethyl-3-(2-(diphenylmethylthio) ethyl-7-methoxybenzofuran (803 mg) was dissolved in DMF (6 ml) and the obtained solution was added to the above-mentioned solution, followed by stirring the resulting solution at 90° C. for 6 hours. The reaction mixture was poured into 5% aqueous citric acid solution and extracted with ethyl acetate. The organic layer was washed with water and with saturated brine and dried over magnesium sulfate. Magnesium sulfate was removed by filtration and the solvent was evaporated off. The residue was purified by column chromatography (solvent: n-hexane/ethyl acetate=1/1) to obtain the phenolic compound (406 mg, yield: 52%). This phenolic compound (406 mg) was dissolved in ethanol (50 ml) and 4N aqueous potassium hydroxide solution (0.3 ml) was added, followed by stirring the resulting solution at room temperature for 30 minutes. The solvent was evaporated off under reduced pressure. DMF (20 ml) was added to the residue to dissolve the same and methyl bromoacetate (0.20 ml) was added to the solution, followed by stirring the resulting solution at room temperature for 90 minutes. The reaction solution was poured into 5% aqueous citric acid solution and extracted with ethyl acetate. The organic layer was washed with water and with saturated brine and dried over magnesium sulfate. Magnesium sulfate was removed by filtration and the solvent was evaporated off. The residue was purified by column chromatography (solvent: n-hexane/ ethyl acetate=1/1) to obtain the phenolic compound (403 mg, yield: 84%).

IR (liquid film method) 3450, 1760, 1591, 1493, 1437, 1388, 1288, 1209, 1096, 1004, 785, 752, 733, 704 cm$^{-1}$ NMR (300 MHz CDCl$_3$) δ7.38–7.18(10H,m),7.08(1H,t, J=8 Hz),6.93(1H,dd,J=1,8 Hz), 6.77(1H,dd,J=1,8 Hz),5.03 (1H,s),4.89(2H,s), 4.67(2H,d,J=6 Hz),3.80(3H,s),2.92(2H,t, J=7 Hz), 2.68(2H,t,J=7 Hz),2.18(1H,t,J=6 Hz)

Reference Example 60

(7-methoxy-benzofuran-3-yl)acetic acid

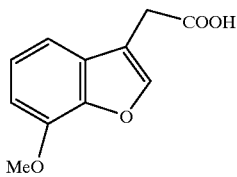

Methyl (7-methoxy-benzofuran-3-yl)acetate (1.12 g) was dissolved in methanol (20 ml). To this solution, 2N aqueous sodium hydroxide solution (5 ml) was added and the resulting solution was stirred at room temperature for 13.5 hours. To this solution, 1N hydrochloric acid (12 ml) was added and the reaction solution was poured into water layer (200 ml), followed by extraction twice with ethyl acetate (50 ml). The organic layers were combined and washed with saturated brine, followed by drying over sodium sulfate. Sodium sulfate was removed by filtration and the solvent was removed under reduced pressure. The residue was recrystallized from hexane/chloroform to obtain the desired compound (0.95 g, yield: 91%).

m.p.: 143–145° C. (recrystallized from hexane/chloroform)

IR (KBr method) 2912, 1715, 1626, 1595, 1497, 1435, 1400, 1284, 1267, 1230, 1178, 1094, 1048, 924, 779, 733, 673 cm$^{-1}$ NMR (90 MHz CDCl$_3$) δ8.78(1H,brm),7.64(1H,s), 7.19–6.75(3H,m),4.00(3H,s), 3.69(2H,d,J=1.1 Hz)

Reference Example 61

3-((4-phenyloxazole-2-yl)methyl)-7-methoxybenzofuran

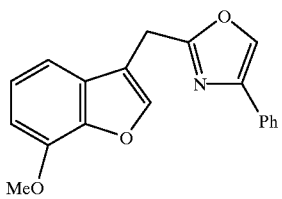

7-methoxy-benzofuran-3-carboxylic acid (294 mg) was dissolved in DMF (5 ml). To this solution, potassium carbonate (237 mg) and phenacyl bromide (342 mg) were added, and the resulting solution was stirred at room temperature for 30 minutes. The reaction mixture was poured into water layer (50 ml) and extracted twice with ethyl acetate (20 ml). The organic layers were combined and washed with saturated brine, followed by drying over sodium sulfate. Sodium sulfate was removed by filtration and the solvent was removed under reduced pressure. The residue was dissolved in acetic acid (5 ml) and ammonium acetate (551 mg) was added, followed by refluxing the resulting solution for 4 hours. After cooling the reaction solution to room temperature, the solution was poured into water layer (100 ml) and extracted twice with ethyl acetate (30 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=5/1) using silica gel to obtain the desired compound (203 mg, yield: 47%).

m.p.: 101–103° C. (recrystallized from hexane/ethyl acetate)

IR (KBr method) 3118, 2968, 2844, 1628, 1591, 1568, 1497, 1477, 1450, 1437, 1417, 1363, 1332, 1317, 1288, 1272, 1224, 1209, 1183, 1170, 1147, 1112, 1100, 1065, 1050, 1033, 959, 942, 919, 905, 820, 789, 754, 733, 690, 673, 632 cm$^{-1}$ NMR (90 MHz CDCl$_3$) δ7.83(1H,s),7.78–6.82(9H,m), 4.23(2H,d,J=1.1 Hz), 4.01(3H)

EI-MS m/e 305(M$^+$)

Reference Example 62

3-((4-phenyloxazole-2-yl)methyl)-7-hydroxybenzofuran

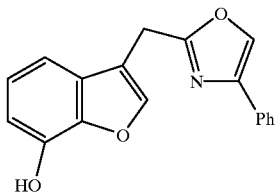

By the method similar to Reference Example 12, the desired compound (242 mg, yield: 91%) was obtained from 3-(4-phenyloxazole-2-yl)methyl-7-methoxybenzofuran (279 mg).

m.p.: 180–181° C. (recrystallized from hexane/ethyl acetate)

IR (KBr method) 3126, 3050, 1597, 1572, 1491, 1448, 1421, 1365, 1346, 1325, 1272, 1181, 1135, 1108, 1075, 971, 951, 795, 756, 731, 690, 677 cm$^{-1}$ NMR (90 MHz CDCl$_3$) δ8.23(1H,m),7.84–6.84(10H,m), 4.22(2H,d,J=0.9 Hz)

EI-MS m/e 291(M$^+$)

Reference Example 63

3-((4-phenyl-2-oxobutoxy)carbonylmethyl)-7-methoxybenzofuran

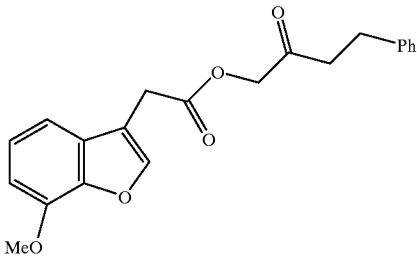

7-methoxybenzofuran-3-carboxylic acid (220 mg) was dissolved in THF (5 ml). To this solution, 4-phenyl-2-oxo-1-butanol (211 mg) and dicyclohexylcarbodiimide (330 mg) were added and the resulting solution was stirred at room temperature for 16 hours. The reaction solution was filtered and the filtrate was poured into water layer (50 ml), followed by extraction twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=3/1) using silica gel to obtain the desired compound (178 mg, yield: 47%).

m.p.: 68–69° C. (recrystallized from hexane/ethyl acetate)

IR (KBr method) 1760, 1725, 1589, 1497, 1439, 1417, 1390, 1270,.1205, 1189, 1160, 1096, 1048, 990, 779, 733 cm$^{-1}$ NMR (90 MHz CDCl$_3$) δ7.67(1H,s),7.29–6.81(8H,m), 4.67(2H,s),4.01(3H,s), 3.82(2H,d,J=1.1 Hz),3.02–2.58(4H,m)

EI-MS m/e 352(M$^+$)

Reference Example 64

3-((4-(2-phenylethyl)oxazole-2-yl)methyl)-7-methoxybenzofuran

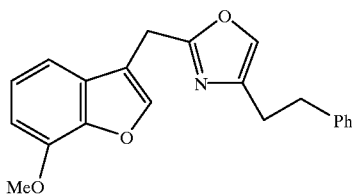

3-((4-phenyl-2-oxo-butoxy)carbonylmethyl-7-methoxy-benzofuran (176 mg) was dissolved in acetic acid (3 ml) and ammonium acetate (373 mg) was added to the solution, followed by refluxing the resulting solution for 4 hours. After cooling the reaction solution to room temperature, the solution was poured into water layer (100 ml) and extracted twice with ethyl acetate (30 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=5/1) using silica gel to obtain the desired compound (96 mg, yield: 58%).

m.p.: 69–70° C. (recrystallized from hexane/ethyl acetate)

IR (KBr method) 3112, 1628, 1591, 1564, 1497, 1456, 1439, 1363, 1286, 1270, 1209, 1183, 1145, 1094, 1048, 789, 754, 733, 712, 692, 663, 625, 603 cm$^{-1}$ NMR (90 MHz CDCl$_3$) δ7.60(1H,s),7.25–6.75(9H,m), 4.14(2H,d,J=1.1 Hz), 4.00(3H),2.95–2.70(4H)

EI-MS m/e 333(M$^+$)

Reference Example 65

3-(2-(2,2-ethylenedioxy-2-phenylethoxy)ethyl)-7-tetrahydropyranyloxybenzofuran

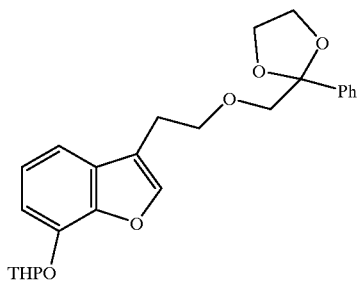

3-(2-hydroxyethyl)-7-tetrahydropyranyloxybenzofuran (319 mg) was dissolved in DMF (2 ml). To this solution, sodium hydride (60%, 59 mg) was added and the solution was stirred at room temperature for 1 hour. To this reaction solution, 1-bromo-acetophenoneethylene acetal (445 mg) was added and the resulting solution was stirred at room temperature for 1 hour and then at 100° C. for 2.5 hours. After cooling the reaction solution to room temperature, the solution was added to water layer (50 ml) and extracted twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=5/1) using silica gel to obtain the desired compound (239 mg, yield: 46%).

Reference Example 66

3-(2-(2,2-ethylenedioxy-2-phenylethoxy)ethyl)-7-hydroxybenzofuran

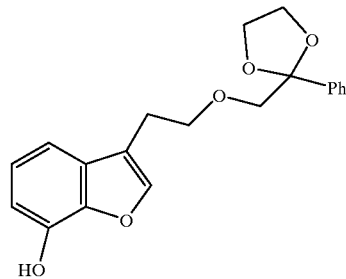

3-(2-(2,2-ethylenedioxy-2-phenylethoxy)ethyl)-7-tetrahydropyranyloxybenzofuran (239 mg) was dissolved in THF (3 ml). To this solution, 6N hydrochloric acid (1 ml) was added and the resulting solution was stirred at room temperature for 30 minutes. The reaction solution was poured into water layer (30 ml) and extracted twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=2/1) using silica gel to obtain the desired compound (189 mg, yield: 98%).

IR (liquid film method) 3550, 2956, 2898, 1624, 1593, 1491, 1448, 1363, 1313, 1238, 1183, 1122, 1093, 1044, 973, 948, 878, 785, 770, 735, 706 cm$^{-1}$ NMR (400 MHz CDCl$_3$) δ7.51–7.49(2H,m),7.36–7.33 (4H,m),7.11–7.04(2H,m), 6.80 (1H,dd,J=8.3 Hz),5.59(1H, s),4.08–4.05(2H,m), 3.87–3.84(2H,m),3.79(2H,t,J=6.4 Hz), 3.71(2H,s)0.88(2H,t, J=6.4 Hz)

Reference Example 67

3-(2-(2-oxo-2-phenylethoxy)ethyl)-7-hydroxybenzofuran

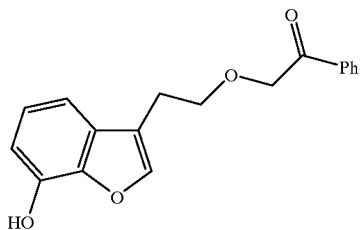

3-(2-(2,2-ethylenedioxy-2-phenylethoxy)ethyl)-7-hydroxybenzofuran (185 mg) was dissolved in THF (3 ml). To this solution, one drop of concentrated hydrochloric acid was added and the solution was stirred at 50° C. for 29 hours, followed by refluxing the solution for 3 hours. The reaction solution was poured into water layer (30 ml) and extracted twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=2/1) using silica gel to obtain the desired compound (111 mg, yield: 69%).

m.p.: 114–115° C. (recrystallized from hexane/ethyl acetate)

IR (KBr method) 3300, 1702, 1622, 1597, 1479, 1446, 1408, 1371, 1274, 1226, 1187, 1131, 1087, 1075, 1044, 1017, 984, 971, 946, 849, 785, 758, 733, 688, 669, 619, 598 cm$^{-1}$ NMR (90 MHz CDCl$_3$) δ7.96–6.97(9H,m),5.60(1H,brs), 4.77(2H,s), 3.88(2H,t,J=6.9 Hz),3.01(2H,t,J=6.8 Hz)

EI-MS m/e 296(M$^+$)

Reference Example 68

3-((3,3-diphenylpropyloxy)methyl)-7-methoxybenzofuran

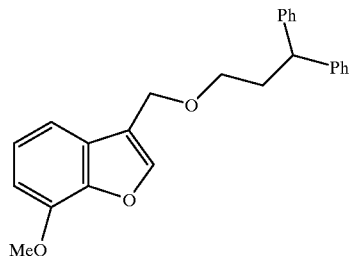

3,3-diphenyl-1-propanol (550 mg) was dissolved in DMF (5 ml) and the obtained solution was cooled to 0° C. To this solution, potassium t-butoxide (291 mg) was added and the solution was stirred at 0° C. for 10 minutes. To the reaction solution, 3-chloromethyl-7-methoxybenzofuran (339 mg) solution in DMF (4 ml) was added dropwise and the resulting solution was stirred at 0° C. for 30 minutes. After neutralizing the reaction solution with 1N hydrochloric acid, the solution was poured into water layer (50 ml) and extracted twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=9/1) using silica gel to obtain the desired compound (547 mg, yield: 85%).

IR (liquid film method) 3062, 3030, 3006, 2942, 2866, 1628, 1593, 1493, 1451, 12435, 1359, 1286, 1270, 1201, 1180, 1151, 1096, 1054, 843, 789, 731, 704 cm$^{-1}$ NMR (90 MHz CDCl$_3$) δ7.50(1H,s),7.25–6.78(13H,m), 4.56(2H,d,J=0.9 Hz), 4.11(1H,m),4.01(3H,s),3.43(2H,t,J= 6.8 Hz),2,46–2.23(2H,m)

EI-MS m/e 372(M$^+$)

Reference Example 69

3-((2-(N,N-diphenylamino)ethoxy)methyl)-7-methoxybenzofuran

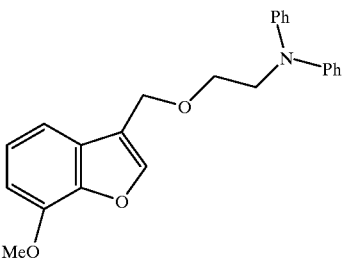

By the method similar to Reference Example 68, the desired compound (185 mg, yield: 70%) was obtained from 2-(N,N-diphenylamino)-1-ethanol (139 mg).

IR (liquid film method) 3062, 2944, 2864, 1628, 1576, 1491, 1464, 1437, 1363, 1253, 1201, 1180, 1152, 1054, 992, 926, 748, 731, 696 cm$^{-1}$ NMR (300 MHz CDCl$_3$) δ7.49(1H,brs),7.25–6.81(13H, m),4.64(2H,d,J=1.1 Hz), 3.96(2H,t,J=6.6 Hz),3.72(2H,t,J= 6.6 Hz)

EI-MS m/e 373(M$^+$)

Reference Example 70

4-benzyloxyindole

Potassium hydroxide (0.42 g) was added to 4-hydroxyindole (1.00 g) in DMF (25 ml), and the solution was stirred at room temperature for 15 minutes. Benzyl bromide (1.00 ml) was added to the solution, and the solution was stirred at room temperature for 1.5 hours. Since the reaction was not completed, benzyl bromide (0.20 ml) was further added and the solution was stirred for 5 hours.

After removing the solvent under reduced pressure, water (50 ml) was added to the residue and the resultant was extracted with ether (3×50 ml). The organic layers were washed with saturated brine, and dried over sodium sulfate. After removing solids by filtration, the solvent was removed under reduced pressure and the obtained crude product was purified by silica gel column chromatography to obtain the desired product (1.43 g, yield: 85%).

IR (liquid film method) 3418, 1589, 1504, 1361, 1243, 1087, 1050, 739 cm$^{-1}$

NMR (90 MHz CDCl$_3$) δ8.16(1H,brs),7.60–7.00(8H,m), 6.80–6.50(2H,m), 5.23(2H,s)

Mass(m/e) 223(M+)

Reference Example 71

1-(2-tetrahydropyranyloxyethyl)-4-benzyloxyindole

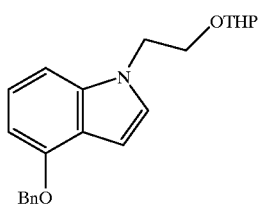

Under argon atmosphere, sodium hydride (121 mg) in DMF (2 ml) was cooled to 0° C. and 4-benzyloxyindole (501 mg) in DMF (5 ml) was added thereto, followed by stirring the resulting solution at 0° C. for 5 minutes. To this solution, 2-tetrahydropyranyloxy-1-bromoethane (599 mg) in DMF (2 ml) was added and the solution was stirred at 0° C. for 30 minutes. The reaction mixture was added to saturated aqueous NH$_4$Cl solution (30 ml) cooled at 0° C., and the resultant was extracted with ethyl acetate (3×20 ml). The obtained organic layers were washed with saturated brine and dried over sodium sulfate. After removing solids by filtration, the solvent was removed under reduced pressure, and the obtained crude product was purified by silica gel column chromatography to obtain the desired compound (722 mg, yield: 92%).

IR (liquid film method) 2944, 1578, 1497, 1441, 1369, 1232, 1125, 1035,737 cm$^{-1}$ NMR (90 MHz CDCl$_3$) δ7.60–6.50(10H,m),5.22(2H,s), 4.60–3.20(7H,m), 1.90–1.30(6H,m)

Mass(m/e) 351(M+)

Reference Example 72

Methyl (1-(2-hydroxyethyl)indole-4-yloxy)acetate

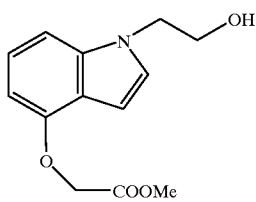

Under argon atmosphere, 1-(2-tetrahydropyranyloxyethyl)-4-benzyloxyindole (85 mg) and 5% Pd-C (10 mg) were added to ethanol (5 ml), and the atmosphere in the reaction vessel was replaced with hydrogen. The mixture was stirred at room temperature for 3 hours and solids were removed by filtration through Celite. The solvent was removed under reduced pressure and the obtained oil was transferred to a reaction vessel having argon atmosphere, followed by dissolving the oil in DMF (2 ml). To this, potassium carbonate (26 mg) was added and the resultant was stirred at room temperature for 10 minutes. Methyl bromoacetate (0.03 ml) was added to the mixture and the resultant was stirred at room temperature for 80 minutes. Since the reaction had not been completed, methyl bromoacetate (0.03 ml) was added and the mixture was stirred at room temperature for 3 hours. To the reaction mixture, saturated aqueous NH$_4$Cl solution (5 ml) was added to stop the reaction, and the resultant was extracted with ethyl acetate (3×10 ml). The obtained organic layers were washed with saturated brine and dried over sodium sulfate. After removing solids by filtration, the solvent was removed under reduced pressure, and the obtained crude product was purified by silica gel column chromatography to obtain the desired compound (25 mg, yield: 41%).

IR (liquid film method) 3520, 2934, 1750, 1578, 1499, 1354, 1220, 1151, 748 cm$^{-1}$ NMR (90 MHz CDCl$_3$) δ7.20–7.00(3H,m),6.69(1H,d,J= 3.1 Hz),6.50–6.30(1H,m), 4.79(2H,s),4.40–40(2H,m), 4.10–3.80(2H,m),3.80(3H,s), 1.56(1H,brs)

EI-MS 249(M+)

Reference Example 73

Methyl (1-(2-bromoethyl)indole-4-yloxy)acetate

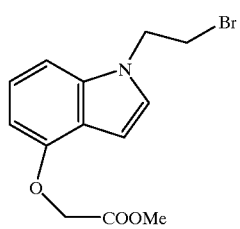

Under argon atmosphere, triphenylphosphine (1.05 g) and tetrabromomethane (2.00 g) were added to methyl (1-(2-hydroxyethyl)indole-4-yloxy)acetate (500 mg) in methylene chloride (10 ml) at room temperature, and the resulting mixture was stirred at room temperature for 15 minutes. Since the reaction had not been completed, triphenylphosphine (1.00 g) was added and the reaction mixture was stirred at room temperature for 30 minutes. To the reaction mixture, aqueous sodium hydrogen carbonate solution (5 ml) and water (10 ml) were added and the resultant was extracted with ethyl acetate (3×20ml). The obtained organic layers were washed with saturated brine and dried over sodium sulfate. After removing solids by filtration, the solvent was removed under reduced pressure, and the obtained crude product was purified by silica gel column chromatography to obtain the desired compound (602 mg, yield: 96%).

IR (liquid film method) 1752, 1578, 1497, 1439, 1257, 1220, 1087, 737 cm$^{-1}$

NMR (90 MHz CDCl$_3$) δ(ppm) 7.30–6.90(3H,m),6.68 (1H,d,J=3.1,0.7 Hz), 6.50–6.30(1H,m),4.78(2H,s),4.46(2H, t,J=6.8 Hz),3.79(3H,s), 3.60(2H,t,J=6.8 Hz)

EI-MS 311(M+)

Reference Example 74

Methyl (1-(2-azidoethyl)indole-4-yloxy)acetate

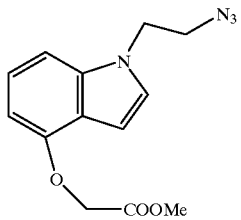

By the method similar to Reference Example 8, the desired compound (597 mg) was obtained from methyl (1-(2-bromoethyl)indole-4-yloxy)acetate (598 mg).

EI-MS 274 (M+)

Reference Example 75

1-(5-phenylpentyl)-4-benzyloxyindole

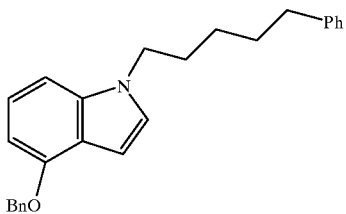

By the method similar to Reference Example 71, the desired compound (330 mg, yield: 100%) was obtained from 4-benzyloxyindole (200 mg).

IR (liquid film method) 2934, 1580, 1497, 1456, 1371, 1234, 1058, 735, 698 cm$^{-1}$ NMR (90 MHz CDCl3) δ(ppm) 7.60–6.90(12H,m), 6.70–6.50(2H,m),5.22(2H,s),4.10–3.90(2H,m),3.51(2H,t,J= 6.4 Hz),2.80–2.40(2H,m),2.20–1.15(6H,m)

EI-MS 369(M+)

Reference Example 76

1-(5-phenylpentyl)-4-hydroxyindole

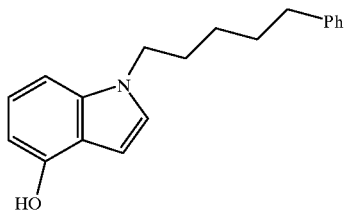

Under argon atmosphere, 1-(5-phenylpentyl)-4-benzyloxyindole (330 mg) and 5% Pd-C (10 mg) were added to methanol (5 ml) and the atmosphere in the reaction vessel was replaced with hydrogen. The mixture was stirred at room temperature for 2 hours and solids were removed by filtration through Celite. The solvent was removed under reduced pressure, and the obtained crude product was purified by silica gel column chromatography to obtain the desired compound (178 mg, yield: 71%).

IR (liquid film method) 3394, 2936, 1580, 1495, 1357, 1257, 982, 737, 700 cm$^{-1}$ NMR (90 MHz CDCl$_3$) δ(ppm) 7.40–6.90(4H,m), 6.60–6.40(1H,m),5.34(1H,brs), 4.02(2H,t,J=6 Hz),2.56(2H, t,J=7.7 Hz),2.00–1.20(6H,m)

EI-MS 279(M+)

Reference Example 77

1-(2-(3-phenylpropyloxy)ethyl)-4-benzyloxyindole

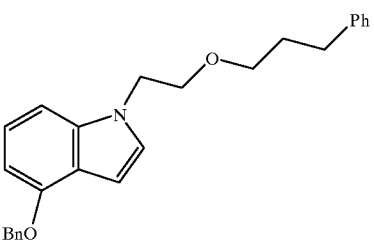

Under argon atmosphere, sodium hydride (40 mg) was added to 1-(2-hydroxyethyl)-4-benzyloxyindole (52 mg) in DMF (3 ml) and the mixture was stirred at room temperature for 15 minutes. To the mixture, 3-phenyl-1-bromopropane (0.15 ml) was added and the resultant was stirred at room temperature for another 18 hours. The reaction mixture was added to saturated aqueous NH$_4$Cl solution (5 ml) to stop the reaction, and the resultant was extracted with ethyl acetate (3×10 ml). The obtained organic layers were washed with saturated brine and dried over sodium sulfate. After removing solids by filtration, the solvent was removed under reduced pressure, and the obtained crude product was purified by silica gel column chromatography to obtain the desired compound (72 mg, yield: 96%).

IR (liquid film method) 2866, 1686, 1560, 1543, 1491, 1056, 735 cm$^{-1}$

NMR (90 MHz CDCl$_3$) δ(ppm) 7.60–6.90(13H,m), 6.75–6.50(2H,m),5.21(2H,s), 4.24(2H,t,J=5.6 Hz),3.68(2H, t,J=5.6 Hz),3.33(2H,t,J=6.2 Hz), 2.68–2.48(2H,m), 2.00–1.62(2H,m)

EI-MS 385(M+)

Reference Example 78

1-(2-(3-phenylpropyloxy)ethyl)-4-hydroxyindole

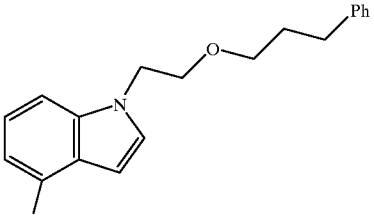

By the method similar to Reference Example 76, the desired compound (180 mg, yield: 74%) was obtained from 1-(2-(3-phenylpropyloxy)ethyl)-4-benzyloxyindole (318 mg).

IR (liquid film method) 3382, 1582, 1495, 1473, 1263, 1114, 737 cm$^{-1}$

NMR (90 MHz CDCl$_3$) δ(ppm) 7.30–6.90(8H,m), 6.60–6.40(2H,m),5.15(1H,brs), 4.26(2H,t,J=5 Hz),3.71(2H, t,J=5.6 Hz),3.35(2H,t,J=6.3 Hz), 2.60(2H,t,J=7.6 Hz), 1.90–1.70(2H,m)

EI-MS 295(M+)

Reference Example 79

4-methoxyindole

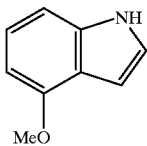

Potassium hydroxide (2.12 g) was added to 4-hydroxyindole (4.99 g) in DMF (100 ml) and the mixture was stirred at room temperature for 30 minutes. Methyl iodide (2.80 ml) was added to the mixture and the resultant was stirred at room temperature for 150 minutes. Since the reaction had not been completed, potassium hydroxide (0.64 g) was added and the mixture was stirred at room temperature for 5 hours. The solvent was removed under reduced pressure and water (20 ml) was added to the residue, followed by extraction with ether (3×30 ml). The organic layers were washed with saturated brine, and dried over sodium sulfate. After removing solids by filtration, the solvent was removed under reduced pressure and the obtained crude product was purified by silica gel column chromatography to obtain the desired product (3.38 g, yield: 61%).

IR (KBr method) 3400, 1591, 1497, 1361, 1284, 1249, 1083, 727 cm$^{-1}$

NMR (90 MHz CDCl$_3$) δ8.50–7.90(1H,m),7.20–7.00(3H,m),6.70–6.40(2H,m), 3.96(3H,s)

EI-MS 147(M+)

Reference Example 80

4-methoxyindoline

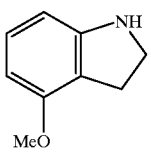

Borane-trimethylamine complex (3.00 g) and 10.5N hydrochloric acid (2.25 ml) were added to 4-methoxyindole (1.29 g) in dioxane (20 ml), and the mixture was heated to reflux for 30 minutes. To this mixture, 6N hydrochloric acid (7.00 ml) was added and the mixture was heated to reflux for 15 minutes. The solvent was removed under reduced pressure and 1N aqueous sodium hydroxide solution was added to change the aqueous layer to alkaline condition, followed by extracting the aqueous layer with ether (3×20 ml). The obtained organic layers were washed with saturated brine and dried over sodium sulfate. After removing solids by filtration, the solvent was removed under reduced pressure, and the obtained crude product was purified by silica gel column chromatography to obtain the desired compound (1.08 g, yield: 83%).

IR (KBr method) 3378, 2943, 1611, 1468, 1336, 1247, 1091, 772, 704 cm$^{-1}$

NMR (90 MHz CDCl$_3$) δ(ppm) 6.98(1H,t,J=8.0 Hz), 6.40–6.20(2H,m),3.80(3H,s), 3.70–3.40(2H,m),3.10–2.80(2H,m)

EI-MS 149(M+)

Reference Example 81

1-(2-diphenylmethoxy)ethyl)-4-methoxyindoline

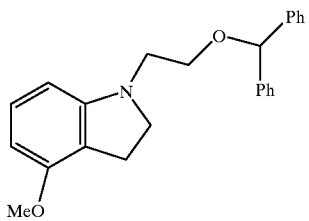

Under argon atmosphere, 4-methoxyindoline (1.08 g) in ether (10 ml) was cooled to 0° C. and phenyllithium (1.77 M solution in ether, 6.0 ml) was added thereto, followed by stirring the resulting mixture at 0° C. for 30 minutes. To this mixture, 2-diphenylmethoxy-1-bromoethane (3.18 g) was added and the mixture was gradually heated to room temperature. After stirring the mixture at room temperature for 1 hour, water (5 ml) was added to the reaction mixture to stop the reaction and the resultant was extracted with ethyl acetate. The obtained organic layer was washed with saturated brine and dried over sodium sulfate. After removing solids by filtration, the solvent was removed under reduced pressure, and the obtained crude product was purified by silica gel column chromatography to obtain the desired compound (1.58 g, yield: 58%).

IR (liquid film method) 2838, 1618, 1458, 1340, 1230, 1073, 743, 511 cm$^{-1}$

NMR (90 MHz CDCl$_3$) δ(ppm) 7.50–7.20(10H,m),7.02 (1H,t,J=8.4 Hz), 6.24(1H,t,J=8.4 Hz),6.15(1H,d,J=8.4 Hz), 5.38(1H,s), 3.80(3H,s),3.80–3.20(6H,m),3.00–2.80(2H,m)

EI-MS 359(M+)

Reference Example 82

1-(2-(diphenylmethoxy)ethyl)-4-hydroxyindoline

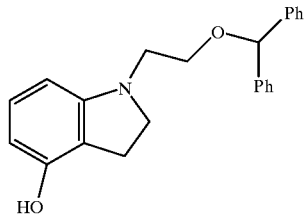

By the method similar to Reference Example 12, the desired compound (855 mg, yield: 89%) was obtained from (2-(diphenylmethoxy)ethyl)-4-methoxyindoline (1.00 g).

IR (liquid film method) 3500, 2858, 1630, 1599, 1466, 1222, 1098, 760, 741, 704 cm$^{-1}$ NMR (90 MHz CDCl$_3$) δ(ppm) 7.40–7.10(10H,m),6.92 (1H,t,J=8.0 Hz), 6.11(1H,t,J=8.0 Hz),6.08(1H,d,J=8.0 Hz), 5.38(1H,s), 4.60(1H,brs),3.80–3.20(6H,m),3.10–2.80(2H,m)

EI-MS 345(M+)

Reference Example 83

1-(2-hydroxyethyl)-4-methoxyindole

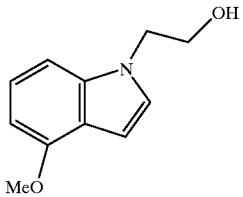

Under argon atmosphere, NaH (283 mg) was added to 4-methoxyindole (516 mg) in DMF (10 ml) and the mixture was stirred at 0° C. for 15 minutes. To this mixture, 2-tetrahydropyranyloxy-1-bromoethane (890 mg) was added and the mixture was gradually heated to room temperature, followed by stirring the mixture at room temperature for 90 minutes. The reaction mixture was added to saturated aqueous NH$_4$Cl solution (5 ml) cooled at 0° C. to stop the reaction, and the resultant was extracted with ethyl acetate (3×10 ml). The obtained organic layers were washed with saturated brine and dried over sodium sulfate. After removing solids by filtration, the solvent was removed under reduced pressure. The obtained oil was transferred to a reaction vessel and dissolved in methanol (10 ml), followed by cooling the obtained solution to 0° C. To this solution, 1N hydrochloric acid (1 ml) was added and the solution was stirred at 0° C. for 2 hours. After removing the solvent under reduced pressure, water (5 ml) was added and the resultant was extracted with ethyl acetate (3×20 ml). The obtained organic layers were washed with saturated brine and dried over sodium sulfate. After removing solids by filtration, the solvent was removed under reduced pressure, and the obtained crude product was purified by silica gel column chromatography to obtain the desired compound (547 mg, yield: 82%).

IR (liquid film method) 3500, 1580, 1497, 1446, 1359, 1257, 1064, 739 cm$^{-1}$

NMR (90 MHz CDCl$_3$) δ(ppm) 7.39–6.95(3H,m), 6.70–6.40(2H,m),4.30–3.70(4H,m), 3.94(3H,s),1.90–1.50 (1H,m)

EI-MS 191(M+)

Reference Example 84

Methyl (1-(2-hydroxyethyl)indole-4-yloxy)acetate

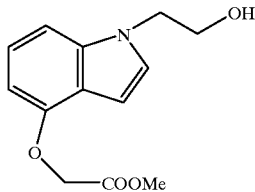

By the method similar to Reference Examples 83 and 45, the desired compound (112 mg, yield: 55%) was obtained from 4-methoxyindole (121 mg).

IR (liquid film method) 2934, 1742, 1615, 1576, 1495, 1437, 1354, 1210, 1060, 737 cm$^{-1}$ NMR (300 MHz CDCl$_3$) δ7.14–7.02(3H,m),6.69(1H,dd, J=3.0,0.9 Hz), 6.42(1H,dd,J=7.5,0.9 Hz),4.80(2H,s),4.26 (2H,t,J=5.4 Hz), 3.97–3.92(2H,m),3.81(3H,s),1.70–1.50 (1H,br s)

EI-MS m/e 249(M$^+$)

Reference Example 85

Methyl (1-(2-hydroxyethyl)indoline-4-yloxy)acetate

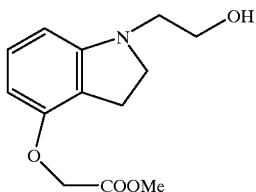

Under argon atmosphere, 1-(2-hydroxyethyl)-4-benzyloxyindoline (369 mg) was dissolved in ethanol and the obtained solution was stirred at room temperature. To this solution, 5% Pd/C (46 mg) was added and the atmosphere in the reaction vessel was replaced with hydrogen. After confirming vanishment of the materials, the atmosphere of the reaction vessel was replaced with argon. Solids were removed by filtration through Celite and the solvent was removed under reduced pressure to obtain a crude product. The crude product was dissolved in DMF and the obtained solution was stirred at room temperature. To this solution, potassium carbonate (368 mg) and methyl bromoacetate (0.26 ml) were added and the mixture was stirred at room temperature. After confirming vanishment of the materials, saturated aqueous ammonium chloride solution (5 ml) was added to the reaction solution and the resultant was extracted three times with ethyl acetate (10 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=1/1) using silica gel to obtain the desired compound (151 mg, yield: 45%).

IR (liquid film method) 2934, 1763, 1655, 1618, 1466, 1437, 1340, 1296, 1212, 1098, 866, 756, 706 cm$^{-1}$ NMR (300 MHz CDCl$_3$) δ7.02(1H,t,J=8.1 Hz),6.28(1H, d,J=8.1 Hz), 6.16(1H,d,J=8.1 Hz),4.65(2H,s),3.90–3.70(2H, m), 3.79(3H,s),3.43(2H,t,J=8.4 Hz),3.24(2H,t,J=5.4 Hz), 3.03(2H,t,J=8.4 Hz)

EI-MS m/e 251(M$^+$)

Reference Example 86

1-(2-(diphenylmethoxy)ethyl)-4-methoxyindole

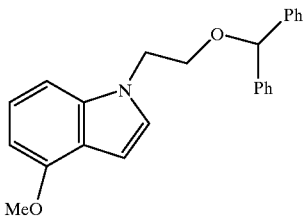

By the method similar to Reference Example 77, the desired compound (309 mg, yield: 55%) was obtained from 1-(2-hydroxyethyl)-4-methoxyindole.

IR (liquid film method) 1686, 1560, 1543, 1491, 1458, 1257, 737 cm$^{-1}$

NMR (90 MHz CDCl₃) δ(ppm) 7.40–6.80(13H,m), 6.70–6.45(2H,m),5.24(1H,s), 4.32(2H,t,J=5.6 Hz),3.96(3H, s),3.74(2H,t,J=5.6 Hz)

EI-MS 357(M+)

Reference Example 87

1-(2-(diphenylmethoxy)ethyl)-4-hydroxyindole

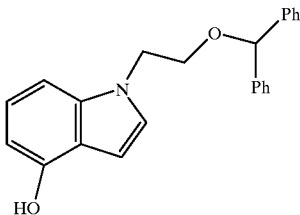

By the method similar to Reference Example 12, the desired compound (263 mg, yield: 42%) was obtained from 1-(2-(diphenylmethoxy)ethyl)-4-methoxyindole (650 ml).

IR (liquid film method) 3400, 1493, 1456, 1263, 1085, 739, 702 cm⁻¹

NMR (90 MHz CDCl₃) δ(ppm) 7.50–6.75(13H,m), 6.60–6.40(2H,m),5.19(1H,s), 4.24(2H,t,J=5.2 Hz),3.69(2H, t,J=5.2 Hz),1.80–1.40(1H,m)

EI-MS 343(M+)

Reference Example 88

1-(4,4-diphenylbutyl)-4-methoxyindole

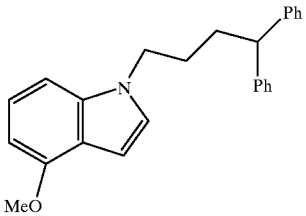

By the method similar to Reference Example 71, the desired compound (176 mg, yield: 36%) was obtained from 4-methoxyindole (200 mg).

IR (liquid film method) 2942, 1736, 1582, 1495, 1454, 1375, 1255, 1183, 1164, 1139, 1065, 911, 845, 735, 702 cm⁻¹

NMR (300 MHz CDCl₃) δ7.27–7.06(11H,m),6.94(1H,d, J=3.3 Hz), 6.87(1H,d,J=8.1 Hz),6.57(1H,dd,J=3.0,0.9 Hz), 6.50(1H,d,J=7.5 Hz),4.07(2H,t,J=6.9 Hz),3.95(3H,s), 3.84 (1H,t,J=7.8 Hz),2.09–2.00(2H,m),1.85–1.75(2H,m)

EI-MS m/e 355(M⁺)

Reference Example 89

1-(4,4-diphenylbutyl)-4-hydroxyindole

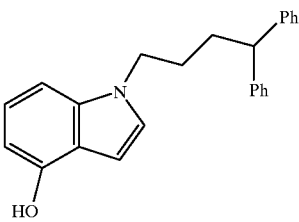

By the method similar to Reference Example 12, the desired compound (16 mg, yield: 83%) was obtained from 1-(4,4-diphenylbutyl)-4-methoxyindole (20 mg).

IR (liquid film method) 3028, 2940, 1700, 1624, 1582, 1495, 1452, 1375, 1249, 1031, 980, 737, 702 cm⁻¹

NMR (300 MHz CDCl₃) δ7.28–7.13(10H,m),7.03(1H,d, J=8.0 Hz), 6.97(1H,d,J=3.0 Hz),6.85(1H,d,J=8.1 Hz), 6.52–6.49(2H,m),4.96(1H,s),4.08(2H,t,J=6.9 Hz), 3.85(1H, t,J=7.8 Hz),2.10–2.02(2H,m),1.85–1.76(2H,m)

EI-MS m/e 341(M⁺)

Reference Example 90

3-(2-(3-phenylpropyloxy)ethyl)-7-hydroxybenzofuran

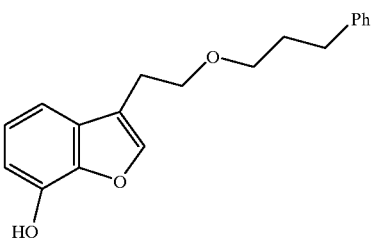

Sodium hydride (60%, 27 mg) was suspended in DMF (1 ml) and the obtained suspension was cooled to 0° C. To this solution, a solution of 3-(2-hydroxyethyl)-7-tetrahydropyranyloxybenzofuran (118 mg) in DMF (0.5 ml) was added dropwise and the obtained mixture was stirred at 0° C. for 10 minutes. To this solution, 1-bromo-3-phenyl-propane (0.27 ml) was added and the solution was stirred at 0° C. for 1 hour and then at room temperature for 45 hours. A catalytic amount of concentrated hydrochloric acid was added to the reaction solution and the solution was stirred for 2 hours. The reaction solution was poured into water layer (30 ml) and the resultant was extracted twice with ethyl acetate (15 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=3/1) using silica gel to obtain the desired compound (106 mg, yield: 80%).

IR (liquid film method) 3210, 3064, 3030, 2944, 2868, 1624, 1595, 1495, 1448, 1363, 1317, 1241, 1185, 1143, 1091, 1048, 971, 946, 847, 787, 733, 700, 679 cm⁻¹

NMR (90 MHz CDCl$_3$) δ7.46(1H,s),7.28–7.16(7H,m), 6.80(1H,dd,J=5.3,4.0 Hz), 5.63(1H,brs),3.71(2H,t,J=7.3 Hz),3.48(2H,t,J=6.4 Hz), 3.01–2.59(4H,m),2.05–1.82(2H, m)

EI-MS m/e 296(M$^+$)

Reference Example 91

3-(2-(4-phenylbenzyloxy)ethyl)-7-methoxybenzofuran

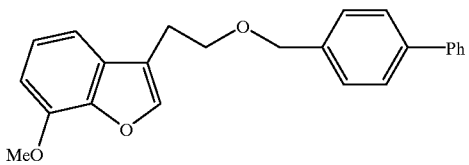

3-(2-hydroxyethyl)-7-methoxybenzofuran (373 mg) was dissolved in DMF (7 ml) and potassium t-butoxide (261 mg) was added to the obtained solution, followed by stirring the resulting solution at room temperature for 20 minutes. To this reaction solution, 4-phenylbenzyl chloride (511 mg) was added and the solution was stirred at room temperature for 1 hour. Acetic acid was added to the reaction solution and the resultant was poured into water layer (50 ml), followed by extraction twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=5/1) using silica gel to obtain the desired compound (613 mg, yield: 88%).

m.p.: 77–78° C. (recrystallized from hexane/ethyl acetate)

IR (KBr method) 2864, 1624, 1589, 1491, 1462, 1446, 1435, 1369, 1280, 1267, 1210, 1180, 1152, 1122, 1106, 1091, 1060, 1035, 1009, 828, 783, 760, 746, 733, 698, 681, 611 cm$^{-1}$ NMR (90 MHz CDCl$_3$) δ7.64–6.75(13H,m),4.58(2H,s), 3.99(3H,s), 3.80(2H,t,J=6.8 Hz),2.99(2H,dd,J=7.3,6.4 Hz)

EI-MS m/e 358(M$^+$)

Reference Example 92

Ethyl 7-methoxybenzofuran-2-carboxylate

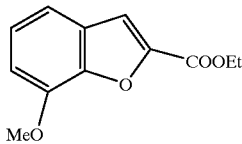

To N,N-dimethylformamide (300 ml), o-vanillin (25.2 g), ethyl chloroacetate (23.5 ml) and potassium carbonate (45 mg) were added and the resulting mixture was stirred at 120° C. for 14 hours. The reaction mixture was filtered to remove insoluble inorganic salts, and 1N hydrochloric acid (50 ml) was added to the mixture to stop the reaction. Distilled water (250 ml) was added and the resulting mixture was extracted 4 times with totally 150 ml of ethyl acetate containing 15% of n-hexane. The organic layers were washed with distilled water (100 ml) and with saturated brine (100 ml), and dried over anhydrous sodium sulfate. The sodium sulfate was removed by filtration and the solvent was concentrated to dryness under reduced pressure. The residue was purified by column chromatography (solvent: n-hexane/ethyl acetate= 10/1 to 5/1) using silica gel to obtain the desired compound (17.4 g, yield: 48%) in the form of colorless needle-shaped crystals.

m.p.: 86.5–87° C. (recrystallized from ethyl acetate/n-hexane)

IR (KBr method) 3132, 3000, 2970, 2846, 1976, 1912, 1711, 1622, 1582, 1495, 1468, 1446, 1371, 1317, 1270, 1224, 1203, 1091, 1058, 1027, 975, 942, 857, 779, 762, 733, 704, 625, 572, 534 cm$^{-1}$ NMR (90 MHz CDCl$_3$) δ7.52(1H,s),7.26–7.19(2H,m), 6.91(1H,dd,J=3.5,5.5 Hz), 4.44(2H,q,J=7.1 Hz),4.02(3H.s.), 1.42(3H,t,J=7.1 Hz)

EI-MS m/e 220(M$^+$)

Reference Example 93

7-methoxy-(2-hydroxymethyl)benzofuran

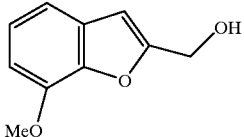

By the method similar to Reference Example 30, the desired compound (11.2 g, yield: 79%) was obtained from ethyl 7-methoxy-benzofuran-2-carboxylate (17.3 g).

IR (liquid film method) 3370, 2926, 2484, 2044, 1636, 1605, 1499, 1454, 1379, 1336, 1319, 1284, 1257, 1195, 1168, 1123, 1050, 1017, 959, 909, 735, 646 cm$^{-1}$ NMR (90 MHz CDCl$_3$) δ7.17–7.11(2H,m),6.87–6.73(1H, m),6.64(1H,s), 4.76(2H,d,J=5.9 Hz),3.99(3H,S),2.32(1H,t, J=5.9 Hz)

EI-MS m/e 178(M$^+$)

Reference Example 94

7-methoxy-2-chloromethylbenzofuran

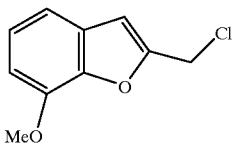

7-methoxy-(2-hydroxymethyl)benzofuran (2.25 g), pyridine (1.12 ml) and thionyl chloride (0.9 ml) were dissolved in dichloromethane (60 ml) and the obtained solution was refluxed under stirring for 23 hours. The reaction mixture was added to saturated aqueous sodium hydrogen carbonate solution (30 ml) and the resulting mixture was separated into aqueous and organic layers, followed by washing the aqueous layer with dichloromethane (30 ml). The organic layers were combined and washed with saturated brine (30 ml), followed by drying over anhydrous sodium sulfate. After removing the sodium sulfate by filtration, the solvent was removed under reduced pressure to dry the residue and the residue was purified by column chromatography (solvent: n-hexane/ethyl acetate=10/1) using silica gel to obtain the desired compound (2.2 g, yield: 87%).

m.p.: 44.5–45° C. (recrystallized from ethyl acetate/n-hexane)

IR (KBr method) 3002, 2960, 2942, 2838, 1918, 1721, 1626, 1601, 1586, 1495, 1466, 1433, 1361, 1330, 1294, 1270, 1253, 1212, 1187, 1174, 1145, 1129, 1098, 1062, 982, 955, 903, 845, 816, 764, 733, 700, 644, 621, 574, 553 cm$^{-1}$ NMR (90 MHz CDCl$_3$) δ7.19–7.13(2H,m),6.82(1H,dd,J=4.4,5.0 Hz),6.74(1H,s), 4.71(2H,s),4.01(3H,S)

EI-MS m/e 196(M$^+$)

Reference Example 95

2-((3,3-diphenylpropyloxy)methyl)-7-methoxybenzofuran

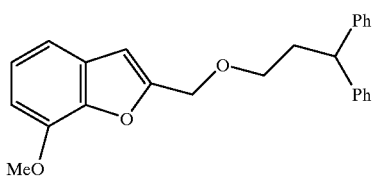

3,3-diphenylpropanol (324 mg) and sodium hydride (60% dispersion in mineral oil, 54 mg) were added to DMF (5 ml) and the obtained mixture was stirred at room temperature for 15 minutes. 7-methoxy-2-chloromethylbenzofuran (250 mg) was then added and the resulting mixture was stirred at room temperature for 3 hours. The reaction mixture was added to saturated aqueous ammonium chloride solution (15 ml) to neutralize the mixture. Distilled water (20 ml) was added to the mixture and the resultant was extracted with 20 ml of ethyl acetate containing 15% of n-hexane three times. The organic layers were combined and washed with distilled water (10 ml) and with saturated brine (10 ml), followed by drying over anhydrous sodium sulfate. After removing the sodium sulfate by filtration, the solvent was removed under reduced pressure to dry the residue and the residue was purified by column chromatography (solvent: n-hexane/ethyl acetate=10/1) using silica gel to obtain the desired compound (394 mg, yield: 83%).

IR (liquid film method) 3062, 3030, 2944, 1951, 1893, 1810, 1738, 1624, 1603, 1589, 1491, 1452, 1437, 1357, 1330, 1292, 1270, 1245, 1209, 1183, 1139, 1094, 1060, 1029, 977, 938, 855, 818, 775, 750, 735, 702, 632, 617 cm$^{-1}$ NMR (90 MHz CDCl$_3$) δ7.23–7.06(12H,m),6.79(1H,dd, J=4.0,4.8 Hz),6.59(1H,s), 4.53(2H,s),4.15(1H,t,J=7.9 Hz), 4.00(3H,S), 3.46(2H,t,J=6.4 Hz),2.34(2H,dt,J=6.4, 7.9 Hz)

EI-MS m/e 372(M$^+$)

Reference Example 96

2-((2,2-diphenylethoxy)methyl)-7-methoxybenzofuran

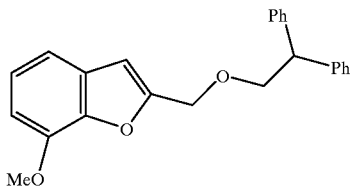

The same procedure as in Reference Example 95 was repeated except that 2,2-diphenylethanol (303 mg) was used in place of 3,3-diphenylpropanol to obtain the desired compound (387 mg, yield: 85%) in the form of a colorless oily product.

IR (liquid film method) 3064, 3030, 2906, 1951, 1885, 1812, 1738, 1624, 1603, 1589, 1495, 1452, 1437, 1357, 1330, 1290, 1270, 1243, 1207, 1183, 1139, 1102, 1060, 1046, 975, 938, 853, 818, 775, 737, 702, 630 cm$^{-1}$ NMR (90 MHz CDCl$_3$) δ7.25–7.10(12H,m),6.76(1H,dd, J=3.8,5.0 Hz),6.56(1H,s), 4.64(2H,d,J=0.4 Hz),4.42–4.24 (1H,m),4.10–4.00(2H,m), 4.03(3H,S)

EI-MS m/e 358(M$^+$)

Reference Example 97

2-((diphenylmethoxy)methyl)-8-methoxybenzofuran

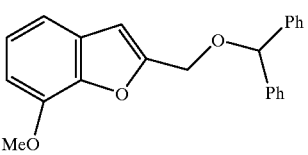

The same procedure as in Reference Example 95 was repeated except that benzhydrol (281 mg) was used in place of 3,3-diphenylpropanol to obtain the desired compound (280 mg, yield: 64%) in the form of a colorless oily product.

IR (liquid film method) 3064, 3030, 2942, 2842, 1891, 1812, 1624, 1589, 1495, 1454, 1437, 1388, 1330, 1288, 1270, 1209, 1183, 1139, 1093, 1060, 1029, 1004, 977, 942, 853, 816, 764, 737, 704, 623, 603 cm$^{-1}$ NMR (90 MHz CDCl$_3$) δ7.40–7.11(12H,m),6.80(1H,q,J=4.3 Hz),6.68(1H,s), 5.54(1H,s),4.64(2H,d,J=0.7 Hz),4.00 (3H,s)

EI-MS m/e 344(M$^+$)

Reference Example 98

2-((3,3-diphenylpropyloxy)methyl)-7-hydroxybenzofuran

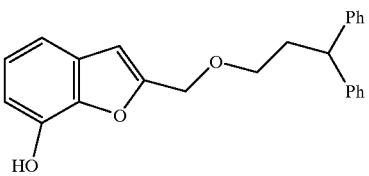

By the method similar to Reference Example 12, the desired compound (242 mg, yield: 64%) was obtained from 2-((3,3-diphenylpropyloxy)methyl)-7-methoxybenzofuran (394 mg)

m.p.: 105–106° C. (recrystallized from n-hexane/ethyl acetate)

IR (KBr method) 3234, 2926, 2362, 1607, 1497, 1448, 1386, 1373, 1332, 1286, 1259, 1228, 1147, 1083, 1052, 975, 938, 861, 820, 770, 731, 698 cm$^{-1}$ NMR (90 MHz CDCl$_3$) δ7.24–7.00(13H,m),6.85(1H,q,J=4.4 Hz),6.60(1H,s), 4.53(2H,d,J=0.4 Hz),4.14(1H,t,J=7.9 Hz),3.47(2H,t,J=6.4 Hz), 2.35(2H,dt,J=6.4, 7.9 Hz)

EI-MS m/e 358(M$^+$)

Reference Example 99

2-((2,2-diphenylethoxy)methyl)-7-hydroxybenzofuran

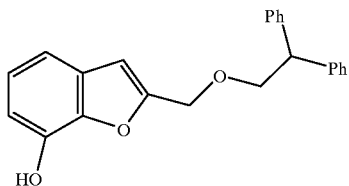

By the method similar to Reference Example 12, the desired compound (115 mg, yield: 35%) in the form of pale yellow oil was obtained from 2-((2,2-diphenylethoxy)methyl)-7-methoxybenzofuran (345 mg).

IR (liquid film method) 3280, 3064, 3030, 2868, 1951, 1897, 1808, 1603, 1495, 1450, 1361, 1307, 1220, 1189, 1162, 1139, 1081, 940, 859, 820, 739, 702 cm$^{-1}$ NMR (90 MHz CDCl3) δ7.23–7.03(12H,m),6.80(1H,q, J=4.3 Hz),6.57(1H,s), 5.71(1H,brs),4.58(2H.s),4.30(1H,m), 4.01(2H,m)

EI-MS m/e 344(M+)

Reference 100

2-((diphenylmethoxy)methyl)-7-hydroxybenzofuran

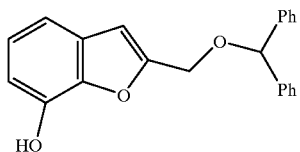

By the method similar to Reference Example 12, the desired compound (227 mg, yield: 85%) in the form of pale yellow oil was obtained from 2-((diphenylmethoxy)methyl)-7-methoxybenzofuran (280 mg). The product was recrystallized from n-hexane/ethyl acetate to obtain colorless crystals.

m.p.: 45–47° C.

EI-MS m/e 330(M$^+$)

Reference Example 101

Methyl (3-((acetylamino)methyl)benzofuran-7-yloxy)acetate

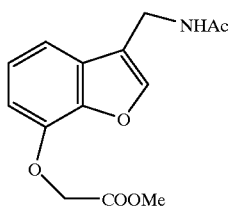

7-acetoxy-3-((acetylamino)methyl)benzofuran (258 mg) and potassium carbonate (82 mg) were added to methanol (5 ml) and the obtained mixture was stirred at room temperature for 1 hour. After removing methanol under reduced pressure, DMF (5 ml) and methyl bromoacetate (0.15 ml) were added to the residue, followed by stirring the resultant for 18 hours. The reaction solution was poured into water layer (30 ml) and the resultant was extracted twice with ethyl acetate (20 ml). The organic layers were combined and washed with saturated brine, followed by drying over anhydrous sodium sulfate. After removing the sodium sulfate by filtration, the solvent was removed under reduced pressure and the residue was purified by column chromatography (solvent: chloroform/methanol=95/5) using silica gel to obtain the desired compound (227 mg, yield: 78%).

m.p.: 139–140° C. (recrystallized from cyclohexane/chloroform)

IR (KBr method) 3292, 1752, 1738, 1649, 1636, 1545, 1510, 1495, 1460, 1433, 1381, 1365, 1321, 1280, 1224, 1193, 1154, 1106, 1087, 783, 729 cm$^{-1}$ NMR (90 MHz CDCl$_3$) δ7.60(1H,s),7.59–7.06(2H,m), 6.80(1H,dd,J=6.8,2.2 Hz), 4.88(2H,s),4.54(2H,d,J=5.1 Hz), 3.81(3H,s),2.01(3H,s)

EI-MS m/e 277(M$^+$)

Reference Example 102

Methyl (3-((acetylamino)methyl)-2-methylbenzofuran-7-yloxy)acetate

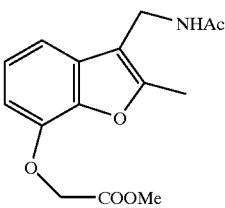

By the method similar to Reference Example 101, the desired compound (1.38 g, yield: 85%) was obtained from 7-acetoxy-3-((acetylamino)methyl)-2-methylbenzofuran (1.46 g).

m.p.: 179–181° C. (recrystallized from hexane/chloroform)

IR (KBr method) 3250, 3080, 3038, 2980, 2960, 2928, 2884, 1750, 1620, 1589, 1549, 1493, 1435, 1379, 1344, 1299, 1263, 1228, 1203, 1183, 1158, 1106, 1093, 1058, 1040, 984, 946, 853, 779, 737, 716, 649, 621, 603 cm$^{-1}$ NMR (90 MHz CDCl$_3$) δ7.15–7.09(2H,m),6.71(1H,dd,J= 5.3,3.8 Hz), 5.70–5.50(1H,brm),4.86(2H,s),4.45(2H,d,J=5.3 Hz), 3.80(3H,s),2.45(3H,s),1.98(3H,s)

EI-MS m/e 291(M$^+$)

Reference Example 103

Methyl (3-((acetylamino)methyl)-2-isopropylbenzofuran-7-yloxy)acetate

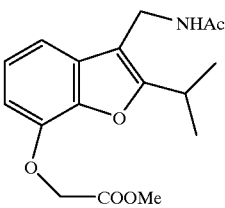

By the method similar to Reference Examples 9 and 101, the desired compound (425 mg, yield: 37%) was obtained from 3-azidomethyl-2-isopropyl-7-methoxybenzofuran (882 mg).

m.p.: 132–133° C. (recrystallized from hexane/chloroform)

IR (KBr method) 3314, 2976, 1742, 1642, 1630, 1593, 1531, 1495, 1470, 1446, 1435, 1371, 1288, 1243, 1201, 1085, 1050, 1023, 996, 725 cm$^{-1}$ NMR (90 MHz CDCl$_3$) δ7.15–7.09(1H,m),6.74(1H,dd,J=5.5,3.7 Hz),5.67(1H,brm), 4.90(2H,s),4.43(2H,d,J=5.1 Hz), 3.81(3H,s),3.27(1H,m), 1.98(3H,s),1.34(3H,d,J=6.8 Hz)

EI-MS m/e 319(M$^+$)

EXAMPLE 1

Methyl (3-((phenoxyacetylamino)methyl)benzofuran-7-yloxy)acetate

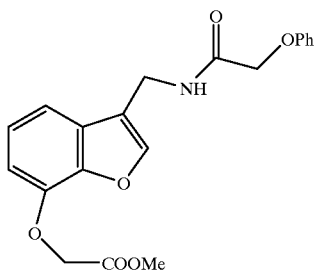

The same procedure as in Reference Example 101 was repeated except that 7-(phenoxyacetoxy)-3-(phenoxyacetylamino)methylbenzofuran (269 mg) was used in place of 7-acetoxy-3-(acetylamino)methylbenzofuran to obtain the desired compound (202 mg, yield: 87%).

m.p.: 101–102° C. (recrystallized from hexane/ethyl acetate)

IR (KBr method) 3266, 3106, 1721, 1659, 1630, 1601, 1591, 1545, 1495, 1450, 1433, 1381, 1365, 1325, 1294, 1270, 1222, 1195, 1178, 1154, 1100, 1096, 1087, 1011, 988, 781, 748, 727, 708, 688, 590 cm$^{-1}$ NMR (90 MHz CDCl$_3$) δ7.57(1H,s),7.30–6.81(8H,m), 4.87(2H,s), 4.65(2H,d,J=5.7 Hz),4.55(2H,s),3.81(3H,s)

EI-MS m/e 369(M$^+$)

EXAMPLE 2

(3-((phenoxyacetylamino)methyl)benzofuran-7-yloxy)acetic acid

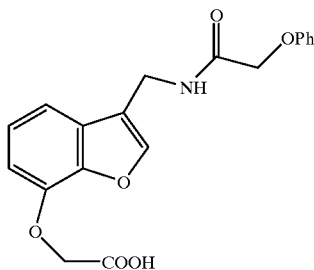

Methyl (3-((phenoxyacetylamino)methyl)benzofuran-7-yloxy)acetate (126 mg) was dissolved in methanol (5 ml) and 1N aqueous sodium hydroxide solution (0.5 ml) was added to the obtained solution, followed by stirring the resulting solution at room temperature for 1 hour. To the reaction solution, 1N hydrochloric acid (1 ml) was added and the solution was poured into water layer (30 ml), followed by extracting the resultant twice with ethyl acetate (20 ml). The organic layers were combined and washed with saturated brine, followed by drying over sodium sulfate. After removing the sodium sulfate by filtration, the solvent was removed under reduced pressure and the residue was recrystallized from cyclohexane/ethyl acetate to obtain the desired compound (108 mg, yield: 89%).

m.p.: 156–157° C.

IR (KBr method) 3412, 3386, 2918, 2760, 2546, 1758, 1742, 1626, 1595, 1551, 1493, 1460, 1439, 1373, 1350, 1278, 1226, 1191, 1151, 1106, 1089, 1058, 1017, 953, 793, 783, 760, 725, 706, 690, 634, 605, 590 cm$^{-1}$ NMR (500 MHz CDCl$_3$) δ7.58(1H,s),7.30–7.24(4H,m), 7.16(1H,t,J=7.9 Hz), 7.01(1H,d,J=7.3 Hz),6.88(1H,d,J=7.9 Hz),6.84(1H,d,J=7.9 Hz), 4.91(2H,s),4.65(2H,d,J=6.1 Hz), 4.56(2H,s),2.01(3H,s)

EI-MS m/e 355(M$^+$)

HR-EI-Ms Calcd. 355.1056 (C$_{19}$H$_{17}$NO$_6$) Found 355.1053 (C$_{19}$H$_{17}$NO$_6$)

Elementary Analysis Calcd. C:64.23% H:4.82% N:3.94% Found C:63.99% H:4.90% N:4.00%

EXAMPLE 3

Methyl (3-(((2-phenoxyethyl)sulfonylamino)methyl)benzofuran-7-yloxy)acetate

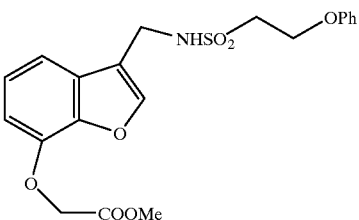

Methyl (3-((acetylamino)methyl)benzofuran-7-yloxy)acetate (224 mg) was dissolved in methanol (4 ml) and hydrogen chloride (2.94N solution in methanol, 0.8 ml) was added thereto, followed by refluxing the resulting solution for 18.5 hours. The reaction solution was poured into water layer (50 ml) and the resultant was extracted twice with ethyl alcohol (20 ml). The organic layers were combined and washed with saturated brine, followed by drying over sodium sulfate. After removing the sodium sulfate by filtration, the solvent was removed under reduced pressure and the residue was dissolved in dichloromethane (5 ml). To this solution, triethylamine (0.23 ml) and 2-phenoxyethylsulfonyl chloride (193 mg) were added and the resulting mixture was stirred at room temperature for 1 hour. The reaction solution was poured into water layer (50 ml) and the resultant was extracted twice with ethyl acetate (20 ml). The organic layers were combined and washed with 1N hydrochloric acid and with saturated brine, followed by drying over sodium sulfate. After removing the sodium sulfate by filtration, the solvent was removed under reduced pressure and the residue was purified by column chromatography (solvent: chloroform/methanol=95/5) using silica gel to obtain the desired compound (85 mg, yield: 25%).

m.p.: 83–84° C. (recrystallized from hexane/ethyl acetate)

IR (KBr method) 3296, 1736, 1601, 1499, 1435, 1394, 1352, 1317, 1296, 1282, 1245, 1187, 1137, 1110, 1081, 1040, 1000, 857, 785, 752, 731, 694, 567 cm$^{-1}$ NMR (90 MHz CDCl$_3$) δ7.57(1H,s),7.30–6.81(8H,m), 4.87(2H,s), 4.65(2H,d,J=5.7 Hz),4.55(2H,s),3.81(3H,s)

EI-MS m/e 419(M$^+$)

EXAMPLE 4

3-(((2-phenoxyethyl)sulfonylamino)methyl)benzofuran-7-yloxy)acetic acid

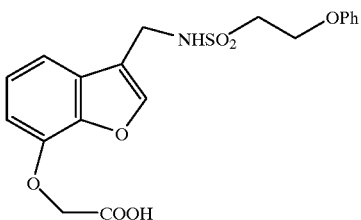

Methyl 3-(((2-phenoxyethyl)sulfonylamino)methyl)benzofuran-7-yloxy)acetate (84 mg) was dissolved in methanol (2.5 ml) and 2N aqueous sodium hydroxide solution (0.2 ml) was added to the obtained solution, followed by stirring the solution at room temperature for 2 hours. To the reaction solution, 1N hydrochloric acid (0.5 ml) was added and the resulting solution was poured into water layer (30 ml), followed by extracting the resultant twice with ethyl acetate (20 ml). The organic layers were combined and washed with saturated brine, followed by drying over sodium sulfate. After removing the sodium sulfate by filtration, the solvent was removed under reduced pressure and the residue was recrystallized from cyclohexane/ethyl acetate to obtain the desired compound (72 mg, yield: 89%).

m.p.: 135–136° C.

IR (KBr method) 3276, 2926, 1736, 1711, 1630, 1601, 1589, 1495, 1475, 1460, 1429, 1398, 1354, 1317, 1267, 1245, 1191, 1156, 1131, 1106, 1062, 959, 783, 752, 729, 690, 542, 505 cm$^{-1}$ NMR (500 MHz DMSO-d$_6$) δ7.93(1H,s),7.76(1H,t,J=6.4 Hz),7.35–7.28(3H,m), 7.15(1H,t,J=7.8 Hz),6.96(1H,t,J=7.3 Hz),6.92(2H,d,J=7.8 Hz), 6.85(1H,d,J=7.8 Hz),4.85(2H,s), 4.32–4.27(4H,m), 3.54(2H,t,J=6.3 Hz)

EI-MS m/e 405(M$^+$)

HR-EI-Ms Calcd. 405.0882 (C$_{19}$H$_{17}$NO$_7$S) Found 405.0909 (C$_{19}$H$_{17}$NO$_7$S)

EXAMPLE 5

Methyl (3-((phenylsulfonylamino)methyl)benzofuran-7-yloxy)acetate

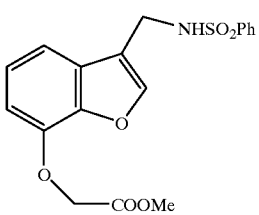

By the method similar to Example 3, the desired compound (119 mg, yield: 52%) was obtained from methyl (3-((phenoxyacetylamino)methyl)benzofuran-7-yloxy)acetate (224 mg).

m.p.: 154–155° C. (recrystallized from cyclohexane/ethyl acetate)

IR (KBr method) 3264, 3116, 1763, 1630, 1586, 1493, 1448, 1433, 1394, 1363, 1323, 1294, 1272, 1226, 1189, 1158, 1096, 1067, 951, 748, 717, 683, 632, 580, 559, 518 cm$^{-1}$ NMR (90 MHz CDCl$_3$) δ7.92–6.72(9H,m),4.85(2H,s), 4.27(2H,brm),3.80(3H,s)

EI-MS m/e 375(M$^+$)

EXAMPLE 6

(3-((phenylsulfonylamino)methyl)benzofuran-7-yloxy)acetic acid

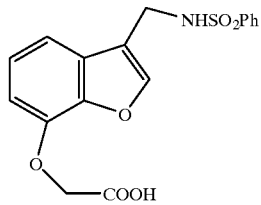

By the method similar to Example 4, the desired compound (73 mg, yield: 83%) was obtained from methyl (3-((phenylsulfonylamino)methyl)benzofuran-7-yloxy)acetate (91 mg).

m.p.: 229–231° C. (recrystallized from ethanol)

IR (KBr method) 3296, 3266, 3116, 2926, 1742, 1709, 1589, 1493, 1448, 1425, 1361, 1321, 1294, 1253, 1199, 1154, 1094, 1052, 957, 855, 785, 746, 721, 683, 667, 632, 580 cm$^{-1}$ NMR (400 MHz DMSO-d$_6$) δ13.06(1H,brm),8.12(1H,t, J=5.9 Hz),7.83–7.54(6H,m), 7.19(1H,d,J=7.4 Hz),7.11(1H, t,J=7.8 Hz),6.83(1H,d,J=7.8 Hz), 4.83(2H,s),4.09(2H,d,J=7.3 Hz)

EI-MS m/e 361(M$^+$)

HR-EI-Ms Calcd. 361.0620 (C$_{17}$H$_{15}$NO$_6$S) Found 361.0640 (C$_{17}$H$_{15}$NO$_6$S)

Elementary Analysis Calcd. C:56.52% H:4.18% N:3.88% S:8.85% Found C:56.48% H:4.30% N:3.97% S:8.80%

EXAMPLE 7

(3-((benzylsulfonylamino)methyl)benzofuran-7-yloxy)acetic acid

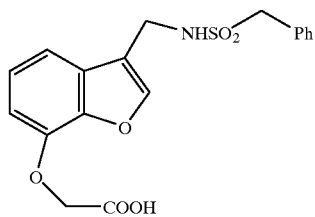

To 1N hydrochloric acid (10 ml), methyl (3-acetylaminomethylbenzofuran-7-yloxy)acetate (145 mg) was added and the obtained mixture was heated to reflux for 5 hours. To the reaction mixture, 2N aqueous sodium hydroxide solution (5 ml) was added to neutralize the mixture, and potassium carbonate (1.46 g) and benzylsulfonyl chloride (1.48 g) were added to the mixture, followed by stirring the resultant at 80° C. for one day and night. To the resulting mixture, 1N hydrochloric acid was added to neutralize the mixture and the resultant was extracted with ethyl acetate (3×20 ml). The organic layers were washed with saturated brine and dried over sodium sulfate. After removing solids by filtration, the solvent was removed under reduced pressure and the obtained solids were purified by recrystallization (ethyl acetate/n-hexane) to obtain the desired compound (85 mg, yield: 43%).

m.p.: 191–192° C.

IR (KBr method) 3248, 1736, 1495, 1429, 1309, 1267, 1125, 1060, 780, 696 cm$^{-1}$ NMR (400 MHz CDCl$_3$) δ(ppm) 13.06(1H,brs)0.8.31 (1H,s)0.7.65(1H,t,J=6.1 Hz), 7.35(5H,s),7.32(1H,d,J=7.8 Hz),7.16(1H,t,J=7.8 Hz), 6.86(1H,d,J=7.8 Hz),4.86(2H,s), 4.36(2H,s), 4.20 (2H,d,J=5.4 Hz)

Mass(m/e) 375(M$^+$)

EXAMPLE 8

(3-(((2-phenylethyl)sulfonylamino)methyl) benzofuran-7-yloxy)acetic acid

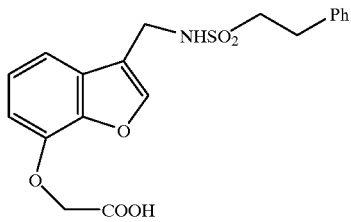

By the method similar to Example 4, the desired compound (73 mg, yield: 83%) was obtained from methyl (3-(((2-phenylethyl)sulfonylamino)methyl)benzofuran-7-yloxy)acetate (91 mg) which can be obtained by the method similar to Example 3.

m.p.: 159–160° C. (recrystallized from hexane/ethyl acetate/methanol)

IR (KBr method) 3286, 3112, 2918, 1740, 1705, 1626, 1586, 1493, 1458, 1431, 1361, 1315, 1294, 1249, 1191, 1156, 1133, 1110, 1094, 1056, 955, 903, 870, 785, 764, 739, 725, 690, 598 cm$^{-1}$ NMR (400 MHz CDCl$_3$) δ7.65(1H,s),7.39(1H,d,J=7.8 Hz),7.25–7.16(1H,m), 7.08(1H,brt,J=5.4 Hz),6.93(2H,d,J=7.3 Hz), 6.83(1H,d,J=7.8 Hz),4.82(2H,s),4.36(2H,d,J=5.4 Hz), 3.14–3.10(2H,m),3.00–2.96(2H,m)

EI-MS m/e 389(M$^+$)

Elementary Analysis Calcd. C:58.62% H:4.92% N:3.94% S:8.21% Found C:58.50% H:5.21% N:3.60% S:8.19%

EXAMPLE 9

(3-((3-phenylpropylsulfonylamino)methyl) benzofuran- 7-yloxy)acetic acid

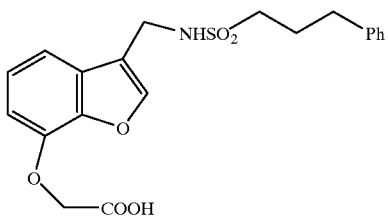

The same procedure as in Example 7 was repeated except that 3-phenylpropanesulfonyl chloride was used in place of benzylsulfonyl chloride to obtain the desired compound (341 mg, yield: 58%) from methyl (3-((acetylamino)methyl) benzofuran-7-yloxy)acetate (401 mg).

m.p.: 135–138° C. (recrystallized from hexane/ethyl acetate)

IR (KBr method) 3284, 1746, 1628, 1593, 1495, 1429, 1313, 1265, 1129, 1060, 702 cm$^{-1}$ NMR (400 MHz CDCl$_3$) δ(ppm) 13.08(1H,brs),7.90(1H, s),7.63(1H,t,J=6.1 Hz), 7.40–7.00(6H,m)0.6.87(1H,d,J=7.8 Hz),4.86(2H,s), 4.23(1H,d,J=5.8 Hz),3.00–2.90(2H,m),2.56 (2H,t,J=7.8 Hz), 1.90–1.80(2H,m)

Mass(m/e) 403(M$^+$)

EXAMPLE 10

(3-((4-phenylbutylsulfonylamino)methyl) benzofuran-7-yloxy)acetic acid

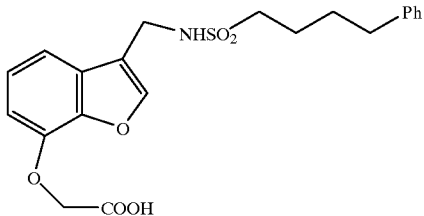

The same procedure as in Example 7 was repeated except that 4-phenylbutanesulfonyl chloride was used in place of benzylsulfonyl chloride to obtain the desired compound (425 mg, yield: 71%) from methyl (3-acetylaminomethylbenzofuran-7-yloxy)acetate (396 mg).

m.p.: 153–154° C. (recrystallized from hexane/ethyl acetate)

IR (KBr method) 3274, 1736, 1497, 1429, 1315, 1267, 1139, 1058, 727, 698 cm$^{-1}$ NMR (400 MHz CDCl$_3$) δ(ppm) 13.07(1H,brs),7.90(1H, s),7.60(1H,t,J=5.9 Hz), 7.40–7.10(6H,m),6.87(1H,d,J=7.8 Hz),4.84(2H,s), 4.24(2H,d,J=5.9 Hz),3.00–2.90(2H,m), 2.50–2.40(2H,m), 1.70–1.50(4H,m)

Mass(m/e) 417(M$^+$)

EXAMPLE 11

Methyl (3-((5-phenylpentylsulfonylamino)methyl)benzofuran-7-yloxy)acetate

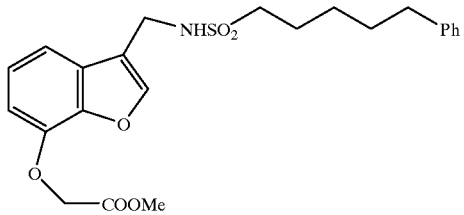

To methyl (3-((acetylamino)methyl)benzofuran-7-yloxy)acetate (298 mg) in methanol (15 ml), trifluoromethanesulfonic acid (0.20 ml) was added and the obtained mixture was heated to reflux overnight. After removing the solvent under reduced pressure, water (10 ml) and 1N aqueous sodium hydroxide solution were added to adjust the pH to 9, and the resultant was extracted with ethyl acetate (3×20 ml). The obtained organic layers were washed with saturated brine and dried over sodium sulfate. Solids were removed by filtration and the solvent was removed under reduced pressure. The obtained oil was transferred to a reaction vessel in which the atmosphere had been replaced with argon, and methylene chloride (10 ml) was added, followed by stirring the resulting mixture at room temperature. To the resultant, triethylamine (0.40 ml) and 5-phenylpentanesulfonyl chloride (607 mg) were added and the resultant was stirred at room temperature for 5 hours. Water (10 ml) was added to stop the reaction, and the resultant was extracted with ethyl acetate (3×10 ml). The obtained organic layers were washed with saturated brine and dried over sodium sulfate. After removing solids by filtration, the solvent was removed under reduced pressure and the obtained crude product was purified by silica gel column chromatography to obtain solids (340 mg). The obtained solids were purified by recrystallization to obtain the desired compound (301 mg, yield: 63%).

m.p.: 84.5–85.5° C. (recrystallized from ethyl acetate/hexane)

IR (KBr method) 3254, 1767, 1742, 1495, 1437, 1319, 1284, 1183, 1154, 1135, 1040, 785, 731 cm$^{-1}$ NMR (400 MHz CDCl$_3$) δ(ppm) 7.63(1H,s),7.40–7.02 (8H m),6.90–6.70(1H,m), 4.85(2H,s),4.42(2H,s)0.3.81(3H, s),3.05–2.82(2H,m), 2.70–2.45(2H,m),2.00–1.10(6H,m)

Mass(m/e) 445(M$^+$)

EXAMPLE 12

(3-((5-phenylpentylsulfonylamino)methyl)benzofuran-7-yloxy)acetic acid

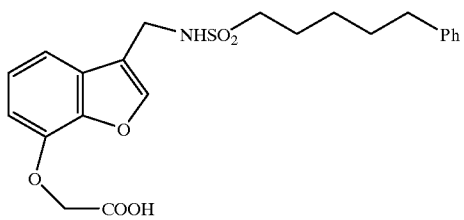

By the method similar to Example 4, the desired compound (168 mg, yield: 87%) was obtained from methyl (3-((5-phenylpentylsulfonylamino)methyl)benzofuran-7-yloxy)acetate (199 mg).

m.p.: 134–135° C. (recrystallized from ethyl acetate/hexane)

IR (KBr method) 3280, 2924, 1713, 1495, 1429, 1301, 1267, 1135, 1056, 727, 696 cm$^{-1}$ NMR (400 MHz CDCl$_3$) δ(ppm) 13.07(1H,brs),7.91(1H, s),7.57(1H,t,J=6.1 Hz), 7.40–7.10(7H,m),6.86(1H,d,J=7.8 Hz),4.84(0.2H,s), 4.24(2H,d,J=5.9 Hz),3.00–2.90(2H,m), 1.70–1.40(4H,m), 1.30–1.20(2H,m)

Mass(m/e) 431(M$^+$)

EXAMPLE 13

(3-(2-methylsulfonylamino)methyl)benzofuran-7-yloxy)acetic acid

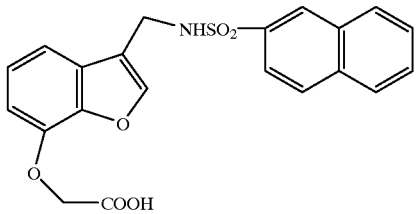

By the method similar to Example 4, the desired compound (143 mg, yield: 82%) was obtained from methyl (3-((2-naphthylsulfonylamino)methyl)benzofuran-7-yloxy)acetate (180 mg) which can be obtained by using 2-naphthalenesulfonyl chloride in place of phenoxyethylsulfonyl chloride in the method of Example 3.

m.p.: 204–206° C. (recrystallized from hexane/chloroform/methanol)

IR (KBr method) 3262, 3114, 1742, 1707, 1628, 1589, 1493, 1435, 1363, 1319, 1253, 1189, 1154, 1131, 1102, 1077, 1056, 957, 866, 785, 743, 727, 661, 547 cm$^{-1}$ NMR (500 MHz DMSO-d$_6$) δ8.45(1H,s),8.21(1H,t,J=5.8 Hz),8.13–8.02(3H,m), 7.83(1H,dd,J=8.3, 1.5 Hz),7.78(1H, m),7.72–7.64(2H,m), 7.19(1H,d,J=7.8 Hz),7.07(1H,t,J=7.8 Hz),6.78(1H,d,J=7.8 Hz), 4.78(2H,s),4.13(2H,d,J=5.9 Hz)

EI-MS m/e 411(M+)

HR-EI-Ms Calcd. 411.0777 (C$_{21}$H$_{17}$NO$_6$S) Found 411.0795 (C$_{21}$H$_{17}$NO$_6$S)

Elementary Analysis Calcd. C:61.32% H:4.17% N:3.40% S:7.77% Found C:61.24% H:4.23% N:3.40% S:7.75%

EXAMPLE 14

(3-((benzylsulfonylamino)methyl)-2-methylbenzofuran-7-yloxy)acetate

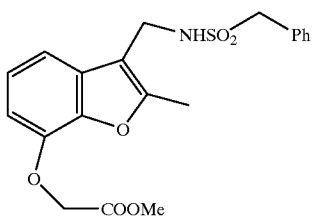

By the method similar to Example 3, the desired compound (196 mg, yield: 27%) was obtained from methyl (3-((acetylamino)methyl)-2-methylbenzofuran-7-yloxy)acetate (488 mg) and benzylsulfonyl chloride.

m.p.: 96–98° C. (recrystallized from hexane/ethyl acetate)

IR (KBr method) 3290, 1717, 1630, 1495, 1450, 1435, 1317, 1272, 1205, 1133, 1104, 1056, 1007, 961, 853, 781, 745, 729, 696, 607, 592, 542, 524 cm$^{-1}$ NMR (90 MHz CDCl$_3$) δ7.37–6.72(8H,m),4.86(2H,s), 4.22–4.17(4H,m), 3.80(3H,s),2.43(3H,s)

EI-MS m/e 403(M$^+$)

EXAMPLE 15

Methyl (3-((benzylsulfonylamino)methyl)-2-methylbenzofuran-7-yloxy)acetic acid

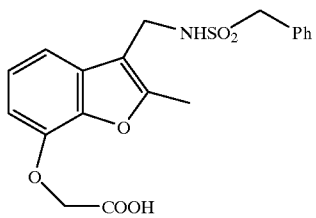

By the method similar to Example 4, the desired compound (175 mg, yield: 93%) was obtained from methyl (3-((benzylsulfonylamino)methyl)-2-methylbenzofuran-7-yloxy)acetate (195 mg).

m.p.: 181–183° C. (recrystallized from cyclohexane/ethyl acetate)

IR (KBr method) 3250, 2928, 1738, 1715, 1638, 1630, 1593, 1495, 1433, 1367, 1342, 1319, 1267, 1209, 1162, 1129, 1112, 1050, 965, 936, 781, 733, 698, 600, 547 cm$^{-1}$ NMR (400 MHz CDCl$_3$) δ7.55–7.26(4H,m),7.23(1H,dd, J=7.3, 1.5 Hz), 7.18(1H,dd,J=7.8,0.9 Hz),7.11(1H,t,J=7.8 Hz), 6.74(1H,d,J=7.3 Hz),5.51(1H,t,J=5.3 Hz),4.81(2H,s), 4.17(2H,d,J=5.4 Hz),4.13(2H,s),2.43(3H,s)

EI-MS m/e 389(M$^+$)

Elementary Analysis Calcd. C:58.62% H:4.92% N:3.60% S:8.21% Found C:58.45% H:4.82% N:3.63% S:8.22%

EXAMPLE 16

(3-(((2-phenylethyl)sulfonylamino)methyl)-2-methylbenzofuran-7-yloxy)acetic acid

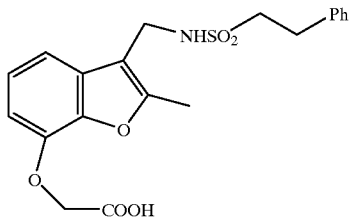

By the method similar to Example 4, the desired compound (121 mg, yield: 91%) was obtained from methyl (3-(((2-phenylethyl)sulfonylamino)methyl)-2-methylbenzofuran-7-yloxy)acetate (137 mg) which can be obtained by using 2-phenylethanesulfonyl chloride in place of phenoxyethylsulfonyl chloride in the method of Example 3.

m.p.: 149–150° C. (recrystallized from hexane/ethyl acetate)

IR (KBr method) 3246, 3064, 2926, 1752, 1711, 1630, 1589, 1493, 1435, 1367, 1342, 1311, 1288, 1251, 1212, 1180, 1127, 1108, 1044, 967, 926, 783, 731, 698, 596, 520 cm$^{-1}$ NMR (400 MHz CDCl$_3$) δ7.28–7.19(4H,m),7.15(1H,t,J= 7.8 Hz), 6.94(2H,d,J=6.4 Hz),6.77(1H,d,J=7.8 Hz),4.90(2H, s), 4.32(1H,m),4.28(2H,d,J=5.3 Hz),3.15, 2.97(each1H, ABq,J=8.8 Hz),3.13,3.00(each1H,ABq,J=4.9 Hz), 2.44(3H, s)

EI-MS m/e 403(M$^+$)

HR-EI-Ms Calcd. 403.1090 (C$_{20}$H$_{21}$NO$_6$S) Found 403.1086 (C$_{20}$H$_{21}$NO$_6$S)

Elementary Analysis Calcd. C:59.56% H:5.25% N:3.47% S:7.93% Found C:59.38% H:5.47% N:3.47% S:7.87%

EXAMPLE 17

(3-(((3-phenylpropyl)sulfonylamino)methyl)-2-methylbenzofuran-7-yloxy)acetic acid

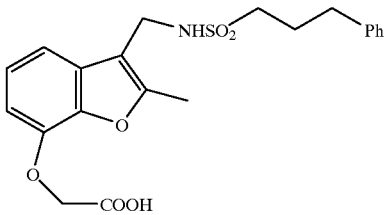

By the method similar to Example 4, the desired compound (176 mg, yield: 92%) was obtained from methyl (3-(((3-phenylpropyl)sulfonylamino)methyl)-2-methylbenzofuran-7-yloxy)acetate (197 mg) which can be obtained by using 3-phenylpropylsulfonyl chloride in place of phenoxyethylsulfonyl chloride in the method of Example 3.

m.p.: 121–122° C. (recrystallized from cyclohexane/chloroform)

IR (KBr method) 3268, 2924, 1750, 1630, 1493, 1460, 1427, 1344, 1317, 1288, 1259, 1241, 1212, 1135, 1110, 1054, 735, 702 cm$^{-1}$ NMR (400 MHz CDCl$_3$) δ7.29–7.11(5H,m),7.04(2H,d,J= 6.8 Hz), 6.75(1H,d,J=7.3 Hz),4.88(2H,s),4.54–4.52(1H,m), 4.28(2H,d,J=5.4 Hz),2.87–2.83(2H,m),2.57(2H,t,J=7.8 Hz), 2.42(3H,s),2.17–1.98(2H,m)

EI-MS m/e 417(M$^+$)

Elementary Analysis Calcd. C:60.44% H:5.55% N:3.36% S:7.66% Found C:60.10% H:5.63% N:3.39% S:7.67%

EXAMPLE 18

Methyl (3-(((2-phenylethyl)sulfonylamino)methyl)-2-isopropylbenzofuran-7-yloxy)acetate

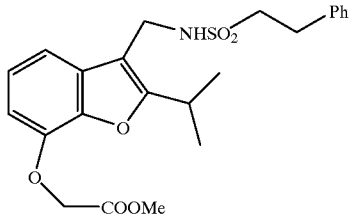

By the method similar to Example 3, the desired compound (217 mg, yield: 60%) was obtained from (3-((acetylamino)methyl)-2-isopropylbenzofuran- 7-yloxy) acetic acid (260 mg).

m.p.: 103–104° C. (recrystallized from hexane/ethyl acetate)

IR (KBr method) 3250, 2974, 1725, 1626, 1510, 1493, 1475, 1458, 1431, 1375, 1342, 1313, 1282, 1212, 1141, 1129, 1093, 1048, 1017, 975, 777, 743, 727, 700, 600, 518 cm$^{-1}$ NMR (400 MHz CDCl$_3$) δ7.28–6.73(8H,m),4.80(2H,s), 4.29(3H,m), 3.80(3H,s),3.32–2.93(4H,m),1.33(6H,d,J=6.8 Hz)

EI-MS m/e 445(M$^+$)

EXAMPLE 19

(3-(((2-phenylethyl)sulfonylamino)methyl)-2-isopropylbenzofuran-7-yloxy)acetic acid

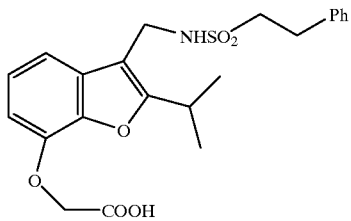

By the method similar to Example 4, the desired compound (171 mg, yield: 83%) was obtained from methyl (3-(((2-phenylethyl)sulfonylamino)methyl)-2-isopropylbenzofuran-7-yloxy)acetate (214 mg).

m.p.: 133–135° C. (recrystallized from hexane/chloroform)

IR (KBr method) 3274, 2978, 2936, 1756, 1626, 1493, 1468, 1458, 1429, 1342, 1311, 1292, 1259, 1216, 1154, 1137, 1100, 1050, 971, 928, 777, 729, 700, 600, 522 cm$^{-1}$ NMR (400 MHz CD$_3$OD) δ7.34(1H,dd,J=7.8,1.0 Hz), 7.20–7.10(4H,m), 6.83(1H,dd,J=7.8,1.0 Hz),6.75–6.73(2H, dd,J=8.3, 1.3 Hz), 4.87(2H,s),4.33(2H,s),3.38–3.33(1H,m), 2.98–2.93(2H,m),2.89–2.80(2H,m),1.34(6H,d,J=6.8 Hz)

EI-MS m/e 431(M$^+$)

HR-EI-Ms Calcd. 431.1403 (C$_{22}$H$_{25}$NO$_6$S) Found 431.1387 (C$_{22}$H$_{25}$NO$_6$S)

Elementary Analysis Calcd. C:61.26% H:5.84% N:3.25% S:7.41% Found C:61.15% H:5.79% N:3.37% S:7.27%

EXAMPLE 20

Methyl (3-(2-(benzylsulfonylamino)ethyl)benzofuran-7-yloxy)acetate

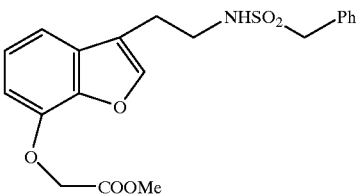

Methyl (3-(2-azidoethyl)benzofuran-7-yloxy)acetate (638 mg) was dissolved in THF-methanol (1:4, 10 ml) and 5% Pd/C (95 mg) was added to the obtained solution, followed by stirring the resulting mixture under hydrogen atmosphere at room temperature for 2 hours. The reaction solution was filtered through Celite and the filtrate was concentrated. The obtained residue was dissolved in THF (8 ml), and triethylamine (2.61 ml) and benzylsulfonyl chloride (885 mg) were added, followed by stirring the resulting mixture at room temperature for 1.5 hours. The reaction solution was poured into water layer (50 ml) and the resultant was extracted twice with ethyl acetate (20 ml). The organic layers were combined and washed with 1N hydrochloric acid and with saturated brine, followed by drying over sodium sulfate. After removing the sodium sulfate by filtration, the solvent was removed under reduced pressure and the residue was purified by column chromatography (solvent: hexane/ethyl acetate=3/2) using silica gel to obtain the desired compound (320 mg, yield: 34%).

IR (liquid film method) 3302, 3036, 2956, 1750, 1628, 1589, 1493, 1458, 1437, 1377, 1359, 1328, 1205, 1152, 1129, 1083, 1048, 924, 785, 733, 700, 605 cm$^{-1}$ NMR (90 MHz CDCl$_3$) δ7.42(1H,s),7.30–7.12(7H,m), 6.79(1H,dd,J=5.1,3.8 Hz), 4.87(2H,s),4.21(2H,s),3.80(3H, s),3.18(2H,m),2.84(2H,m)

EI-MS m/e 403(M$^+$)

EXAMPLE 21

(3-(2-(benzylsulfonylamino)ethyl)benzofuran-7-yloxy)acetic acid

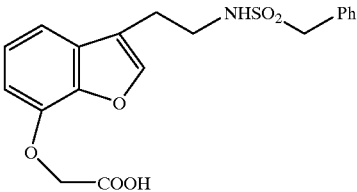

By the method similar to Example 4, the desired compound (110 mg, yield: 74%) was obtained from methyl (3-(2-(benzylsulfonylamino)ethyl)benzofuran-7-yloxy) acetate (153 mg).

m.p.: 132–134° C. (recrystallized from ethanol)

IR (KBr method) 3256, 1738, 1719, 1628, 1589, 1493, 1458, 1431, 1359, 1319, 1265, 1205, 1154, 1125, 1081, 785, 733, 698, 605, 545 cm$^{-1}$ NMR (400 MHz CDCl$_3$) δ7.43(1H,brs),7.31(5H,brs),7.11 (2H,m),6.78(1H,brm), 5.48(1H,brm),4.79(2H,brs),4.20(2H, s), 3.21(2H,dd,J=12.7,6.4 Hz),2.82(2H,brt,J=6.8 Hz)

EI-MS m/e 389(M 4)

HR-EI-Ms Calcd. 389.0933 ($C_{19}H_{19}NO_6S$) Found 389.0914 ($C_{19}H_{19}NO_6S$)

EXAMPLE 22

Methyl (3-(2-(benzylsulfonyl-N-benzyl-amino)ethyl)benzofuran-7-yloxy)acetate

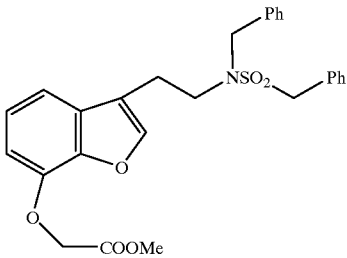

Methyl (3-(2-(benzylsulfonylamino)ethyl)benzofuran-7-yloxy)acetate (143 mg) was dissolved in DMF (3 ml), and potassium carbonate (49 mg) and benzyl bromide (0.13 ml) were added to the obtained solution, followed by stirring the resulting mixture at room temperature for 27 hours and then at 50° C. for 14.5 hours. The reaction solution was poured into water layer (50 ml) and the resultant was extracted twice with ethyl acetate (20 ml). The organic layers were combined and washed with 1N hydrochloric acid and with saturated brine, followed by drying over sodium sulfate. After removing the sodium sulfate by filtration, the solvent was removed under reduced pressure and the residue was purified by column chromatography (solvent: hexane/ethyl acetate=2/1-1/1) using silica gel to obtain the desired compound (100 mg, yield: 57%).

IR (liquid film method) 3034, 2932, 1763, 1736, 1628, 1589, 1508, 1495, 1458, 1437, 1363, 1340, 1296, 1220, 1183, 1151, 1127, 1093, 940, 785, 735, 700 cm$^{-1}$ NMR (90 MHz CDCl$_3$) δ7.42–6.68(14H,m),4.84(2H,s), 4.25(2H,s),4.19(2H,s), 3.79(3H,s),3.32–3.15(2H,m), 2.70–2.52(2H,m)

EXAMPLE 23

(3-(2-(benzylsulfonyl-N-benzyl-amino)ethyl)benzofuran-7-yloxy)acetic acid

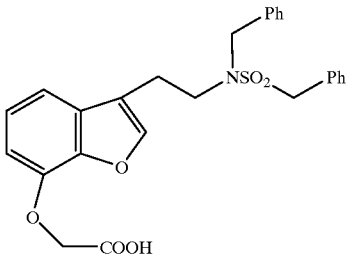

By the method similar to Example 4, the desired compound (103 mg, yield: 82%) was obtained from methyl (3-(2-(benzylsulfonyl-N-benzyl-amino)ethyl)benzofuran-7-yloxy)acetate (130 mg).

m.p.: 155–157° C. (recrystallized from hexane/ethyl acetate)

IR (KBr method) 3130, 3064, 3034, 2954, 2924, 2868, 2788, 1740, 1707, 1628, 1584, 1493, 1456, 1435, 1425, 1408, 1357, 1330, 1296, 1257, 1230, 1197, 1147, 1135, 1122, 1093, 1065, 996, 957, 940, 920, 882, 806785, 737, 702, 603, 542 cm$^{-1}$ NMR (400 MHz CDCl$_3$) δ7.37–7.30(10H,m),7.06(1H,t, J=7.8 Hz), 6.87(1H,d,J=7.8 Hz),6.74(1H,d,J=8.4 Hz),4.77 (2H,s), 4.25(2H,s),4.18(2H,s),3.23(2H,m),2.60(2H,m)

EI-MS m/e 479(M$^+$)

HR-EI-Ms Calcd. 479.1403 ($C_{26}H_{25}NO_6$) Found 479.1425 ($C_{26}H_{25}NO_6$)

Elementary Analysis Calcd. C:65.14% H:5.26% N:2.92% S:6.67% Found C:64.85% H:5.31% N:3.11% S:6.73%

EXAMPLE 24

(3-(2-(benzylsulfonylamino)ethyl)-2-methylbenzofuran-7-yloxy)acetic acid

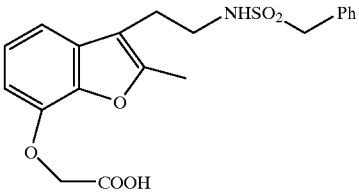

By the method similar to Example 4, the desired compound (104 mg, yield: 86%) was obtained from methyl (3-(2-(benzylsulfonylamino)ethyl)-2-methylbenzofuran-7-yloxy)acetate (125 mg) which is obtained by the method similar to Example 20 from methyl (3-(2-azidoethyl)-2-methylbenzofuran-7-yloxy)acetate.

m.p.: 130–132° C. (recrystallized from chloroform)

IR (KBr method) 3244, 3034, 2980,2042, 1723, 1638, 1628, 1495, 1448, 1323, 1272, 1199, 1172, 1154, 1131, 1112, 1075, 791, 739, 729, 69645 cm$^{-1}$ NMR (400 MHz CD$_3$OD) δ7.34–7.31(5H,m),7.10–7.04 (2H,m), 6.75(1H,dd,J=6.8,3.4 Hz),4.84(2H,s),4.25(2H,s), 3.09(2H,t,J=6.8 Hz),2.76(2H,t,J=7.3 Hz),2.38(3H,s)

EI-MS m/e 403(M$^+$)

HR-EI-Ms Calcd. 403.1090 ($C_{20}H_{21}NO_6$) Found 403.1096 ($C_{20}H_{21}NO_6$)

Elementary Analysis Calcd. C:59.57% H:5.25% N:3.47% S:7.93% Found C:59.21% H:5.26% N:3.57% S:7.61%

EXAMPLE 25

(3-(2-(2-phenylethylsulfonylamino)ethyl)-2-methylbenzofuran-7-yloxy)acetic acid

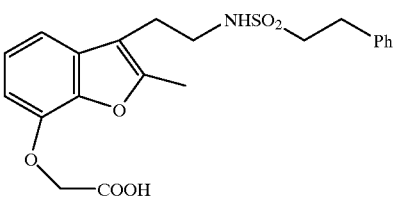

By the method similar to Example 4, the desired compound (130 mg, yield: 86%) was obtained from methyl (3-(2-(2-phenylsulfonylamino)ethyl)-2-methylbenzofuran-7-yloxy)acetate (156 mg) which is obtained by the method similar to Example 20 from methyl (3-(2-azidoethyl)-2-methylbenzofuran-7-yloxy)acetate.

m.p.: 88–90° C. (recrystallized from cyclohexane/chloroform)

IR (KBr method) 3570, 3286, 2926, 1744, 1709, 1638, 1626, 1591, 1493, 1433, 1315, 1263, 1205, 1152, 1131, 1114, 1075, 779, 733, 700 cm$^{-1}$ NMR (400 MHz CDCl$_3$) δ7.24–7.05(7H,m),6.72(1H,d,J=7.8 Hz),4.86(2H,s), 4.13(1 Hrm),3.27–3.19(4H,m),3.02(2H, m), 2.80(2H,t,J=6.9 Hz),2.41(3H,s)

EI-MS m/e 417(M$^+$)

HR-EI-Ms Calcd. 417.1246 (C$_{21}$H$_{23}$NO$_6$) Found 417.1227 (C$_{21}$H$_{23}$NO$_6$)

EXAMPLE 26

(3-(2-((2,2-diphenylethyl)sulfonylamino)ethyl) benzofuran-7-yloxy)acetic acid

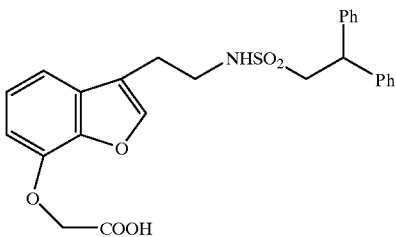

By the method similar to Example 4, the desired compound (153 mg, yield: 70%) was obtained from methyl (3-(2-((2,2-diphenylethyl)sulfonylamino)ethyl)benzofuran-7-yloxy)acetate (225 mg) which is obtained by the method similar to Example 20 from methyl (3-(2-azidoethyl)benzofuran-7-yloxy)acetate.

m.p.: 134–136° C. (recrystallized from hexane/chloroform)

IR (KBr method) 3328, 3030, 2924, 1742, 1628, 1586, 1493, 1454, 1423, 1357, 1323, 1267, 1187, 1137, 1094, 785, 737, 706 cm$^{-1}$ NMR (300 MHz CDCl$_3$) δ7.32(1H,s),7.23–7.06(12H,m), 6.83)1H,dd,J=7.8,0.8 Hz), 4.93(2H,s),4.55(1H,t,J=7.4 Hz), 3.74(2H,d,J=7.4 Hz), 3.37(1H,t,J=6.5 Hz),2.94(2H,q,J=6.6 Hz),2.61(2H,t,J=6.6 Hz)

EI-MS m/e 479(M$^+$)

Elementary Analysis Calcd. C:65.12% H:5.26% N:2.92% S:6.69% Found C:64.55% H:5.26% N:3.21% S:6.55%

EXAMPLE 27

(3-(2-((3,3-diphenylpropyl)sulfonylamino)ethyl) benzofuran-7-yloxy)acetic acid

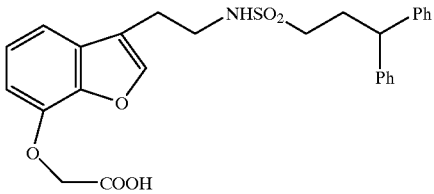

By the method similar to Example 4, the desired compound (172 mg, yield: 84%) was obtained from methyl (3-(2-((3,3-diphenylpropyl)sulfonylamino)ethyl) benzofuran-7-yloxy)acetate (210 mg) which is obtained by the method similar to Example 20 from methyl (3-(2-azidoethyl)benzofuran-7-yloxy)acetate.

m.p.: 95–97° C. (recrystallized from hexane/chloroform)

IR (KBr method) 3280, 3062, 3030, 2930, 1738, 1628, 1586, 1493, 1454, 1425, 1359, 1319, 1263, 1207, 1185, 1149, 1091, 785, 748, 704, 542 cm$^{-1}$ NMR (300 MHz CDCl$_3$) δ7.38(1H,s),7.32–7.12(12H,m), 6.80(1H,dd,J=6.8,2.3 Hz), 4.88(2H,s),4.41(1H,t,J=6.6 Hz), 3.93(1H,t,J=8.0 Hz), 3.34(2H,q,J=6.5 Hz),2.94–2.86(4H, m),2.51–2.43(2H,m)

EI-MS m/e 493(M$^+$)

Elementary Analysis Calcd. C:65.70% H:5.51% N:2.84% S:6.50% Found C:65.56% H:5.53% N:2.70% S:6.50%

EXAMPLE 28

Methyl (3-(2-(2-phenylethylthio)ethyl)-2-methylbenzofuran-7-yloxy)acetate

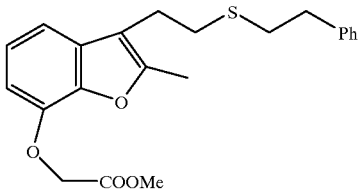

2-phenylethanethiol (0.42 ml) was dissolved in DMF (5 ml) and sodium hydride (60%, 132 mg) was added to the obtained solution, followed by stirring the resulting mixture at room temperature for 40 minutes. To this reaction solution, a solution of methyl 3-(2-bromoethyl)-2-methyl-benzofuran-7-yloxyacetate (900 mg) in DMF (8 ml) was added dropwise and the resulting solution was stirred for 30 minutes. Acetic acid (0.5 ml) was added to the reaction solution and the solution was poured into water layer (100 ml), followed by extraction of the resultant twice with ethyl acetate (30 ml). The organic layers were combined and washed with saturated brine, followed by drying over sodium sulfate. After removing the sodium sulfate by filtration, the solvent was removed under reduced pressure and the residue was purified by column chromatography (solvent: cyclohexane/ethyl acetate=3/1) using silica gel to obtain the desired compound (1.03 g, yield: 98%).

IR (liquid film method) 3030, 2954, 2922, 1763, 1742, 1626, 1591, 1508, 1491437, 1290, 1203, 1100, 731, 698 cm$^{-1}$ NMR (90 MHz CDCl$_3$) δ7.28–7.05(7H,m),6.69(1H,dd,J=5.3,3.8 Hz),4.87(2H,s), 3.80(3H,s),3.02–2.77(6H,m),2.41 (3H,s)

EI-MS m/e 384(M$^+$)

EXAMPLE 29

Methyl (3-(2-(2-phenylethylsulfinyl)ethyl)-2-methylbenzofuran-7-yloxy)acetate

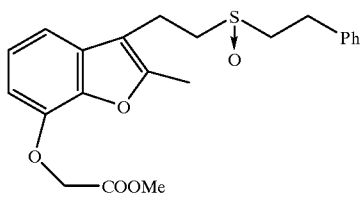

Methyl (3-(2-(2-phenylethylthio)ethyl)-2-methylbenzofuran-7-yloxy)acetate (340 mg) was dissolved in methanol (15 ml) and the obtained solution was cooled to −10° C. To this solution, NBS (190 mg) was added for 5 minutes and the resulting mixture was stirred at −10° C. for 30 minutes. This reaction solution was poured into water layer (100 ml) and the resultant was extracted twice with ethyl acetate (30 ml). The organic layers were combined and washed with saturated brine, followed by drying over sodium sulfate. After removing the sodium sulfate by filtration, the solvent was removed under reduced pressure and the residue was purified by column chromatography (solvent: dichloromethane/ethyl acetate=2/1) using silica gel to obtain the desired compound (225 mg, yield: 64%).

m.p.: 77–78° C. (recrystallized from cyclohexane/ethyl acetate)

IR (KBr method) 2922, 1734, 1632, 1589, 1495, 1450, 1437, 1383, 1371, 1303, 1267, 1214, 1180, 1156, 1093, 1065, 1044, 1025, 1009, 971, 864, 791, 766, 725, 706, 694 cm$^{-1}$ NMR (90 MHz CDCl$_3$) δ7.45–6.64(8H,m),4.87(2H,s), 3.81(3H,s), 3.24–2.79(8H,m),2.45(3H,s)

CI-MS m/e 401(M+H)$^+$

EXAMPLE 30

Methyl (3-(2-(2-phenylethylsulfonyl)ethyl)-2-methylbenzofuran-7-yloxy)acetate

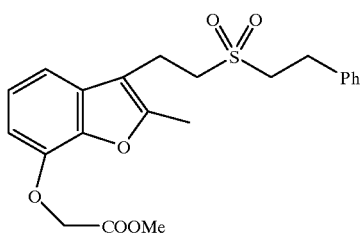

Methyl (3-(2-(2-phenylethylthio)ethyl-2-methylbenzofuran-7-yloxy)acetate (248 mg) was dissolved in dichloromethane (7 ml) and the obtained solution was cooled to 0° C. To this solution, m-chloroperbenzoic acid (350 mg) was added and the resulting solution was stirred at 0° C. for 30 minutes. To this reaction solution, saturated aqueous sodium thiosulfate solution was added and the resulting solution was poured into water layer (50 ml), followed by extraction twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=3/2) using silica gel to obtain the desired compound (248 mg, yield: 88%).

m.p.: 91–92° C. (recrystallized from hexane/ethyl acetate)

IR (KBr method) 1750, 1719, 1702, 1630, 1591, 1510, 1493, 1450, 1315, 1292, 1276, 1253, 1226, 1210, 1125, 1100, 779, 725, 694, 613, 528, 511 cm$^{-1}$ NMR (90 MHz CDCl$_3$) δ7.31–6.63(8H,m),4.86(2H,s), 3.81(3H,s), 3.15–3.11(8H,m)2.42(3H,s)

EI-MS m/e 416(M$^+$)

EXAMPLE 31

(3-(2-(2-phenylethylthio)ethyl)-2-methylbenzofuran-7-yloxy)acetic acid

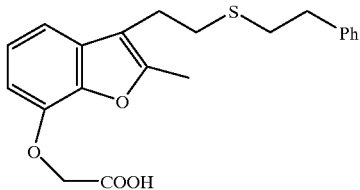

By the method similar to Example 4, the desired compound (141 mg, yield: 88%) was obtained from methyl (3-(2-(2-phenylethylthio)ethyl)-2-methylbenzofuran-7-yloxy)acetate (166 mg).

m.p.: 97–98° C. (recrystallized from cyclohexane/ethyl acetate)

IR (KBr method) 3030, 2930, 1719, 1707, 1636, 1624, 1589, 1288, 1265, 1234, 1201, 1174, 1110, 777, 729, 696 cm$^{-1}$ NMR (500 MHz CDCl$_3$) δ7.31–7.08(7H,m),6.75–6.70 (1H,m),4.92(2H,s), 2.88–2.75(8H,m),2.40(3H,s)

EI-MS m/e 370(M$^+$)

HR-EI-Ms Calcd. 370.1239 (C$_{21}$H$_{22}$O$_4$S) Found 370.1220 (C$_{21}$H$_{22}$O$_4$S)

Elementary Analysis Calcd. C:68.11% H:5.99% S:8.63% Found C:67.68% H:5.92% S:8.65%

EXAMPLE 32

(3-(2-(2-phenylethylsulfinyl)ethyl)-2-methylbenzofuran-7-yloxy)acetic acid

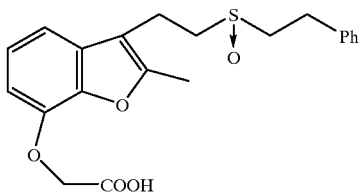

By the method similar to Example 4, the desired compound (188 mg, yield: 89%) was obtained from methyl (3-(2-(2-phenylethylsulfinyl)ethyl)-2-methylbenzofuran-7-yloxy)acetate (220 mg).

m.p.: 139–141° C. (recrystallized from hexane/ethyl acetate)

IR (KBr method) 3054, 2922, 2856,2498, 1734, 1628, 1591, 1495, 1446, 1288, 1261, 1197, 1093, 996, 963, 934, 874, 777, 727, 706 cm$^{-1}$ NMR (400 MHz CDCl₃) δ7.31–7.17(5H,m),7.04–7.00(2H,m),6.74–6.70(1H,m), 4.88(2H,s),3.15–3.01(6H,m),2.92–2.84(2H,m),2.36(3H,s)

FAB-MS m/e 387(M+H)⁺

HR-FAB-Ms Calcd. 387.1308 (C₂₁H₂₃O₅S) Found 387.1287 (C₂₁H₂₃O₅S)

Elementary Analysis Calcd. C:65.29% H:5.74% S:8.28% Found C:65.12% H:5.74% S:8.27%

EXAMPLE 33

(3-(2-(2-phenylethylsulfonyl)ethyl)-2-methylbenzofuran-7-yloxy)acetic acid

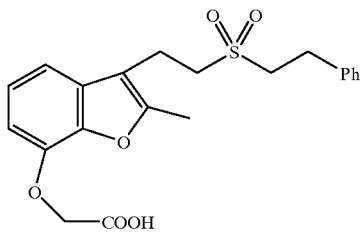

By the method similar to Example 4, the desired compound (204 mg, yield: 81%) was obtained from methyl (3-(2-(2-phenylethylsulfonyl)ethyl)-2-methylbenzofuran-7-yloxy)acetate (260 mg).

m.p.: 155–156° C. (recrystallized from isopropanol)

IR (KBr method) 3270, 1760, 1731, 1628, 1593, 1493, 1452, 1431, 1417, 1336, 1313, 1284, 1272, 1251, 1212, 1172, 1137, 1116, 1096, 777, 729, 694, 615, 528, 511, 485 cm⁻¹

NMR (500 MHz DMSO-d₆) δ7.31–7.09(7H,m),6.78(1H,dd,J=6.9,2.4 Hz), 4.82(2H,s),32–3.34(4H,m),3.06–2.96(4H,m),2.41(3H,s)

EI-MS m/e 402(M⁺)

HR-EI-Ms Calcd. 402.1137 (C₂₁H₂₂O₆S) Found 402.1141 (C₂₁H₂₂O₆S)

Elementary Analysis Calcd. C:62.69% H:5.51% S:7.95% Found C:62.34% H:5.49% S:7.99%

EXAMPLE 34

Methyl (3-(2-(diphenylmethyleneaminoxy)ethyl)-2-methylbenzofuran-7-yloxy)acetate

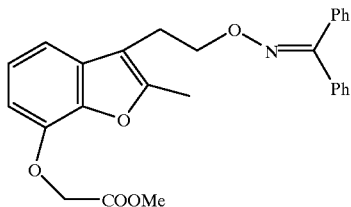

Sodium hydride (60%, 30 mg) was suspended in DMF (1 ml) and a solution of benzophenoneoxime (157 mg) in DMF (2 ml) was added dropwise thereto, followed by stirring the resulting mixture at room temperature for 1 hour. To this solution, a solution of methyl (3-(2-bromoethyl)-2-methylbenzofuran-7-yloxy)acetate (201 mg) in DMF (3 ml) was added dropwise and the solution was stirred at room temperature for 30 minutes. Acetic acid was added to this reaction solution and the resulting solution was added to water layer (50 ml) followed by extraction of the resultant twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=5/1) using silica gel to obtain the desired compound (177 mg, yield: 65%).

IR (liquid film method) 2956, 2926, 2876, 1756, 1622, 1589, 1493, 1446, 1398, 1379, 1350, 1336, 1290, 1274, 1228, 1203, 1170, 1118, 1091, 1071, 1052, 1029, 980, 955, 915, 899, 791, 774, 748, 733, 696, 663, 652, 600 cm⁻¹

NMR (90 MHz CDCl₃) δ7.50–7.02(11H,m),6.67(1H,dd,J=5.3,3.7 Hz),4.87(2H,m), 47(2H,t,J=6.8 Hz),8.80(3H,s),2.99(2H,t,J=6.8 Hz),2.28(3H,s)

EI-MS m/e 443(M⁺)

EXAMPLE 35

(3-(2-(diphenylmethyleneaminoxy)ethyl)-2-methylbenzofuran-7-yloxy)acetic acid

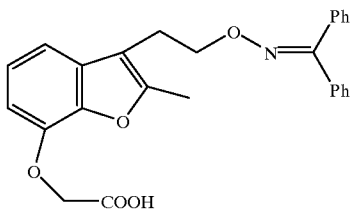

By the method similar to Example 4, the desired compound (159 mg, yield: 82%) was obtained from methyl (3-(2-(diphenylmethyleneaminoxy)ethyl)-2-methylbenzofuran-7-yloxy)acetate (200 mg).

m.p.: 151–152° C. (recrystallized from hexane/ethyl acetate)

IR (KBr method) 3060, 2954, 2936, 2886, 1736, 1711, 1622, 1589, 1493, 1448, 1431, 1365, 1330, 1284, 1245, 1205, 1178, 1116, 1065, 984, 953, 938, 917, 779, 729, 700, 692, 650 cm⁻¹

NMR (400 MHz CDCl₃) δ7.45–7.24(10H,m),7.08(1H,dd,J=8.2,1.5 Hz), 7.04(1H,t,J=7.8 Hz),6.70(1H,dd,J=7.8,1.0 Hz),4.89(2H,s), 4.36(2H,t,J=6.3 Hz),2.99(1H,t,J=6.3 Hz)

EI-MS m/e 429(M⁺)

HR-EI-Ms Calcd. 429.1576 (C₂₆H₂₃NO₅) Found 429.1590 (C₂₆H₂₃NO₅)

Elementary Analysis Calcd. C:72.72% H:5.40% N:3.26% Found C:72.60% H:5.41% N:3.38%

EXAMPLE 36

Methyl (3-((4-phenyloxazole-2-yl)methyl)benzofuran-7-yloxy)acetate

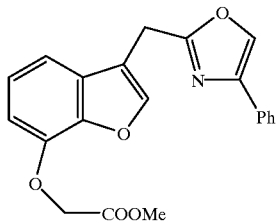

By the method similar to Reference Example 17, the desired compound (250 mg, yield: 83%) was obtained from 7-hydroxy-3-((4-phenyloxazole-2-yl)methyl)benzofuran (242 mg).

m.p.: 95–96° C. (recrystallized from hexane/ethyl acetate)

IR (KBr method) 1729, 1626, 1586, 1562, 1491, 1450, 1435, 1404, 1379, 1309, 1282, 1257, 1195, 1162, 1137, 1114, 1081, 1067, 1011, 959, 942, 864, 818, 777, 770, 731, 704 cm$^{-1}$ NMR (90 MHz CDCl$_3$) δ7.83(1H,s),7.78–6.64(9H,m), 4.88(2H,s), 4.22(2H,d,J=1.0 Hz),3.80(3H,s)

EI-MS m/e 363(M$^+$)

EXAMPLE 37

(3-((4-phenyloxazole-2-yl)methyl)benzofuran-7-yloxy)acetic acid

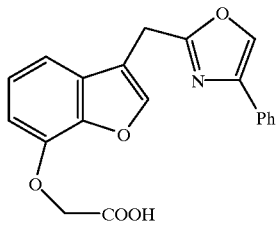

By the method similar to Example 4, the desired compound (209 mg, yield: 90%) was obtained from methyl (3-((4-phenyloxazole-2-yl)methyl)benzofuran-7-yloxy)acetate (243 mg).

m.p.: 165–167° C. (recrystallized from hexane/ethyl acetate)

IR (KBr method) 3118, 2968, 2932, 1765, 1734, 1626, 1591, 1557, 1493, 1450, 1435, 1377, 1365, 1292, 1214, 1195, 1181, 1149, 1118, 1087, 1077, 953, 797, 772, 745, 731, 694, 613 cm$^{-1}$ NMR (400 MHz CDCl$_3$) δ7.84(1H,s),7.71(2H,dd,J=8.3, 1.0 Hz),7.67(1H,s), 7.40(2H,t,J=7.3 Hz),7.31(1H,d,J=7.3 Hz),7.22(1H,d,J=7.8 Hz), 7.14(1H,J=7.8 Hz),6.80(1H,d,J=7.8 Hz),4.83(2H,s),4.23(2H,s)

EI-MS m/e 349(M$^+$)

HR-EI-Ms Calcd. 349.0950 (C$_{20}$H$_{15}$NO$_5$) Found 349.0968 (C$_{20}$H$_{15}$NO$_5$)

Elementary Analysis Calcd. C:68.77% H:4.33% N:4.01% Found C:68.69% H:4.53% N:4.09

EXAMPLE 38

(3-((4-(2-phenylethyl)oxazole-2-yl)methyl)benzofuran-7-yloxy)acetic acid

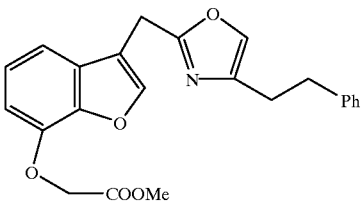

By the method similar to Example 4, the desired compound (56 mg, yield: 68%) was obtained using methyl (3-((4-(2-phenylethyl)oxazole-2-yl)methyl)benzofuran-7-yloxy)acetate (86 mg) which is obtained from 7-methoxy-3-((4-(2-phenylethyl)oxazole-2-yl)methylbenzofuran according to the method similar to Reference Examples 12 and 17.

m.p.: 124–125° C. (recrystallized from hexane/ethyl acetate)

IR (KBr method) 3116, 2936, 2920, 1746, 1601, 1562, 1504, 1437, 1425, 1377, 1363, 1278, 1209, 1193, 1180, 1154, 1100, 787, 754, 733, 72302, 642 cm$^{-1}$ NMR (400 MHz CDCl$_3$) δ7.55(1H,s),7.27–7.10(8H,m), 6.82(1H,dd,J=7.3,1.0 Hz), 4.88(2H,s),4.14(2H,s),2.94–2.90 (2H,m),2.83–2.79(2H,m)

EI-MS m/e 377(M$^+$)

Elementary Analysis Calcd. C:70.02% H:5.07% N:3.71% Found C:69.76% H:5.11% N:3.77

EXAMPLE 39

Methyl (3-(2-(3-phenylpropyloxy)ethyl)benzofuran-7-yloxy)acetate

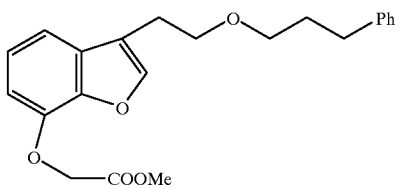

By the method similar to Reference Example 17, the desired compound (123 mg, yield: 93%) was obtained from 3-(2-(3-phenylpropyloxy)ethyl-7-hydroxybenzofuran (106 mg).

IR (liquid film method) 3064, 3030, 2950, 2864, 2802, 1763, 1628, 1591, 1495, 1437, 1361, 1294, 1181, 1151, 1093, 926, 845, 785, 733, 700 cm$^{-1}$ NMR (90 MHz CDCl$_3$) δ7.50(1H,s),7.27–7.03(7H,m), 6.77(1H,dd,J=7.0,2.0 Hz), 4.87(2H,s),3.79(3H,s),3.69(2H,t, J=6.4 Hz), 3.46(2H,t,J=6.4 Hz),2.92(2H,t,J=6.8 Hz), 2.76–2.59(2H,m),1.98–1.81(2H,m)

EI-MS m/e 368(M$^+$)

EXAMPLE 40

(3-(2-(3-phenylpropyloxy)ethyl)benzofuran-7-yloxy) acetic acid

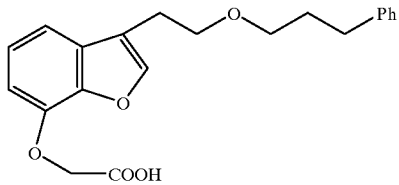

By the method similar to Example 4, the desired compound (95 mg, yield: 81%) was obtained from methyl (3-(2-(3-phenylpropyloxy)ethyl)benzofuran-7-yloxy) acetate (122 mg).

m.p.: 70–71° C. (recrystallized from hexane/ethyl acetate)

IR (KBr method) 3030, 2944, 2876, 2804, 1740, 1715, 1626, 1582, 1493, 1456, 1423, 1363, 1319, 1288, 1261, 1214, 1187, 1151, 1120, 1098, 1062, 938, 911, 787, 743, 716, 692 cm$^{-1}$ NMR (400 MHz CDCl$_3$) δ7.63(1H,s),7.41–7.26(7H,m), 6.93(1H,d,J=7.8 Hz), 5.04(2H),3.83(2H,t,J=6.8 Hz),3.60 (2H,t,J=6.3 Hz), 3.07(2H,t,J=6.8 Hz)0.80(2H,t,J=7.3 Hz), 2.07–2.00(2H,m)

EI-MS m/e 354(M$^+$)

HR-EI-Ms Calcd. 354.1467 (C$_{21}$H$_{22}$O$_5$) Found 354.1479 (C$_{21}$H$_{22}$O$_5$)

Elementary Analysis Calcd. C:71.17% H:6.26% Found C:70.95% H:6.18%

EXAMPLE 41

Methyl (3-(2-benzyloxyethyl)benzofuran-7-yloxy) acetate

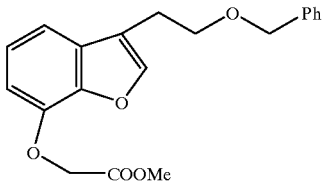

By the method similar to Reference Example 17, the desired compound (176 mg, yield: 96%) was obtained from 3-(2-benzyloxyethyl)-7-hydroxybenzofuran (145 mg) which is obtained by the method similar to Reference Example 90 except that benzyl bromide is used in place of 1-bromo-3-phenyl-propane.

IR (liquid film method) 2862, 1763, 1589, 1493, 1437, 1363, 1294, 1214, 1151, 1093, 733, 698 cm$^{-1}$ NMR (90 MHz CDCl$_3$) δ7.49(1H,s),7.32–7.11(7H,m), 6.77(1H,dd,J=6.6,2.4 Hz), 4.88(2H,s),4.55(2H,s),3.82–3.70 (2H,m),3.80(3H,s), 2.97(2H,dd,J=7.0,5.9 Hz)

EI-MS m/e 340(M$^+$)

EXAMPLE 42

(3-(2-benzyloxyethyl)benzofuran-7-yloxy)acetic acid

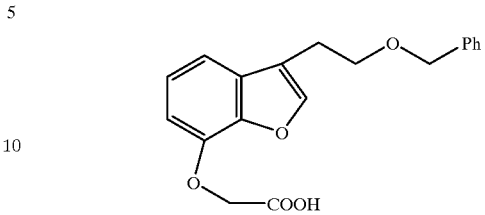

By the method similar to Example 4, the desired compound (128 mg, yield: 76%) was obtained from methyl (3-(2-benzyloxyethyl)benzofuran-7-yloxy)acetate (175 mg).

m.p.: 91–92° C. (recrystallized from hexane/ethyl acetate)

IR (KBr method) 1742, 1711, 1584, 1491, 1423, 1363, 1315, 1267, 1193, 1149, 1120, 1093, 1067, 938, 737 cm$^{-1}$ NMR (400 MHz CDCl$_3$) δ7.49(1H,s),7.36–7.27(5H,m), 7.21(1H,dd,J=7.8,1.0 Hz), 7.13(1H,t,J=7.8 Hz),6.79(1H,d, J=7.3 Hz),4.90(2H,s), 4.55(2H,s),3.77(2H,t,J=6.9 Hz),2.97 (2H,t,J=6.9 Hz)

EI-MS m/e 326(M$^+$)

HR-EI-Ms Calcd. 326.1154 (C$_{19}$H$_{18}$O$_5$) Found 326.1123 (C$_{19}$H$_{18}$O$_5$)

Elementary Analysis Calcd. C:69.93% H:5.56% Found C:69.82% H:5.54%

EXAMPLE 43

(3-(2-(diphenylmethoxy)ethyl)benzofuran-7-yloxy) acetate

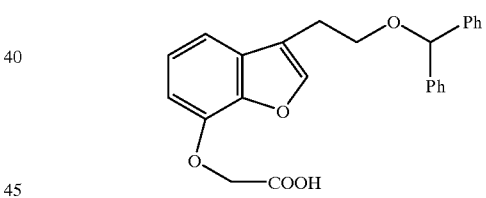

By the method similar to Example 4, the desired compound (104 mg, yield: 74%) was obtained from methyl (3-(2-(diphenylmethoxy)ethyl)benzofuran-7-yloxy)acetate (145 mg) which is obtained by the method similar to Reference Examples 90 and 17 from 3-(2-hydroxyethyl)-7-tetrahydropyranyloxybenzofuran.

m.p.: 121–122° C. (recrystallized from hexane/ethyl acetate)

IR (KBr method) 3062, 2926, 2876, 1740, 1717, 1591, 1493, 1458, 1437, 1367, 1296, 1251, 1220, 1197, 1187, 1151, 1096, 1062, 944, 783, 758, 739, 706 cm$^{-1}$ NMR (400 MHz CDCl$_3$) δ7.49(1H,s),7.32–7.20(10H,m), 7.16(1H,dd,J=7.7,0.8 Hz), 7.10(1H,t,J=7.7 Hz),6.79(1H,dd, J=7.7,0.7 Hz), 5.38(1H,s),4.91(2H,s),3.75(2H,t,J=6.6 Hz), 3.00(2H,t,J=6.6 Hz)

EI-MS m/e 402(M$^+$)

Elementary Analysis Calcd. C:74.61% H:5.51% Found C:74.55% H:5.48%

EXAMPLE 44

(3-(2-(3,3-diphenylpropyloxy)ethyl)benzofuran-7-yloxy)acetic acid

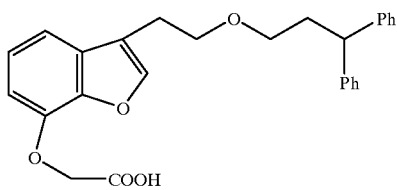

By the method similar to Example 4, the desired compound (71 mg, yield: 60%) was obtained from methyl (3-(2-(3,3-diphenylpropyloxy)ethyl)benzofuran-7-yloxy)acetate (122 mg) which is obtained by the method similar to Reference Examples 90 and 17 from 3-(2-hydroxyethyl)-7-tetrahydropyranyloxybenzofuran.

m.p.: 74–76° C. (recrystallized from cyclohexane/ethyl acetate)

IR (KBr method) 3024, 2940, 2922, 2868, 1742, 1713, 1580, 1493, 1288, 1261, 1207, 1187, 1152, 1120, 1096, 1064, 938, 789, 750, 741, 698, 559 cm$^{-1}$ NMR (400 MHz CDCl$_3$) δ7.46(1H,s),7.26–7.12(12H,m), 6.79(1H,d,J=8.1 Hz), 4.90(2H,s),4.06(1H,t,J=7.7 Hz),3.62 (2H,t,J=6.6 Hz), 3.37(2H,t,J=6.6 Hz),2.89(2H,t,J=7.0 Hz), 2.30(2H,q,J=7.7 Hz)

EI-MS m/e 430(M$^+$)

Elementary Analysis Calcd. C:75.33% H:6.09% Found C:75.28% H:6.05%

EXAMPLE 45

Methyl (3-(2-(4-phenylbenzyloxy)ethyl)benzofuran-7-yloxy)acetate

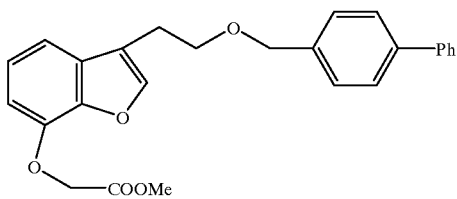

By the method similar to Reference Example 45, the desired compound (519 mg, yield: 95%) was obtained from 3-(2-(4-phenylbenzyloxy)ethyl)-7-methoxybenzofuran (455 mg).

IR (liquid film method) 3032, 2956, 2862, 1767, 1628, 1591, 1491, 1437, 1363, 1294, 1218, 1183, 1151, 1096, 1009, 845, 826, 783, 766, 737, 700 cm$^{-1}$ NMR (90 MHz CDCl$_3$) δ7.67–6.72(13H,m),4.87(2H,s), 4.58(2H,s),3.80(3H,S), 3.97 (2H,m),2.98 (2H,t,J=6.8 Hz)

EI-MS m/e 416(M$^+$)

EXAMPLE 46

(3-(2-(4-phenylbenzyloxy)ethyl)benzofuran-7-yloxy)acetic acid

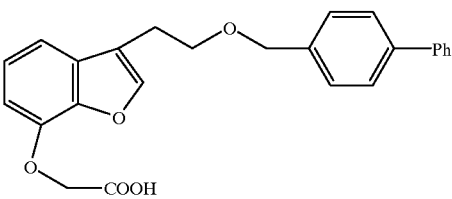

By the method similar to Example 4, the desired compound (435 mg, yield: 89%) was obtained from methyl (3-(2-(4-phenylbenzyloxy)ethyl)benzofuran-7-yloxy)acetate (505 mg).

m.p.: 114–116° C. (recrystallized from hexane/ethyl acetate)

IR (KBr method) 2912, 2864, 1742, 1711, 1686, 1626, 1584, 1562, 1510, 1491, 1460, 1423, 1363, 1315, 1288, 1265, 1191, 1149, 1120, 1106, 1093, 1067, 938, 824, 787, 758, 737, 696, 538 cm$^{-1}$ NMR (400 MHz CDCl$_3$) δ7.59–7.32(10H,m),7.21(1H,dd, J=7.8,1.0 Hz), 7.13(1H,t,J=7.8 Hz),6.79(1H,d,J=7.4 Hz), 4.90(2H,s), 4.59(2H,s),3.80(2H,t,J=6.9 Hz),2.98(2H,t,J=6.9 Hz)

EI-MS m/e 402(M$^+$)

HR-EI-Ms Calcd. 402.1467 (C$_{25}$H$_{22}$O$_5$) Found 402.1476 (C$_{25}$H$_{22}$O$_5$)

Elementary Analysis Calcd. C:74.61% H:5.51% Found C:74.63% H:5.52%

EXAMPLE 47

(3-(2-(2-oxo-2-phenylethoxy)ethyl)benzofuran-7-yloxy)acetic acid

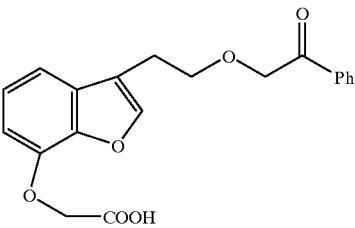

By the method similar to Example 4, the desired compound (100 mg, yield: 80%) was obtained from methyl (3-(2-(2-oxo-2-phenylethoxy)ethyl)benzofuran-7-yloxy)acetate (130 mg) which is obtained by the method similar to Reference Example 17 from 3-(2-(2-oxo-2-phenylethoxy)ethyl)-7-hydroxybenzofuran.

m.p.: 124–126° C. (recrystallized from hexane/ethyl acetate)

IR (KBr method) 2918, 1886, 1742, 1698, 1628, 1582, 1491, 1454, 1425, 1315, 1292, 1267, 1195, 1145, 1093, 1050, 980, 787, 752, 739, 687, 576 cm$^{-1}$ NMR (400 MHz CDCl$_3$) δ7.89(2H,d,J=7.3 Hz),7.58(1H, d,J=7.8 Hz),7.56(1H,s), 7.44(2H,t,J=7.8 Hz),7.23(1H,d,J= 7.8 Hz),7.13(1H,t,J=7.8 Hz), 6.80(1H,d,J=7.8 Hz),4.91(2H, s),4.77(2H,s), 3.88(2H,t.J=6.8 Hz), 3.03(1H,t,J=6.8 Hz)

EI-MS m/e 354(M$^+$)

HR-EI-Ms Calcd. 354.1103 ($C_{20}H_{18}O_6$) Found 354.1097 ($C_{20}H_{18}O_6$)

Elementary Analysis Calcd. C:67.79% H:5.12% Found C:67.64% H:5.11

EXAMPLE 48

(3-((3,3-diphenylpropyloxy)methyl)benzofuran-7-yloxy)acetic acid

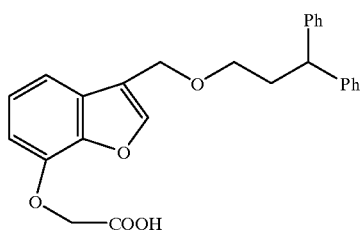

By the method similar to Example 4, the desired compound (465 mg, yield: 89%) was obtained from methyl (3-((3,3-diphenylpropyloxy)methyl)-benzofuran-7-yloxy)acetate (537 mg) which is obtained by the method similar to Reference Example 45 from 3-((3,3-diphenylpropyloxy)methyl)-7-methoxybenzofuran.

m.p.: 147–149° C. (recrystallized from hexane/ethyl acetate)

IR (KBr method) 3028, 2942, 2878, 1748, 1717, 1628, 1593, 1493, 1450, 1431, 1359, 1294, 1257, 1236, 1203, 1156, 1096, 1073, 957, 785, 774, 748, 731 cm$^{-1}$ NMR (400 MHz CDCl$_3$) δ7.51(1H,s),7.31–7.13(12H,m), 6.82(1H,d,J=7.3 Hz), 4.91(2H,s),4.55(2H,s),4.10(1H,t,J=7.8 Hz), 3.43(2H,t.J=6.4 Hz),2.33(2H,dt,J=7.8,6.4 Hz)

EI-MS m/e 416(M$^+$)

HR-EI-Ms Calcd. 416.1624 ($C_{26}H_{24}O_5$) Found 416.1647 ($C_{26}H_{24}O_5$)

Elementary Analysis Calcd. C:74.98% H:5.81% Found C:74.89% H:5.83%

EXAMPLE 49

(3-((2,2-diphenylethoxy)methyl)benzofuran-7-yloxy)acetic acid

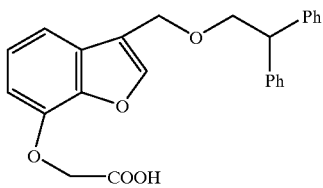

By the method similar to Example 4, the desired compound (118 mg, yield: 80%) was obtained from methyl (3-((2,2-diphenylethoxy)methyl)benzofuran-7-yloxy)acetate (153 mg) which is obtained by the method similar to Reference Examples 68 and 45 except that 2,2-diphenylethanol is used in place of 3,3-diphenylpropanol in Reference Example 68.

m.p.: 160–162° C. (recrystallized from hexane/ethyl acetate)

IR (KBr method) 3118, 3058, 3032, 2898, 2868, 2796, 1742, 1719, 1630, 1599, 1493, 1452, 1435, 1357, 1290, 1259, 1238, 1203, 1185, 1151, 1120, 1098, 1081, 1019, 955, 905, 847, 832, 783, 766, 754, 739, 700, 592 cm$^{-1}$ NMR (400 MHz CDCl$_3$) δ7.47(1H,s),7.28–7.18(10H,m), 7.09–7.01(2H,m), 6.78(1H,dd,J=7.3,1.0 Hz),4.88(2H,s), 4.65(2H,s), 4.31(1H,t,J=7.3 Hz),4.01(2H,d,J=7.3 Hz), 2.33 (2H,dt,J=7.8,6.4 Hz)

EI-MS m/e 402(M$^+$)

HR-EI-Ms Calcd. 402.1467 ($C_{25}H_{22}O_5$) Found 402.1441 ($C_{25}H_{22}O_5$)

Elementary Analysis Calcd. C:74.61% H:5.51% Found C:74.41% H:5.53%

EXAMPLE 50

(3-((diphenylmethoxy)methyl)benzofuran-7-yloxy)acetic acid

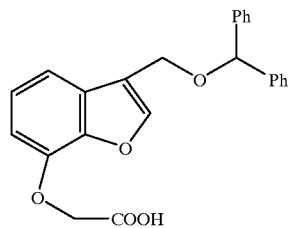

By the method similar to Example 4, the desired compound (216 mg, yield: 83%) was obtained from methyl (3-((diphenylmethoxy)methyl)benzofuran-7-yloxy)acetate (270 mg) which is obtained by the method similar to Reference Examples 68 and 45 except that diphenylmethanol is used in place of 3,3-diphenylpropanol in Reference Example 68.

m.p.: 153–155° C. (recrystallized from hexane/ethyl acetate)

IR (KBr method) 3062, 3032, 2920, 2872, 1746, 1628, 1589, 1493, 1454, 1433, 1354, 1332, 1284, 1255, 1197, 1151, 1091, 1075, 1031, 1006, 901, 801, 777, 743, 731, 702, 652 cm$^{-1}$ NMR (400 MHz CDCl$_3$) δ7.57(1H,s),7.37–7.24(11H,m), 7.15(1H,t,J=7.8 Hz), 6.82(1H,d,J=7.8 Hz),5.48(1H,s),4.91 (2H,s),4.65(2H,s)

EI-MS m/e 388(M$^+$)

HR-EI-Ms Calcd. 388.1311 ($C_{24}H_{20}O_5$) Found 388.1300 ($C_{24}H_{20}O_5$)

Elementary Analysis Calcd. C:74.21% H:5.19% Found C:74.03% H:5.19%

EXAMPLE 51

(R)-(3-((2-phenylpropyloxy)methyl)benzofuran-7-yloxy)acetic acid

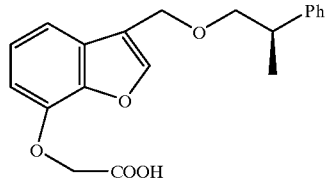

By the method similar to Example 4, the desired compound (275 mg, yield: 87%) was obtained from methyl (R)-(3-((2-phenylpropyloxy)methyl)benzofuran-7-yloxy)acetate (330 mg) which is obtained by the method similar to Reference Examples 68 and 45 except that (R)-2-phenylpropanol is used in place of 3,3-diphenylpropanol in Reference Example 68.

$[\alpha]_D$: -8.82 (c=1.065, CHCl$_3$)

m.p.: 125–127° C. (recrystallized from hexane/ethyl acetate)

IR (KBr method) 3124, 3066, 3032, 2968, 2902, 2872, 2798, 2688, 2586, 1744, 1717, 1628, 1589, 1493, 1454, 1431, 1361, 1294, 1255, 1201, 1187, 1152, 1085, 1004, 957, 897, 830, 785, 766, 739, 702, 565 cm$^{-1}$ NMR (400 MHz CDCl$_3$) δ7.52(1H,s),7.31–7.09(7H,m), 6.80(1H,dd,J=7.8,1.0 Hz), 4.91(2H,s),4.61(2H,s),3.62(1H,dd,J=9.3,6.8 Hz), 3.54(1H,dd,J=9 Hz),3.05(1H,m),1.28(3H,d,J=6.8 Hz)

EI-MS m/e 340(M$^+$)

HR-EI-Ms Calcd. 340.1311 (C$_{20}$H$_{20}$O$_5$) Found 340.1292 (C$_{20}$H$_{20}$O$_5$)

Elementary Analysis Calcd. C:70.57% H:5.92% Found C:70.43% H:5.95%

EXAMPLE 52

(S)-(3-((2-phenylpropyloxy)methyl)benzofuran-7-yloxy)acetic acid

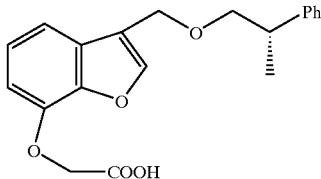

By the method similar to Example 4, the desired compound (280 mg, yield: 92%) was obtained from methyl (S)-(3-((2-phenylpropyloxy)methyl)benzofuran- 7-yloxy)acetate (317 mg) which is obtained by the method similar to Reference Examples 68 and 45 except that (S)-2-phenylpropanol is used in place of 3,3-diphenylpropanol in Reference Example 68.

$[\alpha]_D$:+8.36 (c=1.080, CHCl$_3$)

m.p.: 124–126° C. (recrystallized from hexane/ethyl acetate)

IR (KBr method) 3032, 2968, 2902, 1746, 1719, 1628, 1589, 1493, 1454, 1431, 1361, 1294, 1255, 1203, 1187, 1154, 1083, 785, 766, 739, 70465 cm$^{-1}$ NMR (400 MHz CDCl$_3$) δ7.52(1H,s),7.31–7.09(7H,m), 6.80(1H,dd,J=7.8,1.0 Hz), 4.91(2H,s),4.61(2H,s),3.62(1H,dd,J=9.3,6.8 Hz), 3.54(1H,dd,J=9 Hz),3.05(1H,m),1.28(3H,d,J=6.8 Hz)

EI-MS m/e 340(M$^+$)

HR-EI-Ms Calcd. 340.1311 (C$_{20}$H$_{20}$O$_5$) Found 340.1326 (C$_{20}$H$_{20}$O$_5$)

Elementary Analysis Calcd. C:70.57% H:5.92% Found C:70.37% H:5.90%

EXAMPLE 53

(3-((1-benzyl-2-phenylethoxy)methyl)benzofuran-7-yloxy)acetic acid

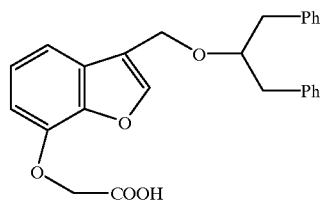

By the method similar to Example 4, the desired compound (247 mg, yield: 89%) was obtained from methyl (3-((1-benzyl-2-phenylethoxy)methyl)benzofuran-7-yloxy)acetate (288 mg) which is obtained by the method similar to Reference Examples 68 and 45 except that 1,3-diphenyl-2-propanol is used in place of 3,3-diphenylpropanol in Reference Example 68.

m.p.: 107–109° C. (recrystallized from hexane/ethyl acetate)

IR (KBr method) 3110, 3062, 3028, 2914, 2856, 2792, 2576, 1740, 1715, 1630, 1599, 1495, 1454, 1435, 1363, 1348, 1321, 1292, 1263, 1238, 1222, 1203, 1187, 1151, 1102, 1079, 1056, 1031, 1013, 961, 878, 853, 835, 783, 754, 735, 702, 501 cm$^{-1}$ NMR (400 MHz CDCl$_3$) δ7.29–7.18(11H,m),7.02(1H,t,J=7.8 Hz), 6.81(1H,d,J=7.8 Hz),6.76(1H,d,J=7.8 Hz),4.89(2H,s), 4.38(2H,s),3.89(1H,quint,J=6 Hz),2.85–2.84(4H,m)

EI-MS m/e 416(M$^+$)

HR-EI-Ms Calcd. 416.1624 (C$_{26}$H$_{24}$O$_5$) Found 416.1629 (C$_{26}$H$_{24}$O$_5$)

Elementary Analysis Calcd. C:74.98% H:5.81% Found C:74.71% H:5.79%

EXAMPLE 54

(S)-(3-((1-methyl-2-phenylethoxy)methyl)benzofuran-7-yloxy)acetic acid

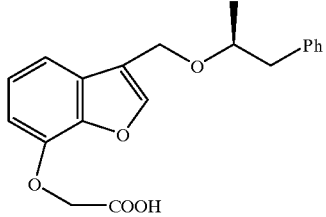

By the method similar to Example 4, the desired compound (83 mg, yield: 77%) was obtained from methyl (S)-(3-((1-methyl-2-phenylethoxy)methyl)benzofuran-7-yloxy)acetate (112 mg) which is obtained by the method similar to Reference Examples 68 and 45 except that (S)-3-phenyl-2-propanol is used in place of 3,3-diphenylpropanol in Reference Example 68.

$[\alpha]_D$: +31.92 (c=0.570, CHCl$_3$)

m.p.: 92–93° C. (recrystallized from hexane/ethyl acetate)

IR (KBr method) 3030, 2974, 2926, 2868, 2802, 1740, 1713, 1628, 1586, 1493, 1456, 1423, 1375, 1359, 1323, 1290, 1265, 1189, 1154, 1131, 1087, 1058, 957, 922, 785, 733, 700 cm$^{-1}$ NMR (400 MHz CDCl₃) δ7.47(1H,s),7.29–7.07(7H,m), 6.80(1H,dd,J=5.3,2.7 Hz), 4.91(2H,s),4.68(1H,dd,J=13.7, 5.9 Hz),4.54(1H,dd,J=13.7,1.0 Hz),3.84–3.76(1H,m),2.92 (1H,dd,J=13.7,6.8 Hz), 2.71(1H,dd,J=13.7,5.9 Hz),1.28(3H, d,J=6.4 Hz)

EI-MS m/e 340(M⁺)

HR-EI-Ms Calcd. 340.1311 (C₂₀H₂₀O₅) Found 340.1312 (C₂₀H₂₀O₅)

Elementary Analysis Calcd. C:70.57% H:5.92% Found C:70.43% H:5.95%

EXAMPLE 55

(3-((1-methyl-2-methoxy-2-phenylethoxy)methyl)benzofuran-7-yloxy)acetic acid

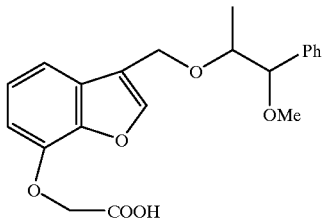

By the method similar to Example 4, the desired compound (78 mg, yield: 62%) was obtained from methyl (3-((1-methyl-2-methoxy-2-phenylethoxy)methyl)benzofuran-7-yloxy)acetate (130 mg) which is obtained by the method similar to Reference Examples 68 and 45 except that (S)-1-phenyl-1-methoxy-2-propanol is used in place of 3,3-diphenylpropanol in Reference Example 68.

m.p.: 104–106° C. (recrystallized from hexane/ethyl acetate)

IR (KBr method) 2986, 2930, 2878, 1740, 1715, 1630, 1586, 1493, 1456, 1427, 1377, 1359, 1288, 1263, 1199, 1187, 1152, 1091, 953, 787, 731, 702 cm⁻¹

NMR (400 MHz CDCl₃) δ7.40(1H,S),7.35–7.25(5H,m), 7.07(1H,t,J=7.8 Hz), 6.98(1Hd,J=7.8,1.0 Hz),6.78(1H,dd,J= 7.8,1.0 Hz),4.89(2H,s), 4.59,4.42(each1H,ABq,J=12.2 Hz), 4.09(1H,d,J=5.8 Hz), 3.70–3.64(1H,m),3.26(3H,s),1.24(3H, d,J=6.3 Hz)

EI-MS m/e 370(M⁺)

HR-EI-Ms Calcd. 370.1416 (C₂₁H₂₃O₆) Found 370.1421 (C₂₁H₂₃O₆)

Elementary Analysis Calcd. C:68.10% H:5.99% Found C:67.97% H:5.96%

EXAMPLE 56

(R)-(3-((2-phenylbutoxy)methyl)benzofuran-7-yloxy)acetic acid

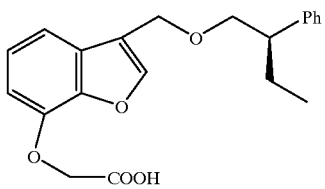

By the method similar to Example 4, the desired compound (275 mg, yield: 89%) was obtained from methyl (R)-(3-((2-phenylbutoxy)methyl)benzofuran-7-yloxy)acetate (320 mg) which is obtained by the method similar to Reference Examples 68 and 45 except that (R)-2-phenyl-1-butanol is used in place of 3,3-diphenylpropanol in Reference Example 68.

[α]_D: −16.63 (c=1.190, CHCl₃)

m.p.: 133–135° C. (recrystallized from hexane/ethyl acetate)

IR (KBr method) 3126, 3030, 2962, 2904, 1746, 1719, 1628, 1589, 1510, 1493, 1454, 1431, 1359, 1292, 1255, 1203, 1187, 1154, 1083, 78533, 700 cm⁻¹

NMR (400 MHz CDCl₃) δ7.50(1H,s),7.30–7.10(7H,m), 6.80(1H,dd,J=5.8,3.4 Hz), 4.91(2H,s),4.59(2H,brs),3.63 (1H,dd,J=6.8,1.0 Hz), 2.81–2.74(1H),1.88–1.79(1H,m), 1.61–1.52(1H,m),0.79(3H,t,J=7.3 Hz)

EI-MS m/e 354(M⁺)

HR-EI-Ms Calcd. 354.1467 (C₂₁H₂₂O₅) Found 354.1489 (C₂₁H₂₂O₅)

Elementary Analysis Calcd. C:71.17% H:6.26% Found C:70.86% H:6.16%

EXAMPLE 57

(R)-(3-((1-methyl-2-(phenylethoxy)methyl)benzofuran-7-yloxy) acetic acid

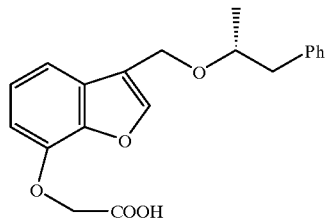

By the method similar to Example 4, the desired compound (215 mg, yield: 88%) was obtained from methyl (R)-(3-((1-methyl-2-phenylethoxy)methyl)benzofuran-7-yloxy)acetate which is obtained by the method similar to Reference Examples 68 and 45 except that (R)-1-phenyl-2-propanol is used in place of 3,3-diphenylpropanol in Reference Example 68. [α]_D: −30.54 (c=1.100, CHCl₃)

m.p.: 90–92° C. (recrystallized from hexane/ethyl acetate)

IR (KBr method) 3064, 3030, 2974, 2926, 2866, 2798, 2682, 2590, 1742, 1713, 1628, 1586, 1493, 1456, 1423, 1377, 1361, 1323, 1288, 1265, 1234, 1189, 1152, 1131, 1085, 1058, 957, 924, 909, 787, 733, 700 cm⁻¹

NMR (400 MHz CDCl₃) δ7.47(1H,s),7.29–7.07(7H,m), 6.79(1H,dd,J=5.9,3.4 Hz), 4.90(2H,s),4.67(1H,d,J=12.2 Hz),4.54(1H,dd,J=12.2,1.0 Hz), 3.84–3.76(1H,m),2.92(1H, dd,J=13.7,6.8 Hz), 2.72(1H,dd,J=13.7,5.9 Hz),1.22(3H,d,J= 5.9 Hz)

EI-MS m/e 340(M⁺)

Elementary Analysis Calcd. C:70.57% H:5.92% Found C:70.35% H:5.86%

EXAMPLE 58

(3-((2-phenoxyethoxy)methyl)benzofuran-7-yloxy) acetic acid

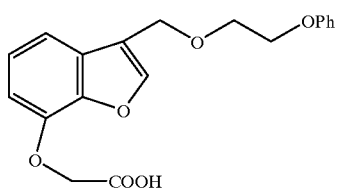

By the method similar to Example 4, the desired compound (286 mg, yield: 92%) was obtained from methyl (3-((2-phenoxyethoxy)methyl)benzofuran-7-yloxy)acetate (325 mg) which is obtained by the method similar to Reference Examples 68 and 45 except that 2-phenoxyethanol is used in place of 3,3-diphenylpropanol in Reference Example 68.

m.p.: 129–131° C. (recrystallized from hexane/ethyl acetate)

IR (KBr method) 2884, 1742, 1605, 1586, 1508, 1493, 1425, 1361, 1292, 1263, 1241, 1193, 1183, 1112, 1081, 1050, 787, 752, 735 cm$^{-1}$ NMR (400 MHz CDCl$_3$) δ7.62(1H,s),7.35(1H,d,J=7.8 Hz),7.29–7.25(2H,m), 7.16(1H=7.8 Hz),6.90(1H,t,J=7.3 Hz),6.82(1H,d,J=7.8 Hz), 4.91(2H,s)0.77(2H,s),4.15,3.85 (each1H,ABq,J=4.9 Hz),4.13, 3.86(each1H,ABq=3.4 Hz)

EI-MS m/e 342(M$^+$)

Elementary Analysis Calcd. C:66.66% H:5.30% Found C:66.35% H:5.29%

EXAMPLE 59

(3-((2-(diphenylmethoxy)ethoxy)methyl)benzofuran-7-yloxy)acetic acid

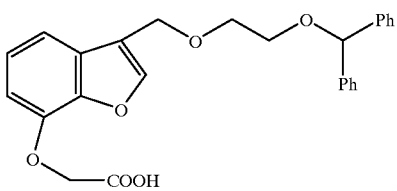

By the method similar to Example 4, the desired compound (282 mg, yield: 82%) was obtained from methyl (3-((2-(diphenylmethoxy)ethoxy)methyl)benzofuran-7-yloxy)acetate (354 mg) which is obtained by the method similar to Reference Examples 68 and 45 except that 2-(diphenylmethoxy)ethanol is used in place of 3,3-diphenylpropanol in Reference Example 68.

m.p.: 95–97° C. (recrystallized from hexane/ethyl acetate)

IR (KBr method) 3030, 2920, 2866, 1746, 1719, 1630, 1589, 1493, 1452, 1431, 1354, 1294, 1257, 1230, 1207, 1187, 1141, 1096, 1087, 1029, 830, 783, 739, 696, 648 cm$^{-1}$ NMR (400 MHz CDCl$_3$) δ7.58(1H,s),7.36–7.21(11H,m), 7.11(1H,t,J=7.8 Hz), 6.80(1H,d,J=7.8 Hz),5.41(1H,s),4.90 (2H,s),4.71(2H,s),3.73, 3.65(each1H,ABq,J=6.4 Hz),3.73, 3.66(each1H,ABq,J=5.4 Hz)

EI-MS m/e 432(M$^+$)

Elementary Analysis Calcd. C:72.21% H:5.59% Found C:71.86% H:5.62%

EXAMPLE 60

(3-((2-methyl-2-phenoxypropyloxy)methyl) benzofuran-7-yloxy)acetic acid

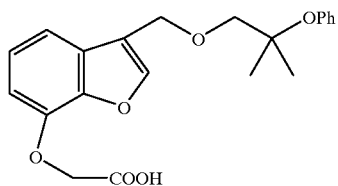

By the method similar to Example 4, the desired compound (260 mg, yield: 85%) was obtained from methyl (3-((2-methyl-2-phenoxypropyloxy)methyl)benzofuran-7-yloxy)acetate (317 mg) which is obtained by the method similar to Reference Examples 68 and 45 except that 2-methyl-2-phenoxy-1-propanol is used in place of 3,3-diphenylpropanol in Reference Example 68.

m.p.: 91–92° C. (recrystallized from hexane/ethyl acetate)

IR (KBr method) 2980, 2928, 2876, 2800, 1738, 1713, 1628, 1593, 1491, 1460, 1423, 1381, 1365, 1352, 1290, 1265, 1226, 1199, 1152, 1110, 1091, 1060, 1025, 957, 922, 891, 787, 743, 731, 721, 700 cm$^{-1}$ NMR (400 MHz CDCl$_3$) δ7.61(1H,s),7.36(1H,dd,J=7.8, 1.0 Hz),7.26–6.99(6H,m), 6.82(1H,d,J=7.3 Hz),4.93(2H,s), 4.75(2H,s),3.46(2H,s), 1.29(6H,s).

EI-MS m/e 370(M$^+$)

Elementary Analysis Calcd. C:68.10% H:5.99% Found C:67.91% H:6.00%

EXAMPLE 61

(3-(2-(2-(diphenylmethoxy)ethoxy)ethyl) benzofuran-7-yloxy)acetic acid

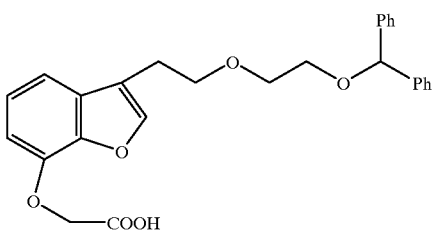

By the method similar to Example 4, the desired compound (185 mg, yield 72%) was obtained from methyl (3-(2-(2-(diphenylmethoxy)ethoxy)ethyl)benzofuran-7-yloxy)acetate (265 mg) which is obtained by the method similar to Reference Examples 90 and 17.

m.p.: 76–78° C. (recrystallized from hexane/ethyl acetate)

IR (KBr method) 3102, 3086, 3064, 3028, 2936, 2910, 2868, 2784, 1756, 1715, 1626, 1584, 1493, 1452, 1427, 1363, 1305, 1288, 1253, 1241, 1205, 1191, 1178, 1145, 1093, 1040, 1027, 1004, 899, 779, 754, 737, 702, 650, 511 cm$^{-1}$ NMR (400 MHz CDCl$_3$) δ7.51(1H,s),7.35–7.22(11H,m), 7,11(1H,t,J=7.8 Hz), 6.80(1H,d,J=7.8 Hz),5.40(1H,s),4.90 (2H,s), 3.78(2H,t,J=6.8 Hz),3.713(each1H,ABq,J=3.9 Hz), 3.70, 3.64(each1H,ABq,J=2.9 Hz),2.94(2H,t,J=6.1 Hz)

EI-MS m/e 446(M$^+$)

Elementary Analysis Calcd. C:72.63% H:5.87% Found C:72.35% H:5.86

EXAMPLE 62

(3-((3-(diphenylmethoxy)propyloxy)methyl)benzofuran-7-yloxy)acetic acid

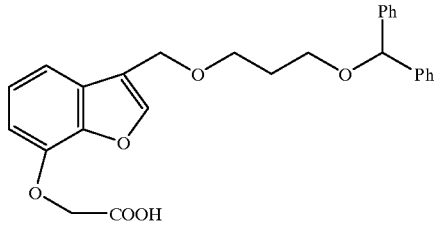

By the method similar to Example 4, the desired compound (309 mg, yield: 89%) was obtained from methyl (3-((3-diphenylmethoxy)propyloxy)methyl)benzofuran-7-yloxy)acetate (359 mg) which is obtained by the method similar to Reference Examples 68 and 45 except that 3-(diphenylmethoxy)-1-propanol is used in place of 3,3-diphenylpropanol in Reference Example 68.

m.p.: 140–141° C. (recrystallized from hexane/ethyl acetate)

IR (KBr method) 3128, 3086, 3064, 3030, 2974, 2924, 2876, 1748, 1628, 1586, 1493, 1452, 1431, 1361, 1294, 1270, 1251, 1236, 1203, 1189, 1154, 1139, 1100, 1089, 1075, 957, 930, 835, 787, 739, 700 cm$^{-1}$ NMR (400 MHz CDCl$_3$) δ7.57(1H,s),7.30–7.21(11H,m), 7.13(1H,t,J=7.8 Hz), 6.81(1H,d,J=7.8 Hz),5.27(1H,s),4.90 (2H,s),4.61(2H,s), 3.66(2H,t,J=6.4 Hz),3.54(2H,t,J=6.4 Hz), 1.94(2H,quint,J=6.4 Hz)

EI-MS m/e 446(M$^+$)

Elementary Analysis Calcd. C:72.63% H:5.87% Found C:72.19% H:5.89%

EXAMPLE 63

Methyl (3-(diphenylmethylthiomethyl)benzofuran-7-yloxy)acetate

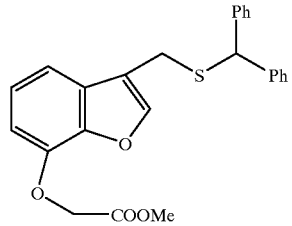

By the method similar to Reference Example 17, the desired compound (73 mg, yield: 90%) was obtained from 3-(diphenylmethylthiomethyl)-7-hydroxybenzofuran (67 mg).

IR (liquid film method) 2956, 1748, 1628, 1595, 1493, 1437, 1381, 1359, 1294, 1183, 1031, 783, 733, 704 cm$^{-1}$ NMR (400 MHz CDCl$_3$) δ7.40–7.12(13H,m),5.00(1H,s), 4.88(2H,s),3.82(3H,s), 3.63(2H,d,J=0.6 Hz)

EI-MS m/e 418(M$^+$)

EXAMPLE 64

(3-(diphenylmethylthiomethyl)benzofuran-7-yloxy)acetic acid

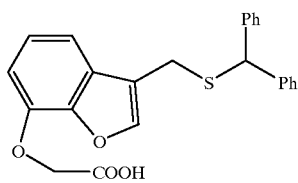

By the method similar to Example 4, the desired compound (70 mg, yield: 99%) was obtained from methyl (3-(diphenylmethylthiomethyl)benzofuran-7-yloxy)acetate (73 mg).

m.p.: 135.5–137.0° C. (recrystallized from hexane/ethyl acetate)

IR (KBr method) 1742, 1626, 1599, 1497, 1450, 1433, 1361, 1294, 1261, 1205, 1139, 1096, 779, 729, 702 cm$^{-1}$ NMR (400 MHz CDCl$_3$) δ7.39–7.14(13H,m),6.83(1H,d, J=5.9 Hz),5.00(1H,s), 4.92(2H,s),3.64(2H,d,J=0.8 Hz)

EI-MS m/e 404(M$^+$)

Elementary Analysis Calcd. C:71.27% H:4.98% S:7.93% Found C:70.99% H:5.00% S:7.97%

EXAMPLE 65

(3-(2,2-diphenylethylthiomethyl)benzofuran-7-yloxy)acetic acid

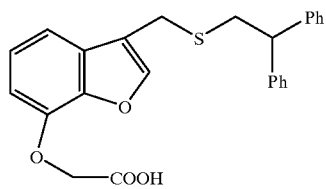

By the method similar to Example 4, the desired compound (144 mg, yield: 89%) was obtained from methyl (3-(2,2-diphenylethylthio)methylbenzofuran-7-yloxy) acetate (167 mg) which can be obtained from 3-bromomethyl-7-methoxybenzofuran by the method similar to Reference Examples 11 and 45.

m.p.: 91.0–93.5° C. (recrystallized from hexane/ethyl acetate)

IR (KBr method) 3392, 2906, 1738, 1628, 1595, 1493, 1425, 1359, 1267, 1201, 1100, 955, 785, 737, 698 cm$^{-1}$ NMR (400 MHz CDCl$_3$) δ7.47(1H,s),7.31–7.13(12H,m), 6.83(1H,d,J=7.8 Hz), 4.92(2H,s),4.11(1H,t,J=7.8 Hz),3.65 (2H,s), 3.13(2H,d,J=7.8 Hz)

EI-MS m/e 418(M$^+$)

EXAMPLE 66

(3-(3,3-diphenylpropylthiomethyl)benzofuran-7-yloxy)acetic acid

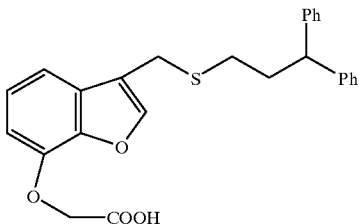

By the method similar to Example 4, the desired compound (140 mg, yield: 96%) was obtained from methyl (3-(3,3-diphenylpropylthiomethyl)benzofuran-7-yloxy)acetate (150 mg) which can be obtained from 3-bromomethyl-7-methoxybenzofuran by the method similar to Reference Examples 11 and 45.

m.p.: 154.5–155° C. (recrystallized from hexane/ethyl acetate)

IR (KBr method) 3028, 2922, 1748, 1626, 1593, 1493, 1433, 1359, 1259, 1201, 1125, 1093, 957, 781, 731, 700 cm$^{-1}$ NMR (400 MHz DMSO-d6) δ13.14–13.02(1H,br s),7.70 (1H,s),7.30–7.10(12H,m), 6.84(1H,d,J=7.8 Hz),4.85(2H,s), 4.02(1H,t,J=6.3 Hz), 3.82(2H,s),2.35–2.15(4H,m)

EI-MS m/e 432(M$^+$)

EXAMPLE 67

Methyl (3-(2-(diphenylmethylthio)ethyl)benzofuran-7-yloxy)acetate

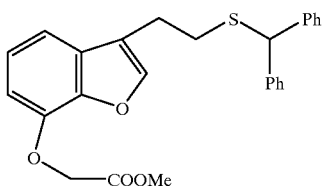

Diphenylmethanethiol (297 mg) was dissolved in DMF (2 ml) and potassium t-butoxide (166 mg) was added to the obtained solution, followed by stirring the resulting solution at room temperature for 5 minutes. To this reaction solution, a solution of 3-(2-bromoethyl)-7-tetrahydropyranyloxybenzofuran (335 mg) in DMF (2.5 ml) was added dropwise for 5 minutes, and the resulting solution was stirred at room temperature for 15 minutes. To this reaction solution, 1N hydrochloric acid (1.5 ml) was added and the solution was stirred at room temperature for 1 hour. The reaction mixture was poured into water layer (50 ml) and the resultant was extracted twice with ethyl acetate (20 ml). The organic layers were combined and washed with saturated brine, followed by drying over sodium sulfate. After removing the sodium sulfate by filtration, the solvent was removed under reduced pressure and the obtained residue was dissolved in DMF (4 ml). To this solution, potassium carbonate (205 mg) and methyl bromoacetate (0.19 ml) were added and the resulting mixture was stirred at room temperature for 3.5 hours. The reaction solution was poured into water layer (50 ml) and the resultant was extracted twice with ethyl acetate (20 ml). The organic layers were combined and washed with saturated saline, followed by drying over sodium sulfate. After removing the sodium sulfate by filtration, the solvent was removed under reduced pressure and the residue was purified by column chromatography (solvent: hexane/ethyl acetate=3/1) using silica gel to obtain the desired compound (255 mg, yield: 60%).

IR (liquid film method) 3064, 3030, 2956, 2926, 1763, 1744, 1628, 1589, 1493, 1437, 1361, 1294, 1220, 1197, 1129, 1079, 789, 704, 627 cm$^{-1}$ NMR (90 MHz CDCl$_3$) δ7.45–6.69(14H,m),5.17(1H,s), 4.87(2H,s), 3.79(3H,s),3.02–2.59(4H,m)

EI-MS m/e 432(M$^+$)

EXAMPLE 68

(3-(2-diphenylmethylthio)ethyl)benzofuran-7-yloxy)acetic acid

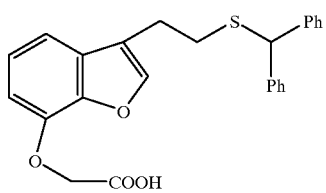

By the method similar to Example 4, the desired compound (209 mg, yield: 86%) was obtained from methyl (3-(2-(diphenylmethylthio)ethyl)benzofuran-7-yloxy)acetate (250 mg).

m.p.: 139–141° C. (recrystallized from hexane/ethyl acetate)

IR (KBr method) 3060, 3030, 2964, 2912, 1738, 1628, 1584, 1493, 1452, 1429, 1361, 1292, 1255, 1199, 1164, 1133, 1096, 955, 789, 746, 73702 cm$^{-1}$ NMR (400 MHz CDCl$_3$) δ7.41–7.21(11H,m),7.09(1H,t, J=7.8 Hz), 6.97(1H,dd,J=7.7,0.9 Hz),6.78(1H,d,J=7.8 Hz), 5.17(1H,s), 4.90(2H,s),2.88(2H,t,J=7.8 Hz),2.57(2H,t,J=7.8 Hz)

EI-MS m/e 418(M$^+$)

Elementary Analysis Calcd. C:71.75% H:5.30% S:7.66% Found C:71.45% H:5.32% S:7.63%

EXAMPLE 69

(3-(2-(diphenylmethylsulfonyl)ethyl)benzofuran-7-yloxy)acetic acid

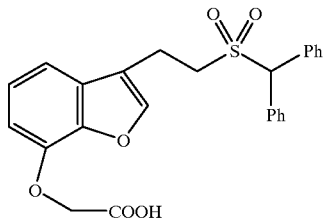

(3-(2-(diphenylmethyl)thioethyl)benzofuran-7-yloxy) acetic acid (126 mg) was dissolved in dichloromethane (2 ml) and the obtained solution was cooled to 0° C. To this solution, m-chloroperbenzoic acid (143 mg) was added and the resulting mixture was stirred for 2 hours. The reaction solution was poured into water layer (30 ml) and the resultant was extracted twice with ethyl acetate (20 ml). The organic layers were combined and washed with saturated aqueous sodium thiosulfate solution and with saturated brine, followed by drying over sodium sulfate. After removing the sodium sulfate by filtration, the solvent was removed under reduced pressure and the residue was purified by column chromatography (solvent: hexane/ethyl acetate=1/2+5% acetic acid) using silica gel to obtain the desired compound (97 mg, yield: 72%).

m.p.: 177–179° C. (recrystallized from hexane/chloroform)

IR (KBr method) 3132, 1771, 1751, 1628, 1588, 1495, 1456, 1437, 1291, 1185, 1165, 1131, 1110, 1097, 1082, 846, 794, 784, 738 cm$^{-1}$ NMR (300 MHz CDCl$_3$) δ7.62–7.58(4H,m),7.44–7.38(7H,m),7.10(1H,t,J=7.7 Hz), 6.89(1H,d,J=7.1 Hz),6.79(1H,d,J=7.4 Hz),5.28(1H,s), 4.88(2H,s),3.22–3.14(4H,m)

EI-MS m/e 450(M$^+$)

EXAMPLE 70

Methyl (3-(2-(bis(4-methoxyphenyl)methylthio)ethyl)benzofuran-7-yloxy)acetate

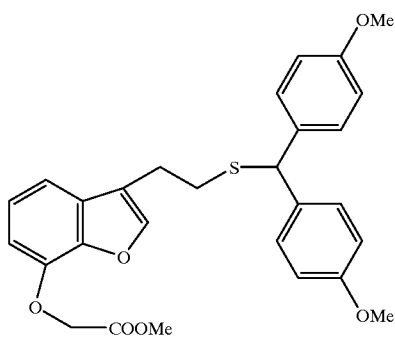

Methyl (3-(2-hydroxyethyl)benzofuran-7-yloxy) acetate (284 mg) and triethylamine (0.242 ml) were dissolved in dichloromethane (4 ml) and the obtained solution was cooled to 0° C. To this solution, methanesulfonyl chloride (0.114 ml) was added and the resulting solution was stirred at 0° C. for 1 hour. The reaction solution was poured into water layer (50 ml) and the resultant was extracted twice with ethyl acetate (20 ml). The organic layers were combined and washed with saturated brine, followed by drying over sodium sulfate. The sodium sulfate was removed by filtration and the solvent was removed under reduced pressure. The obtained residue was dissolved in DMF (2 ml) and the obtained solution was added to a separately prepared solution of bis(4-methoxyphenyl)methanethiol (286 mg) and potassium t-butoxide (140 mg) in DMF (3 ml), followed by stirring the resulting solution at room temperature for 3 hours. The reaction solution was poured into water layer (50 ml) and the resultant was extracted twice with ethyl acetate (20 ml). The organic layers were combined and washed with saturated saline, followed by drying over sodium sulfate. After removing the sodium sulfate by filtration, the solvent was removed under reduced pressure and the residue was purified by column chromatography (solvent: hexane/ethyl acetate=2/1) using silica gel to obtain the desired compound (286 mg, yield: 51%).

IR (liquid film method) 3004, 2956, 2840, 1765, 1742, 1609, 1584, 1512, 1464, 1439, 1361, 1303, 1249, 1178, 1129, 1091, 1035, 816, 785, 733 cm$^{-1}$ NMR (300 MHz CDCl$_3$) δ7.41(1H,brs),7.32–7.27(4H,m),7.08(1H,t,J=8.0 Hz), 6.96(1H,dd,J=7.7,1.1 Hz), 6.86–6.81(4H,m), 6.75(1H,dd,J=8.0,1.1 Hz),5.11(1H,s), 4.88(2H,s),3.80(3H,s), 3.78(6H,s),2.91–2.86(2H, brm), 2.71–2.66(2H,brm)

CI-MS m/e 493(MH$^+$)

EXAMPLE 71

(3-(2-(bis(4-methoxyphenyl)methylthio)ethyl)benzofuran-7-yloxy)acetic acid

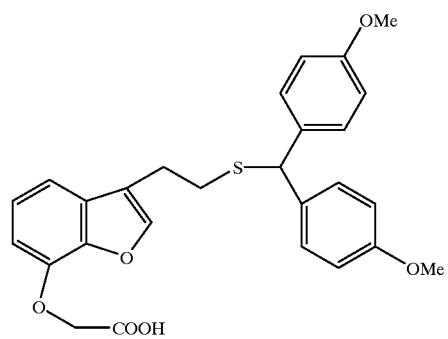

By the method similar to Example 4, the desired compound (175 mg, yield: 70%) was obtained from methyl (3-(2-(bis(4-methoxyphenyl)methylthio)ethyl)benzofuran-7-yloxy)acetate (257 mg).

m.p.: 118–120° C. (recrystallized from hexane/ethyl acetate)

IR (KBr method) 3004, 2908, 2840, 1731, 1610, 1582, 1512, 1438, 1358, 1304, 1258, 1198, 1179, 1087, 1033, 953, 832, 814, 791, 734 cm$^{-1}$ NMR (300 MHz CDCl$_3$) δ7.41(1H,brs),7.32–7.27(4H,m),7.10(1H,t,J=7.7 Hz), 6.99(1H,dd,J=7.7,0.8 Hz), 6.86–6.78(5H,m),5.11(1H,s), 4.91(2H,s), 3.78(6H,s), 2.91–2.85(2H,brm), 2.72–2.66(2H,brm)

EI-MS m/e 478(M$^+$)

Elementary Analysis Calcd. C:67.76% H:5.48% S:6.70% Found C:67.66% H:5.47% S:6.64%

EXAMPLE 72

Methyl (3-(2-(bis(4-hydroxyphenyl)methylthio)ethyl)-2-methylbenzofuran-7-yloxy)acetate

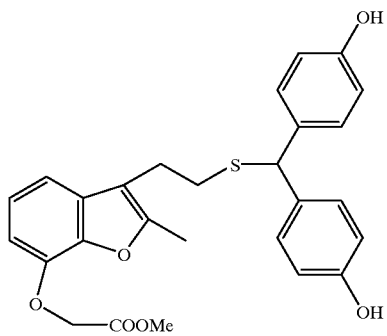

Methyl (3-(2-hydroxyethyl)-2-methylbenzofuran-7-yloxy)acetate (203 mg) and triethylamine (0.16 ml) were dissolved in dichloromethane (4 ml) and the obtained solution was cooled to 0° C. To this solution, methanesulfonyl chloride (0.071 ml) was added and the solution was stirred at 0° C. for 20 minutes. The reaction solution was poured into water layer (50 ml) and the resultant was extracted twice with ethyl acetate (20 ml). The organic layers were combined and washed with saturated brine, followed by drying over sodium sulfate. The sodium sulfate was removed by filtration and the solvent was removed under reduced pressure. The obtained residue was dissolved in DMF (2.5 ml) and the obtained solution was added to a separately prepared solution of bis($^4$-tetrahydropyranyloxyphenyl)methanethiol (369 mg) and potassium t-butoxide (104 mg) in DMF (2 ml), followed by stirring the resulting solution at room temperature for 30 minutes. To this reaction solution, 1N hydrochloric acid (1.5 ml) was added and the solution was stirred for 1 hour. The reaction solution was poured into water layer (50 ml) and the resultant was extracted twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=1/1)using silica gel to obtain the desired compound (54 mg, yield: 15%).

m.p.: 178–180° C. (recrystallized from hexane/ethyl acetate)

IR (KBr method) 3378, 3352, 1754, 1611, 1595, 1514, 1491, 1435, 1357, 1294, 1241, 1214, 1174, 1102, 839, 774, 735 cm$^{-1}$ NMR (300 MHz CDCl$_3$) δ7.17–7.13(4H,m),7.00(1H,t,J= 7.7 Hz), 6.81(1H,dd,J=7.7,0.8 Hz),6.71–6.67(4H,m), 6.64–6.61(1H,brm),5.00(1H,s),4.88(2H,s),3.82(3H,s), 2.81–2.76(2H,brm),2.67–2.62(2H,brm),2.36(3H,s)

EI-MS m/e 478(M$^+$)

EXAMPLE 73

(3-(2-bis(4-hydroxyphenyl)methylthio)ethyl)-2-methylbenzofuran-7-yloxy)acetic acid

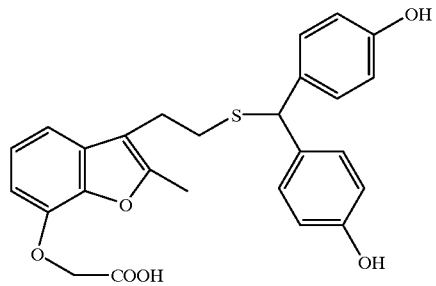

By the method similar to Example 4, the desired compound (175 mg, yield: 60%) was obtained from methyl (3-(2-(bis(4-hydroxyphenyl)methyl)ethyl)-2-5 methylbenzofuran-7-yloxy)acetate (210 mg). Decomposition Point: 213–215° C. (recrystallized from methanol/chloroform/hexane)

IR (KBr method) 3494, 3446, 2922, 1727, 1612, 1592, 1513, 1438, 1359, 1277, 1256, 1215, 1171, 1104, 966, 829, 785, 732 cm$^{-1}$ NMR (300 MHz CD$_3$OD) δ7.16(4H,m),7.01(1H,t,J=7.7 Hz),6.82(1H,dd,J=7.7,0.8 Hz), 6.74(1H,dd,J=8.0,0.8 Hz), 6.71–6.66(4H,m),5.00(1H,s), 4.84(2H,s),2.85–2.79(2H, brm),2.59–2.54(2H,brm),2.32(3H,s)

EI-MS m/e 464(M$^+$)

EXAMPLE 74

Methyl (3-(2-(bis(4-chlorophenyl)methylthio)ethyl) benzofuran-7-yloxy)acetate

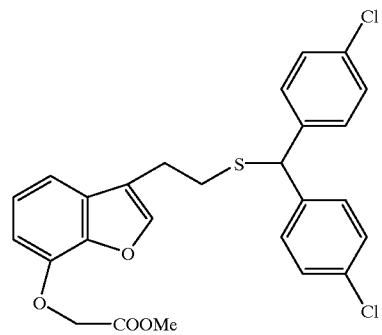

Methyl (3-(2-methanesulfonyloxyethyl)benzofuran-7-yloxy)acetate (203 mg) and diphenylmethanethiol (250 mg) were dissolved in DMF and potassium carbonate (288 mg) was added to this solution, followed by stirring the resulting solution at room temperature for 21 hours and then at 30° C. for 3.5 hours. The reaction solution was poured into water layer (50 ml) and the resultant was extracted twice with ethyl acetate (20 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=3/1) using silica gel to obtain the desired compound (118 mg, yield: 38%).

m.p.: 68–69° C. (recrystallized from hexane/ethyl acetate)

IR (KBr method) 1763, 1628, 1586, 1491, 1437, 1426, 1361, 1299, 1263, 1220, 1203, 1185, 1164, 1135, 1093, 1013, 948, 801, 787, 737 cm$^{-1}$ NMR (300 MHz CDCl$_3$) δ7.43(1H,s),7.32–7.26(8H,m), 7.11(1H,t,J=7.7 Hz), 6.95(1H,dd,J=7.7,0.8 Hz),6.79–6.76 (1H,m),5.05(1H,s), 4.88(2H,s),3.81(3H,s),2.92–2.87(2H, brm),2.72–2.67(2H,brm)

EI-MS m/e 500(M$^+$)

EXAMPLE 75

(3-(2-bis (4-chlorophenyl)methylthio)ethyl) benzofuran-7-yloxy)acetic acid

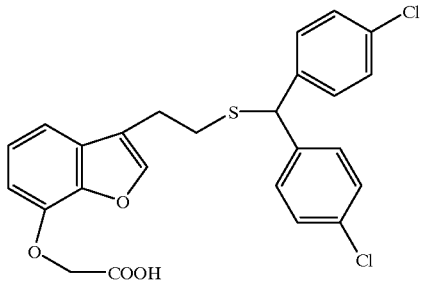

By the method similar to Example 4, the desired compound (75 mg, yield: 67%) was obtained from methyl (3-(2-(bis(4-chlorophenyl)methylthio)ethyl)benzofuran-7-yloxy)acetate (115 mg).

m.p.: 130–132° C. (recrystallized from hexane/ethyl acetate)

IR (KBr method) 3094, 3034, 2920, 2854, 1736, 1626, 1591, 1491, 1437, 1406, 1359, 1292, 1197, 1164, 1129, 1091, 1015, 953, 814, 799, 733 cm$^{-1}$ NMR (300 MHz CDCl$_3$) δ7.44(1H,s),7.27(8H,brs),7.12 (1H,t,J=8.0 Hz), 6.98(1H,dd,J=7.7,0.8 Hz),6.80(1H,dd,J= 8.0,0.8),5.06(1H,s), 4.92(2H,s),2.92–2.86(2H,brm), 2.73–2.67(2H,brm)

EI-MS m/e 486(M$^+$)

EXAMPLE 76

(3-(2-(bis(4-fluorophenyl)methylthio)ethyl)-benzofuran-7-yloxy)acetic acid

By the method similar to Example 4, the desired compound (171 mg, yield: 93%) was obtained from methyl (3-(2-(bis(4-fluorophenyl)methylthio)ethyl)-benzofuran-7-yloxy)acetate (195 mg) which can be obtained by the method similar to Example 74 from methyl (3-(2-methanesulfonyloxyethyl)benzofuran-7-yloxy)acetate.

m.p.: 132–134° C. (recrystallized from ethyl acetate/n-hexane).

IR (KBr method) 3114, 3046, 2914, 1740, 1628, 1603, 1506, 1435, 1415, 1359, 1294, 1257, 1224, 1201, 1156, 1133, 1093, 953, 835, 789, 733 cm$^{-1}$ NMR (300 MHz CDCl$_3$) δ7.42(1H,brs),7.03–7.28(4H, m),7.11(1H,t,J=8.0 Hz),7.03–6.95(5H,m), 6.80(1H,dd,J= 8.0,0.8 Hz),5.10(1H,s),4.91(2H,s), 2.92–2.86(2H,m), 2.72–2.66(2H,m)

EI-MS m/e 454(M$^+$)

EXAMPLE 77

(3-(2-(dicyclohexylmethylthio)ethyl)-benzofuran-7-yloxy)acetic acid

By the method similar to Example 4, the desired compound (131 mg, yield: 96%) was obtained from methyl 3-(2-dichclohexylmethylthioethyl)-benzofuran-7-yloxyacetate (140 mg) which can be obtained by the method similar to Example 74 from methyl (3-(2-methanesulfonyloxyethyl)benzofuran-7-yloxy)acetate.

m.p.: 131.0° C. (recrystallized from ethyl acetate/n-hexane)

IR (KBr method) 3400, 2926, 2854, 1709, 1497, 1439, 1234, 1195, 1085, 783, 725 cm$^{-1}$ NMR (300 MHz CDCl$_3$) δ7.50(1H,s),7.21(1H,dd,J=1,8 Hz),7.16(1H,t,J=8 Hz), 6.82(1H,dd,J=1,8 Hz),4.92(2H,s), 2.90–2.95(2H,m), 2.79–2.85(2H,m),2.11(1H,t,J=6 Hz),1.93 (2H,m), 1.54–1.76(10H,m),1.04–1.34(10H,m)

EI-MS m/e 430(M$^+$)

EXAMPLE 78

3-(2-(phenyl(2-thienyl)methylthio)ethyl)-benzofuran-7-yloxyacetic acid

By the method similar to Example 4, the desired compound (163 mg, yield: 98%) was obtained from methyl 3-(2-(phenyl(2-thienyl)methylthio)ethyl)-benzofuran-7-yloxy acetate (172 mg) which can be obtained by the method similar to Example 74 from methyl (3-(2-methanesulfonyloxyethyl)benzofuran-7-yloxy)acetate.

m.p.: 111.0° C. (recrystallized from ethyl acetate/n-hexane)

IR (KBr method) 2914, 1738, 1626, 1593, 1493, 1452, 1431, 1361, 1261, 1199, 1089, 955, 791, 733, 700 cm$^{-1}$ NMR (300 MHz CDCl$_3$) δ7.45(3H,m),7.22–7.36(4H,m), 7.11(1H,t,J=8 Hz),7.03(1H,dd,J=1,8 Hz),6.91(2H,m), 6.80 (1H,dd,J=1,8 Hz),5.36(1H,s),4.91(2H,s),2.90(2H,m), 2.77 (2H,m)

EI-MS m/e 424(M$^+$)

EXAMPLE 79

Methyl (3-(2-(diphenylmethylthio)ethyl)benzofuran-6-yloxy)acetate

By the method similar to Example 70, the desired compound (191 mg, yield: 81%) was obtained from methyl (3-(2-hydroxyethyl)benzofuran-6-yloxy)acetate (137 mg) which can be obtained by the method similar to Reference Examples 13, 16 and 17 from 6-hydroxy-2,3-dihydrobenzofuran-3-one.

m.p.: 88–89° C. (recrystallized from hexane/ethyl acetate)

IR (KBr method) 2944, 1763, 1626, 1599, 1582, 1489, 1454, 1439, 1381, 1340, 1296, 1284, 1265, 1222, 1209, 1156, 1143, 1123, 1075, 1054, 1029, 975, 930, 820, 808, 799, 775, 754, 725, 708, 675 cm$^{-1}$ NMR (300 MHz CDCl$_3$) δ7.42–7.20(11H,m),7.16(1H,d, J=8.5 Hz), 6.96(1H,d,J=1.8 Hz),6.86(1H,dd,J=8.5,2.3 Hz), 5.17(1H,s), 4.67(2H,s),3.82(3H,s),2.90–2.86(2H,m), 2.74–2.67(2H,m)

EI-MS m/e 432(M$^+$)

EXAMPLE 80

(3-(2-(diphenylmethylthio)ethyl)benzofuran-6-yloxy)acetic acid

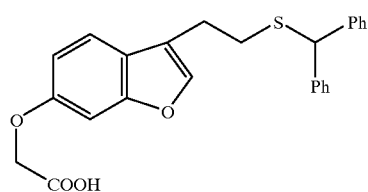

By the method similar to Example 4, the desired compound (170 mg, yield: 94%) was obtained from methyl (3-(2-(diphenylmethylthio)ethyl)benzofuran-6-yloxy) acetate (188 mg).

m.p.: 133–135° C. (recrystallized from hexane/ethyl acetate)

IR (KBr method) 3060, 3030, 2906, 2778, 2584, 1748, 1626, 1597, 1582, 1491, 1446, 1427, 1338, 1294, 1257, 1232, 1154, 1122, 1075, 1058, 951, 926, 832, 810, 799, 754, 702 cm$^{-1}$ NMR (300 MHz CDCl$_3$) δ7.42–7.20(11H,m),7.18(1H,d, J=8.5 Hz), 6.99(1H,d,J=1.9 Hz),6.87(1H,dd,J=8.5,2.2 Hz), 5.17(1H,s), 4.71(2H,s),2.89–2.84(2H,m),2.73–2.67(2H,m)

EI-MS m/e 418(M$^+$)

Elementary Analysis Calcd. C:71.75% H:5.30% S:7.66% Found C:71.46% H:5.28% S:7.58%

EXAMPLE 81

(3-(2-(diphenylmethylthio)ethyl)-2-methylbenzofuran-7-yloxy)acetic acid

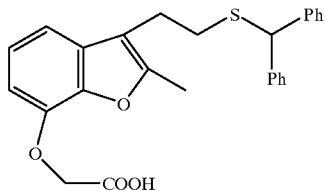

By the method similar to Example 4, the desired compound (196 mg, yield: 88%) was obtained from methyl (3-(2-(diphenylmethylthio)ethyl)-2-methylbenzofuran-7-yloxy)acetate (230 mg) which can be obtained by the method similar to Reference Example 11 from methyl (3-(2-bromoethyl)-2-methylbenzofuran-7-yloxy)acetate.

m.p.: 146–148° C. (recrystallized from hexane/ethyl acetate)

IR (KBr method) 3064, 3030, 2924, 1742, 1713, 1630, 1589, 1493, 1452, 1431, 1361, 1288, 1247, 1232, 1212, 1164, 1106, 1081, 965, 907, 787, 768, 750, 733, 725 cm$^{-1}$ NMR (300 MHz CDCl$_3$) δ7.40–7.19(10H,m),7.03(1H,t, J=7.7 Hz), 6.84(1H,dd,J=7.7,1.1 Hz),6.69(1H,dd,J=8.0,1.1 Hz), 5.15(1H,s),4.88(2H,s),2.84–2.78(2H,brm), 2.65–2.59 (2H,brm),2.31(3H,s)

EI-MS m/e 432(M$^+$)

Elementary Analysis Calcd. C:72.20% H:5.59% S:7.41% Found C:72.01% H:5.55% S:7.35%

EXAMPLE 82

Methyl (2-hydroxymethyl-3-(2-(diphenylmethylthio) ethyl)benzofuran-7-yloxy)acetate

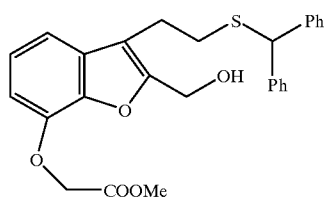

Potassium t-butoxide (465 mg) was dried under reduced pressure. In DMF (5 ml), n-propanethiol (0.4 ml) was dissolved and the obtained solution was added to the potassium t-butoxide, followed by stirring the resulting mixture at room temperature. 2-hydroxymethyl-3-(2-(diphenylmethylthio)ethyl)-7-methoxybenzofuran (803 mg) was dissolved in DMF (6 ml) and the obtained solution was added to the above-mentioned solution, followed by stirring the resulting solution at 90° C. for 6 hours. The reaction solution was poured into 5% aqueous citric acid solution and the resultant was extracted with ethyl acetate. The organic layer was washed with water and with saturated brine and dried over magnesium sulfate. The magnesium sulfate was removed by filtration and the solvent was evaporated off. The obtained residue was purified by column chromatography (solvent: n-hexane/ethyl acetate=1/1) to obtain the phenol compound (406 mg, yield: 52%). This phenol compound (406 mg) was dissolved in ethanol (50 ml) and 4N aqueous potassium hydroxide solution (0.3 ml) was added thereto, followed by stirring the resulting solution at room temperature for 30 minutes. The solvent was evaporated off under reduced pressure. Dimethylformamide (20 ml) was added to the obtained residue to dissolve the same and methyl bromoacetate (0.20 ml) was added to the obtained solution, followed by stirring the solution at room temperature for 90 minutes. The reaction solution was poured into 5% aqueous citric acid solution, and the resultant was extracted with ethyl acetate. The organic layer was washed with water and with saturated brine, and dried over magnesium sulfate. The magnesium sulfate was removed by filtration and the solvent was evaporated off. The obtained residue was purified by column chromatography (solvent: n-hexane/ethyl acetate= 1/1)to obtain the phenol compound (403 mg, yield: 84%).

IR (thin film method) 3450, 1760, 1591, 1493, 1437, 1388, 1288, 1209, 1096, 1004, 785, 752, 733, 704 cm$^{-1}$ NMR (300 MHz CDCl$_3$) δ7.38–7.18(10H,m),7.08(1H,t, J=8 Hz),6.93(1H,dd,J=1,8 Hz), 6.77(1H,dd,J=1,8 Hz),5.03 (1H,s),4.89(2H,s), 4.67(2H,d,J=6 Hz),3.80(3H,s),2.92(2H,t, J=7 Hz), 2.68(2H,t,J=7 Hz),2.18(1H,t,J=6 Hz)

EXAMPLE 83

(2-hydroxymethyl-3-(2-(diphenylmethylthio)ethyl) benzofuran-7-yloxy)acetic acid

By the method similar to Example 4, the desired compound (343 mg, yield: 80%) was obtained from methyl (2-hydroxymethyl-3-(2-(diphenylmethylthio)ethyl) benzofuran-7-yloxy)acetate (446 mg).

m.p.: 144.0° C. (recrystallized from ethyl acetate/n-hexane)

IR (KBr method) 3400, 3026, 2924, 1736, 1657, 1628, 1591, 1493, 1452, 1439, 1286, 1209, 1096, 748, 729, 704, 692, 623 cm$^{-1}$ NMR (300 MHz CDCl$_3$) δ7.36–7.19(10H,m),7.07(1H,t, J=8 Hz),6.92(1H,dd,J=1,8 Hz), 6.77(1H,dd,J=1,8 Hz),5.04 (1H,s),4.85(2H,s),4.65(2H,s), 2.88(2H,t,J=7 Hz),2.66(2H,t, J=7 Hz)

Elementary Analysis Calcd. C:68.93% H:5.45% S:7.08% Found C:68.86% H:5.55% S:7.36%

EXAMPLE 84

Methyl (2-(2-acetoxyethyl)-3-(2-(diphenylmethyl) thioethyl)benzofuran-7-yloxy)acetate By the method similar to Example 70, the desired compound (125 mg, yield: 42%) was obtained from methyl (2-(2-acetoxyethyl)-3-(2-hydroxyethyl)benzofuran-7-yloxy)acetate (195 mg).

IR (liquid film method) 3064, 3030, 2958, 1765, 1742, 1628, 1591, 1493, 1441, 1367, 1338, 1238, 1201, 1100, 1042, 787, 762, 733, 704, 629 cm$^{-1}$ NMR (300 MHz CDCl$_3$) δ7.41–7.19(10H,m),7.04(1H,t, J=8.0 Hz), 6.83(1H,dd,J=7.6,0.8 Hz),6.70(1H,dd,J=8.0,1.1 Hz), 5.20(1H,s),4.86(2H,s),4.31(2H,t,J=6.6 Hz),3.80(3H,s), 2.99(2H,t,J=6.6 Hz),2.86–2.81(2H,m),2.66–2.61(2H,m), 1.99(3H,s)

EI-MS m/e 518(M$^+$)

EXAMPLE 85

(3-(2-(diphenylmethyl)thioethyl)-2-(2-hydroxyethyl))benzofuran-7-yloxy)acetic acid By the method similar to Example 4, the desired compound (208 mg, yield: 94%) was obtained from methyl (2-(2-acetoxyethyl)-3-(2-(diphenylmethyl)thioethyl)) benzofuran-7-yloxy)acetate (247 mg).

m.p.: 148–150° C. (recrystallized from hexane/ethyl acetate)

IR (KBr method) 3340, 2904, 1742, 1711, 1628, 1589, 1493, 1450, 1303, 1274, 1232, 1209, 1098, 1035, 1019, 748, 727, 702 cm$^{-1}$ NMR (300 MHz CD$_3$OD) δ7.38–7.16(10H,m),7.00(1H, t,J=8.0 Hz), 6.81(1H,dd,J=7.7,0.8 Hz),6.75(1H,dd,J=7.7,0.8 Hz), 5.17(1H,s),4.85(2H,s),3.82(2H,t,J=6.6 Hz), 2.93–2.85 (4H,m),2.66–2.60(2H,m), EI-MS m/e 462(M$^+$)

Elementary Analysis Calcd. C:70.11% H:5.67% S:6.93% Found C:69.91% H:5.65% S:6.88%

EXAMPLE 86

Methyl (2-(3-acetoxypropyl)-3-(2-(diphenylmethyl) thioethyl)benzofuran-7-yloxy)acetate Methyl (2-(3-acetoxypropyl)-3-(2-hydroxyethyl) benzofuran-7-yloxy)acetate (78 mg) was dissolved in dichloromethane (1 ml) and the obtained solution was cooled to 0° C. To this solution, triethylamine (0.02 ml) and methanesulfonyl chloride (0.047 ml) were added and the resulting mixture was stirred for 30 minutes. The reaction solution was poured into water (50 ml) and extracted twice with ethyl acetate (20 ml). The organic layers were combined and washed with saturated aqueous sodium hydrogen carbonate solution and with saturated brine, followed by drying over sodium sulfate. After removing the sodium sulfate by filtration, the solvent was removed under reduced pressure and the obtained residue was dissolved in DMF (2 ml). To this solution, diphenylmethanethiol (89 mg) and potassium carbonate (37 mg) were added and the resultant was stirred at room temperature for 22 hours. The reaction mixture was poured into water (50 ml) and the resultant was extracted twice with ethyl acetate (20 ml). The organic layers were combined and washed with saturated aqueous sodium hydrogen carbonate solution and with saturated brine, followed by drying over sodium sulfate. After removing the sodium sulfate by filtration, the solvent was removed under reduced pressure and the residue was purified by column chromatography (solvent: hexane/ethyl acetate=2/1) using silica gel to obtain the desired compound (83 mg, yield: 70%).

IR (liquid film method) 3062, 3030, 2958, 1765, 1734, 1628, 1591, 1493, 1448, 1369, 1243, 1201, 1102, 1079, 1044, 779, 750, 733, 704 cm$^{-1}$ NMR (300 MHz CDCl$_3$) δ7.41–7.19(10H,m),7.02(1H,t,J=8.0 Hz), 6.80(1H,dd,J=8.0,1.1 Hz),6.68(1H,dd,J=8.0,0.8 Hz), 5.16(1H,s),4.86(2H,s),4.05(2H,t,J=6.3 Hz),3.80(3H,s), 2.85–2.71(4H,m),2.64–2.59(2H,m),2.05(3H,s), 2.06–1.95 (2H,m)

EI-MS m/e 532(M$^+$)

EXAMPLE 87

(3-(2-(diphenylmethyl)thioethyl)-2-(2-hydroxypropyl)benzofuran-7-yloxy)acetic acid

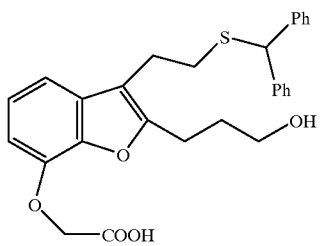

By the method similar to Example 4, the desired compound (67 mg, yield: 79%) was obtained from methyl (2-(2-acetoxypropyl)-3-(2-(diphenylmethyl)thioethyl) benzofuran-7-yloxy)acetate (95 mg).

m.p.: 154–156° C. (recrystallized from hexane/ethyl acetate)

IR (KBr method) 3448, 3034, 2928, 2584, 1748, 1627, 1590, 1493, 1450, 1431, 1377, 1356, 1285, 1240, 1208, 1158, 1098, 1059, 1005, 911, 775, 749, 731, 703 cm$^{-1}$ NMR (300 MHz CD$_3$OD) δ7.39–7.17(10H,m),7.00(1H, t,J=8.0 Hz), 6.82(1H,dd,J=7.7,1.1 Hz),6.75(1H,dd,J=8.0,0.8 Hz), 5.19(1H,s),4.84(2H,s),3.56(2H,t,J=6.3 Hz), 2.90–2.85 (2H,brt),2.78–2.73(2H,brt),2.64–2.59(2H,brt), 1.93–1.84 (2H,m)

EI-MS m/e 476(M$^+$)

EXAMPLE 88

(3-(2-(2,2-diphenylethylthio)ethyl)benzofuran-7-yloxy)acetic acid

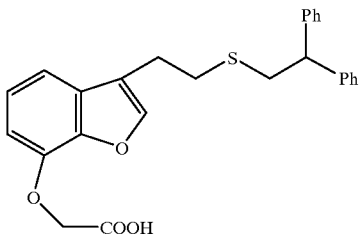

By the method similar to Example 4, the desired compound (100 mg, yield: 78%) was obtained from methyl (3-(2-(2,2-diphenylethylthio)ethyl)benzofuran-7-yloxy) acetate (133 mg) which can be obtained by the method similar to Reference Examples 11 and 45 from 3-(2-bromoethyl)-7-methoxybenzofuran.

m.p.: 116.0–118.0° C. (recrystallized from hexane/ethyl acetate)

IR (KBr method) 2906, 1744, 1630, 1591, 1493, 1427, 1359, 1259, 1197, 1125, 1089, 957, 748, 733, 698 cm$^{-1}$ NMR (400 MHz CDCl$_3$) δ7.40(1H,s),7.32–7.12(12H,m), 6.82(1H,dd,J=6.6,2.2 Hz), 4.91(2H,s),4.16(1H,t,J=7.8 Hz), 3.24(2H,d,J=7.8 Hz), 2.91–2.87(2H,m),2.79–2.74(2H,m)

EI-MS m/e 432(M$^+$)

EXAMPLE 89

(3-(2-(3,3-diphenylpropylthio)ethyl)benzofuran-7-yloxy)acetic acid

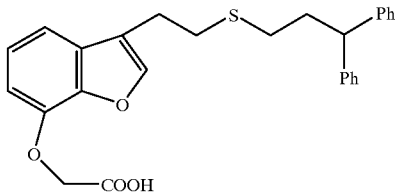

By the method similar to Example 4, the desired compound (61 mg, yield: 97%) was obtained from methyl (3-(2-(3,3-diphenylpropylthio)ethyl)benzofuran-7-yloxy) acetate (65 mg) which can be obtained by the method similar to Reference Examples 11 and 45 from 3-(2-bromoethyl)-7-methoxybenzofuran.

m.p.: 61.0–62.0° C. (recrystallized from hexane/ethyl acetate)

IR (KBr method) 2368, 1734, 1532, 1493, 1363, 1245, 1185, 1087, 733, 700, 586, 509, 445, 426 cm$^{-1}$ NMR (400 MHz CDCl$_3$) δ7.44(1H,s),7.30–7.11(12H,m), 6.82(1H,dd,J=6.8,2.0 Hz), 4.91(2H,s),4.07(1H,t,J=7.8 Hz), 2.89–2.78(4H,m), 2.49(2H,dd,J=8.8,6.8 Hz),2.36–2.29(2H, m)

EI-MS m/e 446(M$^+$)

EXAMPLE 90

Methyl (3-(3-diphenylmethylthiopropyl)benzofuran-7-yloxy)acetate

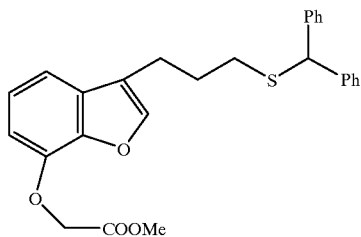

By the method similar to Reference Example 11, the desired compound (177 mg, yield: 89%) was obtained from methyl (3-(3-bromopropyl)benzofuran-7-yloxy)acetate (145 ml).

IR (liquid film method) 2928, 1763, 1740, 1628, 1589, 1493, 1437, 1375, 1292, 1245, 1183, 1091, 1046, 1031, 785, 733, 702, 586 cm$^{-1}$ NMR (300 MHz CDCl$_3$) δ7.0–7.5(13H,m),6.77(1H,dd,J=2,6 Hz),5.13(1H,s), 4.88(2H,s),3.82(3H,s),2.72(2H,t,J=7 Hz),2.46(2H,t,J=7 Hz), 1.93(2H,quint,J=7 Hz)

EI-MS m/e 446(M$^+$)

EXAMPLE 91

(3-(3,3-diphenylmethylthiopropyl)benzofuran-7-yloxy)acetic acid

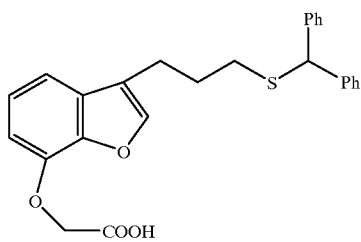

By the method similar to Example 4, the desired compound (142 mg, yield: 85%) was obtained from methyl (3-(3,3-diphenylmethylthiopropyl)benzofuran-7-yloxy)acetate (171 mg).

m.p.: 112.0° C. (recrystallized from ethyl acetate/n-hexane)

IR (KBr method) 1738, 1715, 1628, 1584, 1493, 1433, 1259, 1201, 1185, 1093, 955, 781, 739, 700 cm$^{-1}$ NMR (300 MHz CDCl$_3$) δ7.10–7.42(13H,m),6.81(1H,d, J=7 Hz),5.14(1H,s), 4.91(2H,s),2.72(2H,t,J=7 Hz),2.46(2H, t,J=7 Hz), 1.93 (2H, sept,J=7 Hz)

EI-MS m/e 432(M$^+$)

Elementary Analysis Calcd. C:71.81% H:5.62% S:7.37 Found C:71.81% H:5.59% S:7.32

EXAMPLE 92

(3-(3-(2,2-diphenylethylthio)propyl)benzofuran-7-yloxy)acetic acid

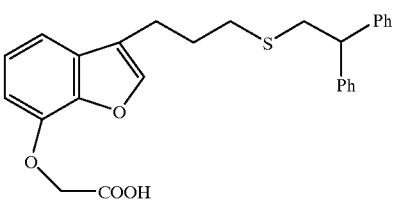

By the method similar to Example 4, the desired compound (92 mg, yield: 84%) was obtained from methyl (3-(3-(2,2-diphenylethylthio)propyl)benzofuran-7-yloxy)acetate (114 mg) which can be obtained by the method similar to Reference Example 11 from methyl (3-(3-bromopropyl)benzofuran-7-yloxy)acetate and 2,2-diphenylethanethiol.

m.p.: 94° C. (recrystallized from ethyl acetate/n-hexane)

IR (KBr method) 2924, 1740, 1713, 1626, 1584, 1493, 1452, 1423, 1354, 1267, 1195, 1094, 783, 735, 702 cm$^{-1}$ NMR (300 MHz CDCl$_3$) δ7.10–7.40(13H,m),6.81(1H,d, J=7 Hz),4.92(2H,s), 4.17(1H,t,J=8 Hz),3.21(2H,d,J=8 Hz), 2.72(2H,t,J=7 Hz), 2.51(2H,t,J=7 Hz),1.94(2H,quint,J=7 Hz)

EI-MS m/e 446(M$^+$)

EXAMPLE 93

(3-(3-(3,3-diphenylpropylthio)propyl)benzofuran-7-yloxy)acetic acid

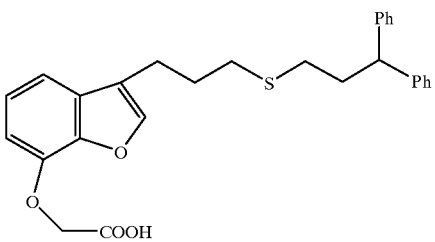

By the method similar to Example 4, the desired compound (54 mg, yield: 85%) was obtained from methyl (3-(3-(3,3-diphenylpropylthio)propyl)benzofuran-7-yloxy)acetate (66 mg) which can be obtained by the method similar to Reference Example 11 from methyl (3-(3-bromopropyl)benzofuran-7-yloxy)acetate and 3,3-diphenylpropanethiol.

m.p.: 94° C. (recrystallized from ethyl acetate/n-hexane)

IR (KBr method) 2930, 1738, 1582, 1493, 1423, 1263, 1023, 801, 700 cm$^{-1}$

NMR (300 MHz CDCl$_3$) δ7.10–7.40(13H,m),6.81(1H,d, J=7 Hz),4.91(2H,s), 4.08(1H,t,J=8 Hz),2.74(2H,t,J=7 Hz), 2.54(2H,t,J=7 Hz), 2.45(2H,t,J=7 Hz),2.32(2H,q,J=7 Hz), 1.92(2H,quint,J=7 Hz)

EI-MS m/e 460(M$^+$)

Elementary Analysis Calcd. C:73.02% H:6.13% S:6.96 Found C:73.04% H:6.14% S:6.93

EXAMPLE 94

(3-((3,3-diphenyl-2-propenyloxy)methyl)
benzofuran-7-yloxy)acetic acid

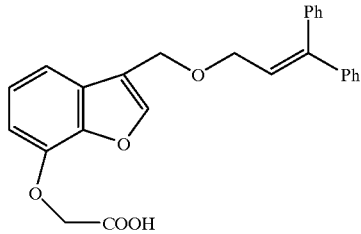

By the method similar to Example 4, the desired compound (286 mg, yield: 94%) was obtained from methyl (3-((3,3-diphenyl-2-propenyloxy)methylbenzofuran-7-yloxy)acetate (315 mg) which is obtained by the method similar to Reference Examples 68 and 59 except that 3,3-diphenyl-2-propene-1-ol is used in place of 3,3-diphenylpropanol.

m.p.: 112–115° C. (recrystallized from hexane/ethyl acetate)

IR (KBr method) 3120, 3060,3 028, 2918, 2868, 1748, 1719, 1628, 1589, 1493, 1431, 1359, 1294, 1253, 1199, 1154, 1096, 1079, 955, 828, 781, 772, 764, 735, 702 cm$^{-1}$ NMR (400 MHz CDCl$_3$) δ7.47(1H,s),7.36–7.12(12H,m), 6.82(1H,d,J=7.8 Hz), 6.23(1H,t,J=6.8 Hz),4.90(2H,s),4.60 (2H,s), 4.11(2H,d,J=6.8 Hz)

EI-MS m/e 414(M$^+$)

EXAMPLE 95

(S)-(3-((2-(diphenylmethoxy)propyloxy)methyl)
benzofuran-7-yloxy)acetic acid

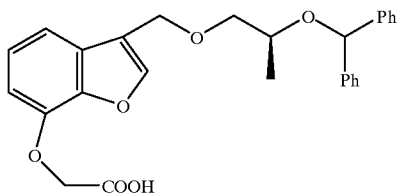

By the method similar to Example 4, the desired compound (74 mg, yield: 68%) was obtained from methyl (S)-(3-((2-(diphenylmethoxy)propyloxy)mcthyl) benzofuran-7-yloxy)acetate (112 mg) which is obtained by the method similar to Reference Examples 68 and 45 except that (S)-2-diphenylmethoxy-1-propanol is used in place of 3,3-diphenylpropanol.

[α]$_D$: −8.17 (c=0.881, CHCl$_3$)

m.p.: 105–107° C.

IR (KBr method) 3500, 1746, 1493, 1431, 1361, 1253, 1187, 1081, 733 cm$^{-1}$

NMR (400 MHz, CDCl$_3$) δ(ppm) 7.55(1H,s),7.40–7.20 (1H,m),7.12(1H,t,J=7.8 Hz), 6.82(1H,d,J=7.8 Hz),5.60(1H, s),4.92(2H,s),4.65(2H,s), 3.7–3.8(1H,m),3.62(1H,dd,J= 10.0, 5.8 Hz), 3.49(1H,dd,J=10.0,4.4 Hz),1.19(3H,d,J=6.4 Hz)

Mass(m/e) 446(M$^+$)

EXAMPLE 96

(R)-(3-((2-(diphenylmethoxy)propyloxy)methyl)
benzofuran-7-yloxy)acetic acid

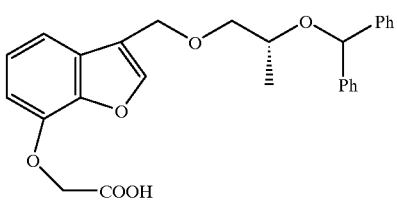

By the method similar to Example 4, the desired compound (72 mg, yield: 46%) was obtained from methyl (R)-(3-((2-(diphenylmethoxy)propyloxy)methyl) benzofuran-7-yloxy)acetate (160 mg) which is obtained by the method similar to Reference Examples 68 and 45 except that (R)-2-diphenylmethoxy-1-propanol is used in place of 3,3-diphenylpropanol.

[α]$_D$: +8.78 (c=0.957, CHCl$_3$)

m.p.: 105–106.5° C.

IR (KBr method) 3500, 1744, 1493, 1431, 1361, 1253, 1187, 1079, 739 cm$^{-1}$

NMR (400 MHz CDCl$_3$) δ(ppm) 7.55(1H,s),7.20–7.40 (11H,m),7.12(1H,t,J=7.8 Hz), 6.82(1H,d,J=7.8 Hz),5.60 (1H,s),4.92(2H,s),4.65(2H,s), 3.7–3.8(1H,m),3.62(1H,dd,J= 10.0,5.8 Hz), 3.49(1H,dd,J=10.0,5.8 Hz),1.19(3H,d,J=6.4 Hz)

Mass(m/e) 447((M+H)$^+$)

EXAMPLE 97

(R)-(3-((2-(diphenylmethoxy)-1-methylethoxy)
methyl)benzofuran-7-yloxy)acetic acid

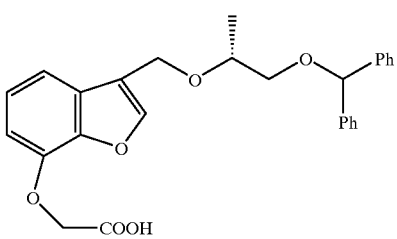

By the method similar to Example 4, the desired compound (74 mg, yield: 42%) was obtained from methyl (R)-(3-((1-(diphenylmethoxy)-1-methylethoxy)methyl) benzofuran-7-yloxy)acetate (180 mg) which is obtained by the method similar to Reference Examples 68 and 45 except that (R)-1-diphenylmethoxy-2-propanol is used in place of 3,3-diphenylpropanol.

[α]$_D$: −11.44 (c=0.769, CHCl$_3$)

m.p.: 91–92.5° C.

IR (KBr method) 2868, 1746, 1717, 1628, 1591, 1543, 1495, 1454, 1431, 1363, 1292, 1261, 1203, 1154, 1096, 1048, 998, 959, 826, 783, 731 cm$^{-1}$ NMR (400 MHz CDCl₃) δ(ppm) 7.56(1H,s),7.20–7.40 (11H,m),7.09(1H,t,J=7.8 Hz), 6.81(1H,d,J=7.3 Hz),5.38 (1H,s),4.90(2H,s),4.75(2H,s), 3.90–3.80(1H,m),3.54(1H,dd, J=10.0,6.3 Hz), 3.45(1H,dd,J=10.0,4 Hz),1.21(3H,d,J=6.4 Hz)

Mass(m/e) 446(M⁺)

EXAMPLE 98

(S)-(3-((2-(diphenylmethoxy)-1-methylethoxy) methyl)benzofuran-7-yloxy)acetic acid

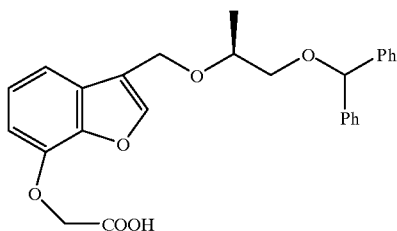

By the method similar to Example 4, the desired compound (40 mg, yield: 30%) was obtained from methyl (R)-(3-((1-(diphenylmethoxy)-1-methylethoxy)methyl) benzofuran-7-yloxy)acetate (136 mg) which is obtained by the method similar to Reference Examples 68 and 45 except that (S)-1-diphenylmethoxy-2-propanol is used in place of 3,3-diphenylpropanol. [α]_D : +11.69 (c=0.872, CHCl₃)

m.p.: 89.5–92° C.

IR (KBr method) 2868, 1746, 1717, 1628, 1591, 1543, 1495, 1454, 1431, 1363, 1292, 1261, 1203, 1154, 1096, 1048, 998, 959, 826, 783, 731 cm⁻¹

NMR (400 MHz CDCl₃) δ7.56(1H,s),7.20–7.40(11H,m), 7.09(1H,t,J=7.3 Hz), 6.81(1H,d,J=7.3 Hz),5.38(1H,s),4.90 (2H,s),4.75(2,s), 3.90–3.80(1H,m),3.54(1H,dd,J=10.0, 6.3 Hz), 3.45(1H,dd,J=10.0,4 Hz),1.21(3H,d,J=6.4 Hz)

Mass(m/e) 446(M⁺)

EXAMPLE 99

(3-(((2-(N,N-diphenylamino)ethoxy)methyl) benzofuran-7-yloxy)acetic acid

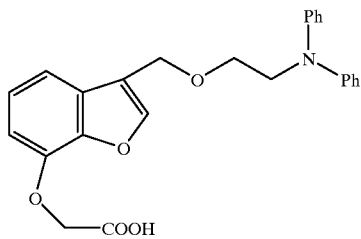

By the method similar to Example 4, the desired compound (68 mg, yield: 68%) was obtained from methyl (3-(((2-(N,N-diphenylamino)ethoxy)methyl)benzofuran-7-yloxy)acetate (103 mg) which is obtained by the method similar to Reference Examples 68 and 45 except that 2-(N, N-diphenylamino)-1-ethanol is used in place of 3,3-diphenylpropanol.

m.p.: 109–110° C. (recrystallized from hexane/ethyl acetate)

IR (KBr method) 2910, 2868, 1731, 1628, 1586, 1495, 1433, 1363, 1323, 1263, 1224, 1195, 1154, 1094, 1077, 791, 750, 733, 704 cm⁻¹

NMR (300 MHz CDCl₃) δ7.50(1H,1Hbrs),7.27–6.80 (13H,m),4.91(2H,s), 4.63(2H,d,J=0.8 Hz),3.96(2H,t,J=6.3 Hz),3.72(2H,t,J=6.3 Hz)

EI-MS m/e 417(M⁺)

Elementary Analysis Calcd. C:71.93% H:5.55% N:3.36% Found C:71.63% H:5.56% N:3.69%

EXAMPLE 100

Methyl (3-(2-hydroxy-5, 5-diphenylpentyl) benzofuran-7-yloxy)acetate

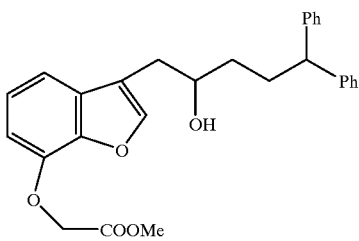

3-(2-acetoxy-5, 5-diphenylpentyl)-7-acetoxybenzofuran (184 mg) was dissolved in methanol (5 ml) and the obtained solution was stirred at room temperature. To this solution, 1N aqueous sodium hydroxide solution (1 ml) was added and the resulting solution was stirred at room temperature. After confirming vanishment of the materials, the solvent was removed under reduced pressure. Water (5 ml) was added to the obtained residue and the resultant was extracted three times with ethyl acetate (10 ml). The organic layers were combined and washed with saturated brine, followed by drying over sodium sulfate. The sodium sulfate was removed by filtration and the solvent was removed under reduced pressure to obtain a crude product. The obtained crude product was dissolved in DMF (3 ml) and the obtained solution was stirred at room temperature. To this solution, potassium carbonate (100 mg) and methyl bromoacetate (0.10 ml) were added and the resultant was stirred at room temperature. After confirming vanishment of the materials, the reaction solution was poured into saturated aqueous ammonium chloride solution and extracted three times with ethyl acetate (10 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=3/1–2/1) using silica gel to obtain the desired compound (184 mg, yield: 100%).

IR (liquid film method) 2948, 1763, 1628, 1591, 1493, 1437, 1361, 1294, 1183, 1143, 1093, 911, 845, 783, 733, 702 cm⁻¹

NMR (300 MHz CDCl₃) δ7.50–7.10(13H,m),6.78(1H,dd, J=7.2,2.4 Hz),4.88(2H,s), 3.90(1H,t,J=7.8 Hz),3.81(3H,s), 2.86–2.78(1H,m), 2.68(1H,dd,J=14.4,7.5 Hz),2.38–2.07 (2H,m),1.60–1.40(2H,m)

EI-MS m/e 444(M⁺)

EXAMPLE 101

(3-(2-hydroxy-5,5-diphenylpentyl)benzofuran-7-yloxy)acetic acid

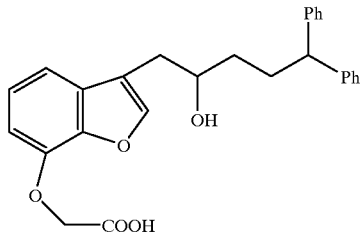

By the method similar to Example 4, the desired compound (116 mg, yield: 78%) was obtained from methyl (3-(2-hydroxy-5,5-diphenylpentyl)benzofuran-7-yloxy) acetate.

m.p.: 155.0–157.0° C. (recrystallized from hexane/ethyl acetate)

IR (KBr method) 3342, 1736, 1620, 1584, 1493, 1433, 1363, 1232, 1195, 1141, 1079, 781, 748, 729 cm$^{-1}$ NMR (400 MHz CDCl$_3$) δ7.46(1H,s),7.29–7.10(12H,m), 6.80(1H,dd,J=7.1,1.7 Hz),4.85(2H,s),3.94–3.87(2H,m), 3.42–3.41(1H,m),2.81(1H,dd,J=14.6,4.2 Hz), 2.69(1H,dd, J=14.6,8.11 Hz),2.33–2.04(3H,m),1.57–1.49(2H,m)

EI-MS m/e 430(M$^+$)

Elementary Analysis Calcd. C:75.33% H:6.09% Found C:75.01% H:6.07%

EXAMPLE 102

Methyl (1-(2-p-toluenesulfonylamino)ethyl)indole-4-yloxy)acetate

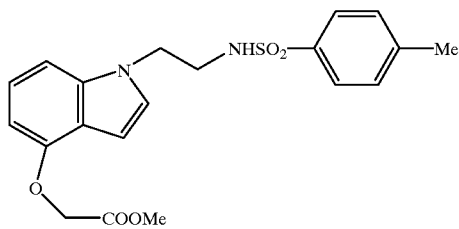

By the method similar to Example 20, the desired compound (200 mg, yield: 46%) was obtained from methyl (1-(2-azideethyl)indole-4-yloxy)acetate (297 mg).

IR (KBr method) 3258, 1740, 1497, 1280, 1249, 1091, 741, 547 cm$^{-1}$

NMR (90 MHz CDCl$_3$) δ7.70–7.60(2H,m),7.40–7.20(5H, m),7.00–6.90(1H), 6.70–6.40(2H,m),4.78(2H,s),4.30–4.10 (2H,m), 3.81(3H,s),3.70–3.40(2H,m),2.41(3H,s)

EI-MS 402(M$^+$)

EXAMPLE 103

(1-(2-p-toluenesulfonylamino)ethyl)indole-4-yloxy) acetic acid

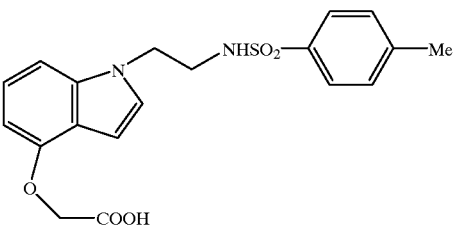

By the method similar to Example 4, the desired compound (114 mg, yield: 79%) was obtained from methyl (1-(2-(p-toluenesulfonylamino)ethyl)indole-4-yloxy)acetate (149 mg).

m.p.: 157–158° C.

IR (KBr method) 3298, 1711, 1497, 1437, 1325, 1224, 1154, 1094, 737 cm$^{-1}$

NMR (400 MHz CDCl$_3$) δ(ppm) 12.97(1H,brs),7.76(1H, t,J=5.9 Hz), 7.61(2H,d,J=8.3 Hz),7.33(2H,d,J=8.3 Hz),7.21 (2H,d,J=3.4 Hz), 7.00(1H,d,J=2.2 Hz),6.99(1H,s),6.43(1H, d,J=3.4 Hz), 4.75(2H,s),3.04(2H,q,J=6.4 Hz),2.36(3H,s)

EI-MS 388(M$^+$)

EXAMPLE 104

(1-(2-(phenylsulfonylamino)ethyl)indole-4-yloxy) acetic acid

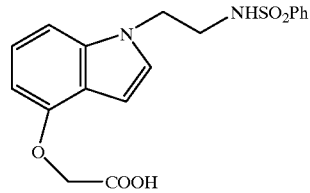

By the method similar to Example 4, the desired compound (105 mg, yield: 77%) was obtained from methyl (1-(2-(phenylsulfonylamino)ethyl)indole-4-yloxy)acetate (141 mg) which can be obtained by the method similar to Example 20.

NMR (400 MHz DMSO-d$_6$) δ(ppm) 12.98(1H,brs),7.86 (1H,t,J=5.9 Hz), 7.77–7.70(2H),7.66–7.50(3H,m),7.21(1H, d,J=2.9 Hz), 7.00(2H,d,J=4.9 Hz),6.43(1H,d,J=2.9 Hz),6.40 (1H,t,J=4.4 Hz), 4.75(2H,s),4.20(2H,t,J=6.4 Hz),3.10–3.04 (2H,m)

EI-MS 374(M$^+$)

EXAMPLE 105

(1-(2-(benzylsulfonylamino)ethyl)indole-4-yloxy) acetic acid

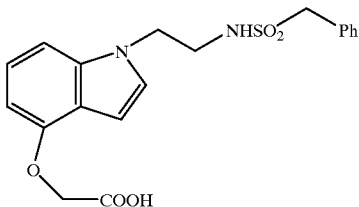

By the method similar to Example 4, the desired compound (72 mg, yield: 65%) was obtained from methyl (1-(2-(benzylsulfonylamino)ethyl)indole-4-yloxy)acetate (114 mg) which can be obtained by the method similar to Example 20.

NMR (400 MHz DMSO-$d_6$) δ(ppm) 12.96(1H,brs), 7.40–7.25(5H,m), 7.25(1H,d,J=3.4 Hz),7.10–7.00(2H,m), 6.46(1H,d,J=2.9 Hz), 6.41(1,dd,J=6.3, 1.4 Hz)0.4.75(2H,s), 4.25(2H,s), 4.18(2H,t,J=6.6 Hz),3.22(2H,q,J=6.3 Hz)

EI-MS 388(M$^+$)

EXAMPLE 106

Methyl (1-(2-(3-phenylpropyloxy)ethyl)indole-4-yloxy)acetate

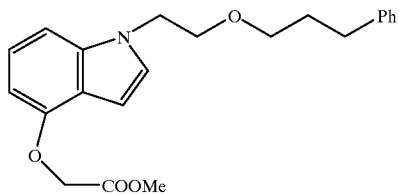

By the method similar to Reference Example 17, the desired compound (196 mg, yield: 88%) was obtained from 1-(2-(3-phenylpropyloxy)ethyl)-4-hydroxyindole (180 mg).

IR (liquid film method) 2952, 1742, 1497, 1212, 1106, 739 cm$^{-1}$

NMR (400 MHz CDCl$_3$) δ(ppm) 7.30–6.90(8H,m),6.66 (1H,d), 6.41(1H,dd,J=5.9,2.3 Hz),4.78(2H,s),4.26(2H,t,J=5 Hz), 3.78(3H,s),3.69(2H,t,J=5.5 Hz),3.34(2H,t,J=6.3 Hz), 2.58(2H,t,J=7.6 Hz),2.00–1.50(2H,m)

EI-MS 367(M$^+$)

EXAMPLE 107

(1-(2-(3-phenylpropyloxy)ethyl)indole-4-yloxy) acetic acid

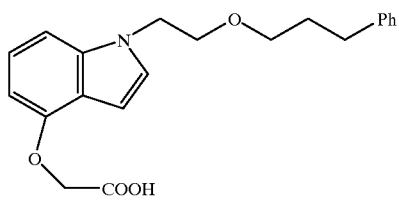

By the method similar to Example 4, the desired compound (152 mg, yield: 81%) was obtained from methyl (1-(2-(3-phenylpropoxy)ethyl)indole-4-yloxy)acetate (196 mg).

m.p.: 89.5–91.0° C. (recrystallized from hexane/ethyl acetate)

IR (KBr method) 2944, 2886, 1713, 1497, 1228, 1123, 1106, 893, 735, cm$^{-1}$

NMR (400 MHz CDCl$_3$) δ(ppm) 7.26–7.00(8H,m),6.64 (1H,d,J=0.7 Hz), 6.50–6.45(1H,m),4.81(2H,s),4.28(2H,t,J= 5.5 Hz), 3.72(2H,t,J=5.5 Hz),3.35(2H,t,J=6.2 Hz),2.58(2H, t,J=7.7 Hz), 1.82(2H,tt,J=7.7.6.7 Hz)

EI-MS 353(M$^+$)

EXAMPLE 108

(1-(2-(2-phenylethoxy)ethyl)indole-4-yloxy)acetic acid

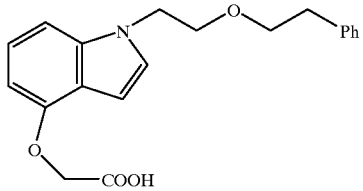

By the method similar to Example 4, the desired compound (119 mg, yield: 58%) was obtained from methyl (1-(2-(2-phenylethoxy)ethyl)indole-4-yloxy)acetate (214 mg) which can be obtained by the method similar to Reference Example 17 from 1-(2-(2-phenylethoxy))ethyl-4-hydroxyindole (201 mg).

m.p.: 76–78° C. (recrystallized from hexane/ethyl acetate)

IR (KBr method) 2868, 1711, 1497, 1454, 1357, 1226, 1104, 891, 77735, 694, 619 cm$^{-1}$ NMR (400 MHz CDCl$_3$) δ(ppm) 7.30–7.02(8H,m),6.60 (1H,d,J=3.9 Hz), 6.47(1H,d=7.3 Hz),4.83(2H,s),4.25(1H,t, J=5.6 Hz), 3.74(2H,t,J=5.6 Hz),38(1H,t,J=6.8 Hz),2.81(2H, t,J=6.8 Hz)

EI-MS 339(M$^+$)

EXAMPLE 109

(1-(2-(2,2-diphenylethoxy)ethyl)indole-4-yloxy) acetic acid

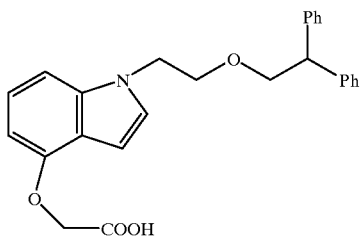

By the method similar to Example 4, the desired compound (150 mg, yield: 76%) was obtained from methyl (1-(2-(2,2-diphenylethoxy)ethyl)indole-4-yloxy)acetate (204 mg) which can be obtained by the method similar to Reference Example 17 from 1-(2-(2,2-diphenylethoxy) ethyl)-4-hydroxyindole.

NMR (400 MHz CDCl$_3$) δ(ppm) 7.30–7.10(8H,m),7.07 (1H,t,J=8.1 Hz), 6.96(1H,d=8.6 Hz),6.90(1H,d,J=2.9 Hz), 6.60–6.50(1H,m),6.45(1H,d,J=7.8 Hz),4.82(2H,s), 4.15–4.23(3H,m),3.90(2H,d,J=7.3 Hz),3.75'2H,t,J=5.6 Hz)

EI-MS 415(M$^+$)

EXAMPLE 110

(1-(2-(3,3-diphenylpropyloxy)ethyl)indole-4-yloxy) acetic acid

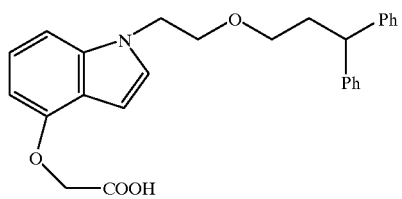

By the method similar to Example 4, the desired compound (40 mg, yield: 47%) was obtained from methyl (1-( 2-(3,3-diphenylpropyloxy)ethyl)indole-4-yloxy)acetate (88 mg) which can be obtained by the method similar to Reference Example 17 from 1-(2-(3,3-diphenylpropyloxy) ethyl)-4-hydroxyindole.

m.p.: 107–109° C. (recrystallized from hexane/ethyl acetate)

IR (KBr method) 1742, 1574, 1497, 1433, 1373, 1354, 1251, 1127, 1106, 739, 698, 538 cm$^{-1}$ NMR (400 MHz CDCl$_3$) δ(ppm) 7.24–7.02(13H,m), 6.66–6.64(1H,m), 6.50(1H,d,J=6.8 Hz),4.82(2H,s),4.25(2H, t,J=5.4 Hz), 3.92(1H,t,J=8.0 Hz),34(2H,t,J=5.4 Hz),3.26 (2H,t,J=6.2 Hz), 2.20(2H,dt,J=8.0, 6.2 Hz)

Mass(m/e) 429(M$^+$)

EXAMPLE 111

Methyl (1-(2-(diphenylmethylthio)ethyl)indole-4-yloxy)acetate

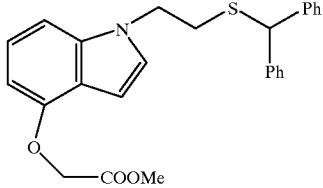

By the method similar to Example 70, the desired compound (122 mg, yield: 73%) was obtained from methyl (1-(2-hydroxyethyl)indole-4-yloxy)acetate (96 mg).

IR (liquid film method) 1763, 1717, 1700, 1686, 1655, 1618, 1560, 1543, 1508, 1495, 1437, 1375, 1210, 1096, 737, 704 cm$^{-1}$ NMR (300 MHz CDCl$_3$) δ7.30–7.14(10H,m),7.06–7.00 (2H,m),6.77(1H,d,J=8.7 Hz), 6.70(1H,dd,J=3.3,0.6 Hz),6.43 (1H,d,J=7.5 Hz),4.80(2H,s), 4.60–4.50(1H,s),4.21(2H,t,J= 6.9 Hz),3.79(3H,s), 2.74(2H,d,J=6.9 Hz)

EI-MS m/e 431(M$^+$)

EXAMPLE 112

(1-(2-(diphenylmethylthio)ethyl)indole-4-yloxy) acetate

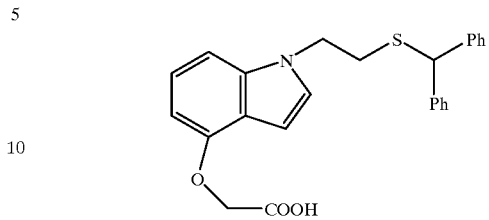

By the method similar to Example 4, the desired compound (103 mg, yield: 87%) was obtained from methyl (1-(2-(diphenylmethylthio)ethyl)indole-4-yloxy)acetate (122 mg).

m.p.: 163.0–165.0° C. (recrystallized from hexane/ethyl acetate)

IR (KBr method) 2562, 1744, 1578, 1495, 1433, 1357, 1245, 1207, 1133, 1096, 739, 702 cm$^{-1}$ NMR (400 MHz CDCl$_3$) δ7.29–7.18(10H,m),7.04(1H,t, J=8.1 Hz), 7.01(1H,d,J=3.4 Hz),6.80(1H,d,J=7.8 Hz),6.66 (1H,d,J=3.0 Hz), 6.47(1H,d,J=7.8 Hz),4.83(2H,s),4.63(1H, s), 4.21(2H,t,J=7.1 Hz),2.75(2H,t,J=7.1 Hz)

EI-MS m/e 419(M$^+$)

Elementary Analysis Calcd. C:71.92% H:5.55% N:3.35% S:7.68% Found C:71.78% H:5.69% N:3.47% S:7.68%

EXAMPLE 113

Methyl (1-(2-(N-(diphenylmethyl)amino)ethyl) indole-4-yloxy)acetate

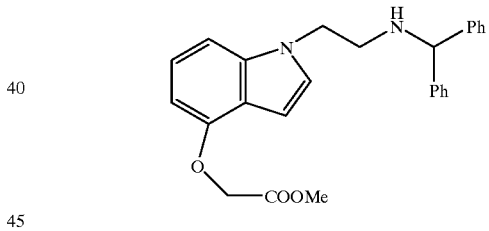

Under argon atmosphere, methyl (1-(2-(azido)ethyl) indole-4-yloxy)acetate (432 mg) was dissolved in a mixed solvent of ethanol (10 ml) and THF (1 ml), and the obtained solution was stirred at room temperature. To this solution, 5% Pd/C (68 mg) was added and the atmosphere in the reaction vessel was replaced with hydrogen. After confirming vanishment of the materials, the atmosphere in the reaction vessel was replaced with argon. Solids were removed by filtration through Celite, and the solvent was removed under reduced pressure to obtain a crude product (362 mg). Under argon atmosphere, the crude product (40 mg) was dissolved in acetonitrile and the obtained solution was stirred at room temperature. To this solution, potassium carbonate (24 mg) and diphenylmethyl bromide (48 mg) were added and the resulting mixture was stirred at room temperature. After confirming vanishment of the materials, phosphate buffer (pH 7, 2 ml) and water (5 ml) were added to the reaction mixture, and the resultant was extracted three times with ethyl acetate (10 ml). The organic layers were combined and washed with saturated brine, followed by drying over sodium sulfate. After removing the sodium sulfate by filtration, the solvent was removed under reduced pressure and the residue was purified by column chromatography (solvent: hexane/ethyl acetate=3/1) using silica gel to obtain the desired compound (23 mg, yield: 32%).

IR (liquid film method) 3062, 2930, 1763, 1740, 1615, 1580, 1495, 1452, 1354, 1284, 1210, 1154, 1100, 1029, 739, 704 cm$^{-1}$ NMR (300 MHz CDCl$_3$) δ7.31–6.97(13H,m),6.67–6.65 (1H,m), 6.41(1H,d,J=7.5 Hz),4.79(2H,s),4.74(1H,s), 4.24 (2H,t,J=6.1 Hz),3.80(3H,s),2.98(2H,t,J=6.1 Hz)

EI-MS m/e 414(M$^+$)

EXAMPLE 114

(1-(2-(N-(diphenylmethyl)amino)ethyl)indole-4-yloxy)acetic acid

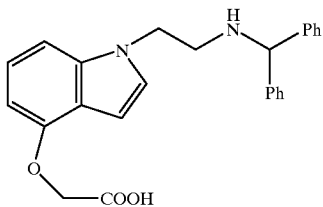

Methyl (1-(2-(N-(diphenylmethyl)amino)ethyl)indole-4-yloxy)acetate (99 mg) was dissolved in a mixed solvent of ethanol (5 ml) and THF (2 ml), and the obtained solution was stirred at room temperature. To this solution, 1N aqueous sodium hydroxide solution was added and the resulting solution was stirred at room temperature. After confirming vanishment of the materials, the solvent was removed under reduced pressure. Water (5 ml) was added to the obtained residue and 1N hydrochloric acid was added to the mixture to neutralize the same. The precipitated solids were collected by centrifugation and washed twice with water and twice with methanol. The solids were dried under reduced pressure to obtain the desired compound (58 mg, yield: 61%)

m.p.: 213.0–215.0° C.

IR (KBr method) 1582, 1495, 1454, 1410, 1267, 1234, 1079, 741, 702, 563, 453, 422 cm$^{-1}$ NMR (400 MHz DMSO-d6) δ7.32–7.14(11H,m), 7.13–6.96(2H,m),6.44(1H,d,J=3.0 Hz), 6.37(1H,d,J=7.3 Hz),4.78(1H,s),4.73(2H,s), 4.24(2H,t,J=6.3 Hz),2.76(2H,t, J=6.3 Hz)

EI-MS m/e 400(M$^+$)

EXAMPLE 115

(1-(2-N,N-dibenzylamino)ethyl)indole-4-yloxy) acetic acid

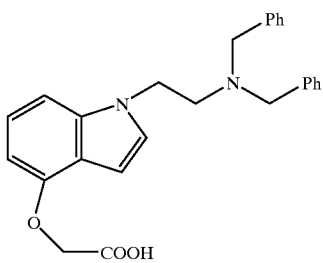

By the method similar to Example 4, the desired compound (187 mg, yield: 100%) was obtained from methyl (1-(2-(N,N-dibenzylamino)ethyl)indole-4-yloxy)acetate (189 mg) which can be obtained by the method similar to Example 113 except that benzylbromide is used in place of diphenylmethyl bromide.

m.p.: 83.0–85.0° C. (recrystallized from hexane/ethyl acetate)

m.p.: 83.0–85.0° C. (recrystallized from hexane/ethyl acetate)

IR (KBr method) 2924, 1721, 1580, 1495, 1450, 1359, 1232, 1123, 1083, 1029, 737, 700, cm$^{-1}$ NMR (400 MHz CDCl$_3$) δ7.40–7.15(10H,m),6.94(1H,t, J=8.1 Hz), 6.87(1H,d,J=3.3 Hz),6.63(1H,d,J=8.4 Hz), 6.56 (1H,dd,J=3.3,0.9 Hz),6.43(1H,d,J=7.5 Hz),4.80(2H,s), 4.10–4.00(2H,m),3.85–3.60(4H,m),3.00–2.80(2H,m)

EI-MS m/e 414(M$^+$)

Elementary Analysis Calcd. C:75.34% H:6.32% N:6.76% Found C:75.12% H:6.38% N:7.05%

EXAMPLE 116

(1-(5-phenylpentyl)indole-4-yloxy)acetic acid

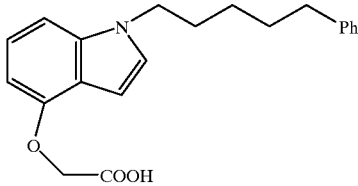

By the method similar to Example 4, the desired compound (112 mg, yield: 69%) was obtained from methyl (1-(5-phenylpentyl)indole-4-yloxy)acetate (170 mg) which can be obtained by the method similar to Reference Example 17 from 1-(5-phenylpentyl)-4-hydroxyindole.

m.p.: 109–110° C. (recrystallized from hexane/ethyl acetate)

IR (KBr method) 2932, 1748, 1711, 1574, 1499, 1247, 1093, 913, 735 cm$^{-1}$

NMR (400 MHz CDCl$_3$) δ(ppm) 7.33–6.95(8H,m),6.61 (1H,d,J=2.9 Hz), 6.46(1H,d=7.4),4.82(2H,s),4.08(2H,t,J= 7.1 Hz), 2.58(2H,t,J=7.8 Hz),1.85(2H,quint,J=6.8 Hz), 1.68–1.59(2H,m)

EI-MS 337(M$^+$)

EXAMPLE 117

Methyl (1-(4,4-diphenylbutyl)indole-4-yloxy)acetate

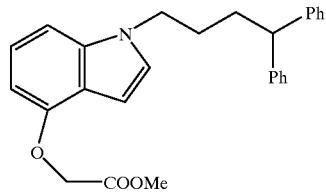

By the method similar to Reference Example 17, the desired compound (60 mg, yield: 88%) was obtained from 1-(4,4-diphenylbutyl)-4-hydroxyindole (56 mg).

IR (liquid film method) 2938, 1763, 1576, 1560, 1497, 1437, 1375, 1212, 1093, 737, 704 cm$^{-1}$ NMR (300 MHz CDCl$_3$) δ7.27–7.13(10H,m),7.05(1H,d, J=8.0 Hz), 6.97(1H,d,J=3.3 Hz),6.91(1H,d,J=8.4 Hz),6.64

(1H,d,J=3.3 Hz), 6.40(1H,d,J=7.8 Hz),4.79(2H,s),4.08(2H, t,J=7.1 Hz), 3.84(1H,t,J=7.7 Hz),3.80(3H,s),2.09–2.01(2H, m), 1.86–1.75 (2H,m)

EI-MS m/e 413(M+)

EXAMPLE 118

(1-(4,4-diphenylbutyl)indole-4-yloxy)acetic acid

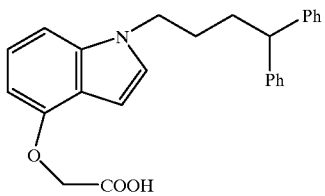

By the method similar to Example 4, the desired compound (67 mg) was obtained from ethyl (1-(4,4-diphenylbutyl)indole-4-yloxy)acetate (73 mg).

m.p.: 123.0–125.5° C. (recrystallized from hexane/ethyl acetate)

IR (KBr method) 2928, 1740, 1715, 1618, 1495, 1446, 1423, 1379, 1313, 1247, 1137, 1091, 781, 741, 700, 667 cm$^{-1}$ NMR (300 MHz CDCl$_3$) δ7.28–7.05(11H,m),6.99(1H,d, J=3.0 Hz), 6.95(1H,d,J=8.1 Hz),6.60(1H,dd,J=3.0,0.9 Hz), 6.46(1H,d,J=7.5 Hz),4.82(2H,s),4.10(2H,t,J=6.9 Hz), 3.85 (1H,t,J=7.8 Hz),2.10–2.01(2H,m),1.86–1.76(2H,m)

EI-MS m/e 399(M+)

Elementary Analysis Calcd. C:78.17% H:6.31% N:3.51% Found C:76.97% H:6.35% S:3.84%

EXAMPLE 119

(1-(2-(2-phenylethylsulfonylamino)ethyl)indole-4-yloxy)acetic acid

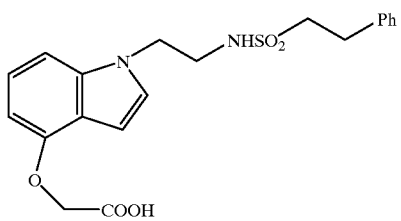

By the method similar to Example 4, the desired compound (115 mg, yield: 56%) was obtained from methyl (1-(2-(2-phenylethylsulfonylamino)ethyl)indole-4-yloxy) acetate (211 mg) which can be obtained by the method similar to Example 20.

m.p.: 167–168.5° C. (recrystallized from hexane/ethyl acetate)

NMR (400 MHz DMSO-d$_6$) δ(ppm) 12.97(1H,brs), 7.40–7.00(8H,m), 6.46–6.41(2H,m)0.73(2H,s),4.24(2H,t,J= 6.4 Hz), 3.24–3.40(4H,m),3.16–3.05(2H,m),2.86–2.76(2H, m)

EI-MS 402(M+)

EXAMPLE 120

Methyl (1-(2-(diphenylmethoxy)ethyl)indoline-4-yloxy)acetate

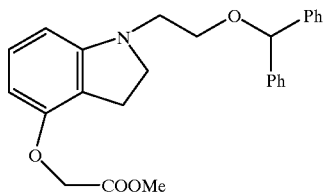

Under argon atmosphere, potassium t-butoxide (586 mg) and methyl bromoacetate (2.50 ml) were added to 1-(2-(diphenylmethoxy)ethyl)-4-hydroxyindoline (855 mg) in DMF (15 ml), and the obtained mixture was stirred at room temperature for 2 hours. To the reaction mixture, saturated aqueous ammonium chloride solution (5 ml) was added to stop the reaction and the resultant was extracted with ethyl acetate. The obtained organic layer was washed and dried over sodium sulfate. After removing solids by filtration, the solvent was removed under reduced pressure and the obtained crude product was purified by silica gel column chromatography to obtain the desired compound (571 mg, yield: 55%)

IR (liquid film method) 2856, 1763, 1618, 1508, 1437, 1209, 1102, 745, 704 cm$^{-1}$ NMR (90 MHz CDCl$_3$) δ(ppm) 7.40–7.10(10H,m), 7.10–6.80(1H,m), 6.20–6.00(2H,m),5.38(1H,s),4.63(2H,s), 3.78(3H,s), 3.20–3.70(6H,m),3.10–2.80(2H,m)

EI-MS 417(M+)

EXAMPLE 121

(1-(2-(diphenylmethoxy)ethyl)indoline-4-yloxy) acetic acid

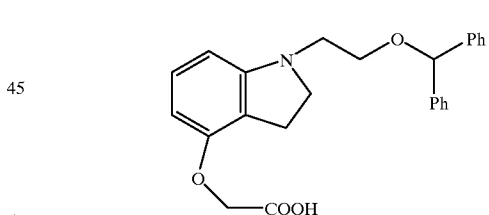

By the method similar to Example 4, the desired compound (406 mg, yield: 74%) was obtained from methyl (1-(2-(diphenylmethoxy)ethyl)indoline-4-yloxy)acetate (571 mg).

m.p.: 109–111° C. (recrystallized from hexane/ethyl acetate)

IR (KBr method) 3500, 2852, 1742, 1620, 1491, 1261, 1238, 1102, 756, 704 cm$^{-1}$ NMR (400 MHz CDCl$_3$) δ(ppm) 7.38–7.20(10H,m),7.00 (1H,t,J=8.1 Hz), 6.19(1H,t,J=7.8 Hz),6.13(1H,d,J=7.8 Hz), 5.38(1H,s), 4.66(2H,s),3.65(2H,t,J=5.9 Hz),3.49(2H,t,J=8.5 Hz), 3.35(2H,t,J=5.9 Hz),2.98(2H,J=8.5 Hz)

EI-MS 403(M+)

EXAMPLE 122

(1-(2-(2,2-diphenylethoxy)ethyl)indoline-4-yloxy) acetic acid

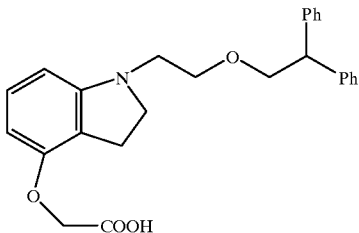

By the method similar to Example 4, the desired compound (100 mg, yield: 96%) was obtained from methyl (1-(2-(2,2-diphenylethoxy)ethyl)indoline-4-yloxy)acetate (108 mg) which can be obtained by the method similar to Example 120 from 1-(2-(2,2-diphenylethoxy))ethyl)-4-hydroxyindoline.

NMR (400 MHz CDCl$_3$) δ(ppm) 7.31–7.10(10H,m),6.91 (1H,t,J=8.1 Hz), 6.10–6.05(2H,m),4.52(2H,s),4.26(1H,t,J= 7.3 Hz), 3.98(2H,d,J=7.3 Hz),31(2H,t,J=5.9 Hz),3.21(2H,t, J=8.4 Hz), 3.15(2H,t,J=5.9 Hz),2.82(1H,t,J=8.4 Hz), 2.60–1.40(1H,brs)

EXAMPLE 123

(1-(2-(3,3-diphenylpropyloxy)ethyl)indoline-4-yloxy)acetic acid

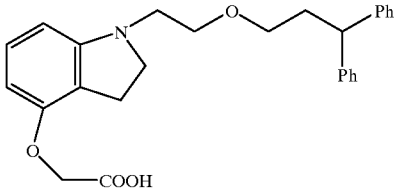

By the method similar to Example 4, the desired compound (461 mg, yield: 89%) was obtained from methyl (1-(2-(3,3-diphenylpropyloxy)ethyl)indoline-4-yloxy) acetate (533 mg) which can be obtained by the method similar to Example 120 from 1-(2-(3,3-diphenylpropyloxy) ethyl-4-hydroxyindoline.

NMR (400 MHz CDCl$_3$) δ(ppm) 7.31–7.11(10H,m), 7.04–6.99(1H,m), 6.21(1H,d,J=7.8 Hz),6.14(1H,d,J=8.3 Hz),4.66(2H,s), 4.12–4.07(1H,m),3.55(2H,t,J=5.9 Hz),3.47 (2H,t,J=8.6 Hz), 3.38(2H,t,J=6.4 Hz),3.24(2H,t,J=5.9 Hz), 2.99(2H,t,J=8.6 Hz), 2.35–2.25(2H,m)

EXAMPLE 124

Methyl (1-(2-(diphenylmethylthio)ethyl)indoline-4-yloxy)acetate

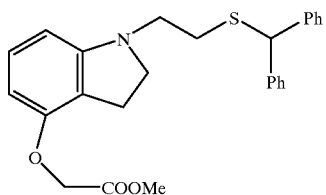

By the method similar to Example 70, the desired compound (219 mg, yield: 84%) was obtained from methyl (1-(2-hydroxyethyl)indoline-4-yloxy)acetate (151 mg).

IR (liquid film method) 2956, 1763, 1742, 1618, 1597, 1485, 1466, 1452, 1294, 1270, 1207, 1156, 1106, 1031, 1004, 924, 845, 787, 752, 702, 629, 586 cm$^{-1}$ NMR (300 MHz CDCl$_3$) δ7.46–7.20(10H,m),6.94(1H,t, J=8.1 Hz), 6.08(1H,d,J=8.1 Hz),5.98(1H,d,J=8.1 Hz),5.25 (1H,s), 3.78(3H,s),3.31(2H,t,J=8.6 Hz),3.23(2H,dd,J=8.7, 7.5 Hz), 2.96(2H,t,J=8.6 Hz),2.60(2H,dd,J=7.5,6.0 Hz)

EI-MS m/e 433(M$^+$)

EXAMPLE 125

(1-(2-(diphenylmethylthio)ethyl)indoline-4-yloxy) acetic acid

By the method similar to Example 4, the desired compound (181 mg, yield: 87%) was obtained from methyl (1-(2-(diphenylmethylthio)ethyl)indoline-4-yloxy)acetate (216 mg).

m.p.: 158.0–161.5° C. (recrystallized from hexane/ethyl acetate)

IR (KBr method) 2786, 2592, 1744, 1711, 1620, 1485, 1452, 1431, 1352, 1251, 1224, 1154, 1108, 917, 752, 704 cm$^{-1}$ NMR (400 MHz CDCl$_3$) δ7.45–7.21(10H,m),6.96(1H,t, J=8.1 Hz), 6.12(1H,d,J=8.1 Hz),6.00(1H,d,J=8.1 Hz),5.25 (1H,s), 4.64(2H,s),3.33(2H,t,J=6.4 Hz),3.22(2H,t,J=5.5 Hz), 2.95(2H,t,J=6.4 Hz),2.62–2.57(2H,m)

EI-MS m/e 419(M$^+$)

Elementary Analysis Calcd. C:71.57% H:6.01% N:3.34% S:7.64% Found C:71.21% H:6.01% N:3.49% S:7.66%

EXAMPLE 126

Ethyl (2-((3,3-diphenylpropyloxy)methyl)benzofuran-7-yloxy)acetate

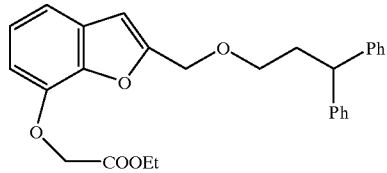

By the method similar to Reference Example 17, the desired compound (235 mg, yield: 95%) was obtained from 2-(3,3-diphenylpropyloxy)methyl-7-hydroxybenzofuran (200 mg).

IR (liquid film method) 3062, 3030, 2982, 2940, 2868, 1953, 1889, 1763, 1626591, 1493, 1437, 1379, 1330, 1296, 1191, 1139, 1116, 1062, 1031, 940, 855, 816, 775, 752, 733, 702, 630, 617, 514, 451 cm$^{-1}$ NMR (90 MHz CDCl$_3$) δ7.26–7.06(12H,m),6.75(1H,dd, J=6.4,2.6 Hz), 6.59(1H,s),4.85(2H,s),4.54(2H.s),4.27(2H,q, J=7.0,7.3 Hz), 4.15(1H,t,J=7.7 Hz),3.47(2H,t,J=6.3 Hz), 2.35(2H,dt,J=6.3,7.7 Hz),1.27(3H,t,J=7.0 Hz)

EI-MS m/e 444(M$^+$)

EXAMPLE 127

(2-((3,3-diphenylpropyloxy)methyl)benzofuran-7-yloxy)acetic acid

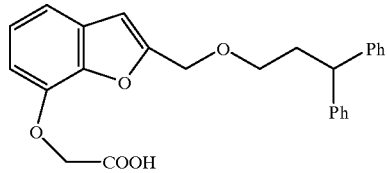

By the method similar to Example 4, the desired compound (208 mg, yield: 97%) was obtained from ethyl (2-((3,3-diphenylpropyloxy)methyl)benzofuran-7-yloxy)acetate (230 mg).

m.p.: 116–118° C. (recrystallized from ethyl acetate/n-hexane)

IR (KBr method) 3062, 3030, 2922, 2866, 1750, 1493, 1456, 1427, 1361, 1332, 1296, 1251, 1201, 1118, 1058, 940, 777, 733, 706, 629, 538 cm$^{-1}$ NMR (400 MHz CDCl$_3$) δ7.24–7.10(12H,m),6.78(1H,dd, J=7.8,1.0 Hz), 6.59(1H,s),4.87(2H,s),4.52(2H.s),4.13(1H,t, J=7.8 Hz), 4.2–3.3(1H,br),3.46(2H,t,J=6.4 Hz),2.34(2H,dt, J=6.4,7.8 Hz)

EI-MS m/e 416(M$^+$)

High Resolution Mass Spectrum Calcd. (C$_{26}$H$_{24}$O$_5$M$^+$): 416.1624 Found: 416.1637

Elementary Analysis Calcd. (as C$_{26}$H$_{24}$O$_5$) Found C: 74.98 74.73 H: 5.81 5.82

EXAMPLE 128

(2-((2,2-diphenylethoxy)methyl)benzofuran-7-yloxy)acetic acid

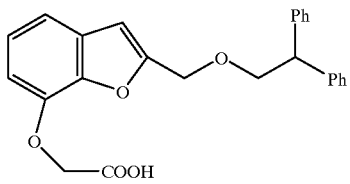

By the method similar to Reference Example 17 and Example 4, the desired compound (178 mg, yield: 97%) was obtained from 2-(2,2-diphenylethoxy)methyl-7-hydroxybenzofuran.

m.p.: 141–142° C. (recrystallized from ethyl acetate/n-hexane)

IR (KBr method) 3028, 2890, 1740, 1626, 1603, 1586, 1493, 1454, 1429, 1371, 1296, 1261, 1197, 1141, 1116, 1087, 1013, 953, 928, 853, 830, 791, 779, 739, 700, 630, 561,472 cm$^{-1}$ NMR (400 MHz CDCl$_3$) δ7.28–7.16(11H,m),7.11(1H,t, J=7.8 Hz), 6.77(1H,dd,J=7.8,1 Hz),6.57(1H,s),4.86(2H,s), 4.62(2H.s), 4.5–3.6(1H,br),4.31(1H,t,J=7.3 Hz),4.06(2H,d, J=7.3 Hz)

EI-MS m/e 402(M$^+$)

High Resolution Mass Spectrum Calcd. (C$_{25}$H$_{22}$O$_5$M$^+$): 402.1467 Found: 402.1468

Elementary Analysis Calcd. (as C$_{25}$H$_{22}$O$_5$) Found C: 74.61 74.28 H: 5.52 5.51

EXAMPLE 129

(2(diphenylmethoxymethyl)benzofuran-7-yloxy)acetic acid

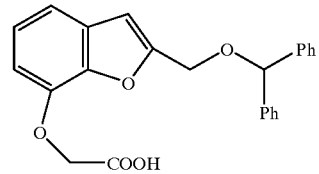

By the method similar to Reference Example 17 and Example 4, the desired compound (202 mg, yield: 95%) was obtained from 2-(diphenylmethoxymethyl)-7-hydroxybenzofuran (192 mg).

m.p.: 98–99° C. (recrystallized from ethyl acetate/n-hexane)

IR (KBr method) 3030, 2926, 1744, 1626, 1591, 1493, 1441, 1394, 1301, 1249, 1199, 1120, 1089, 1067, 1011, 942, 855, 806, 766, 735, 702, 634, 501, 464, 418 cm$^{-1}$ NMR (400 MHz CDCl$_3$) δ7.39–7.20(11H,m),7.12(1H,t, J=7.8 Hz), 6.79(1H,dd,J=7.8,1 Hz),6.69(1H,s),5.53(1H,s), 4.89(2H.s), 4.64(2H,s),4.6–3.4(1Hrs)

EI-MS m/e 488(M$^+$)

High Resolution Mass Spectrum Calcd. (C$_{24}$H$_{20}$O$_5$M$^+$): 388.1311 Found: 388.1331

Elementary Analysis Calcd. (as C$_{24}$H$_{20}$O$_5$) Found C: 74.21 74.17 H: 5.81 5.82

EXAMPLE 130

(2-(2-diphenylmethoxyethoxymethyl)benzofuran-7-yloxy)acetic acid

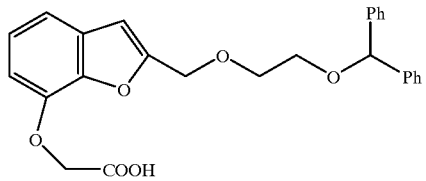

By the method similar to Example 4, the desired compound (256 mg, yield: 91%) was obtained from ethyl 2-(2-diphenylmethoxyethoxymethyl)-benzofuran-7-yloxyacetate (298 mg) which can be obtained by the method similar to Reference Examples 68 and 45 from 2-(2-chloromethyl)-7-methoxybenzofuran.

m.p.: 102.0–103.0° C. (recrystallized from hexane/ethyl acetate)

IR (KBr method) 2922, 2866, 1742, 1717, 1493, 1296, 1259, 1197, 1108, 743, 700 cm$^{-1}$ NMR (400 MHz CDCl$_3$) $\delta$7.16–7.38(11H,m),7.11(1H,t, J=7.8 Hz), 6.78(1H,d,J=7.8 Hz),6.67(1H,s),5.42(1H,s),4.86 (2H,s), 4.68(2H,s),3.72–3.81(2H,m),3.61–3.71(2H,m)

FAB-MS m/e 431((M–H)$^-$)

Elementary Analysis Calcd. C:72.21% H:5.59% Found C:71.89% H:5.56%

EXAMPLE 131

(2-(3-diphenylmethoxypropoxymethyl)benzofuran-7-yloxy)acetic acid

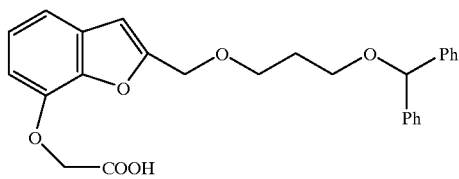

By the method similar to Example 4, the desired compound (186 mg, yield: 81%) was obtained from ethyl (2-(3-diphenylmethoxypropoxymethyl)benzofuran-7-yloxy)acetate (246 mg) which can be obtained by the method similar to Reference Examples 68 and 45 from 2-(2-chloromethyl)-7-methoxybenzofuran.

m.p.: 78.5–79.5° C. (recrystallized from hexane/ethyl acetate)

IR (KBr method) 3064, 2962, 2952, 2926, 2910, 2868, 1748, 1586, 1493, 1456, 1429, 1369, 1313, 1292, 1259, 1197, 1139, 1118, 1093, 1071, 1040, 932, 828, 779, 746, 737, 729, 702 cm$^{-1}$ NMR (400 MHz CDCl$_3$) $\delta$7.19–7.34(10H,m),7.19(1H,dd, J=7.8, 1.0 Hz), 7.11(1H,t,J=7.8 Hz),6.77(1H,dd,J=7.8, 1.0 Hz),6.65(1H,s), 5.33(1H,s),4.86(2H,s),4.58(2H,s),3.69(2H, t,J=6.4 Hz), 3.57(2H,t,J=6.4 Hz),1.94(2H,quint,J=6.4 Hz)

FAB-MS m/e 446((M–H)$^-$)

Elementary Analysis Calcd. C:72.63% H:5.87% Found C:72.40% H:5.91%

EXAMPLE 132

Platelet Aggregation-inhibition Action 1

Blood collected from medial cubital vein is centrifuged at 800 rmp for 10 minutes and the upper portion of the resultant is collected as platelet-rich plasma (PRP). The PRP is dividedly poured into small test tubes and a TXA$_2$ agonist U-46619 is added thereto (final concentration: 1–4 $\mu$M) so as to induce platelet aggregation. The degree of platelet aggregation is measured in terms of change in turbidity by a platelet aggregation measuring apparatus (Hematoracer, NIKO BIOSCIENCE). The compound is added one minute before the addition of U-46619 and the concentration of the compound at which the aggregation is inhibited by 50% is calculated as IC$_{50}$ value.

The results of the evaluation of the activities of the compounds of the present invention by this method are summarized in Table 1.

TABLE 1

| Example No. | Platelet Aggregation-Inhibition Action IC$_{50}$ ($\mu$M) |
|---|---|
| 4 | 1.1 |
| 8 | 1.0 |
| 9 | 0.3 |
| 13 | 7.2 |
| 15 | 1.0 |
| 16 | 0.5 |
| 17 | 0.14 |
| 19 | 1.4 |
| 24 | 0.088 |
| 25 | 0.14 |
| 31 | 0.44 |
| 32 | 1.6 |
| 33 | 1.1 |
| 35 | 4.5 |
| 43 | 4.0 |
| 48 | 4.8 |
| 59 | 0.33 |
| 68 | 0.9 |
| 81 | 0.64 |
| 83 | 0.46 |
| 85 | 0.62 |
| 88 | 0.51 |
| 94 | 0.71 |
| 97 | 1.6 |
| 101 | 1.5 |
| 103 | 1.3 |
| 104 | 5.1 |
| 112 | 0.84 |
| 118 | 1.7 |
| 122 | 1.4 |
| 125 | 0.72 |
| 130 | 18 |

EXAMPLE 113

Platelet Aggregation-Inhibition Action 2

Blood collected from medial cubital vein is centrifuged at 800 rmp for 10 minutes and the upper portion of the resultant is collected as platelet-rich plasma PRP). The PRP is dividedly poured into small test tubes and ADP is added thereto (final concentration: 1–3 $\mu$M) so as to induce platelet aggregation. The degree of platelet aggregation is measured in terms of change in turbidity by a platelet aggregation measuring apparatus Hematoracer, NIKO BIOSCIENCE). The compound is added one minute before the addition of ADP the concentration of the compound at which the aggregation is inhibited by 50% is calculated as IC$_{50}$ value.

The results of the evaluation of the activities of the compounds of the present invention by this method are summarized in Table 2.

TABLE 2

| Example No. | Platelet Aggregation Inhibition Action IC$_{50}$ ($\mu$M) |
|---|---|
| 8 | 305 |
| 15 | 201 |
| 16 | 403 |
| 31 | 265 |
| 35 | 7.8 |
| 48 | 7.8 |
| 49 | 8.2 |
| 59 | 0.6 |
| 68 | 6.2 |
| 81 | 4.5 |
| 83 | 3.3 |
| 85 | 0.75 |
| 88 | 0.73 |
| 91 | 1.9 |
| 97 | 3.4 |
| 101 | 1.8 |
| 109 | 27.9 |
| 112 | 4.5 |
| 118 | 3.6 |
| 122 | 2.7 |
| 125 | 3.1 |

EXAMPLE 134

TXA$_2$ Receptor Binding Test 1

Blood from a New Zealand White rabbit is taken in a vessel containing ACD solution (prepared by dissolving 1.175 g of sodium citrate, 0.685 g of citric acid and 1 g of dextrose in 50 ml of distilled water) and centrifuged at 180×g for 10 minutes at room temperature to obtain platelet-rich plasma. The obtained platelet-rich plasma is centrifuged at 180×g at room temperature to precipitate platelets. The platelets are then suspended in 50 mM Tris-HCl buffer (pH 7.2, containing 0.154M of NaCl) and the suspension is centrifuged at 2800×g for 15 minutes at 4° C. These operations are repeated twice to prepare washed platelets and the concentration of the platelets are adjusted to a final concentration of 10 mg/ml (wet weight).

As the ligand of TXA$_2$, tritium-labelled SQ29548 ([$^3$H] SQ29548) is used. In the antagonism test, 20 $\mu$l of [$^3$H] SQ29548 having a final concentration of 3 nM is added to 500 $\mu$l of a platelet suspension having a platelet concentration of 10 mg/ml and 2.6 $\mu$l of a solution of a test compound dissolved in an appropriate solvent is added thereto. After incubating the resulting mixture at 25° C. for 60 minutes, the mixture is filtered through a glass filter by the cell harvester method. After washing the filter with 50 mM Tris-HCl buffer (3×4 ml), the radioactivity of the filter is measured by a scintillation counter, thereby measuring the amount of the [$^3$H]SQ29548 bound to platelets. In the saturation test, 20 $\mu$l of [$^3$H]SQ29548 is added to a final concentration of 0.1–50 nM and 2.6 $\mu$l of BM13505 having a final concentration of 1 $\mu$M is added so as to check non-specific binding, followed by carrying out the binding test. The concentration of the test compound at which binding of [$^3$H]SQ29548 is inhibited by 50% is determined as the IC$_{50}$ value.

The results of the evaluation of the activities of the compounds of the present invention by this method are summarized d in Table 3.

TABLE 3

| Example No. | TXA$_2$ Receptor Binding Test IC$_{50}$ ($\mu$g/$\mu$l) |
|---|---|
| 9 | 0.0018 |
| 13 | 0.012 |
| 15 | 0.43 |
| 16 | 0.022 |
| 17 | 0.0008 |
| 19 | 0.34 |
| 24 | 0.0075 |
| 25 | 0.002 |
| 31 | 0.019 |
| 32 | 0.22 |
| 33 | 0.037 |
| 43 | 0.028 |
| 46 | 0.24 |
| 47 | 1.3 |
| 51 | 0.078 |
| 53 | 0.84 |
| 103 | 0.0012 |
| 104 | 0.01 |

EXAMPLE 135

TXA$_2$ Receptor Binding Test 2

Blood collected from human forearm vein and ACD solution (85 mM trisodium citrate, 65 mM citric acid, 2% glucose) in an amount of ¹/₁₀ volume of the blood were mixed the resultant was dividedly poured into Spitz tubes an amount of 8 ml/tube. The mixture was centrifuged at 200×g for 10 minutes at room temperature to obtain platelet-rich plasma and the obtained platelet-rich plasma was centrifuged at 1000×g for 15 minutes to obtain platelets. The platelets were washed by centrifugation using a washing buffer (115 mM sodium chloride, 4.3 mM potassium dihydrogen phosphate, 5.5 mM glucose, 1 mM disodium EDTA, 10 $\mu$M indomethacin, pH 6.5) and 1 ml of a melting buffer (10 mM Tris(hydroxymethyl)aminomethane, 5 mM magnesium chloride, 2 mM disodium EDTA, pH 7.4) was added. The resultant was frozen in liquid nitrogen and thawed at room temperature. By repeating freezing in liquid nitrogen and thawing totally three times, the platelets were ruptured. The resultant was washed three times by ultracentrifugation (40,000×g, each 20 minutes) using iced 5 mM Tris-HCl buffer, and the finally obtained precipitate was collected as the platelet membrane fraction.

As the ligand of TXA$_2$, tritium-labelled SQ29548 ([$^3$H] SQ29548) was used. As the solvent for the receptor binding reaction, 50 mM Tris-HCl buffer (5 mM magnesium chloride, pH 7.4) was used. The saturation test was carried out by reacting [$^3$H]SQ29548 (100 $\mu$l) having a final concentration of 3–100 nM with 0.1 mg protein/ml of a suspension of the platelet membrane fraction (100 $\mu$l) at 25° C. for 30 minutes under shaking. The binding test was carried out by mixing a mixture (100 $\mu$l) of a test compound dissolved in an appropriate solvent and then diluted and [$^3$H]SQ29548, and the suspension of platelet membrane fraction (100 $\mu$l) having a concentration of 0.1 mg protein/ml, and allowing the mixture to react at 25° C. for 30 minutes under shaking. After the reaction, the resultant was filtered through a glass filter using a cell harvester to collect the membrane fraction on the glass filter. The filter was washed with a iced buffer and radioactivity was measured by scintillation counter. The non-specific binding to substances other than the platelets was measured by the reaction in the presence of SQ29548 having a final concentration of 10 nM. The IC$_{50}$ value of the test compound and Hill coefficient in the binding test was determined by Pseudo-Hill plot. The receptor dissociation constant (Ki value) was calculated according to the following equation from the IC$_{50}$ value and the receptor dissociation constant (Kd value) of [³H] SQ29548 determined in the saturation test.

Ki=IC₅₀/[1+(radioactive ligand concentration/Kd)]

The results of the evaluation of the activities of the compounds of the present invention by this method are summarized in Table 4.

TABLE 4

| Example No. | TXA₂ Receptor Binding Test Ki (μM) |
|---|---|
| 48 | 7.7 |
| 67 | 0.31 |
| 118 | 3.6 |

EXAMPLE 136

PGI₂ Receptor Binding Test

As the ligand of PGI₂ receptor, tritium-labelled (1R,2R,3aS,8bS)-2,3,3a,8-tetrahydro-2-hydroxy-1-[(E)-(3S,4S)-3-hydroxy-4-methyl-1-octene-6-ynyl]-1H-cyclopenta[b]benzofuran-5-butanoic acid ([³H]APS-314d) was used. The saturation test was carried out by reacting [³H]APS-314d (100 μl) having a final concentration of 3–100 nM with a suspension (100 μl) of platelet membrane fraction having a concentration of 0.1 mg protein/ml at 4° C. for 60 minutes under shaking. The competition test was carried out by mixing a mixture (100 μl) of a test compound dissolved in an appropriate solvent and then diluted and [³H]APS-314d, and the suspension of platelet membrane fraction (100 μl) having a concentration of 0.1 mg protein/ml, and allowing the mixture to react at 4° C. for 60 minutes under shaking. After the reaction, the resultant was filtered through a glass filter using a cell harvester to collect the membrane fraction on the glass filter. The filter was washed with a iced buffer and radioactivity was measured by scintillation counter. The non-specific binding to substances other than the platelets was measured by the reaction in the presence of sodium beraprost having a final concentration of 10 nM. The IC₅₀ value of the test compound and Hill coefficient in the binding test was determined by Pseudo-Hill plot. The receptor dissociation constant (Ki value) was calculated according to the following equation from the IC₅₀ value and the receptor dissociation constant (Kd value) of [³H]APS-314d determined in the saturation test.

Ki=IC₅₀/[1+(radioactive ligand concentration/Kd)]

The results of the evaluation of the activities of the compounds of the present invention by this method are summarized in Table 5.

TABLE 5

| Example No. | PGI₂ Receptor Binding Test Ki (μM) |
|---|---|
| 48 | 0.38 |
| 68 | 0.41 |
| 118 | 0.44 |

Industrial Availability

The compounds of the present invention have strong TXA₂ receptor antagonist activities and PGI₂ receptor agonist activities, so that they are effective for therapy and prevention of diseases related to TXA₂.

What is claimed is:

1. A benzene-condensed heterocyclic derivative of the formula (I):

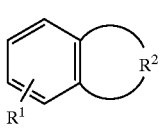

(I)

wherein R¹ is —X—(CH₂)ₙCOOR³ wherein X is —O—, —S—, or —CH₂—, R³ is hydrogen, C₁–C₅ lower alkyl, or an atom or group which gives a pharmaceutically acceptable salt, and n is an integer of 1 to 3;

R² is —NR⁴—CR⁵R⁶—CHR⁷— wherein

R⁴ is —(CH₂)ₘ—Y—R⁸ wherein m is an integer of 1 to 4,

Y is
1) —O—,
2) —CH₂—,
3) —S(O)ₚ— and p is an integer of 0 to 2,
4) —CO—,
5) —CH(OH)—,
6) —NR⁹SO₂—,
7) —NR⁹CO—,
8) —CONR⁹,
9) —NR⁹—,
10) —O—N=CR⁹—, wherein R⁹ is
 a) hydrogen,
 b) C₁–C₅ alkyl,
 c) phenyl or substituted phenyl,
 d) C₁–C₅ alkyl substituted with a phenyl or with a substituted phenyl group, or
11) the group represented by the formula (IIa) and (IIb)

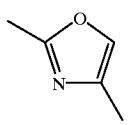

(IIa)

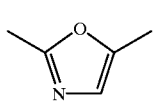

(IIb)

R⁸ is
1) phenyl, thienyl, furyl, naphthyl or C₃–C₈ cycloalkyl,
2) substituted phenyl, substituted thienyl, substituted furyl or substituted naphthyl,
3) C₁–C₅ alkyl which is substituted with one or two substituents selected from the group consisting of phenyl, substituted phenyl, thienyl, substituted thienyl, furyl, substituted furyl, naphthyl, substituted naphthyl, C₃–C₈ cycloalkyl and phenoxy;
4) C₂–C₅ alkenyl which is substituted with one or two substituents selected from the group consisting of phenyl, substituted phenyl, thienyl, substituted thienyl, furyl, substituted furyl, naphthyl, substituted naphthyl, C₃–C₈ cycloalkyl and phenoxy;
5) C₃–C₅ alkynyl which is substituted with one or two substituents selected from the group consisting of phenyl, substituted phenyl, thienyl, substituted thienyl, furyl, substituted furyl, naphthyl, substituted naphthyl, C₃–C₈ cycloalkyl and phenoxy;

6) $C_2$–$C_8$ alkoxyalkyl which is substituted with one or two substituents selected from the group consisting of phenyl, substituted phenyl, thienyl, substituted thienyl, furyl, substituted furyl, naphthyl, substituted naphthyl, $C_3$–$C_8$ cycloalkyl and phenoxy;

7) $C_1$–$C_5$ hydroxyalkyl which is substituted with one or two substituents selected from the group consisting of phenyl, substituted phenyl, thienyl, substituted thienyl, furyl, substituted furyl, naphthyl, substituted naphthyl, $C_3$–$C_8$ cycloalkyl and phenoxy;

8) $C_2$–$C_8$ alkylthioalkyl which is substituted with one or two substituents selected from the group consisting of phenyl, substituted phenyl, thienyl, substituted thienyl, furyl, substituted, naphthyl, substituted naphthyl, $C_3$–$C_8$ cycloalkyl and phenoxy;

9) $C_1$–$C_5$ aminoalkyl which is substituted with one or two substituents selected from the group consisting of phenyl, substituted phenyl, thienyl, substituted thienyl, furyl, substituted furyl, naphthyl, substituted naphthyl, $C_3$–$C_8$ cycloalkyl and phenoxy;

10) —$CH_2$—C(O)—$R^{10}$ wherein $R^{10}$ is phenyl or substituted phenyl or $C_1$–$C_5$ alkyl substituted with one or two phenyl groups or substituted phenyl;

$R^5$ is
1) hydrogen,
2) $C_1$–$C_5$ alkyl,
3) $C_1$–$C_5$ hydroxyalkyl or acetoxyalkyl,
4) $C_1$–$C_5$ alkyl substituted with one or two phenyl groups or substituted phenyl; or
5) $C_2$–$C_8$ alkoxyalkyl substituted with one or two phenyl groups or substituted phenyl groups; and $R^6$ and $R^7$ represent hydrogen or $R^6$ and $R^7$ are covalently bonded to represent a double bond, with the proviso that when X is $CH_2$, Y is not $CH_2$.

2. The compound according to claim 1, wherein X is —O—.

3. The compound according to claim 1, wherein Y is —O— or —$CH_2$—.

4. The compound according to claim 1, wherein Y is —S(O)$_p$—.

5. The compound according to claim 1, wherein Y is —$NR^9SO_2$— or —$NR^9CO$—.

6. The compound according to claim 1, wherein Y is —$NR^9$— or —$CONR^9$—.

7. The benzene-condensed heterocylic derivative according to claim 1, wherein when $R^8$ is a substituted phenyl, wherein the phenyl group is substituted with at least one substituent selected from the group consisting of $C_1$–$C_5$alkyl, phenyl, hydroxy, $C_1$–$C_5$ alkyloxy, phenoxy, halogen, trifluoromethyl, cyano, nitro, amino and $C_1$–$C_5$ alkylamino.

8. A thromboxane $A_2$ receptor antagonist comprising the compound according to claim 1 as an active ingredient.

9. A pharmaceutical composition comprising the compound according to claim 1 as an active ingredient.

10. A pharmaceutical composition for therapy or prevention of hypertension, thrombosis, ischemic heart diseases, cerebral circulatory diseases, peripheral circulatory diseases, arteriosclerosis, platelet function disorder, hyperlipidemia, nephritis or asthma comprising the compound of claim 1.

11. A method for antagonizing activity of a thromboxane $A_2$ receptor comprising contacting said thromboxane $A_2$ receptor with a compound according to claim 1.

12. A method for preventing or treating a disease resulting from excessive thromboxane $A_2$ activity resulting in abnormal platelet activation, thrombus formation or vasoconstriction comprising administering to a subject suffering from said disease an effective amount of the composition of claim 9 for inhibiting platelet activation, thrombus formation or vasoconstriction.

13. A method according to claim 12, wherein said disease is selected from the group consisting of hypertension, thrombosis, ischemic heart diseases, cerebral circulatory diseases, peripheral circulatory diseases, arteriosclerosis, platelet function disorder, hyperlipidemia, nephritis and asthma.

\* \* \* \* \*